US012778997B2

(12) United States Patent
Maresso et al.

(10) Patent No.: US 12,778,997 B2
(45) Date of Patent: *Nov. 3, 2026

(54) BACTERIOPHAGE COMPOSITIONS AND METHODS FOR TREATMENT OF BACTERIAL INFECTIONS

(71) Applicants: Baylor College of Medicine, Houston, TX (US); The United States of America as Represented by the Department of Veterans Affairs, Washington, DC (US)

(72) Inventors: Anthony Maresso, Houston, TX (US); Robert Ramig, Houston, TX (US); Sabrina Green, Houston, TX (US); Austen Terwilliger, Houston, TX (US); Keiko Salazar, Houston, TX (US); Justin R. Clark, Houston, TX (US); Barbara Trautner, Houston, TX (US)

(73) Assignees: Baylor College of Medicine, Houston, TX (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,659

(22) Filed: Mar. 12, 2024

(65) Prior Publication Data

US 2025/0041366 A1 Feb. 6, 2025

Related U.S. Application Data

(63) Continuation of application No. 18/053,245, filed on Nov. 7, 2022, now abandoned, which is a continuation of application No. PCT/US2022/076048, filed on Sep. 7, 2022.

(60) Provisional application No. 63/274,815, filed on Nov. 2, 2021, provisional application No. 63/241,209, filed on Sep. 7, 2021.

(51) Int. Cl.

| | |
|---|---|
| ***A61K 35/76*** | (2015.01) |
| ***A61P 31/04*** | (2006.01) |
| ***C12N 7/00*** | (2006.01) |

(52) U.S. Cl.

CPC .............. *A61K 35/76* (2013.01); *A61P 31/04* (2018.01); *C12N 7/00* (2013.01); *C12N 2795/10232* (2013.01)

(58) Field of Classification Search

None

See application file for complete search history.

(56) References Cited

U.S. PATENT DOCUMENTS

| | | | | |
|---|---|---|---|---|
| 2005/0136037 | A1 | 6/2005 | Holland et al. | |
| 2014/0199360 | A1 | 7/2014 | Donlan et al. | |
| 2017/0000831 | A1* | 1/2017 | Pouillot | C12Q 1/18 |
| 2021/0062160 | A1* | 3/2021 | Rohwer | C12N 7/00 |
| 2025/0281555 | A1 | 9/2025 | Maresso et al. | |

FOREIGN PATENT DOCUMENTS

| | | | |
|---|---|---|---|
| WO | 2020264096 | A1 | 12/2020 |
| WO | 2021163663 | A2 | 8/2021 |
| WO | 2023039427 | A1 | 3/2023 |

OTHER PUBLICATIONS

Cieplak et al., "A bacteriophage cocktail targeting *Escherichia coli* reduces *E. coli* in simulated gut conditions, while preserving a non-targeted representative commensal normal microbiota", Gut Microbes, vol. 9, No. 5, pp. 391-399. (Year: 2018).

Gibson et al., "Constructing and Characterizing Bacteriophage Libraries for Phage Therapy of Human Infections," Frontiers in Microbiology, Nov. 12, 2019 (Nov. 12, 2019), vol. 10, Art. No. 2537, pp. 1-14.

Green et al: "Bacteriophages from ExPEC Reservoirs Kill Pandemic Multidrug-Resistant Strains of Clonal Group ST131 in Animal Models of Bacteremia", Nature.come, Scientific Reports, 7:46151, published Apr. 12, 2017.

Green et al: "Targeting of Mammalian Glycans Enhances Phage Predation in the Gastrointestinal Tract", American Society for Microbiology, Therapeutics and Prevention, Jan./Feb. 2021, vol. 12, Issue 1, e03474-20, mbio.asm.org.

International Application No. PCT/US2022/080888 filed Dec. 5, 2022.

International Search Report dated Dec. 29, 2022 during examination of related application PCT/US2022/076048.

International Search Report dated May 4, 2023 during examination of International Appl. No. PCT/US22/80888.

(Continued)

*Primary Examiner* — Grant C Currens

(74) *Attorney, Agent, or Firm* — Norton Rose Fulbright US LLP

(57) ABSTRACT

Disclosed are compositions, devices, kits, and methods for treatment of Enterobacteriaceae infection. Aspects of the present disclosure are directed to bacteriophage compositions comprising one or more of ES17, ES19, HP3, HP3.1, and HP3.2. Certain aspects of the disclosure are directed to compositions comprising (a) bacteriophage ES17 or bacteriophage ES19, (b) bacteriophage HP3, and (c) bacteriophage HP3.1. Also disclosed are compositions comprising bacteriophage HP 3.2. Further disclosed are devices and kits comprising such compositions and methods for use of such compositions in treatment and prevention of pathogenic *E. coli* infection.

12 Claims, 37 Drawing Sheets

Specification includes a Sequence Listing.

(56) References Cited

OTHER PUBLICATIONS

Ma et al., "Metals Enhance the Killing of Bacteria by Bacteriophage in Human Blood", Scientific Reports, vol. 8, Article 2326, pp. 1-11. (Year: 2018).
Rosner et al., "Formulations for Bacteriophage Therapy and the Potential Uses of Immobilization", Pharmaceuticals, vol. 14, No. 359, pp. 1-19. (Year: 2021).
Ryan et al., "Recent advances in bacteriophage therapy: how delivery routes, formulation, concentration and timing influence the success of phage therapy", Journal of Pharmacy and Pharmacology, vol. 63, pp. 1253-1264. (Year: 2011).
Salazar et al., Antiviral Resistance and Phage Counter Adaptation to Antibiotic-Resistant Extraintestinal Pathogenic *Escherichia coli*. mBio. Apr. 27, 2021, vol. 12, No. 2, e00211-21, p. 1-20.
Terwilliger et al., "Phage Therapy Related Microbial Succession Associated with Successful Clinical Outcome for a Recurrent Urinary Tract Infection," Viruses, Oct. 12, 2021 (Oct. 12, 2021), vol. 13, No. 13, pp. 1-14.

* cited by examiner

FIG. 11C

| Strains | Mutated or missing genes | Earliest LPS knockout | Hypothetical LPS structure | LPS phenotype | ompA mutation? |
|---|---|---|---|---|---|
| JJ2050, JJ2528, JJ2547 | Wild type | | 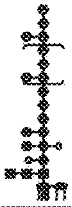 | Smooth | No |
| JJ2528-1, -2, -3, -4, -6, -7, -12 | *waaH, rfaD, waaF, waaC, waaL* | *waaC* | 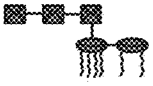 | Deep-rough | No |
| JJ2528-8 | *rfaD, waaF, waaC, waaL, waaU, waaZ, waaY, waaR, waaaO, waaB, waaS, waaP, waaG* | *waaC* | 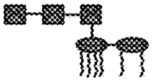 | Deep-rough | No |
| JJ2528-10, -11 | *waaC, waaL* | *waaC* | 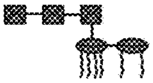 | Deep-rough | No |
| JJ2547-5 | *waaC* | *waaC* | 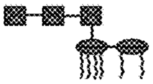 | Deep-rough | No |
| JJ2547-1, -2, -3, -4 | *waaF, waaC, waaL* | *waaC* |  | Deep-rough | No |
| JJ2050-1, -2, JJ2528-5, JJ2547-6 | *hldE* | *hldE* | 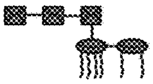 | Deep-rough | No |
| JJ2050-3, JJ2528-9 | *wzy O-antigen polymerase* | *wzy* | 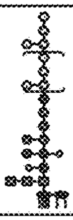 | Semi-smooth | Downstream (JJ2050-3 and JJ2528-9) Truncation (JJ2050-3) |

iii.

iii.

FIG. 13A

| | | |
|---|---|---|
| 1 | MSNNTYQHVSNESKYCKFDPTGSNPGTVTTVQSALSKISNGVNGIPDATMEVKGIAMI | 60 |
| 1 | MSNNTYQHVSNESKYCKFDPTGSNPGTVTTVQSALSKISNGVNGIPDATMEVKGIAMI | 60 |
| 61 | ASEQEVLDGTNNSKIVTPATLATRLLYPNATETKYGLTRYSTNEETLKGSDNNSSITPQK | 120 |
| 61 | ASEQEVLDGTNNSKIVTPATLATRLLYPNATETKYGLTRYSTNEETLKGSDNNSSITPQK | 120 |
| 121 | LKYHTDDVFKNRYSSESSNGVIKISSTPAALAGVDDTTAMTPLKTQKLAIKLISQIAPSE | 180 |
| 121 | LKYHTDDVFKNRYSSESSNGVIKISSTPAALAGVDDTTAMTPLKTQKLAIKLISQIAPSE | 180 |
| 181 | DTATESVRGVVQLSTVAQIRQGTLREGYAISPYTFMNSVATHEYKGVIRLGTQTEINNNL | 240 |
| 181 | DTATESVRGVVQLSTVAQIRQGTLREGYAISPYTFMNSVATHEYKGVIRLGTQTEINNNL | 240 |
| 241 | GGVAVTGETNGRGATGMRGVVKLTTQAGIAPEGDSSGALWNADVINTRGGQTINGSL | 300 |
| 241 | GGVAVTGETNGRGATGMRGVVKLTTQAGIAPEGDSSGALWNADVINTRGGQTINGSL | 300 |
| 301 | NLDHLTANGIWSRGGMWKNGDQPVATERYASERVPVGTIMMFAGDSAPPGWIMCHGGTVS | 360 |
| 301 | NLDHLTANGIWSRGGMWKNGDQPVATERYASERVPVGTIMMFAGDSAPPGWIMCHGGTVS | 360 |
| 361 | GDQPDYRNVVGTRFGGDWNPGVPDMRGLFVRGAGTGGHILNQRGQDGYGKDRLGVGCD | 420 |
| 361 | GDQPDYRNVVGTRFGGDWNPGVPDMRGLFVRGAGTGGHILNQRGQDGYGKDRLGVGCD | 420 |
| 421 | GMHVGGQAQQMSYHKHAGGWGEYNRSEGPFGASVYQGYLGTRKYSDWDNASYFTNDGFE | 480 |
| 421 | GMHVGGQAQQMSYHKHAGGWGEYNRSEGPFGASVYQGYLGTRRHSDWDNASYFTNDGFE | 480 |
| 481 | LGGPRDAHGTLNREGLIGYETRPWNISLNYIIKVHY SEQ ID NO:1 HP3 | 516 |
| 481 | LGGPRDAHGTLNREGLIGYETRPWNISLNYIIKVHY SEQ ID NO:2 HP3.1 | 516 |

FIG. 15

| Isolate | Isolation Strategy | Organ |
|---|---|---|
| JJ2050 | | |
| JJ2050-1 | Culture | |
| JJ2050-2 | Animal | Liver |
| JJ2050-3 | Animal | Spleen |
| JJ2528 | | |
| JJ2528-1 | Culture | |
| JJ2528-2 | Culture | |
| JJ2528-3 | Culture | |
| JJ2528-4 | Culture | |
| JJ2528-5 | Culture | |
| JJ2528-6 | Culture | |
| JJ2528-7 | Culture | |
| JJ2528-8 | Animal | Liver |
| JJ2528-9 | Animal | Liver |
| JJ2528-10 | Animal | Spleen |
| JJ2528-11 | Animal | Liver |
| JJ2528-12 | Animal | Mix |
| JJ2547 | | |
| JJ2547-1 | Culture | |
| JJ2547-2 | Culture | |
| JJ2547-3 | Culture | |
| JJ2547-4 | Culture | |
| JJ2547-5 | Animal | Liver |
| JJ2547-6 | Animal | Spleen |

| ExPEC Isolate | Spot Assay (PFU/mL) | | | | EOP (HP3.1 vs HP3) |
|---|---|---|---|---|---|
| | HP3 | HP3.1 | EC1 | ES17 | |
| *JJ2050* | 6.73E10 | 4.74E9 | 5.61E9 | 2.56E10 | 7.04% |
| JJ2050-1 | | 4.16E8 | | | |
| JJ2050-2 | | 3.34E8 | | | |
| JJ2050-3 | | 9.29E8 | | | |
| ***JJ2528*** | 8.32E10 | 4.47E10 | 8.20E9 | 2.07E10 | 53.73% |
| JJ2528-1 | | 3.56E9 | | | |
| JJ2528-2 | | 3.78E9 | | | |
| JJ2528-3 | | 4.45E9 | | | |
| JJ2528-4 | | 5.42E9 | | | |
| JJ2528-5 | | 1.39E9 | | | |
| JJ2528-6 | | 6.61E8 | | | |
| JJ2528-7 | | 6.53E8 | | | |
| JJ2528-8 | | 1.9E9 | | | |
| JJ2528-9 | | 1.93E9 | | | |
| JJ2528-10 | | 1.48E9 | | | |
| JJ2528-11 | | 1.25E9 | | | |
| **JJ2528-12** | | 2.47E9 | | | |
| *JJ2547* | 3.16E11 | 3.01E10 | 5.80E9 | 3.47E10 | 39.52% |
| JJ2547-1 | | 6.32E9 | | | |
| JJ2547-2 | | 4.27E10 | | | |
| JJ2547-3 | | 9.51E9 | | | |
| JJ2547-4 | | 1.07E10 | | | |
| JJ2547-5 | | 8.13E9 | | | |
| JJ2547-6 | | 2.67E9 | | | |

FIG. 16

BACTERIOPHAGE COMPOSITIONS AND METHODS FOR TREATMENT OF BACTERIAL INFECTIONS

CROSS-REFERENCE TO RELATED APPLICATIONS

This application is a continuation of U.S. Non-Provisional application Ser. No. 18/053,245 filed Nov. 7, 2022, which is a continuation of International Application No. PCT/US2022/076048 filed Sep. 7, 2022, which claims priority to U.S. Provisional Application No. 63/241,209 filed Sep. 7, 2021 and U.S. Provisional Application No. 63/274,815 filed Nov. 2, 2021, the disclosures of which are hereby incorporated by reference in their entirety.

SEQUENCE LISTING

The instant application contains a Sequence Listing which has been submitted in XML format and is hereby incorporated by reference in its entirety. Said XML copy, created on May 28, 2024, is named BAYMP0340USC1_SL.xml and is 172,008 bytes in size.

BACKGROUND

I. Field of the Invention

Aspects of this invention relate to at least the fields of microbiology and virology.

II. Background

Multidrug-resistant (MDR) bacteria infect millions of people around the world, yearly. Many of these infections caused by these bacteria have become untreatable due to resistance to last resort antibiotics. Exacerbating this crisis, the pipeline for antibiotic development is slow and resistant strains rapidly develop in the wake of new drugs. The family Enterobacteriaceae provides an urgent threat of MDR infections, due in part to strains of *Escherichia* (*E.*) *coli*. Extraintestinal pathogenic *E. coli* (ExPEC), a pathotype of the larger *E. coli* superfamily, is a natural inhabitant of the human gastrointestinal microbiome. ExPEC strains are unique in their ability to translocate and cause subsequent infections in immunocompromised individuals. When they do, they cause an array of serious illnesses including urinary tract infections (UTI), bacteremia, sepsis, and neonatal meningitis. New treatments are needed to contain the threat of MDR bacteria.

A promising response to MDR infections is bacteriophage (phage) therapy. Viruses which infect bacteria, phages are environmentally ubiquitous, host-specific, and effective at infecting MDR bacterial strains. Importantly, they have been shown to be safe and effective in animal and compassionate-use human trials. Because they use the replication machinery of their bacterial host, phage mutation rates are directly influenced by those of that host; as such, phages may rapidly adapt to target strains of bacteria. However, due to the cognate rates of evolution between a phage and its host, a mixed population of phages and bacteria will result in an evolutionary arms race. Consequently, phage-resistant bacteria are likely to develop.

There exists a need for new and improved methods and compositions for treatment of bacterial infections, including *E. coli* infections such as ExPEC.

SUMMARY

Aspects of the present disclosure are directed to bacteriophage compositions, kits and devices comprising such compositions, and methods for use of such compositions for treatment or prevention of pathogenic infections. In some aspects, disclosed is a composition comprising (a) bacteriophage ES17 or bacteriophage ES19, (b) bacteriophage HP3, and (c) bacteriophage HP3.1. In some embodiments, the composition comprises bacteriophages ES17, HP3, and HP3.1. In some embodiments, the composition comprises bacteriophages ES19, HP3, and HP3.1 Also disclosed are compositions comprising bacteriophage HP3.2. Further disclosed are methods of treating or preventing an *E. coli* infection in an individual comprising administering (a) bacteriophage ES17 or bacteriophage ES19, (b) bacteriophage HP3, and (c) bacteriophage HP3.1. Certain aspects disclose methods of treating or preventing an *E. coli* infection in an individual comprising administering bacteriophage HP3.2.

Embodiments of the disclosure include bacteriophages, bacteriophage compositions, kits, devices, medical devices, therapeutic devices, polynucleotides, methods for preparing a device, methods for treatment of an *E. coli* infection, and methods for prevention of an *E. coli* infection. Compositions of the disclosure can include at least 1, 2, 3, or more of the following components: bacteriophage ES17, bacteriophage ES19, bacteriophage HP3, bacteriophage HP3.1, bacteriophage HP3.2, an additional bacteriophage, a metal, and a pharmaceutical excipient. Any one or more of the preceding components may be excluded from certain embodiments. Methods of the disclosure can include at least 1, 2, 3, or more of the following steps: detecting an infection in an individual, diagnosing an individual as having an *E. coli* infection, generating a bacteriophage composition, coating a device with a bacteriophage composition, providing a device to an individual, formulating a bacteriophage composition for therapeutic administration, and administering a bacteriophage composition to an individual. Any one or more of the preceding steps may be excluded from certain embodiments.

Disclosed herein, in some embodiments, is a composition comprising (a) bacteriophage ES17 or bacteriophage ES19, (b) bacteriophage HP3, and (c) bacteriophage HP3.1. In some embodiments, the composition comprises bacteriophage ES17. In some embodiments, the composition comprises bacteriophage ES19. In some embodiments, the composition further comprises HP3.2. In some embodiments, the amount of the bacteriophages in the composition are substantially the same. In some embodiments, the amount of the bacteriophages in the composition are not substantially the same. Also disclosed, in some embodiments, is a composition comprising bacteriophage HP3.2. In some embodiments, the composition further comprises a pharmaceutically acceptable excipient. In some embodiments, the pharmaceutical composition further comprises one or more metals. In some embodiments, the one or more metals comprise calcium, magnesium, iron, sodium, and/or potassium. In some embodiments, the composition is in a liquid formulation. In some embodiments, the composition is in a solid formulation. In some embodiments, the composition is housed in a delivery apparatus. Also disclosed is a method of treating or preventing an *E. coli* infection in an individual, comprising administering to the individual a composition of the disclosure.

Further disclosed herein, in some embodiments, is a device comprising (a) bacteriophage ES17 or bacteriophage ES19, (b) bacteriophage HP3, and (c) bacteriophage HP3.1 that are on, in, and/or around the device. In some embodiments, the device comprises bacteriophage ES17. In some embodiments, the device comprises bacteriophage ES19. In some embodiments, the device further comprises bacteriophage HP3.2. Also disclosed is a device comprising bacteriophage HP3.2 that is on, in, and/or around the device. In some embodiments, the device is a catheter, drive line, syringe, tube, implant, defibrillator, artificial joint, pacemaker, screw, rod, disc, intrauterine device, pin, plate, stent, dental device, eye lens, shunt, valve, neurological or neurosurgical device, gastrointestinal device, genitourinary device, catheter cuff, vascular access device, or wound drain. In some embodiments, the device is further defined as having a coating comprising the bacteriophages.

Also disclosed herein, in some embodiments, is a kit comprising (a) bacteriophage ES17 or bacteriophage ES19, (b) bacteriophage HP3, and (c) bacteriophage HP3.1, housed in a suitable container. In some embodiments, the kit comprises bacteriophage ES17. In some embodiments, the kit comprises bacteriophage ES19. In some embodiments, the kit further comprises HP3.2. Also disclosed is a kit comprising bacteriophage HP3.2. In some embodiments, the kit further comprises a device. In some embodiments, the device comprises the bacteriophages. In some embodiments, the bacteriophages are separate from the device.

Disclosed herein, in some embodiments, is a method of treating or preventing an *E. coli* infection in an individual, comprising the step of administering to the individual (a) bacteriophage ES17 or bacteriophage ES19, (b) bacteriophage HP3, and (c) bacteriophage HP3.1. In some embodiments, the method comprises administering bacteriophage ES17. In some embodiments, the method comprises administering bacteriophage ES19. In some embodiments, the method further comprises administering to the individual the bacteriophage HP3.2. In some embodiments, the bacteriophages are in the same formulation. In some embodiments, the bacteriophages are not in the same formulation. In some embodiments, each of the bacteriophages are administered to the individual at the same time. In some embodiments, each of the bacteriophages are administered to the individual at different times. In some embodiments, the bacteriophages are administered to the individual intravenously, orally, and/or upon a device. In some embodiments, the bacteriophages are administered multiple times to the individual. In some embodiments, the bacteriophages are administered once a day, twice a day, once a week, twice a week, once a month, or twice a month. In some embodiments, the bacteriophages are administered twice a week for 6-12 weeks. Also disclosed is a method of treating or preventing an *E. coli* infection in an individual, comprising the step of administering to the individual the bacteriophage HP3.2.

In some embodiments, the individual has an infection in the urinary tract, blood, gut, abdomen, stomach, lungs, skin, kidneys, prostate, bladder, brain, vaginal tract, heart, liver, spleen, or a combination thereof. In some embodiments, the individual has a catheter-associated urinary tract infection. In some embodiments, the *E. coli* is multidrug-resistant. In some embodiments, the *E. coli* is an extraintestinal pathogenic *E. coli*. In some embodiments, the *E. coli* is ST69, ST73, ST96, or ST131. In some embodiments, the *E. coli* is ST131. In some embodiments, the individual has a urinary tract infection, neonatal meningitis, a blood-stream infection, pneumonia, sepsis, a surgical wound infection, a skin infection, a prostate infection, meningitis, a vaginal infection or a combination thereof. In some embodiments, the individual has diarrhea, stomach cramping, nausea, and/or vomiting. In some embodiments, the individual is immunosuppressed. In some embodiments, the individual has an immune cell defect, asplenia, impaired splenic function, nephrotic syndrome, or an autoimmune condition. In some embodiments, the individual is administered the bacteriophages prior to a medical procedure or regimen. In some embodiments, the individual will be subject to immunosuppressive conditions. In some embodiments, the individual is taking or will be taking chemotherapy. In some embodiments, the individual is taking or will be taking an immunosuppressant. In some embodiments, the immunosuppressant is a glucocorticoid, a calcineurin inhibitor, an antimetabolite, or an antibody therapy. In some embodiments, the medical procedure comprises insertion of a device in the individual. In some embodiments, the source of the *E. coli* was from a beverage, comestible, another individual, or an environment. In some embodiments, the environment is ground or surface water, water used to irrigate crops, a public water system, a hospital, a school, a nursing home, a petting zoo, a cruise ship, a train, or an airplane. In some embodiments, the individual is at a higher risk for *E. coli* infection than the general population. In some embodiments, the individual is younger than 12 years of age or is 65 years of age or older. In some embodiments, the individual is 1, 2, 3, 4, 5, 6, 7, 8, 9, 10, 11, or 12 years of age. In some embodiments, the individual is 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years of age, or older. In some embodiments, the individual has consumed undercooked meat, unpasteurized milk, apple juice or cider; or soft cheese made from raw milk. In some embodiments, the individual is taking a medication to reduce stomach acid (e.g., a proton pump inhibitor).

Also disclosed herein, in some embodiments, is a method of reducing the level of a drug-resistant and/or pathogenic *E. coli* strain in an individual, comprising the step of administering to the individual a therapeutically effective amount of (a) bacteriophage ES17 or bacteriophage ES19, (b) bacteriophage HP3, and (c) bacteriophage HP3.1. In some embodiments, the method comprises administering bacteriophage ES17. In some embodiments, the method comprises administering bacteriophage ES19. In some embodiments, administering to the individual a therapeutically effective amount of the bacteriophage HP3.2. Also disclosed, in some embodiments, is a method of reducing the level of a drug-resistant and/or pathogenic *E. coli* strain in an individual, comprising the step of administering to the individual a therapeutically effective amount of the bacteriophage HP3.2. In some embodiments, the reduction is in the intestine of the individual. In some embodiments, the individual has been subject to insertion of a device or will be subjected to insertion of a device. In some embodiments, the individual will be subject to immunosuppressive conditions. In some embodiments, the *E. coli* strain is an extraintestinal pathogenic *E. coli*. In some embodiments, the *E. coli* strain is ST69, ST73, ST96, or ST131. In some embodiments, the *E. coli* strain is ST131.

Further described herein, in some embodiments, is a method of preparing a device, comprising the step of subjecting a device to (a) bacteriophage ES17 or bacteriophage ES19, (b) bacteriophage HP3, and (c) bacteriophage HP3.1. In some embodiments, the method comprises subjecting the device to bacteriophage ES17. In some embodiments, the method comprises subjecting the device to bacteriophage ES19. In some embodiments, the bacteriophages are placed on, in, and/or around the device. In some embodiments, one or more surfaces of the device are coated with the bacteriophages. In some embodiments, the device is a catheter, drive line, syringe, tube, implant, defibrillator, artificial joint, pacemaker, screw, rod, disc, intrauterine device, pin, plate, stent, dental device, or eye lens. In some embodiments, the method further comprises delivering the device to an individual in need thereof.

Throughout this application, the term “about” is used to indicate that a value includes the inherent variation of error for the measurement or quantitation method.

The use of the word “a” or “an” when used in conjunction with the term “comprising” may mean “one,” but it is also consistent with the meaning of “one or more,” “at least one,” and “one or more than one.”

The phrase “and/or” means “and” or “or”. To illustrate, A, B, and/or C includes: A alone, B alone, C alone, a combination of A and B, a combination of A and C, a combination of B and C, or a combination of A, B, and C. In other words, “and/or” operates as an inclusive or.

The words “comprising” (and any form of comprising, such as “comprise” and “comprises”), “having” (and any form of having, such as “have” and “has”), “including” (and any form of including, such as “includes” and “include”) or “containing” (and any form of containing, such as “contains” and “contain”) are inclusive or open-ended and do not exclude additional, unrecited elements or method steps.

The compositions and methods for their use can “comprise,” “consist essentially of,” or “consist of” any of the ingredients or steps disclosed throughout the specification. Compositions and methods “consisting essentially of” any of the ingredients or steps disclosed limits the scope of the claim to the specified materials or steps which do not materially affect the basic and novel characteristic of the claimed invention.

“Individual, “subject,” and “patient” are used interchangeably and can refer to a human or non-human.

Any method in the context of a therapeutic, diagnostic, or physiologic purpose or effect may also be described in “use” claim language such as “Use of” any compound, composition, or agent discussed herein for achieving or implementing a described therapeutic, diagnostic, or physiologic purpose or effect.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Any embodiment discussed with respect to one aspect of the disclosure applies to other aspects of the disclosure as well and vice versa. For example, any step in a method described herein can apply to any other method. Moreover, any method described herein may have an exclusion of any step or combination of steps. Aspects of an embodiment set forth in the Examples are also embodiments that may be implemented in the context of embodiments discussed elsewhere in a different Example or elsewhere in the application, such as in the Summary, Detailed Description, Claims, and Brief Description of the Drawings.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Mice were orally gavaged on day 0 with $10^9$ CFU of ExPEC JJ1901 and then monitored for colonization by plating fecal pellets for colony counts on selective medium (LB plus chloramphenicol). Starting on day 1, groups received either daily phage dose ($10^9$ PFU), phage in water ($10^9$ PFU/ml), or antibiotic (ABX), 2 mg/ml ampicillin in water, until day 5. On day 6, mice were euthanized and their organs were homogenized and plated for CFU levels or PFU levels (plaque assay). (FIG. 1B) Intestinal (fecal) colonization of ExPEC. Colored dots represent means. ExPEC plus phage gavage, ExPEC1U(G); ExPEC plus phage in water, ExPEC1U(W); ExPEC plus antibiotic in water, ExPEC1ABX(W). (FIG. 1C) Intestinal tissue and contents phage levels. (FIG. 1D) Intestinal tissue and contents ExPEC levels. N=8 to 10. Open squares represent individual mice, bars represent means. #, missing values due to histological analysis. (FIG. 1E) ExPEC levels after 4.5 h of growth (shaking, 37° C.) in LB, fecal medium, or cecal medium with or without phage (MOI 10). (FIG. 1F) PFU counts of phage HP3 after 4.5 h of growth in different medium. Open squares represent independent cultures (N=3). Bars represent means±standard deviation (SD). NS, not significant; ", none detected. One-way ANOVA used for statistical analysis.

(FIG. 2A) Cecal medium (CM) was prepared, heat treated (HT CM) at 100° F. for 20 min or centrifuged (6,000×g; 5 min), filtered (0.22-mm filter treated or FT), and then used for a 4.5-h growth assay. (FIG. 2B) Cecal medium was centrifuged at a high speed (9,000×g, 5 min) separated into pellet (insoluble [Ins]) and supernatant (soluble [Sol]). The Ins was resuspended in saline±NAC (N-acetyl cysteine, 5 mg/ml), the soluble±mucin (porcine gastric mucin, 1% [wt/vol]). ExPEC levels are after a 4.5-h assay. (FIG. 2C) ExPEC levels following a 4.5-h assay screen with phages in mucin (1.5% [wt/vol] in LB). For all experiments, MOI of 10. Open squares represent independent cultures. Mean (bars) 6SD shown throughout, N=3 to 9. ", none detected. One-way ANOVA used for statistical analysis.

(FIG. 3A) Transmission electron microscopy (TEM) image of phage ES17. (FIG. 3B) Mucin (0%, 0.5% and 1.5% [wt/vol]) was added to the ExPEC cultures for 10 min at RT with shaking (255 rpm). The cultures were centrifuged (6,000×g for 5 min) and gently washed with PBS. Adsorption curve (MOI, 1) was constructed using mid-log-phase cultures and samples taken every 5 min for 10 min. ExPEC coated with mucin pictured in TEM image. White bar, 1 mm. (FIG. 3C) Adsorption phage ES17. (FIG. 3D) Adsorption phage HP3. Adsorption constant (K) and percent adsorbed (% Ads) in 10 min for 0% and 1.5% mucin indicated above the curves. Regression lines generated from mean values of phage remaining for time points indicated. Open squares represent individual values from separate cultures. Dashed lines, 0% mucin; red lines, 0.5% mucin; blue lines, and 1.5% mucin in bacteria. Two biological replicates for 0% and 1.5%. (FIG. 3E) ELISA with 1.5% mucin-coated wells. Different phages were incubated overnight on coated wells and then washed, and the assay was performed. Open squares represent biological replicates.

Different concentrations of phages incubated on wells indicated on x axis. N=6. Bars represent means±SD shown throughout. Simple linear regression was used to calculate if slope is significantly nonzero for FIGS. 3C and 3D. Two-way ANOVA used for statistical analysis in FIG. 3E.

Figure 4A:
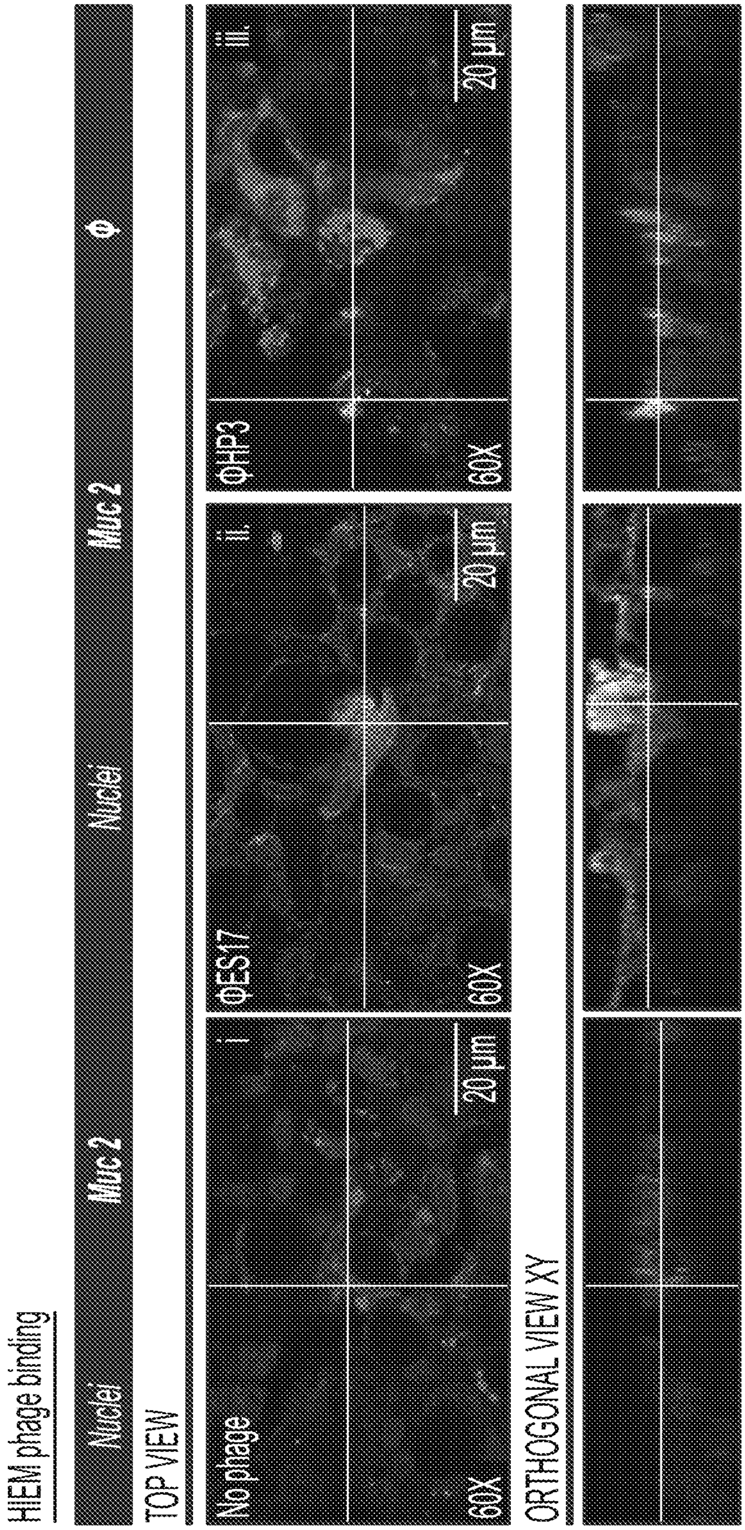
Figure 4B:
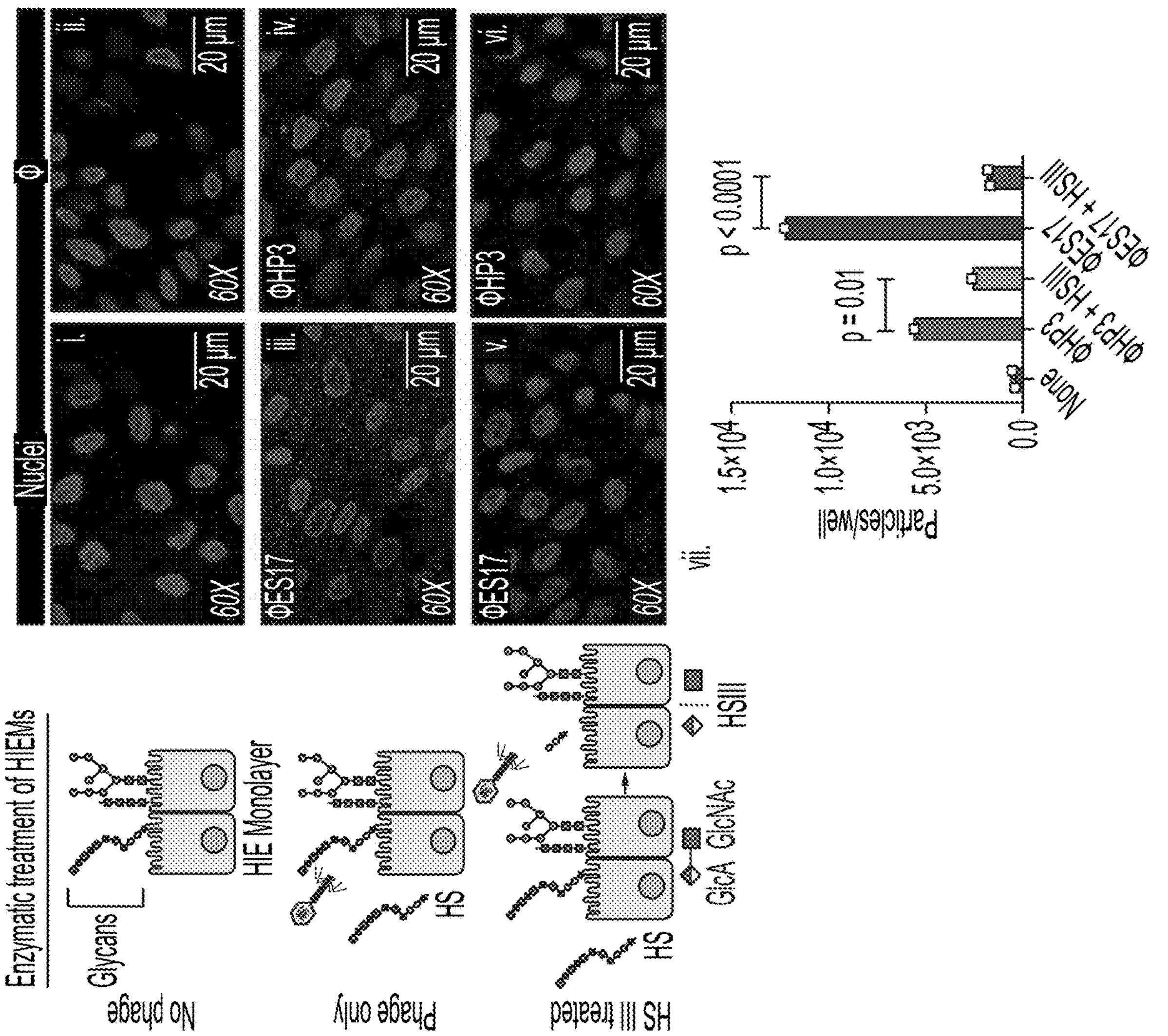

FIGS. 4A and 4B. ES17 binds to the surface of human intestinal enteroids (HIEMs). Differentiated HIEMs were incubated with phages ($10^8$ PFU/ml for 1 h) at 37° C., 5% $CO_2$, in a humidified incubator. Afterwards, HIEMs were washed, fixed in Clark's solution, stained, and imaged for phage (Alexa Fluor 488; green), intestinal cells (DAPI; blue), and Muc2 (Alexa Fluor 594; red). Image magnification, ×60. Orthogonal view XY shown below. (FIG. 4A) No phage added (i), phage ES17 added (ii), and phage HP3 added (iii). (FIG. 4B) To selectively removed HSPG from GAG chains, enteroid cultures were pretreated with heparinase III (Hep III; 2 U/ml) for 2 h at 37° C., 5% $CO_2$, in a humidified incubator and then incubated with or without phage as described above. No phage (i and ii), phage ES17 added (iii), phage HP3 added (iv), Hep III-treated HIEMs incubated with ES17 (v), and Hep Ill-treated HIEMs incubated with HP3 (vi). Image magnification, ×60. (vii) Quantification of particles (phage) per well using FIJI software. Means±SDs shown (N=1 to 2). Open squares represent independent cultures. One-way ANOVA used for statistical analysis. FIG. 4B created with BioRender software.

FIGS. 5A-5D. (FIG. 5A) ExPEC levels after 4.5-h growth assay in cecal medium or LB (MOI, 10). Bars indicate the means, and open squares represent independent cultures. N=3. (FIG. 5B) Mice were orally gavaged on day 0 with $10^9$ CFU of ExPEC JJ1901. Starting on day 1, mice received either daily dose (gavage) of phages (HP3 or ES17 at $10^{10}$ PFU) or none until day 5. On day 6, mice were euthanized and their organs were homogenized and plated for CFU levels or plaque assay for PFU levels. (FIG. 5C) Intestinal (tissue) and contents phage levels. (FIG. 5D) Intestinal (tissue) and contents ExPEC levels. N=10 mice per group. Bars indicate the means±SD, and open squares indicate individual mice. ", none detected. One-way ANOVA used for statistical analysis.

Figure 6:
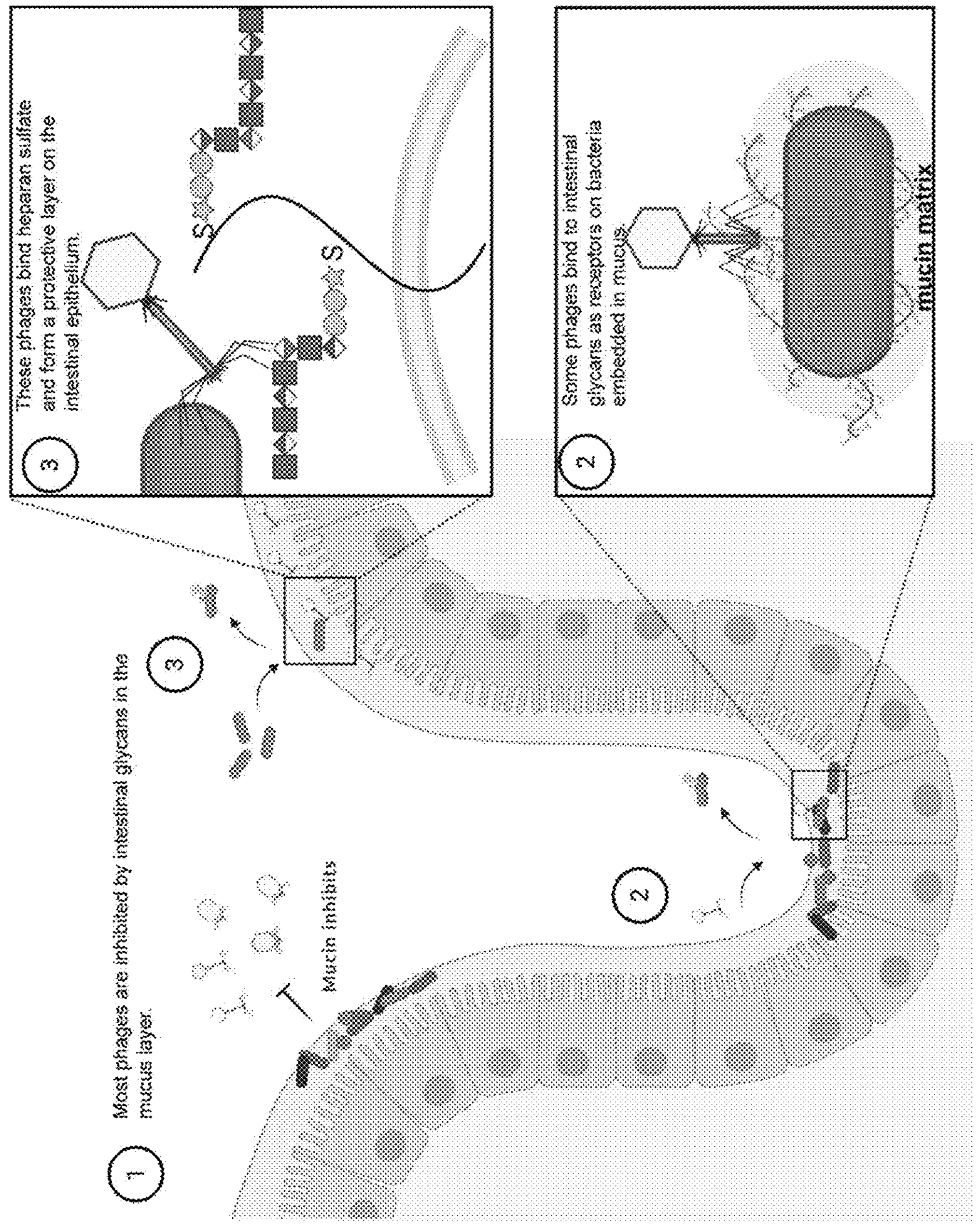

FIG. 6. Model showing (1) mucins from the intestinal mucus layer inhibit phage infection, (2) phage ES17 can bind to mucin and utilize other intestinal glycans as a receptor to infect and kill mucus-embedded bacteria, and (3) phages like ES17 can be utilized to coat the intestinal epithelium by binding heparan sulfate glycans to protect from invasive pathogen infection.

Figure 7A:
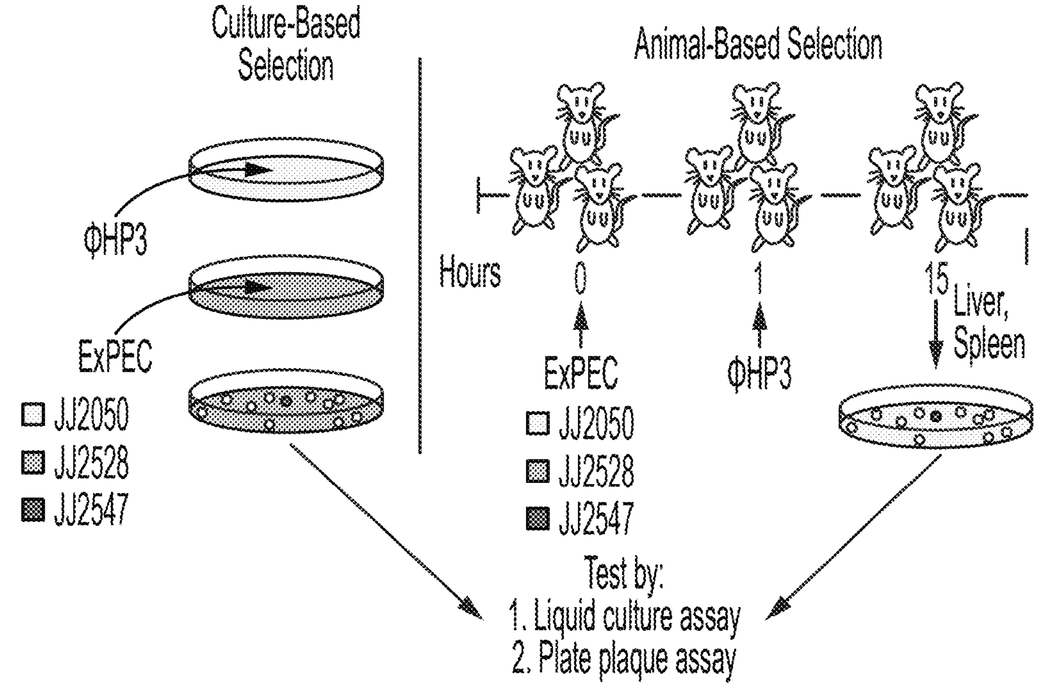
Figure 7B:
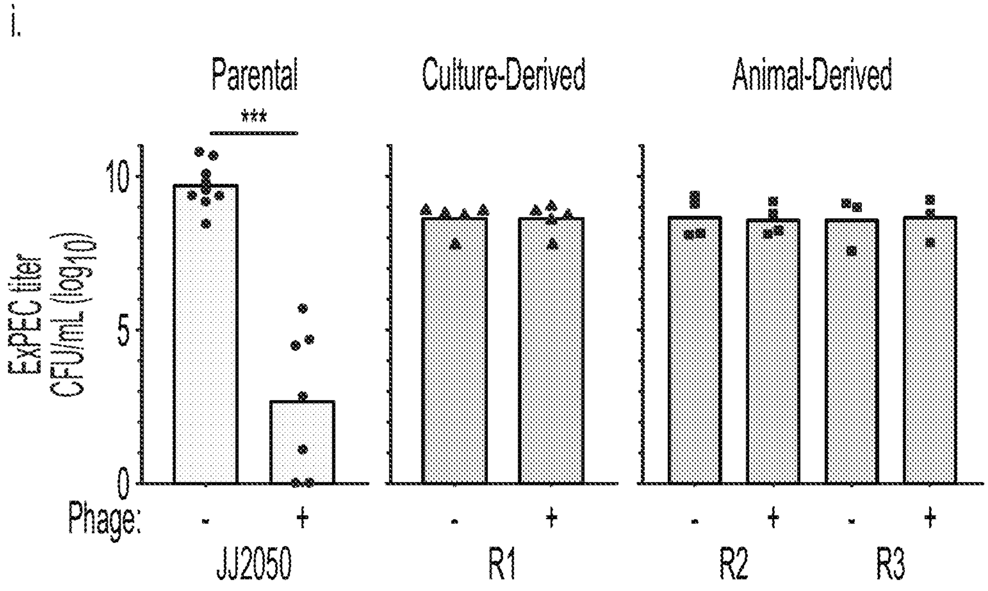
Figure 7B:
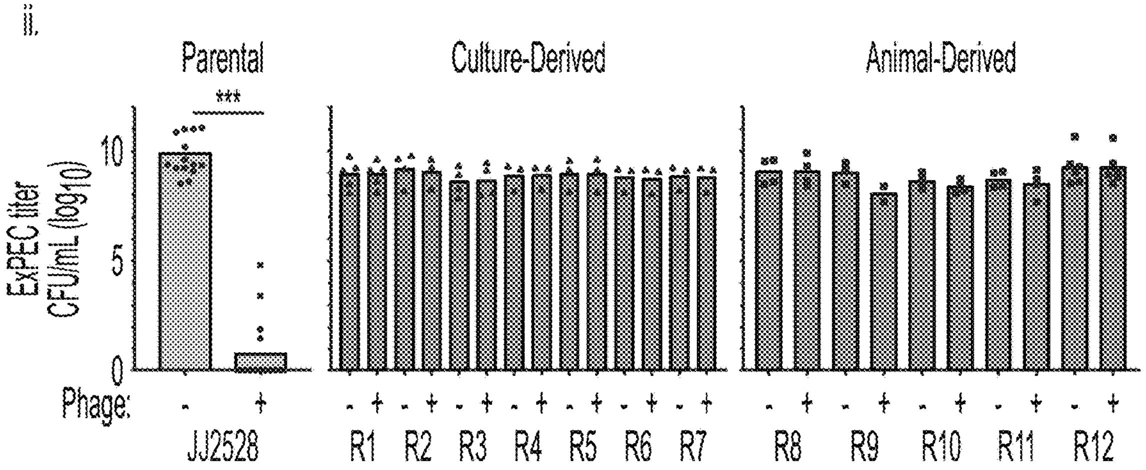
Figure 7B:
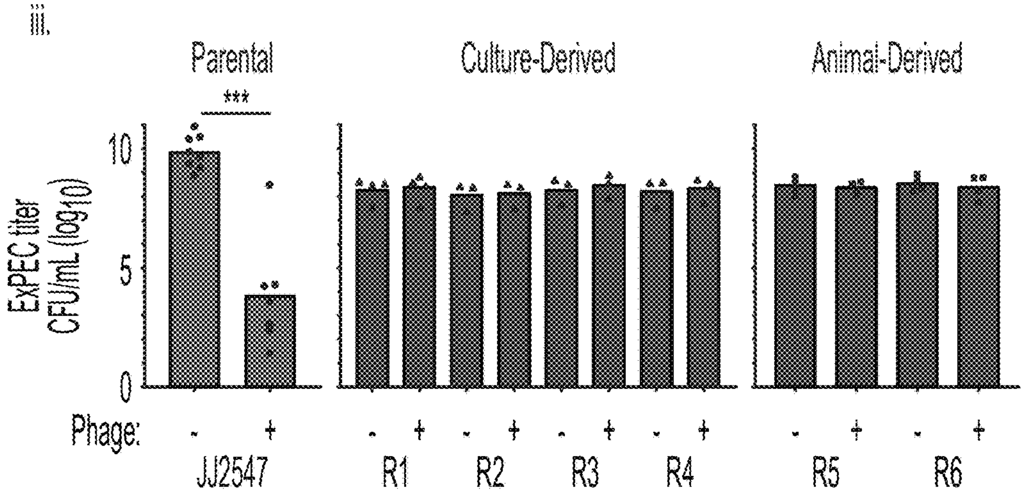

FIGS. 7A and 7B. Three clinical ExPEC isolates—JJ2050, JJ2528, and JJ2547—were used to develop resisters against ϕHP3. (FIG. 7A) Resisters were isolated using either a culture- or murine-based method. In both cases, parental strains were subjected to selective pressure in the presence of ϕHP3. (FIG. 7B) Isolate titers were determined in liquid culture after 4.5 h of incubation in LB, with or without the presence of 0HP3. Panel B is grouped by parental isolate: JJ2050 (i), JJ2528 (ii), and JJ2547 (iii). P values were determined by Student t test or Mann-Whitney test, where necessary. *, P, 0.05; , P, 0.01; *, P, 0.01. Bars represent the average titers. Each data point represents the average of three parallel technical replicates.

Figure 8:
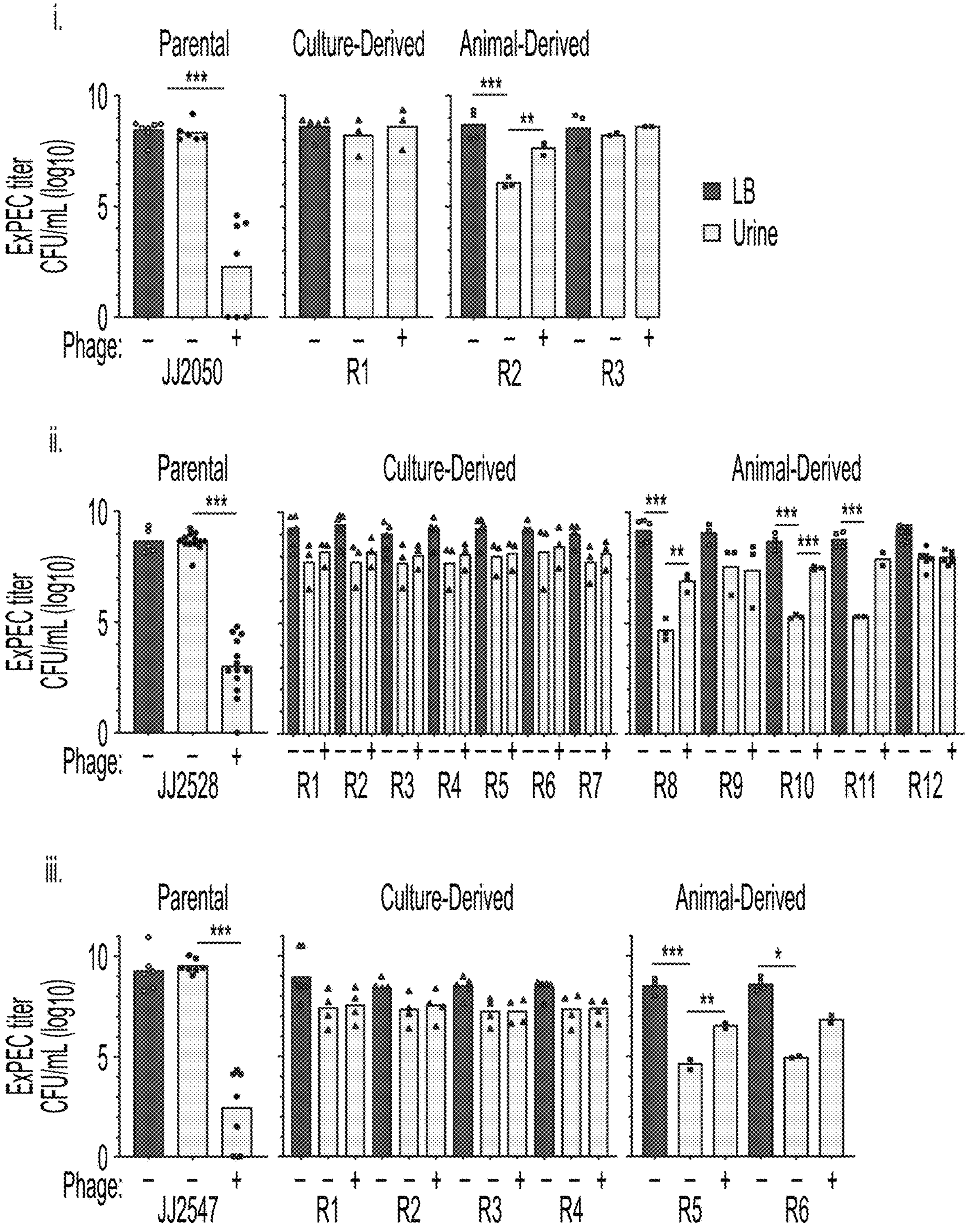

FIG. 8. Isolate titers were determined in liquid culture after 4.5 h of incubation in LB (black) or human urine (yellow), with or without f HP3. Each panel is grouped by parental isolate: JJ2050 (i), JJ2528 (ii), and JJ2547 (iii). P values were determined by Student t test or Mann-Whitney test, where necessary. *, P<0.05; , P<0.01; *, P<0.01. Each data point represents the average of three parallel technical replicates.

Figure 9A:
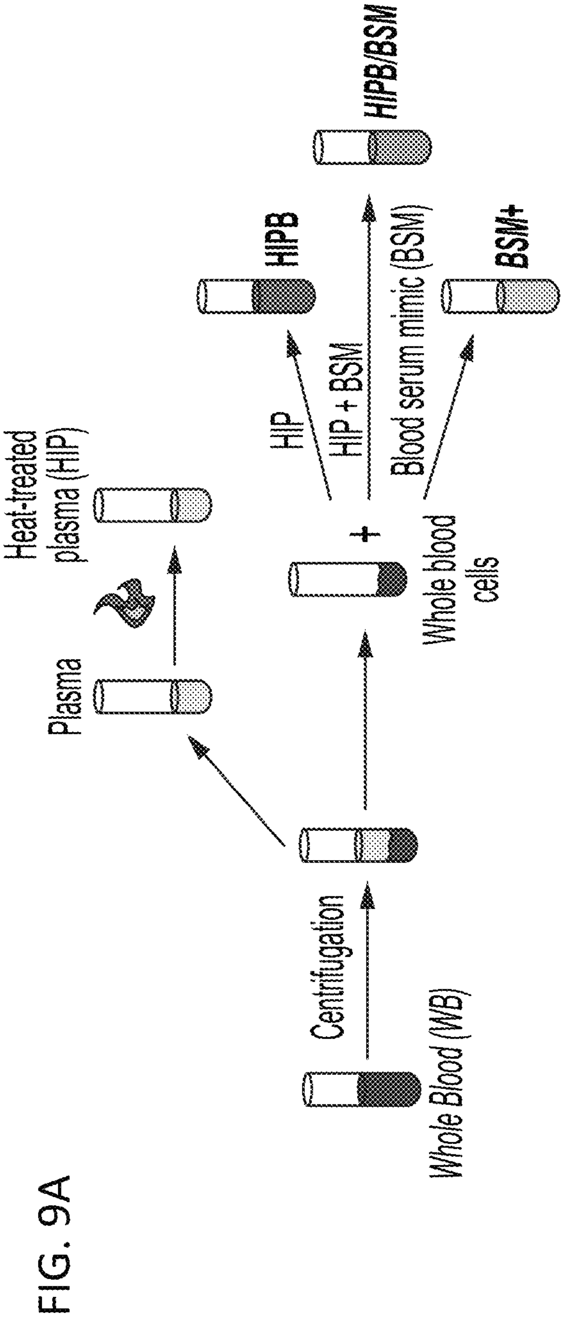
Figure 9B:
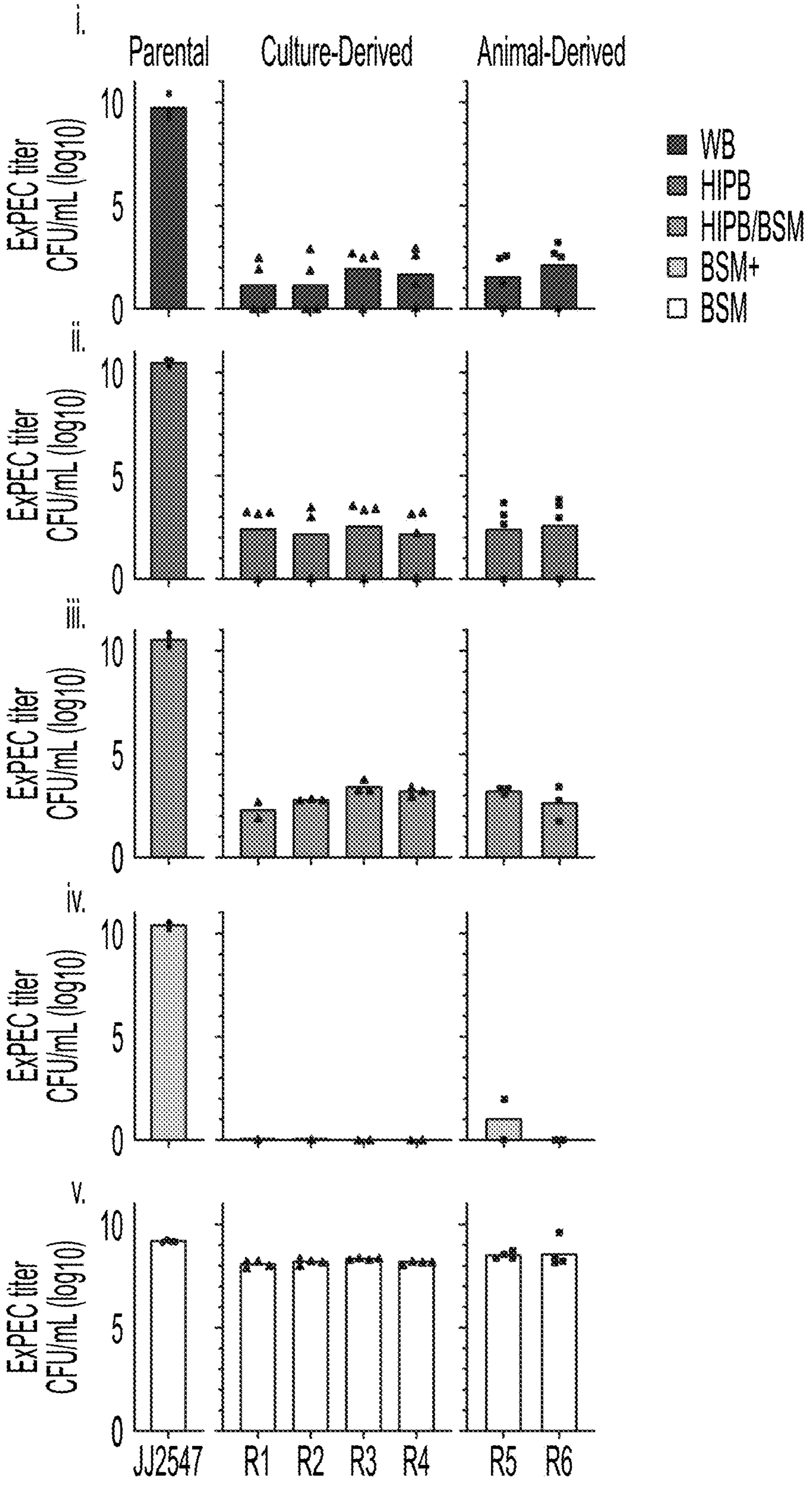

FIGS. 9A and 9B. (FIG. 9A) Human whole blood was separated by centrifugation and the plasma heat-treated to inactivate complement. The whole blood cells (WBCs) were then resuspended in heat-treated plasma (HIP), blood serum mimic (BSM), or a 1:1 mix of HIP and BSM. (FIG. 9B) JJ2547 and resisters' titers were determined after 24 h of incubation in different blood media: whole blood (WB, dark red) (i), HIP blood (HIPB, red) (ii), HIP/BSM blood (HIPB/BSM, orange) (iii), BSM (BSM1, light orange) (iv), or BSM with no blood cells (BSM, white) (v). P values were determined by Student t test or Mann-Whitney test, where necessary. *, P<0.05; , P<0.01; *, P<0.01. Each data point represents the average of three parallel technical replicates.

FIGS. 10A-10D. Two representative resisters, JJ2528-8 ("Resister 8", dark gray, ompA truncated) and JJ2528-12 ("Resister 12", black, waaC truncated), and their parental isolate (light gray) were tested for virulence in the murine sepsis model. (FIG. 10A) Swiss-Webster mice were infected with $3.5\times10^7$ CFU log-phage cultures, suspended in PBS. Animals were observed for 72 h and then euthanized unless moribund. Livers and spleens were homogenized and plated to determine bacterial burden. (FIG. 10B) Animals infected with the parental isolate showed a survival rate of only 20%, whereas the resister-infected animals had a survival rate of 100%. (FIG. 10C) Infected animals were observed and given a health score using the four parameters outlined in the NIH Animal Research Advisory Committee Guidelines. A score of 4 or greater is considered moribund and requires euthanasia. (FIG. 10D) Livers and spleens of infected animals were collected after euthanasia, weighed, homogenized, and plated on LB to determine bacterial burden. Shown is the titer per gram weight. The P values in FIG. 10B were determined by log-rank (Mantel-Cox) test. P values in FIG. 10D were determined by a Student t test or Mann-Whitney test, where necessary. *, P<0.05; , P<0.01; *, P<0.01.

Figures 1, 11A:
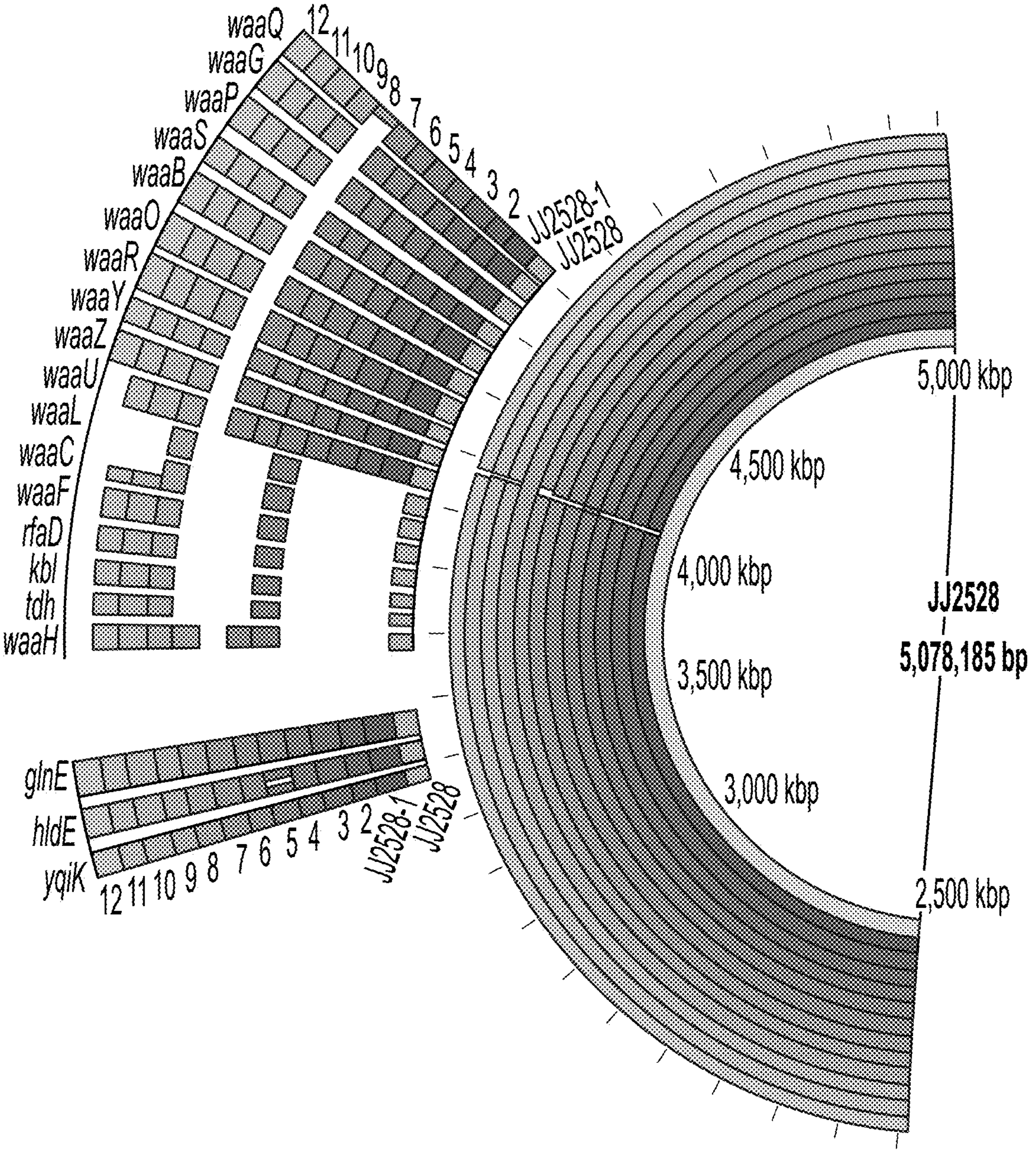
Figures 2, 11A:
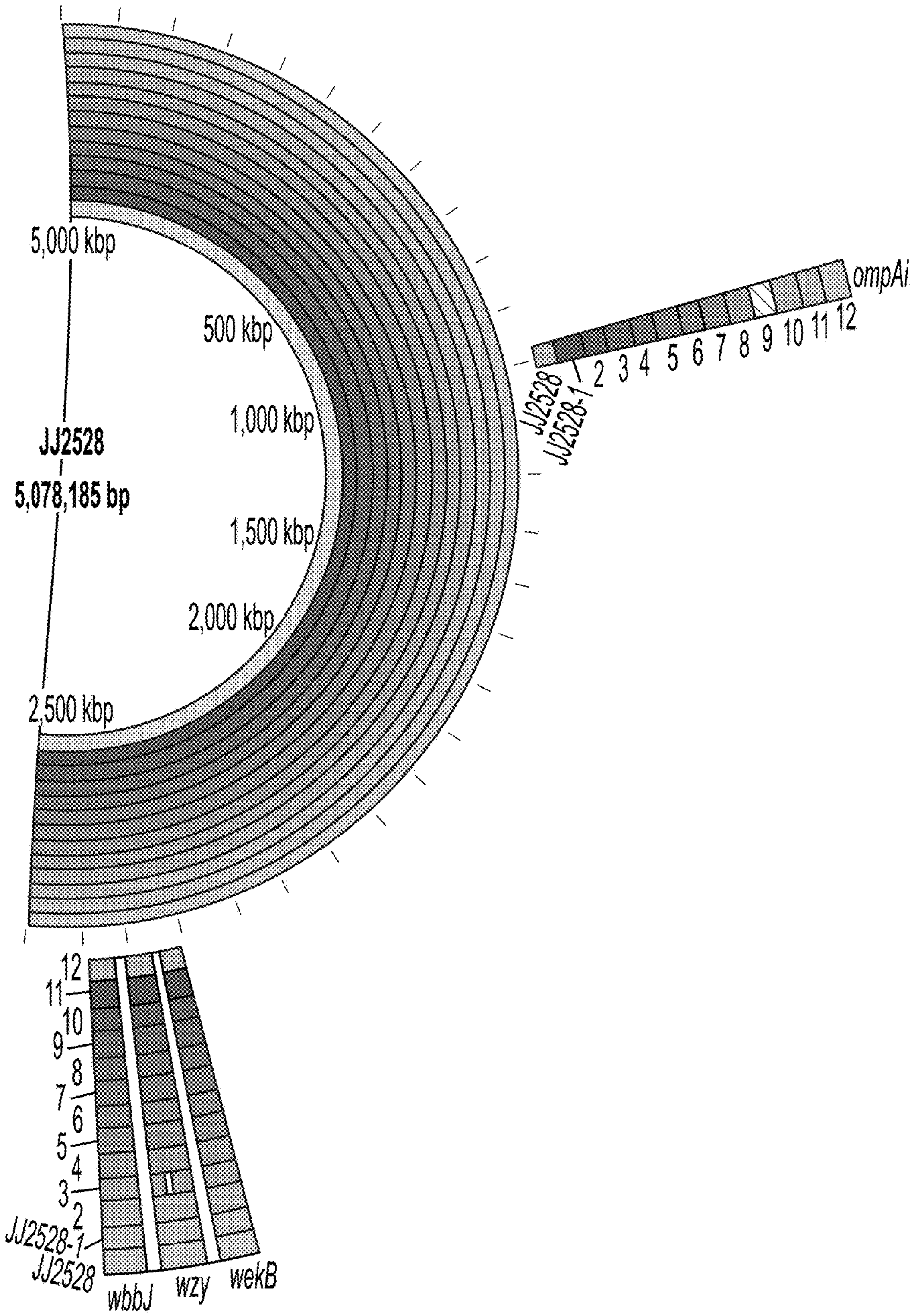
Figure 11B:
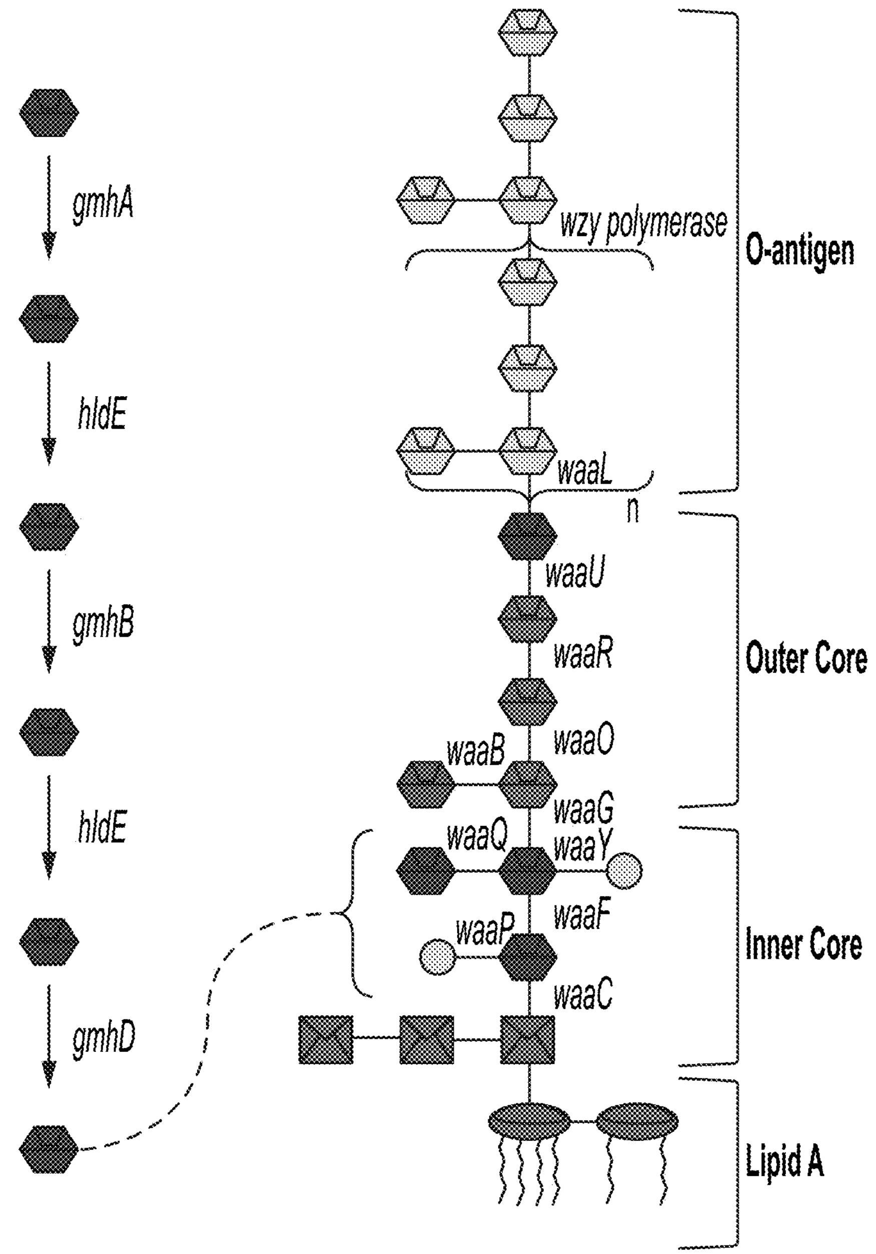

FIGS. 11A-11C. The genomes of all 21 resisters and their parental isolates were sequenced. (FIG. 11A) JJ2528 and its resistant isolates were aligned to reveal several truncations of interest, particularly in the waa operon, hldE, and ompA. Dashed fill for panel indicates the downstream SNP in ompA. (FIG. 11B) Structure of LPS, naming the enzyme responsible for forming each linkage. Also shown are several steps in the construction of LD-Hep (left).

Figure 12A:
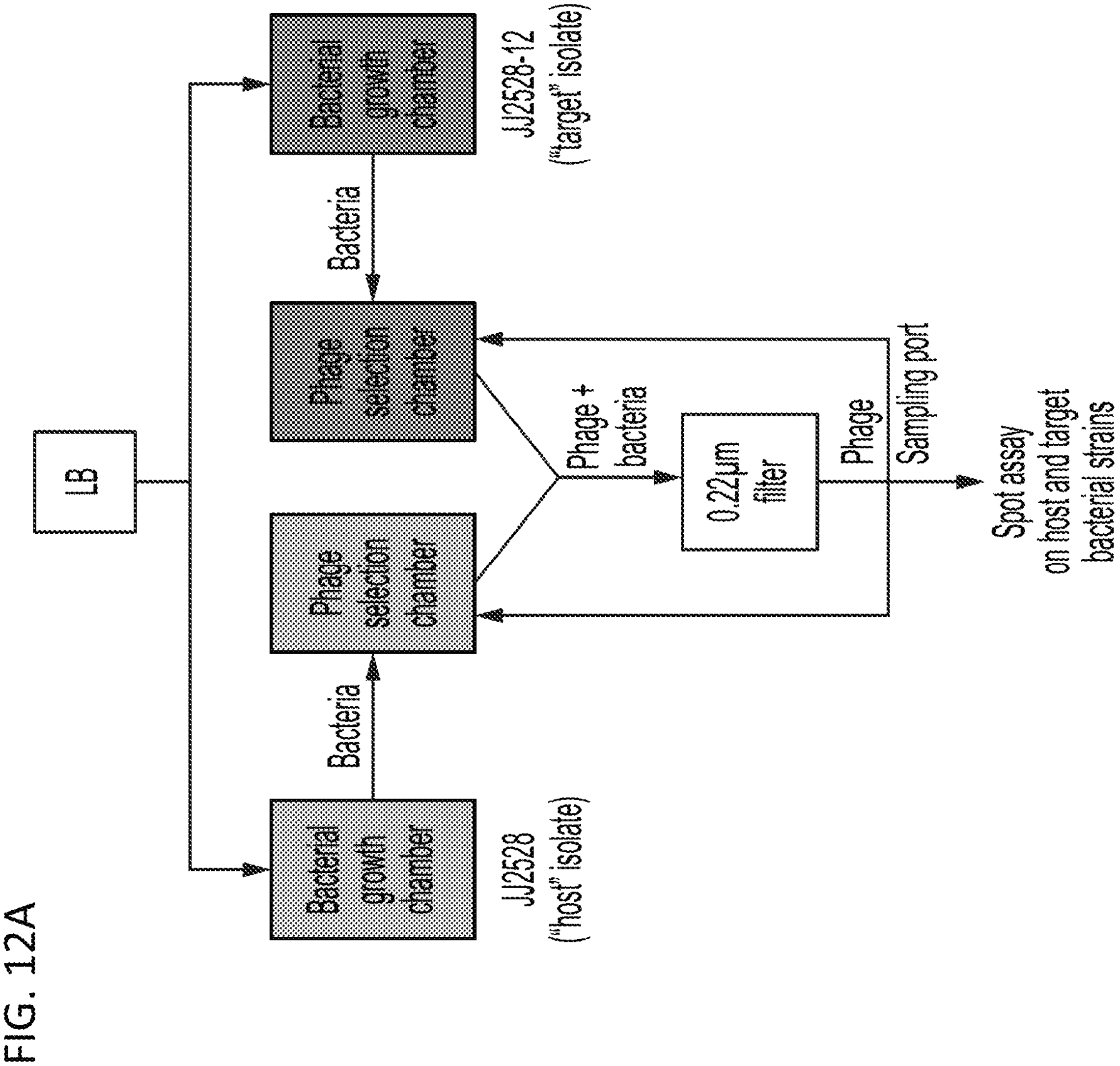
Figure 12B:
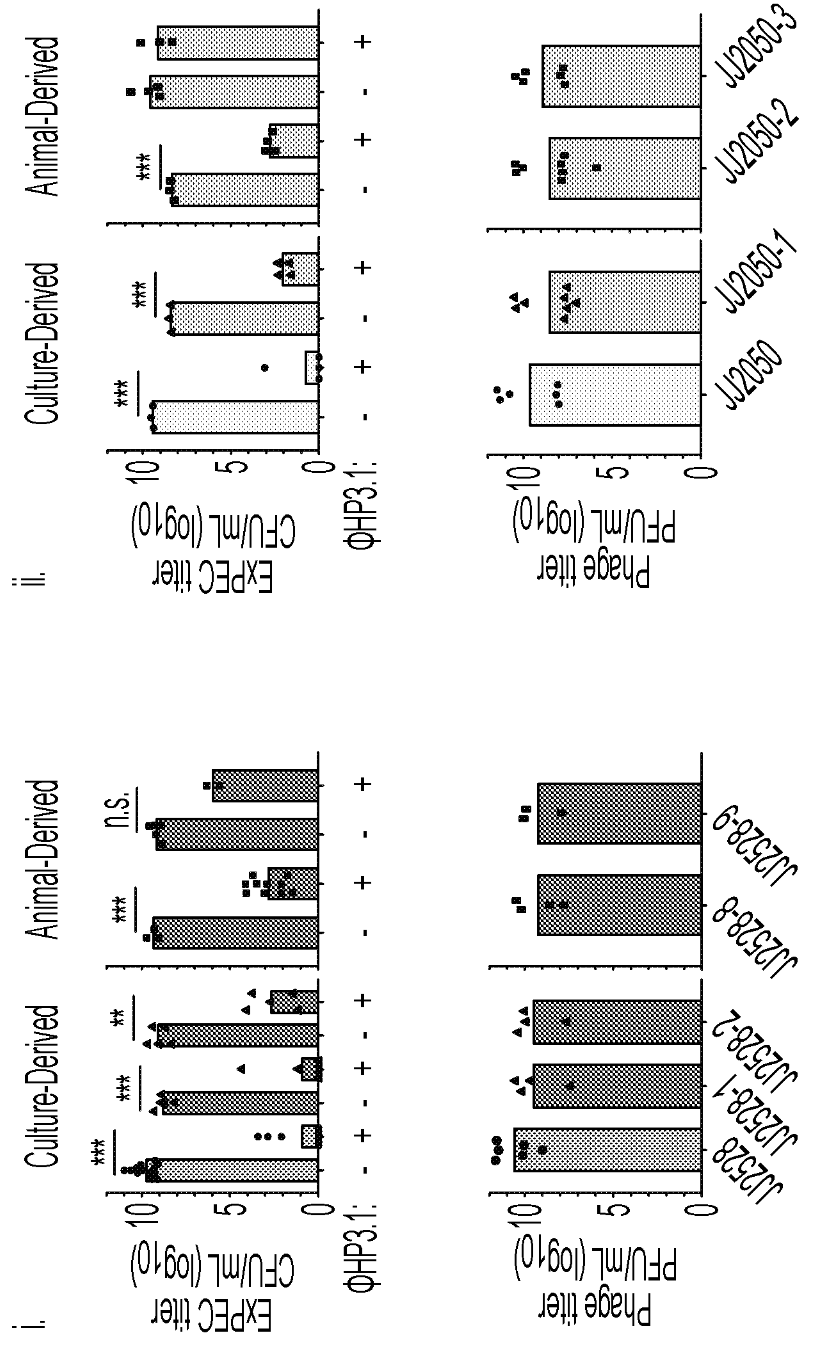
Figure 12B:
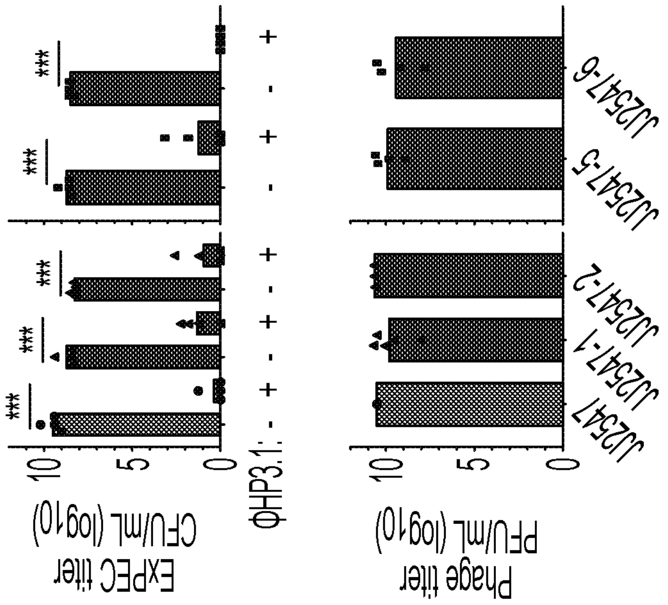
Figure 12B:
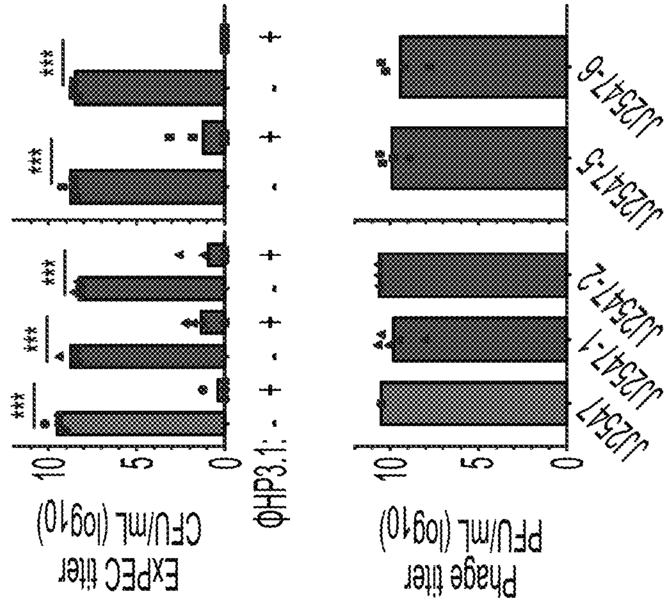

FIGS. 12A and 12B. (FIG. 12A) Resister JJ2528-12 was used as a target for the evolution of φHP3. PHP3 was allowed to adapt to the target in a continuous-flow bioreactor, in a method similar to the Appelman's protocol. (FIG. 12B) Isolate titers were determined in liquid culture after 4.5 h of incubation in LB with or without the presence of the evolved φHP3.1 (top panels). The φHP3.1 titer was also determined on these isolates using a standard phage spot assay (bottom panels). FIG. 12B is grouped by parental isolate: JJ2050 (i), JJ2528 (ii), and JJ2547 (iii). The P values were determined by a Student t test or Mann-Whitney test, where necessary. *, P<0.05; , P<0.01; *, P<0.01. Each data point represents the average of three parallel technical replicates.

Figure 13B:
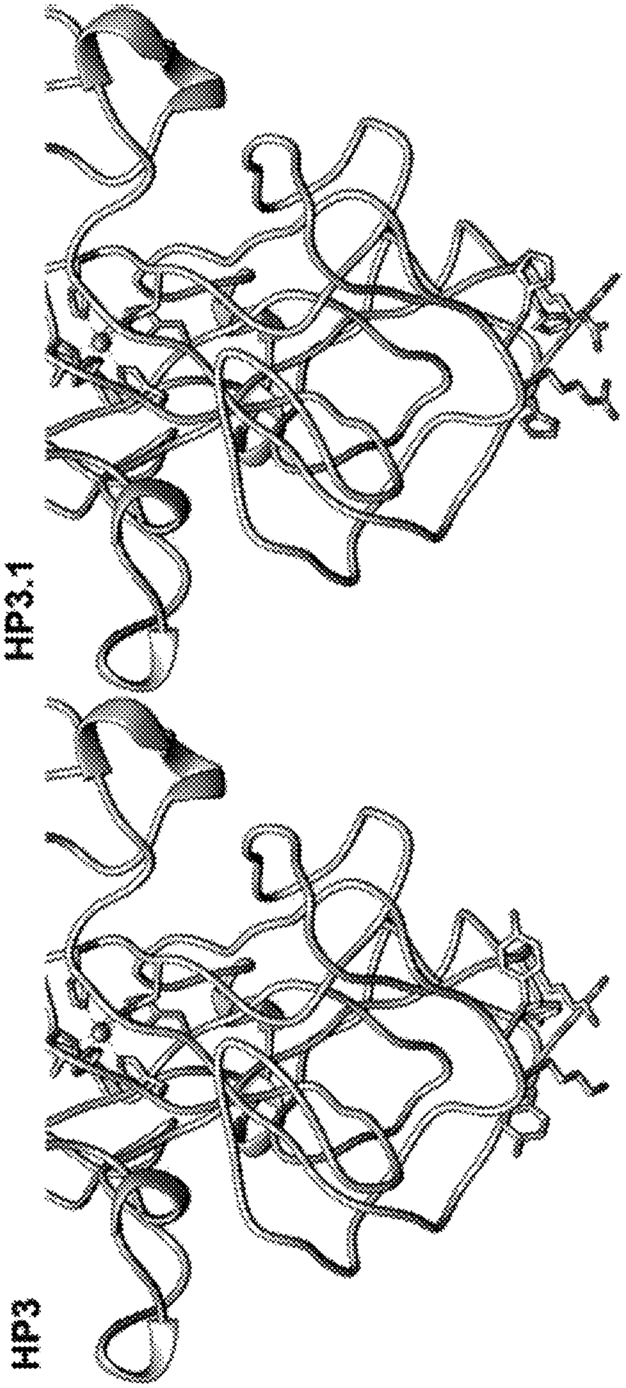

FIGS. 13A and 13B. (FIG. 13A) Sequencing revealed a key missense mutation in the binding spike of φHP3.1 (red highlight). (FIG. 13B) Residue substitutions were determined to be located at the binding region of the tail protein by protein modeling, based on the structure of the tail spike of φT4.

Figure 14A:
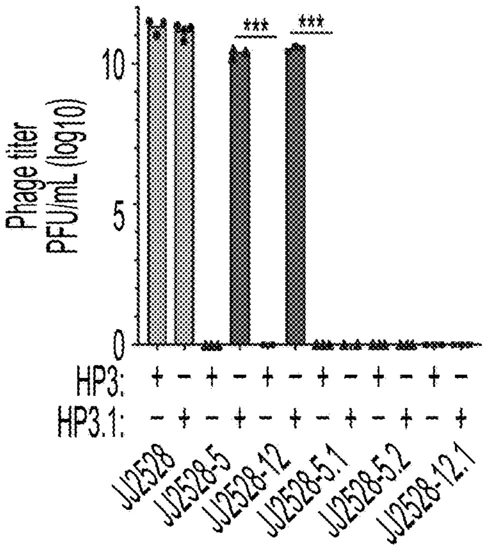
Figure 14B:
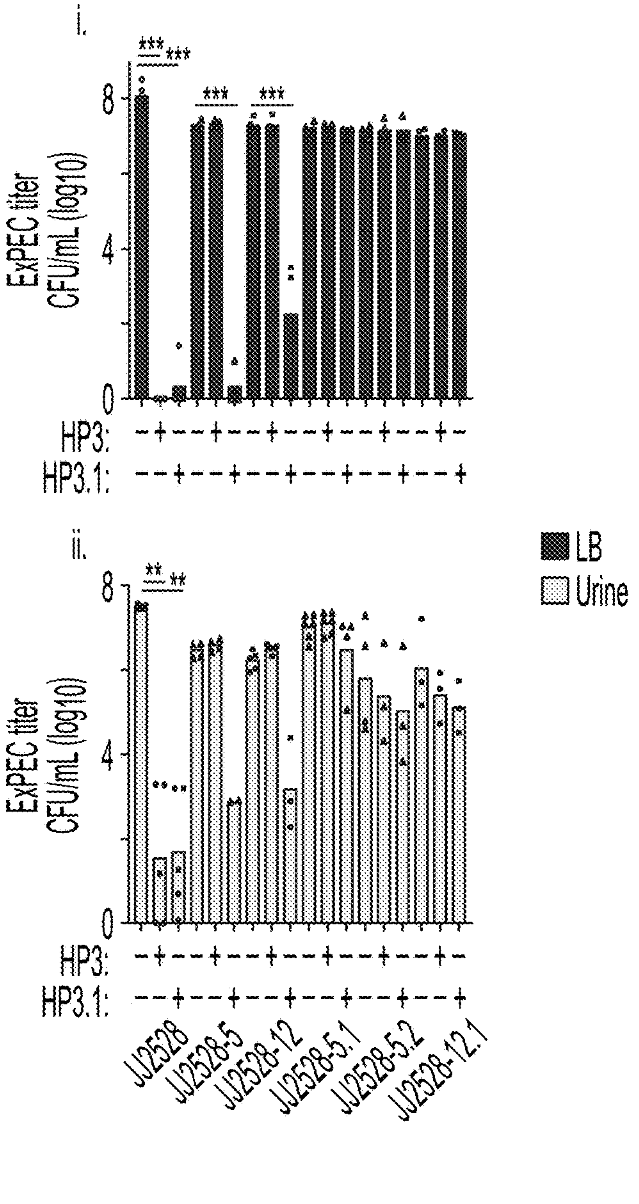
Figures 1, 14C:
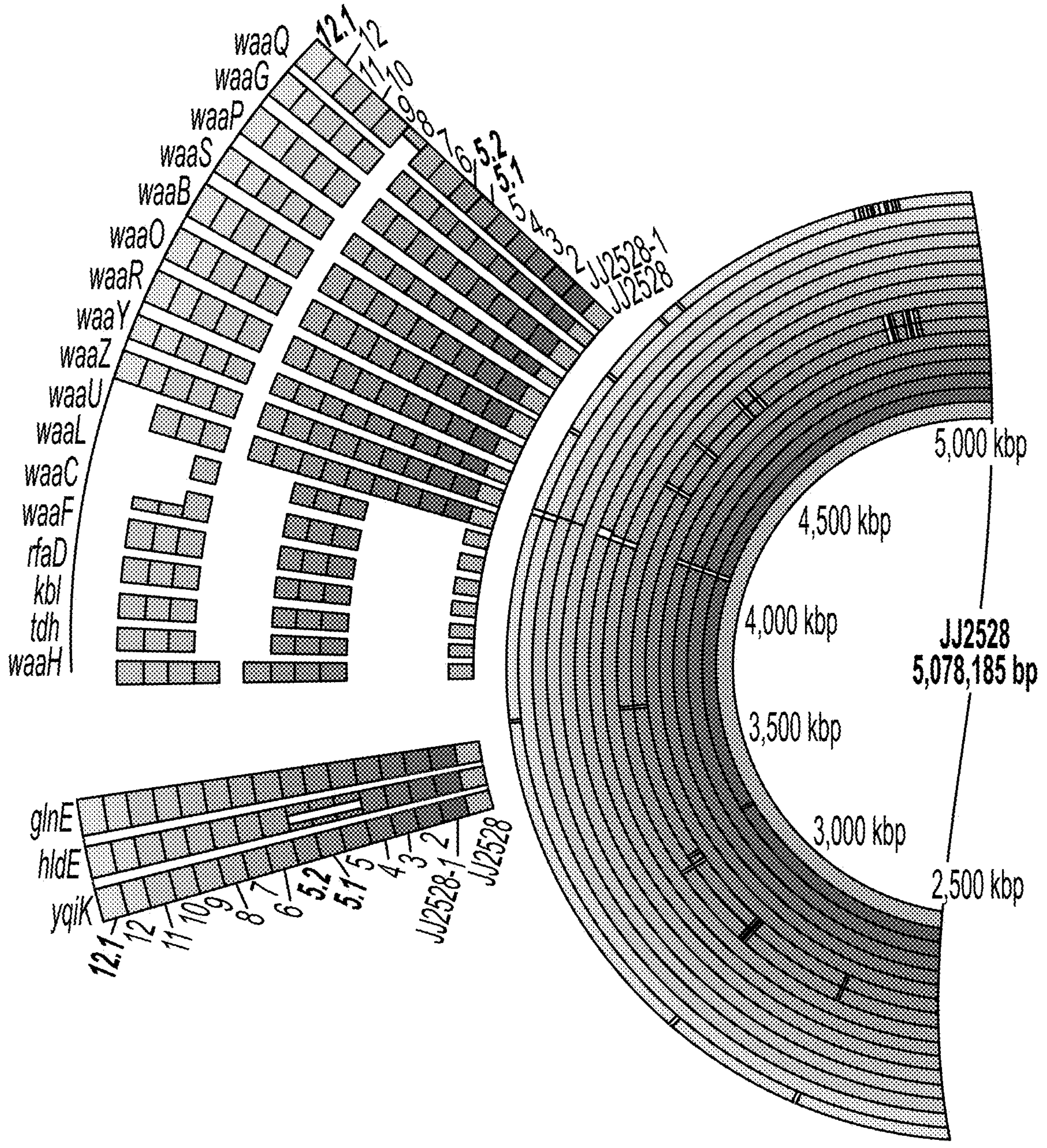
Figures 2, 14C:
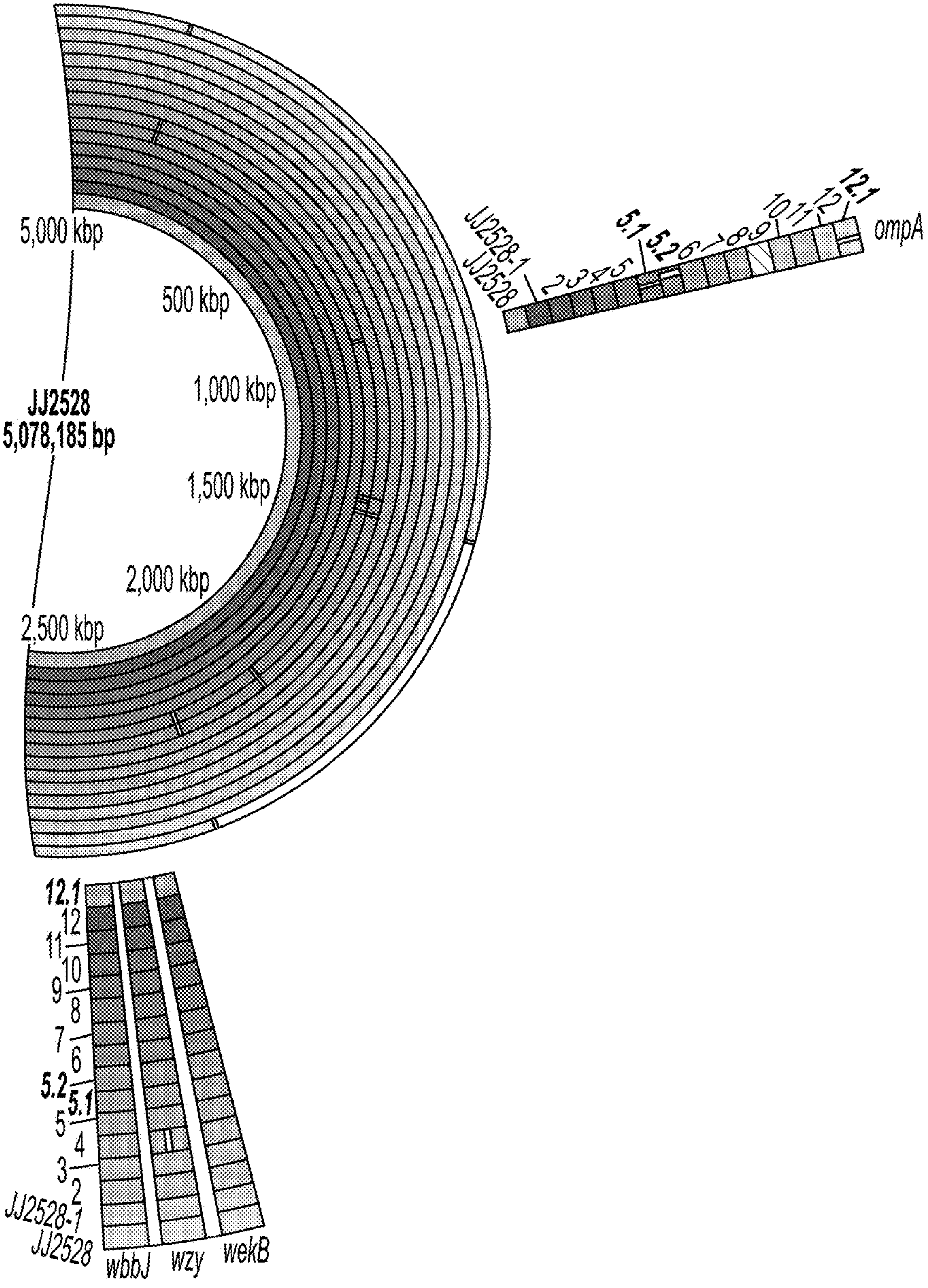

FIGS. 14A-14C. Two φHP3 resisters, JJ2528-5 and JJ2528-12, were used to select φHP3.1-resistant isolates using the culture-derived method depicted in FIG. 7B. (FIG. 14A) Phage (φHP3 and φHP3.1) titers were determined by spot assay on the parental isolate and primary and secondary resisters. (FIG. 14B) Isolate titers were determined in liquid culture after 4.5 h of incubation in LB (black) or urine (yellow), with or without the presence of either φHP3 or φHP3.1. (FIG. 14C) Whole-genome sequencing was performed on the secondary resisters, and they were aligned with the parental isolate and primary resisters. The secondary resisters retained truncations in the waa operon and acquired truncations in ompA. A dashed fill for panel indicates the downstream SNP in ompA. The P values in FIGS. 14A and 14B were determined by a Student t test or Mann-Whitney test, where necessary. *, P<0.05; , P<0.01; *, P<0.01. Each data point represents the average of three parallel technical replicates.

FIG. 15 shows phage-resistant isolates. A total of 21 combined φHP3-resistant isolates were collected from the three parental isolates and two selection methods. Each isolate and its source is listed.

FIG. 16 shows results from a phage screen against resistant isolates. Resisters were screened against φHP3, φHP3.1, φEC1 (similar to φHP3), and φES17 (dissimilar to φHP3) by phage spot assay. The phage titer is shown, where applicable. Green squares indicate plaque formation, and red squares indicate resistance to the phage. The φHP3.1 efficiency of plating is shown relative to that of φHP3 on parental ExPEC isolates.

Figure 17A:
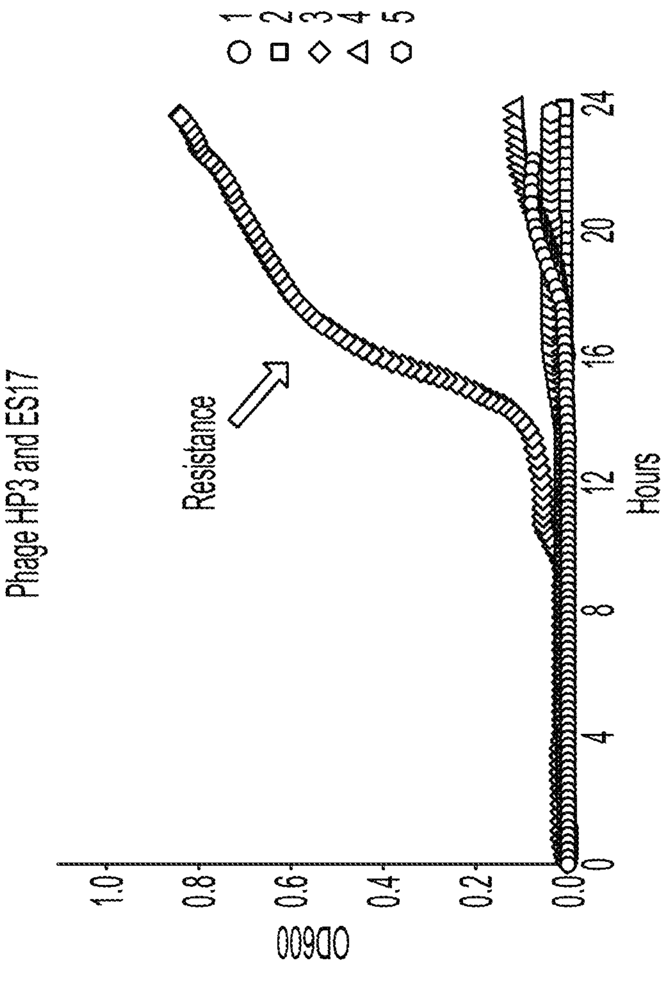
Figure 17B:
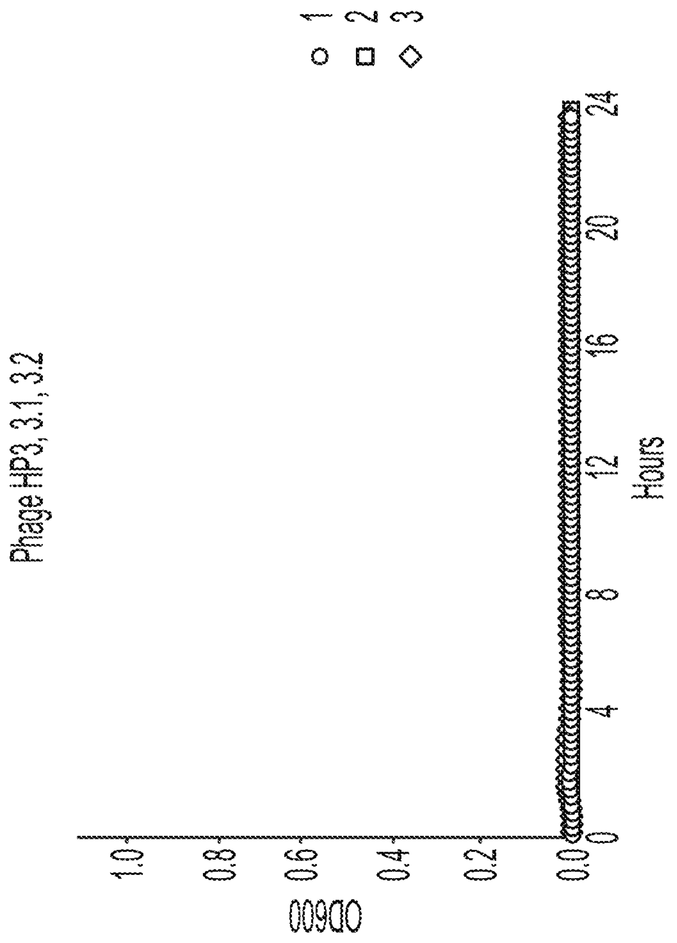

FIG. 17A shows growth of *E. coli* (measured by OD600) treated with a phage cocktail of HP3 and ES17. FIG. 17B shows growth of *E. coli* treated with a phage cocktail of φHP3, φHP3.1, and φHP3.2.

Figure 18:
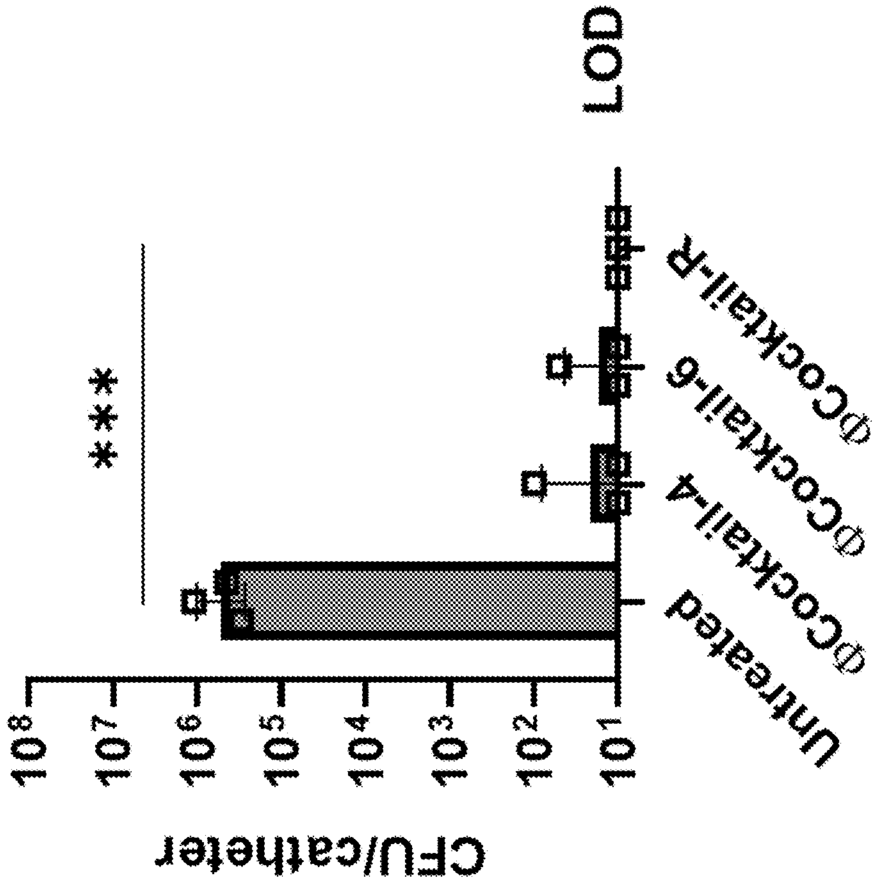

FIG. 18 shows *E. coli* colony forming units (CFU) from growth on human catheters, either untreated or treated with the phage cocktails shown.

Figure 19:
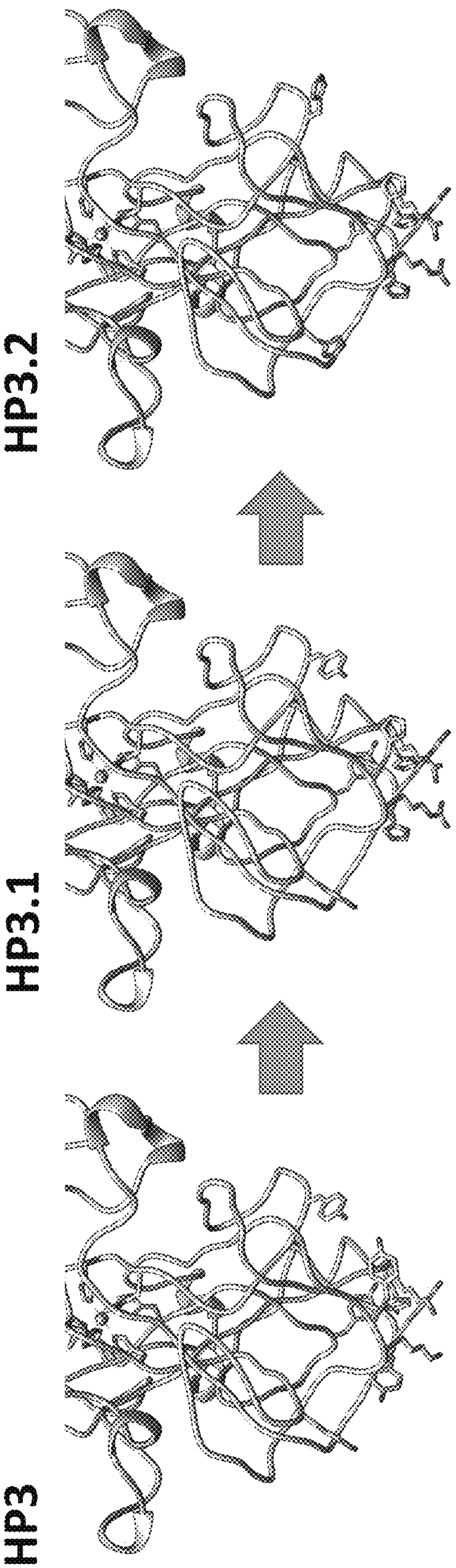

FIG. 19 shows a molecular model of the tail fiber gene protein product from φHP3, φHP3.1, and φHP3.2. φHP3.1 and φHP3.2 each contain a mutation in the tail giber gene, the protein product of which is believed to interact with its *E. coli* receptor.

Figure 20:
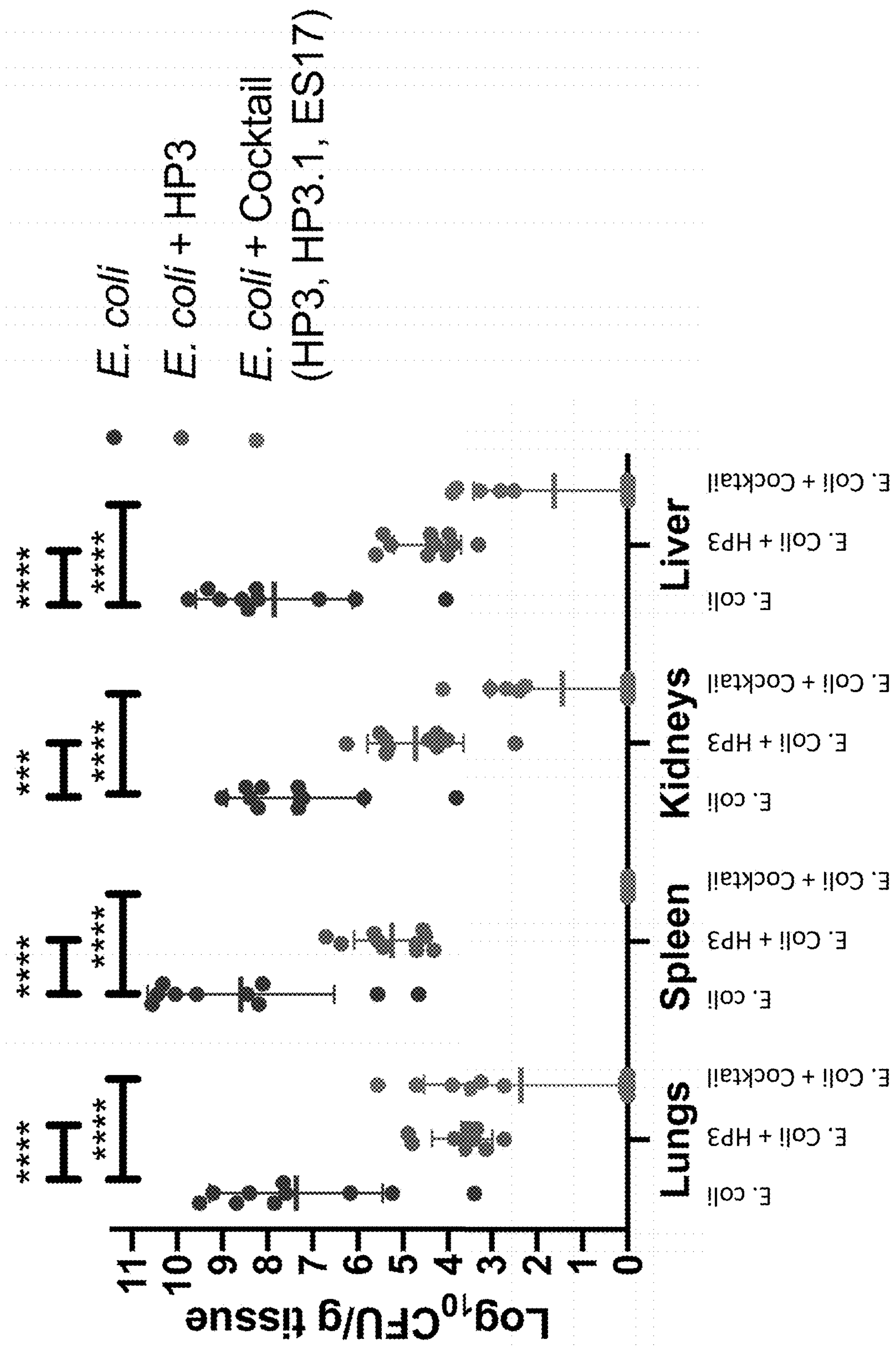

FIG. 20 shows results from analysis of mice infected with *E. coli* and treated with HP3 phage or a phage cocktail comprising HP3, HP3.1, and ES17. Standard deviation and mean pictured. N=10 for each group. Significance was determined using two-way ANOVA *p<0.001, **P<0.0001.

Figure 21:
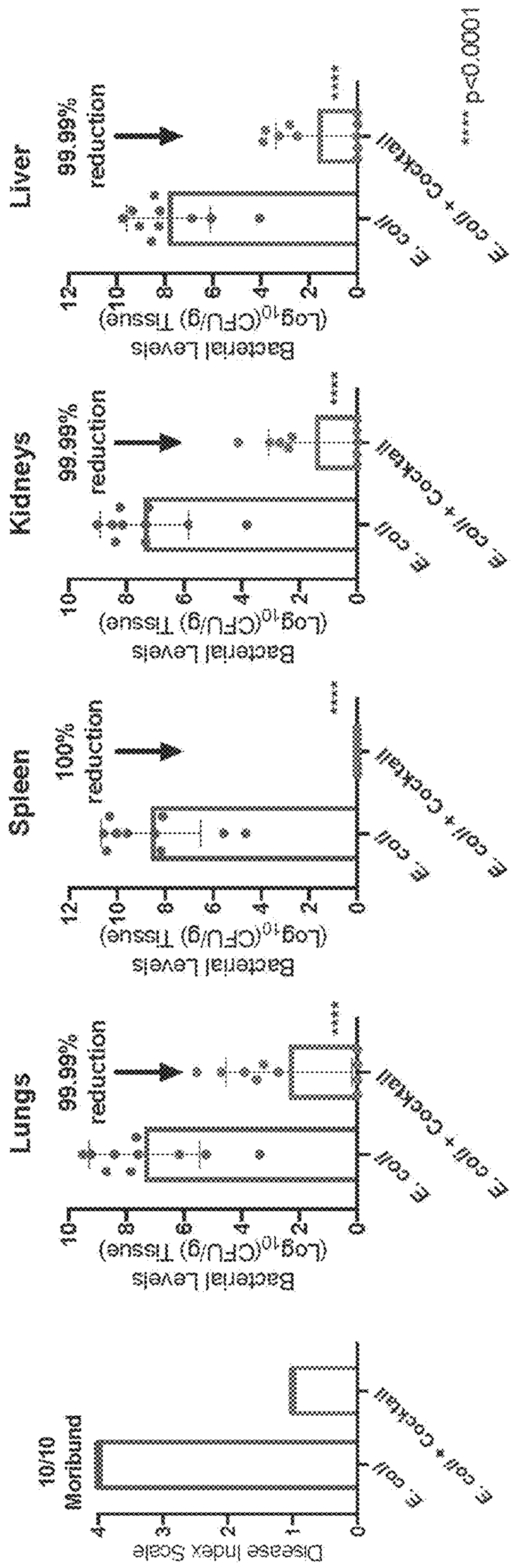

FIG. 21 shows efficacy of phage cocktail HP3, HP3.1, and ES17 in reducing bacterial levels in mice infected with pathogenic *E. coli*. Mice were infected with 1×10^8 colony forming units of ExPEC strain 2050, a pathogenic pandemic ST131 *E. coli*. After 24 hrs, mice were either treated or not with 1×10^8 PFU (total) SC of phages 3, 3.1, and ES17. Bacterial levels were recorded 24 hrs later by necropsy and plating of organs to determine bacterial levels.

DETAILED DESCRIPTION OF THE INVENTION

The present disclosure is based, at least in part, on the discovery and development of novel bacteriophages and bacteriophage combinations for treatment and prevention of *E. coli* infection, including multidrug-resistant (MDR) *E. coli* infection. Accordingly, disclosed herein, in some embodiments, are bacteriophage compositions comprising one or more of ES17, ES19, HP3, HP3.1, and HP3.2. Certain aspects of the disclosure are directed to compositions comprising (a) bacteriophage ES17 or bacteriophage ES19, (b) bacteriophage HP3, and (c) bacteriophage HP3.1. Also disclosed are compositions comprising bacteriophage HP3.2. Further disclosed are devices and kits comprising such compositions and methods for use of such compositions in treatment and prevention of pathogenic *E. coli* infection.

I. Bacteriophage Compositions

Aspects of the disclosure are directed to compositions comprising one or more bacteriophage. As used herein, a "bacteriophage composition" describes any composition comprising one or more bacteriophage (also "phage"). A bacteriophage of the present disclosure may be a lytic phage. A bacteriophage of the present disclosure may be a phage capable of infecting one or more pathogenic bacteria. A bacteriophage of the present disclosure may be a phage capable of infecting one or more bacteria of the family Enterobacteriaceae. In some embodiments, a bacteriophage of the disclosure is a phage capable of infecting *Escherichia coli* (*E. coli*), such as a multidrug-resistant (MDR) *E. coli* and/or extraintestinal pathogenic *E. coli* (ExPEC). A bacteriophage composition may comprise, for example, a bacteriophage generated using a method or system described in PCT Publication No. WO 2020/264096, titled "Systems And Methods For Generating Bacteriophages Adapted To Infect A Target Bacterial Strain", incorporated herein by reference in its entirety.

A bacteriophage composition of the disclosure may comprise, for example, one or more bacteriophage capable of lysing a pathogenic bacteria. A bacteriophage composition of the present disclosure may comprise at least, at most, or exactly 1, 2, 3, 4, 5, 6, 7, 8, 9, or 10 different bacteriophages, or more. In some embodiments, a bacteriophage composition of the disclosure comprises one or more of ES17, ES19, HP3, HP3.1, and HP3.2. In some embodiments, a bacteriophage composition of the disclosure comprises ES17. In some embodiments, a bacteriophage composition of the disclosure comprises ES19. In some embodiments, a bacteriophage composition of the disclosure comprises HP3. In some embodiments, a bacteriophage composition of the disclosure comprises HP3.1. In some embodiments, a bacteriophage composition of the disclosure comprises HP3.2. In some embodiments, a bacteriophage composition comprises two or more of ES17, ES19, HP3, HP3.1, and HP3.2. In some embodiments, a bacteriophage composition comprises three or more of ES17, ES19, HP3, HP3.1, and HP3.2. In some embodiments, a bacteriophage composition comprises four or more of ES17, ES19, HP3, HP3.1, and HP3.2. In some embodiments, a bacteriophage composition comprises (a) ES17 or ES19, (b) HP3, and (c) HP3.1. In some embodiments, a bacteriophage composition comprises ES17, HP3, and HP3.1. In some embodiments, a bacteriophage composition comprises ES19, HP3, and HP3.1. In some embodiments, a bacteriophage composition comprises ES17, HP3, HP3.1, and HP3.2. In some embodiments, a bacteriophage composition comprises ES19, HP3, HP3.1, and HP3.2. In some embodiments, a bacteriophage composition comprises ES17, ES19, HP3, HP3.1, and HP3.2.

A bacteriophage composition of the disclosure may comprise, in addition to one or more of ES17, ES19, HP3, HP3.1, and HP3.2, one or more additional bacteriophages (e.g., additional bacteriophages capable of lysing pathogenic *E. coli*). Additional bacteriophages contemplated herein include, but are not limited to, bacteriophages EC1, CF2, ES12, ES21, and ES26, which bacteriophages are described in, for example, Gibson S B, Green S I, Liu C G, et al. Constructing and Characterizing Bacteriophage Libraries for Phage Therapy of Human Infections. Front Microbiol. 2019; 10:2537., incorporated herein by reference in its entirety.

A bacteriophage composition of the disclosure may comprise, in addition to one or more bacteriophages, one or more metals. The one or more metals may include, for example, calcium, magnesium, iron, sodium, and/or potassium. A bacteriophage composition comprising two or more different bacteriophages may comprise various amounts of each bacteriophage. For example, a composition may comprise substantially the same amount of each bacteriophage. Alternatively, a composition may comprise substantially different amounts of each bacteriophage.

A bacteriophage composition may comprise at least, at most, or about $10^3$, $10^4$, $10^5$, $10^6$, $10^7$, $10^8$, $10^9$, $10^{10}$, $10^{11}$, or $10^{12}$ plaque forming units (PFU) of each of the one or more bacteriophage in the composition, or more. In some embodiments, a bacteriophage composition comprises at least, at most, or about $10^3$, $10^4$, $10^5$, $10^6$, $10^7$, $10^8$, $10^9$, $10^{10}$, $10^{11}$, or $10^{12}$ PFU of ES17. In some embodiments, a bacteriophage composition comprises at least, at most, or about $10^3$, $10^4$, $10^5$, $10^6$, $10^7$, $10^8$, $10^9$, $10^{10}$, $10^{11}$, or $10^{12}$ PFU of ES19. In some embodiments, a bacteriophage composition comprises at least, at most, or about $10^3$, $10^4$, $10^5$, $10^6$, $10^7$, $10^8$, $10^9$, $10^{10}$, $10^{11}$, or $10^{12}$ PFU of HP3. In some embodiments, a bacteriophage composition comprises at least, at most, or about $10^3$, $10^4$, $10^5$, $10^6$, $10^7$, $10^8$, $10^9$, $10^{10}$, $10^{11}$, or $10^{12}$ PFU of HP3.1. In some embodiments, a bacteriophage composition comprises at least, at most, or about $10^3$, $10^4$, $10^5$, $10^6$, $10^7$, $10^8$, $10^9$, $10^{10}$, $10^{11}$, or $10^{12}$ PFU of HP3.2.

A. ES17

Aspects of the present disclosure comprise bacteriophage ES17 (also "*Escherichia* phage ES17," "(ES17," or "ES17," used synonymously herein), compositions, kits, and devices comprising ES17, and methods for use. An ES17 genome sequence is described by GenBank accession number MN508615 and provided as SEQ ID NO: 3.

B. ES19

Aspects of the present disclosure comprise bacteriophage ES19 (also "*Escherichia* phage ES19," "qES19," or "ES19," used synonymously herein), compositions, kits, and devices comprising ES19, and methods for use. An ES19 genome sequence is described by GenBank accession number MN508616 and provided as SEQ ID NO: 7.

C. HP3

Aspects of the present disclosure comprise bacteriophage HP3 (also "*Escherichia* phage HP3," "φHP3," or "HP3," used synonymously herein), compositions, kits, and devices comprising HP3, and methods for use. An HP3 genome sequence is described by GenBank accession number NC_041920 and provided as SEQ ID NO: 4.

D. HP3.1

Aspects of the present disclosure comprise bacteriophage HP3.1 (also "*Escherichia* phage HP3," "φHP3.1," or "HP3.1," used synonymously herein), compositions, kits, and devices comprising HP3.1, and methods for use. The HP3.1 genome sequence is described by GenBank accession number OK275722.1 and provided as SEQ ID NO: 5.

E. HP3.2

Aspects of the present disclosure comprise bacteriophage HP3.2 (also "*Escherichia* phage HP3," "φHP3.2," or "HP3.2," used synonymously herein), compositions, kits, and devices comprising HP3.2, and methods for use. The HP3.2 genome sequence is described by GenBank accession number OP978391.1 and provided as SEQ ID NO: 6.

II. Treatment and Prevention of Bacterial Infection

Aspects of the present disclosure are directed to methods for treatment and prevention of a bacterial infection in an individual. In some embodiments, disclosed are methods for treatment or prevention of an *E. coli* infection in an individual. In particular aspects, the present disclosure provides methods for treatment or prevention of an *E. coli* infection in an individual comprising administering to the individual an effective amount of one or more bacteriophages, including bacteriophages disclosed herein. Bacteriophages useful for such treatment methods include those described herein, for example ES17, ES19, HP3, HP3.1, and/or HP3.2. Accordingly, in some embodiments, disclosed herein is a method for treatment or prevention of an *E. coli* infection in an individual comprising administering to the individual an effective amount of ES17, ES19, HP3, HP3.1, and/or HP3.2. In some embodiments, the method comprises administering (a) ES17 or ES19, (b) HP3, and (c) HP3.1. In some embodiments, the method comprises administering ES17, HP3, and HP3.1. In some embodiments, the method comprises administering ES17, HP3, and HP3.2. In some embodiments, the method comprises administering HP3.2. In some embodiments, the method comprises administering ES17, HP3, HP3.1, and HP3.2. In some embodiments, the method comprises administering ES19, HP3, HP3.1, and HP3.2. In some embodiments, the method comprises administering ES17, ES19, HP3, HP3.1, and HP3.2.

In some embodiments, multiple bacteriophage (e.g., two or more of ES17, ES19, HP3, HP3.1, and HP3.2) are administered to an individual in the same formulation. Alternatively, multiple bacteriophage may be administered to an individual in different formulations (e.g., 2, 3, or more formulations). Multiple bacteriophage may be administered to an individual at the same time or may be administered at different times.

Multiple bacteriophage may be administered to an individual substantially simultaneously, for example via a single composition. For example, ES17, HP3, and HP3.1 may be administered to an individual having a pathogenic *E. coli* infection at the same time, as a single composition. As another example, ES19, HP3, and HP3.1 may be administered to an individual having a pathogenic *E. coli* infection at the same time, as a single composition. As yet another example, ES17, HP3, HP3.1, and HP3.2 may be administered to an individual having a pathogenic *E. coli* infection at the same time, as a single composition. As a further example, ES19, HP3, HP3.1, and HP3.2 may be administered to an individual having a pathogenic *E. coli* infection at the same time, as a single composition.

Multiple bacteriophage may be administered to an individual sequentially in any order. For example, an individual having a pathogenic *E. coli* infection may be administered ES17, followed by HP3, followed by HP3.1. Example administration sequences of ES17, HP3, and HP3.1 include: ES17, HP3, HP3.1; HP3, ES17, HP3.1; HP3.1, ES17, HP3; ES17, HP3.1, HP3; HP3, HP3.1, ES17; and HP3.1, HP3, ES17. Example administration sequences of ES19, HP3, and HP3.1 include ES19, HP3, HP3.1; HP3, ES19, HP3.1; HP3.1, ES19, HP3; ES19, HP3.1, HP3; HP3, HP3.1, ES19; and HP3.1, HP3, ES19. Example administration sequences of ES17, HP3, HP3.1, and HP3.2 include: ES17, HP3, HP3.1, HP3.2; HP3, ES17, HP3.1, HP3.2; HP3.1, ES17, HP3, HP3.2; ES17, HP3.1, HP3, HP3.2; HP3, HP3.1, ES17, HP3.2; HP3.1, HP3, ES17, HP3.2; HP3.2, HP3, ES17, HP3.1; HP3, HP3.2, ES17, HP3.1; ES17, HP3.2, HP3, HP3.1; HP3.2, ES17, HP3, HP3.1; HP3, ES17, HP3.2, HP3.1; ES17, HP3, HP3.2, HP3.1; ES17, HP3.1, HP3.2, HP3; HP3.1, ES17, HP3.2, HP3; HP3.2, ES17, HP3.1, HP3; ES17, HP3.2, HP3.1, HP3; HP3.1, HP3.2, ES17, HP3; HP3.2, HP3.1, ES17, HP3; HP3.2, HP3.1, HP3, ES17; HP3.1, HP3.2, HP3, ES17; HP3, HP3.2, HP3.1, ES17; HP3.2, HP3, HP3.1, ES17; HP3.1, HP3, HP3.2, ES17; and HP3, HP3.1, HP3.2, ES17. Example administration sequences of ES19, HP3, HP3.1, and HP3.2 include ES19, HP3, HP3.1, HP3.2; HP3, ES19, HP3.1, HP3.2; HP3.1, ES19, HP3, HP3.2; ES19, HP3.1, HP3, HP3.2; HP3, HP3.1, ES19, HP3.2; HP3.1, HP3, ES19, HP3.2; HP3.2, HP3, ES19, HP3.1; HP3, HP3.2, ES19, HP3.1; ES19, HP3.2, HP3, HP3.1; HP3.2, ES19, HP3, HP3.1; HP3, ES19, HP3.2, HP3.1; ES19, HP3, HP3.2, HP3.1; ES19, HP3.1, HP3.2, HP3; HP3.1, ES19, HP3.2, HP3; HP3.2, ES19, HP3.1, HP3; ES19, HP3.2, HP3.1, HP3; HP3.1, HP3.2, ES19, HP3; HP3.2, HP3.1, ES19, HP3; HP3.2, HP3.1, HP3, ES19; HP3.1, HP3.2, HP3, ES19; HP3, HP3.2, HP3.1, ES19; HP3.2, HP3, HP3.1, ES19; HP3.1, HP3, HP3.2, ES19; and HP3, HP3.1, HP3.2, ES19. One or more of the preceding administration sequences may be excluded from embodiments of the disclosure.

Bacteriophages of the disclosure may be administered to an individual once, or may be administered multiple times (e.g., 2, 3, 4, 5, 6, 7, 8, 9, 10, 11, 12, 13, 14, 15, or more times). Bacteriophages may be administered via an appropriate treatment regimen for an appropriate length of time, e.g., for effective treatment or prevention of a pathogenic *E. coli* infection. For example, a bacteriophage composition may be administered to an individual 1, 2, 3, or 4 times per day (or more); 1, 2, 3, 4, 5, 6, or 7 times per week (or more); or 1, 2, 3, 4, 5, 6, 7, 8, 9, 10, 11, 12, 13, 14, 15, 16, 17, 18, 19, or 20 times per month (or more). A bacteriophage composition may be administered for at least, at most, or exactly 1, 2, 3, 4, 5, 6, 7, 8, 9, 10, 11, 12, 13, or 14 days (or more); 1, 2, 3, 4, 5, 6, 7, 8, 9, 10, 11, 12, 13, 14, 15, 16, 17, 18, 19, 20, or 21 weeks (or more); or 1, 2, 3, 4, 5, 6, 7, 8, 9, 10, 11, or 12 months (or more). In some embodiments, a bacteriophage is administered twice per week for between 6 and 12 weeks.

An individual receiving a treatment of the disclosure may have an infection in, for example, one or more of a urinary tract, blood, gut, abdomen, stomach, lungs, skin, kidneys, prostate, bladder, brain, vaginal tract, heart, liver, and spleen. In some embodiments, an individual has a urinary tract infection. In some embodiments, an individual has a catheter-associated urinary tract infection. An individual may have one or more of a urinary tract infection, neonatal meningitis, a blood-stream infection, pneumonia, sepsis, a surgical wound infection, a skin infection, a prostate infection, meningitis, and a vaginal infection. An individual may have one or more symptoms of a pathogenic infection, for example diarrhea, stomach cramping, nausea, and/or vomiting. In some embodiments, an individual does not have any symptoms of a pathogenic infection.

In some embodiments, an individual receiving a treatment of the disclosure has an *E. coli* infection. In some embodiments, an individual has been diagnosed with an *E. coli* infection. In some embodiments, an individual has one or more symptoms of an *E. coli* infection (including, e.g., diarrhea, stomach cramping, nausea, and/or vomiting). In some embodiments, the individual does not have any symptoms of an *E. coli* infection. In some embodiments, the *E. coli* is multidrug-resistant (i.e. is a multidrug-resistant *E. coli*). In some embodiments, the *E. coli* is an extraintestinal pathogenic *E. coli*. Extraintestinal pathogenic *E. coli* are described in, for example, Smith J L, Fratamico P M, Gunther N W. Extraintestinal pathogenic *Escherichia coli*. *Foodborne Pathog Dis.* 2007; 4 (2): 134-163, incorporated herein by reference in its entirety. An individual may have received an *E. coli* infection from various sources. For example, in some embodiments, the *E. coli* was from a beverage, comestible (e.g., undercooked meat, unpasteurized milk, apple juice or cider; or soft cheese made from raw milk), another individual, or an environment (e.g., ground or surface water, water used to irrigate crops, a public water system, a hospital, a school, a nursing home, a petting zoo, a cruise ship, a train, or an airplane).

An individual receiving a treatment of the disclosure may be an immunosuppressed individual. An immunosuppressed individual may be an individual having, for example, an immune cell defect, asplenia, impaired splenic function, nephrotic syndrome, or an autoimmune condition. An immunosuppressed individual may be an individual subject to immunosuppressive conditions, for example chemotherapeutic agents or immunosuppressant agents (e.g., a glucocorticoid, a calcineurin inhibitor, an antimetabolite, a medication to reduce stomach acid such as a proton pump inhibitor, or an antibody therapy). Accordingly, in certain embodiments, bacteriophages of the disclosure may be administered to an individual before, during, and/or after subjecting the individual to immunosuppressive conditions. For example, bacteriophages of the disclosure (e.g., ES17, ES19, HP3, HP3.1, and/or HP3.2) may be administered to an individual having cancer during treatment with chemotherapy, thereby treating or preventing a pathogenic *E. coli* infection.

III. Devices

Also contemplated herein, in some embodiments, are devices (e.g., medical devices) comprising one or more bacteriophages or bacteriophage compositions of the present disclosure. A device of the disclosure may comprise one or more of ES17, ES19, HP3, HP3.1, and HP3.2. In some embodiments, the device comprises (a) ES17 or ES19, (b) HP3, and (c) HP3.1. In some embodiments, the device comprises ES17, HP3, and HP3.1. In some embodiments, the device comprises ES19, HP3, and HP3.1. In some embodiments, the device comprises HP3.2. In some embodiments, the device comprises ES17, HP3, HP3.1, and HP3.2. In some embodiments, the device comprises ES19, HP3, HP3.1, and HP3.2. A device is described herein as "comprising" a bacteriophage or bacteriophage composition where the device has in, on, or around it, or is attached to, the bacteriophage or bacteriophage composition. In some embodiments, a device of the disclosure is a medical device. In such cases, it may be desirable for a medical device to comprise bacteriophages capable of treating or preventing a pathogenic infection, such as an *E. coli* infection. Various medical devices are recognized in the art and contemplated herein. Examples of devices contemplated herein include, but are not limited to, a catheter, drive line, syringe, tube, implant, defibrillator, artificial joint, pacemaker, screw, rod, disc, intrauterine device, pin, plate, stent, dental device, eye lens, shunt, valve, neurological or neurosurgical device, gastrointestinal device, genitourinary device, catheter cuff, vascular access device, and wound drain. In some embodiments, the device is a stent. In some embodiments, the device is a catheter. In some embodiments, the device is an implant.

Aspects of the disclosure comprise methods for preparing a device comprising subjecting a device to a bacteriophage composition of the disclosure (e.g., a bacteriophage composition comprising ES17, HP3, and HP3.1). Disclosed are methods comprising placing a bacteriophage composition on a device, placing a bacteriophage composition around a device, placing a bacteriophage composition in a device, and coating a device with a bacteriophage composition (e.g., coating one or more surfaces of a device). Aspects further comprise delivering the device to an individual following such preparation.

IV. Pharmaceutical Compositions

In certain aspects, the compositions or agents for use in the disclosed methods, such as bacteriophage(s) (e.g., ES17, ES19, HP3, HP3.1, and/or HP3.2), are suitably contained in a pharmaceutically acceptable carrier. In some embodiments, the carrier is non-toxic, biocompatible and is selected so as not to detrimentally affect the biological activity of the agent. The agents in some aspects of the disclosure may be formulated into preparations for local delivery (i.e. to a specific location of the body) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable or solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, nontoxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol may be between about 0.01 ml and 0.5 ml, for example.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

A. Other Agents

It is contemplated that other agents may be used in combination with certain aspects of the present embodiments to improve the therapeutic efficacy of treatment. These additional agents include agents having antibacterial properties (e.g., antibiotics). For example, one or more therapeutic phage of the disclosure may be used in combination with one or more antibiotics. Various antibiotics are recognized in the art and contemplated herein including, for example, ceftazidime, ciprofloxacin, kanamycin, colistin (polymyxin E), trimethoprim, cefepime, sulfamethoxazole, levofloxacin, and polymyxin B.

V. Kits

Certain aspects of the present disclosure also concern kits containing compositions of the disclosure or compositions to implement methods disclosed herein. In some embodiments, kits can be used to evaluate one or more biomarkers. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules or inhibitors, or any value or range and combination derivable therein. In some embodiments, there are kits for evaluating biomarker activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

In some embodiments, kits of the disclosure comprise one or more bacteriophages housed in a suitable container. A kit may comprise, comprise at least, or comprise at most 1, 2, 3, 4, 5, 6, 7, 8, 9, or 10 different bacteriophages, or more. In some embodiments, a kit of the disclosure comprises 1, 2, 3, 4, or all of ES17, ES19, HP3, HP3.1, and HP3.2. One or more phage may be specifically excluded from certain embodiments. In some embodiments, a kit of the disclosure comprises ES17, HP3, and HP3.1. In some embodiments, a kit of the disclosure comprises ES19, HP3, and HP3.1. In some embodiments, a kit of the disclosure comprises HP3.2. In some embodiments, a kit of the disclosure comprises ES17, HP3, HP3.1, and HP3.2. In some embodiments, a kit of the disclosure comprises ES19, HP3, HP3.1, and HP3.2. In some embodiments, a kit of the disclosure comprises ES17, HP3, HP3.1, and HP3.2. Phage may be housed in a suitable container. A kit of the disclosure may further comprise a device. A kit may comprise a device having one or more bacteriophages of the disclosure on, in, and/or around the device. A kit may comprise a device separate from one or more bacteriophages.

VI. Biological Deposit

Representative materials of the present disclosure were deposited in the American Type Culture Collection, 10801 University Boulevard, Manassas, VA 20110-2209, USA, on Dec. 14, 2023. Phage "HP3.1" having ATCC Accession No. OK275722.1_comprises a bacteriophage having genome sequence shown by SEQ ID NO: 5. Phage "HP3.2" having ATCC Accession No. OP978391.1_comprises a bacteriophage having genome sequence shown by SEQ ID NO: 6.

| Bacteriophage | SEQ ID NO (genome) | ATCC Accession No. |
|---|---|---|
| HP3.1 | 5 | OK275722.1 |
| HP3.2 | 6 | OP978391.1 |

Aspects of the present disclosure include compositions comprising one or more of the abovementioned deposited materials, as well as methods of use thereof in treatment and prevention of pathogenic infections. In some embodiments, disclosed is a bacteriophage having all of the identifying characteristics of one of the abovementioned deposited bacteriophage.

The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions; the materials will be promptly replaced on notification with another of the same. Availability of the deposited material is not to be construed as a license to practice the invention in contravention of the rights granted under the authority of any government in accordance with its patent laws.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute certain modes for its practice. However, those of skill in the art should, in light of the present disclosure, appreciate that many changes can be made in the specific embodiments which are disclosed and still obtain a like or similar result without departing from the spirit and scope of the invention.

Example 1—Targeting of Mammalian Glycans Enhances Phage Predation in the Gastrointestinal Tract The gastrointestinal tract is prohibitive to phage therapy. Previous studies reported that phage HP3, a lytic myovirus isolated from environmental reservoirs of ExPEC, reduces ST131 bacteremia and disease severity in murine models of infection. Since the human gastrointestinal tract is the primary reservoir of ExPEC ST131, the inventors wondered if phage HP3 could act prophylactically to reduce or eliminate ExPEC burden in the intestine. To test this, mice were orally gavaged with an ExPEC ST131 clinical isolate JJ1901, and then treated with phage or an antibiotic as illustrated in FIG.

Figure 1A:
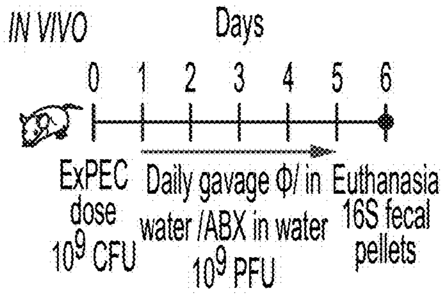
FIGS. 1A-1F.
Figure 1B:
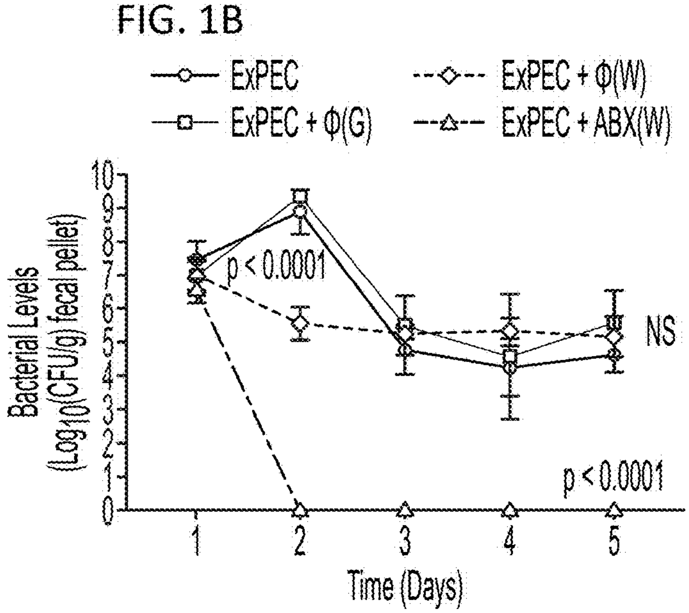
Figure 1C:
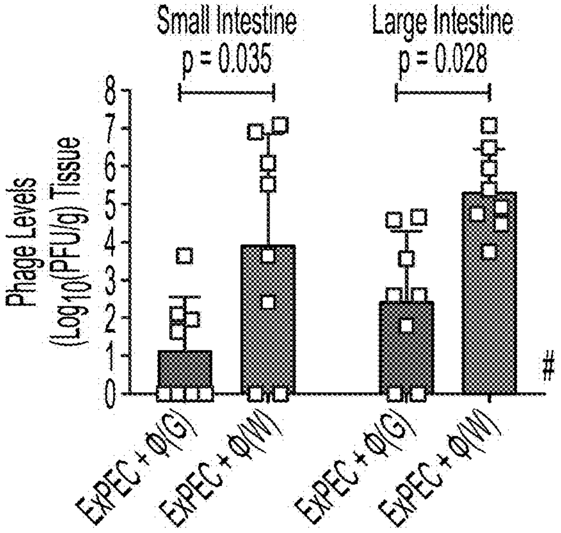
Figure 1D:
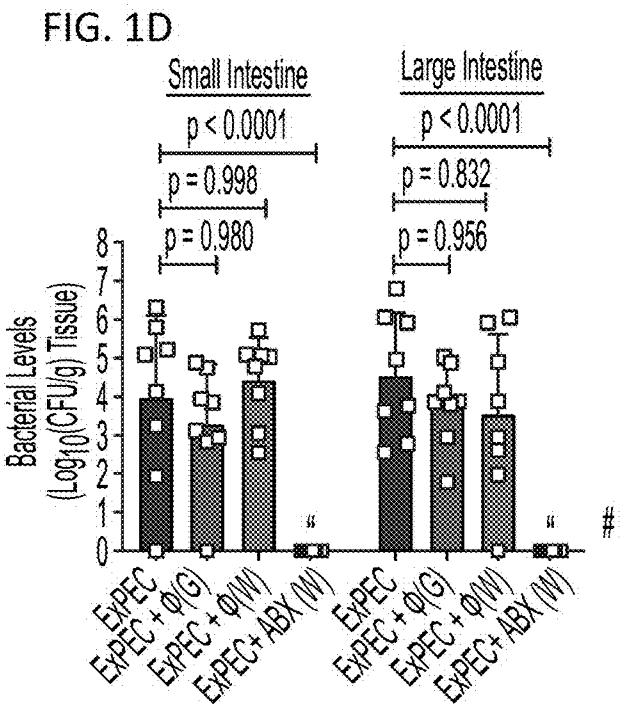
Figure 1E:
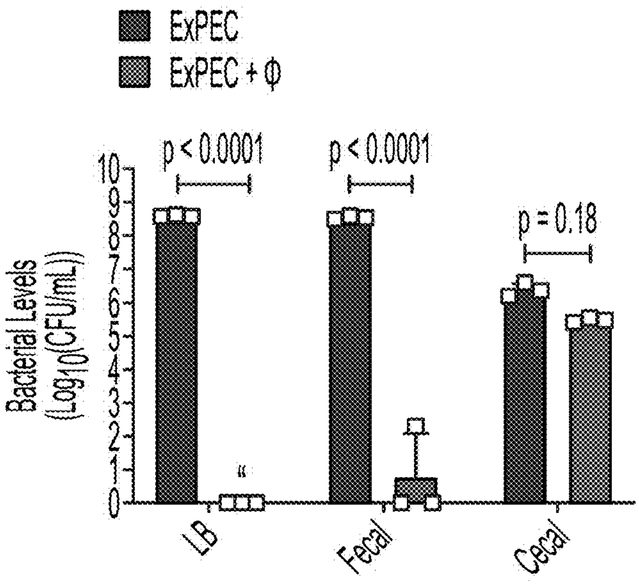
Figure 1F:
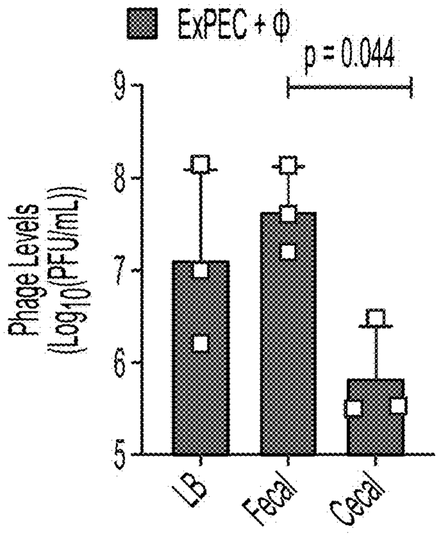

1A. Untreated mice sustained stable bacterial colonization during the course of the experiment (6 days) (FIG. 1B). When phage HP3 was given to animals via water or a daily gavage, the levels of ExPEC were indistinguishable from that of the untreated control at the end of the experiment. An uptick in CFU was noted on day 2; however, all groups leveled out by day 3 until the end of the experiment. No ExPEC was detected at any time point in the antibiotic-treated group. Interestingly, phage HP3 was detected and active as determined via plaque assay by plating the stool of phage-treated mice on an overlay of ExPEC bacteria, even on day 4, indicating that the lack of ExPEC reduction was not due to a lack of delivery to the intestinal environment or to inactivation of the phage. It should also be noted that despite having higher levels of phage upon gavage during days 1 to 4, the phage was no more effective at removing ExPEC than phage given in the water, suggesting that in this experiment, there was no dose-dependent effect of phage. In addition, as many as $10^5$ PFU/g phage were found in the murine intestinal tissue (including cecum and colon) on day 6, the final day of the study, yet there was little to no clearing of ExPEC compared to that in these tissues of the untreated control FIGS. 1C and 1D. Importantly, antibiotic treatment significantly reduced the number of operational taxonomic units (OTUs) and diversity, as determined by the Shannon diversity index, which takes into account species richness and distribution (P=0.007, P=0.009). Also, a principal-component analysis (PCA) of beta diversity demonstrated that mice in the antibiotic cohort clustered together and away from the untreated and phage groups, suggesting antibiotics had a more profound effect on the microbiome than phage. Finally, the inventors assessed phage killing in a modified "cecal medium" (CM) that is derived from the cecal contents from recently euthanized mice. These cecal contents were pooled and homogenized in sterile saline solution and then centrifuged to remove large particulates. This medium is designed to simulate the luminal complexity of the mammalian intestine, since it contains fecal matter, a microbiome, mucus, and likely many of the small molecules and proteins present in an intestinal lumen. Whereas phage HP3 completely abolished ExPEC in LB (nearly a 9-log drop in levels and no detectable live bacteria) and nearly abolished it in a slurry of fecal pellets taken from the same murine host (~8-log drop in levels), there was little to no phage-based killing in CM, despite recovering nearly $10^6$ to $10^{7.5}$ PFU/ml of phage FIGS. 1E and 1F These results mirrored those from the ExPEC colonization model and indicate there is a factor(s) present in the mammalian GI that inhibits this lytic phage.

Figure 2A:
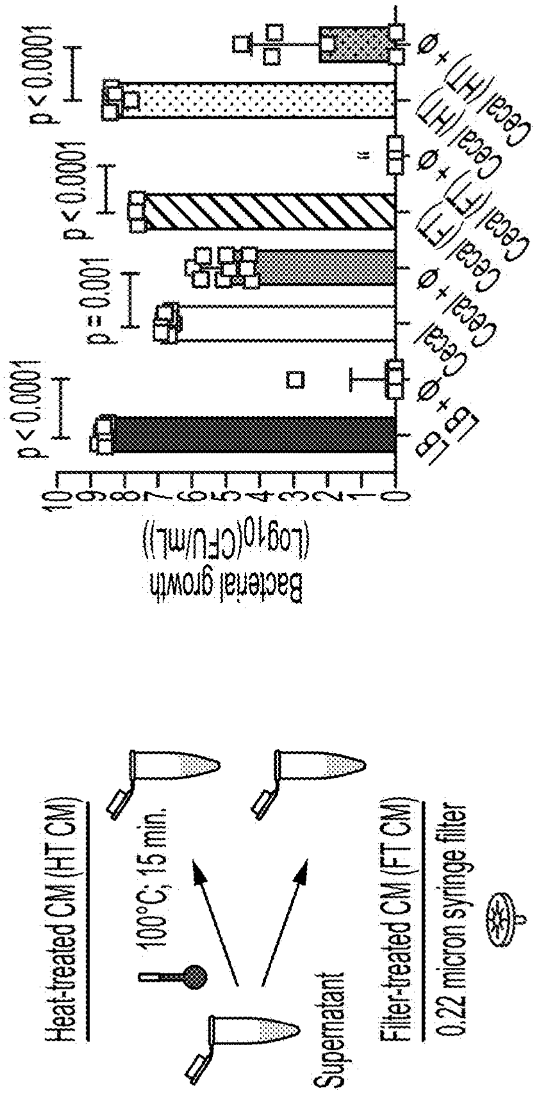
FIGS. 2A-2C.

The inhibitory component is mucin. The inventors wished to understand the reasons phage HP3 was ineffective in this intestinal microenvironment. The inventors next tested whether the inhibition might be related to the presence of live bacterial microbiota in CM. However, ExPEC killing with phage was not enhanced with removal of the microbiota with a broad range of antibiotics, including inhibitors of protein synthesis, cell wall, and DNA synthesis. (Note that the antibiotics efficiently killed a commensal, antibiotic-sensitive, *E. coli* that was spiked into the CM). Arriving at no resolution as to what the inhibitory factor may be, the inventors decided to test more drastic treatments for their ability to restore phage killing in CM. First, the CM was heat treated (HT CM) (FIG. 2A). Interestingly, heat treatment led to a 0.6-log improvement in ExPEC killing by phage HP3 (P<0.0001). Similarly, when CM was filter treated (0.22-mm filter) (FT CM), there was no detectable level of ExPEC in the medium after treatment with phage HP3 (FIG. 2A), and this observation was extended to another phage showing inhibition in CM, EC1 (P<0.0001). Thus, the inhibitory component was large (retained on 0.22-mm filter) and sensitive to boiling.

Figure 2B:
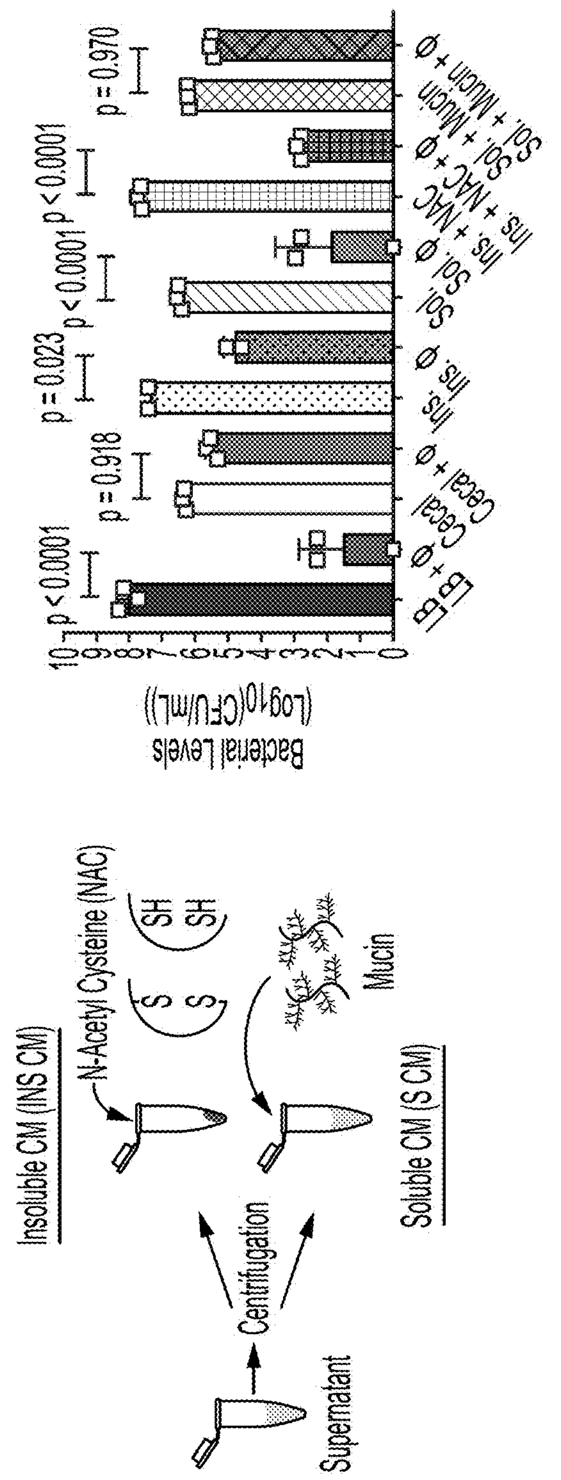

The inventors reasoned intestinal mucins might fit this profile due to their highly associative and sticky properties (captured on a filter), and as proteins, they would be sensitive to heat. Mucins are glycoproteins found throughout the gastrointestinal system which form a layer between the intestinal epithelial cells (IECs) and the commensal or pathogenic microbiota. Also, they can function as receptors for microbes. To test whether mucins were inhibiting bacterial killing by phage, the inventors devised another method whereby CM was separated via high-speed centrifugation into soluble (S CM) and insoluble (INS CM) forms (FIG. 2B). The inventors hypothesized that INS CM would contain mucin, since large intestinal mucins are normally present in this portion, and be inhibitory to phage killing, whereas the S CM would not have these properties. Indeed, phage killing in unprocessed CM or INS CM was inhibited to a greater extent than in S CM (FIG. 2B). To more directly test the hypothesis that mucin was the inhibitory factor, the mucolytic drug N-acetyl cysteine (NAC) was added to INS CM, and porcine gastric mucin (1.5% [wt/vol]) was added to S CM. Indeed, a 5-log reduction in phage killing of ExPEC was observed in INS CM upon addition of NAC, which also improved killing to that seen in S CM (P<0.0001). Perhaps more compelling, the addition of mucin to S CM abrogated bacterial killing by phage to levels originally observed in CM alone (not significant, P=0.970). These results indicate that the inhibitor of phage killing in cecal medium is intestinal mucin.

Along these lines, *E. coli* is known to use mucins as a source of carbon. The inventors reasoned that a murine host colonized with ExPEC may see a bloom upon NAC treatment due to the drug liberating the mucins for bacterial consumption and thus serve as a system to test if the reduction in aggregated mucin would promote phage HP3's ability to kill ExPEC. Upon treatment with NAC for 2 weeks, ExPEC levels in the small intestine of mice were increased, and phage HP3 reduced ExPEC levels, although it was not significant. A similar trend was observed in the large intestine. The less pronounced effect in the large intestine compared to that in the small intestine may be due to the thickness of mucus and thus the lower likelihood for NAC to be effective at breaking up this mucus. Also, NAC is known to be rapidly absorbed in the small intestinal tissue, thereby losing its effect in the more distal large intestine.

Figure 2C:
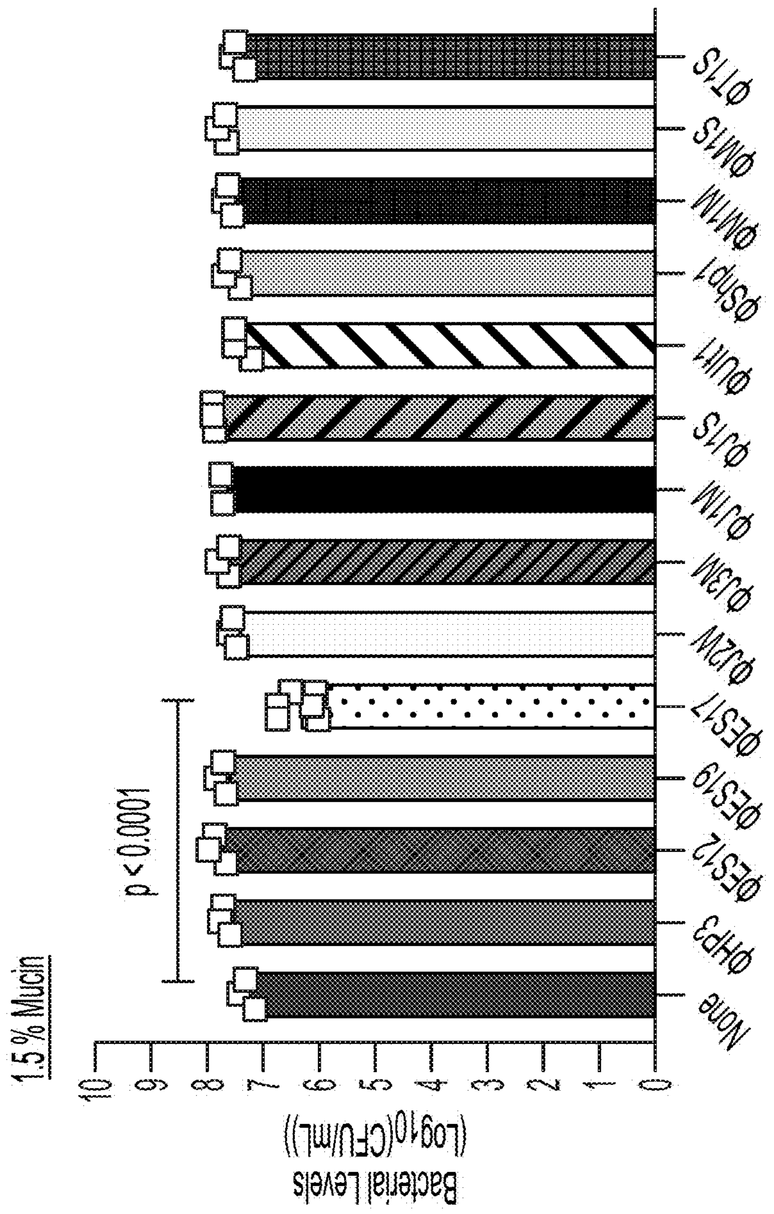

Discovery of a mucin-enhanced phage. Reasoning that human sewage or the feces of animals may contain phage that have evolved to target their host in high mucin environments, such as the intestinal tract, the inventors screened their phage library and other phages recently isolated from these environments for enhanced activity in LB containing 1.5% mucin (FIG. 2C). This is the same concentration that prevented phage HP3 activity in soluble cecal medium and was shown to provide strong inhibition in LB for up to 8 h. Surprisingly, only a single phage, designated phage ES17 (GenBank Accession No. MN508615), significantly reduced bacteria in the LB mucin medium (FIG. 2C) (P<0.0001, approximately 1 log). Phage ES17 was active in mucin despite being much less effective (0.3 log) than phages HP3, J2W, Ult1, Shp1, or M1S, which completely killed ExPEC to undetectable levels in LB medium alone. Consistent with these data, when the amount of mucin was varied from 0% to 2% and phages HP3 and ES17 were compared for lytic activity against ExPEC, phage HP3 was highly effective as the concentration of mucin was lowered to 0.5% but completely inhibited at higher levels. However, phage ES17 was most effective at concentrations in which HP3 was inactive (0.5% to 1% mucin) and least active at concentrations lower or higher than in this range. Taken together, these data suggest that phage ES17 harbors unique properties that facilitate its ability to efficiently be lytic in the presence of mucin.

Figure 3A:
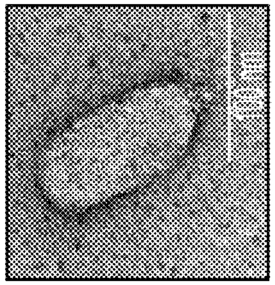
FIGS. 3A-3E.

Phage ES17 is a C3-type phage whose activity is enhanced by mucin. The inventors sought to understand the molecular mechanism of phage ES17's enhanced ability to find and lyse its bacterial host in mucin. Phage ES17 was determined to be a double-stranded (dsDNA) virus of the order Caudovirales, family Podoviridae, genus *Kuravirus*. PhiEco32, another *Kuravirus* phage, shows close genetic similarity to ES17. *Kuravirus* phages have elongated C3-type capsids, an uncommon morphology, short tail fibers, and small genomes. ES17 has these similar morphological characteristics (capsid of 0.100 nm) (FIG. 3A). ES17 has a small genome size consisting of 75,007 bp with 123 predicted open reading frames (ORFs) (MN508615).

Figure 3B:
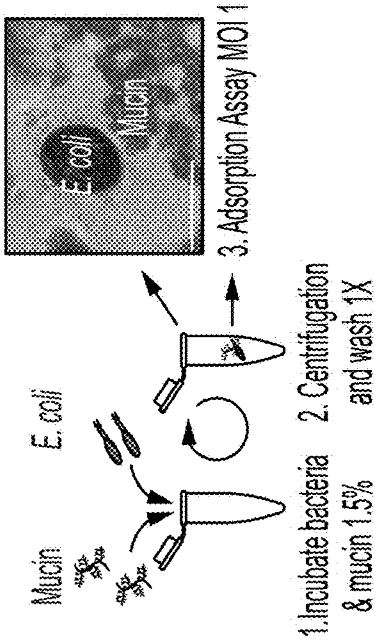
Figure 3C:
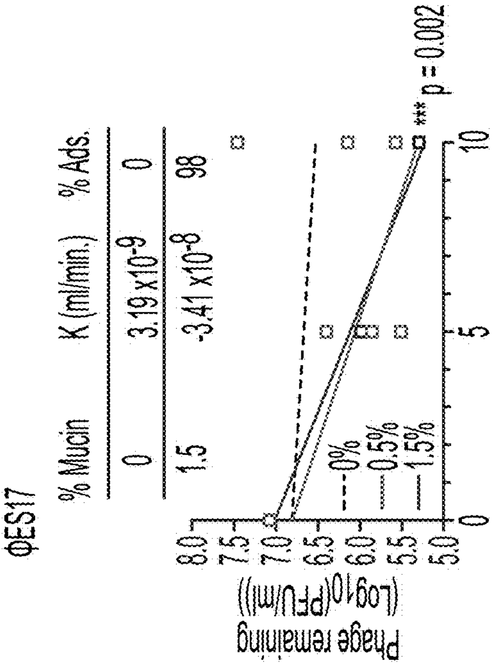
Figure 3D:
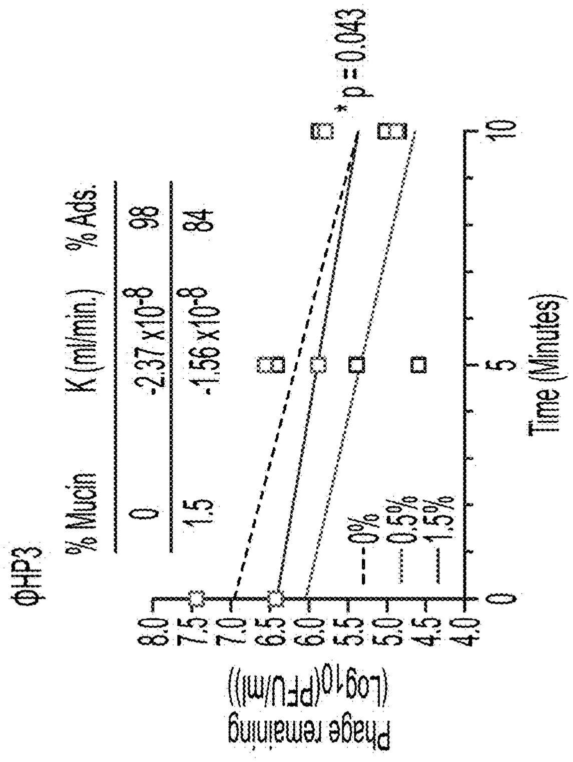

To determine why this phage is distinct from other phages that lack activity in mucin-rich environments, the inventors examined the ability of phages ES17 and HP3 to adsorb to their *E. coli* hosts. Previous data had shown that 98% of HP3 was adsorbed in 10 min, whereas only 32% of ES17 was adsorbed in that time. Additionally, no major differences were previously found between ES17 and HP3 as determined by one-step growth curve parameters such as burst size (ES17, 36; HP3, 60) or latent period (ES17, 32 min; HP3, 22.5 min). The inventors wondered whether the addition of mucin could improve phage ES17 adsorption and inhibit the adsorption of phage HP3. A modified adsorption assay was utilized for this experiment using ExPEC and mucin. Briefly, the bacteria were incubated in different concentrations of mucin (0% to 1.5%), pelleted, and washed to remove any mucin that did not adhere to the bacterial surface (FIG. 3B). Next, a standard adsorption assay was conducted with phages ES17 and HP3. Interestingly, phage ES17 showed no adsorption to ExPEC in 10 min in the absence of mucin; however, if first incubated with 1.5% mucin, adsorption increased to 98% (FIG. 3C). In contrast, 98% of phage HP3 was adsorbed without mucin, and the adsorption dropped to 84% in its presence (FIG. 3D). Finally, the inventors adapted an enzyme-linked immunosorbent assay (ELISA)-like approach to determine if phage ES17 preferred binding to surfaces coated with mucin, a hypothesis consistent with the inventors' data. Indeed, when mucin was bound to an ELISA plate, phage ES17 bound to the mucin surface at higher levels than phage HP3 (FIG. 3E) (P=0.041 and P=0.002). Taken together, using these different approaches, the data suggest that phage ES17 binds mucin, a property that may enhance its ability to infect *E. coli* in mucin-rich environments.

Phage ES17 binds human heparan sulfated proteoglycans. Phage ES17 harbors an enhanced ability relative to that of other *E. coli* phages to find its bacterial host in environments in which carbohydrates are a prominent chemical component (examples from above include cecal medium and mucin-rich broth). ES17's putative tail fiber protein (ES17-TFP) showed high similarity, based on a BLAST analysis (64% similar; E value, 0), to a tail fiber protein in another lytic podophage, the T7-like bacteriophage LM33_P1 (YP_009324518.1), which also targets ST131 strains. T7-like phage tail fibers have been shown to possess endosialidases that target surface sugars, such as capsule-forming polysaccharides. A BLAST analysis revealed that ES17-TFP contains a putative pectinesterase (E value, 7.45e203; 369 bp). This domain was only found in four other phages, myPSH1131, myPSH2311, vB_EcoS_Golestand, and LM33_P1, and of those, only myPSH1131 has it in the same tail fiber protein as ES17.

A structural analysis of modeled ES17-TFP showed a high similarity to a phage K5 lyase binding domain (E value=4e212). Phage K5 binds K5 capsular polysaccharide and acts as a K5 polysaccharide lyase. The K5 *E. coli* capsule is made of a repeating disaccharide that is identical to the precursor of heparin and heparan sulfate (HS), a linear polysaccharide present in glycosaminoglycans (heparan sulfate proteoglycans [HSPGs]). These proteoglycans are found on mammalian cells and in mucus. Also, mucins with similar structures to that of heparan sulfate/heparin (a-linked GlcNAc or N-acetyl-D-glucosamine) are present intestinally and found in porcine gastric mucin (PGM).

The inventors reasoned that ES17's enhanced activity might be due to an ability to bind mammalian polysaccharides found on glycoproteins, as other groups have found with different phage types. However, none of these groups had identified heparan sulfate proteoglycans, ubiquitous glycoproteins present at the basement membranes and surfaces of various cell types, as likely receptors for this interaction. Using this mechanism, phage could localize to its host, thereby explaining its enhanced activity in a mucin-rich environment. The inventors wished to extend these observations further and specifically pinpoint the exact type of carbohydrate that might mediate the hypothesized activity. To test this idea, the inventors cloned and purified ES17-TFP (FIG. S4E) and assessed the ability of purified ES17-TFP to bind to a glycan array containing more than; 860 unique glycan structures from porcine gastric mucin (PGM), glycosaminoglycans (GAGs) and a variety of synthetic and naturally sourced glycans generated by the Consortium for Functional Glycomics (CFG). No or very low relative fluorescent units (RFU), a proxy for binding, was observed for a wide array of mammalian glycans, including those purified from porcine gastric mucin. However, surprisingly, there was an increase of several orders of magnitude in RFU (RFU>2,000) observed for binding to the GAGs containing heparan sulfate (identification numbers [ID no.] 64 to 173) but not the structurally similar GAGs hyaluronic acid no. 1 to 20 or chondroitin sulfate no. 21 to 63 (FIG. S4Fiii). The finding that purified ES17-TFP binds human heparan sulfated proteoglycans provides a possible mechanism to explain why phage ES17 demonstrates enhanced activity in intestinal environments.

ES17 binds to the surface of human intestinal enteroids. Human intestinal enteroids (HIEs) are organotypic higher-order cultures that have become popular as surrogates to model the human intestine. They can be grown as 3-dimensional structures complete with a lumen and crypt/villus axis or as 2-dimensional monolayers that facilitate host-pathogen interactions. These cultures are also useful because they express a variety of glycans found in the human intestine, including mucins and proteoglycans. Human intestinal enteroid monolayers (HIEMs) were derived from colonic stem cells following differentiation for 5 days in high-Wnt medium. Phage ES17 or HP3 was added to confluent HIEMs for 1 h, extensively washed, and visualized by immunofluorescence microscopy using antibodies raised against each phage. Little to no detectable phage HP3 was observed on the HIEMs intestinal epithelial cell (IEC) surface, though antibodies generated robust signal and specificity toward the phage when HP3 was fixed on slides alone FIG. 4A). Phage ES17 (green) bound evenly to the IECs on the apical side, including areas where prominent Muc2 (red) localization was observed, but also on areas where there was no Muc2 staining (FIG. 4A). To determine whether phage ES17 bound to the IECs of HIEMs via heparan sulfate, the inventors pretreated the HIEMs with heparinase III to enzymatically remove HSPGs and then assessed phage binding. Indeed, HIEMs treated with heparinase significantly reduced the levels of bound ES17, both qualitatively and quantitatively (FIG. 4B) ($P<0.0001$). This finding is consistent with the purified tail fiber protein specifically binding to HSPGs. The localization of ES17 to both the mucus layer and to the IEC surface was by binding to HSPGs, which likely position the phage to be in the exact location needed to find its bacterial target in the intestinal microenvironment. To show that ES17 when bound to HIEMs could still infect bacteria, the inventors utilized the diarrhea-causing pathogen enteroaggregative *Escherichia coli* (EAEC), which adheres to HIEMs robustly in an aggregative mesh-like pattern unlike ExPEC. For this experiment, the inventors precoated HIEMs with phage ES17, washed them, as detailed above, and then infected them with EAEC strain 042. HIEMs were fixed and stained using a Giemsa-Wright stain to visualize cells and bacteria, as previously described. Infected HIEMs showed robust bacterial adhesion to cells with an aggregative phenotype (FIG. S4Hii, red arrows). Phage-coated HIEMs, however, showed significantly reduced EAEC on the surface of the organoid ($P=0.007$), demonstrating that bound ES17 is still infectious to this significant biofilm-forming pathogen.

Figure 5A:
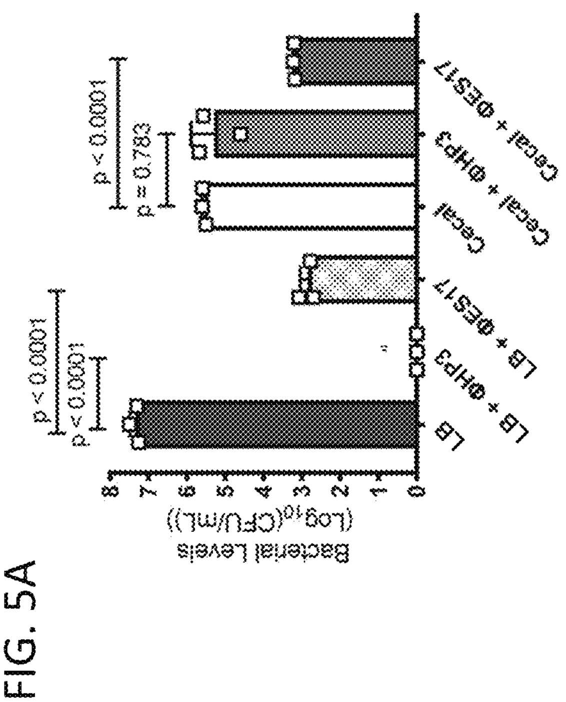
Figure 5B:
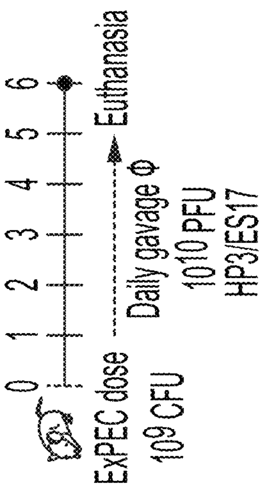
Figure 5C:
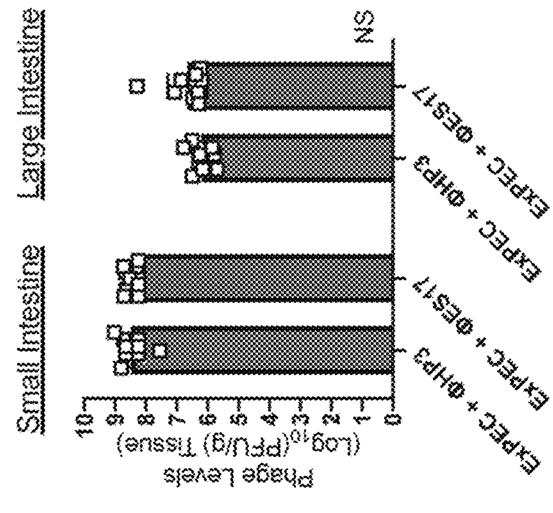
Figure 5D:
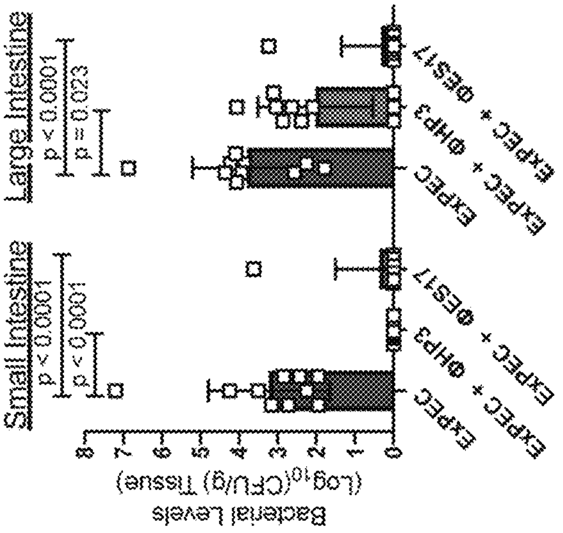

Phage ES17 kills ExPEC in the mammalian intestine. The finding that phage ES17 demonstrated enhanced lytic activity in the presence of mucins, was the best of several screened phages in a mock luminal environment rich in mucins, and binds the human organotypic culture IECs via HSPGs prompted an examination into whether this phage could overcome the intestine-induced inhibition of phage lytic activity toward colonized ExPEC that was observed for phage HP3. The inventors first tested if ES17 was effective in cecal medium. Indeed, phage ES17 showed a 2.5-log improvement in ExPEC removal in this environment compared to that of phage HP3 (FIG. 5A) ($P<0.0001$). There was no effect on the number of OTUs or the Shannon diversity index in this experiment, suggesting phage ES17 was highly selective at removing only the target ExPEC strain. The inventors next tested the effect of phage ES17 on ExPEC in a murine intestine. Animals were colonized with ExPEC as in FIG. 1A and treated with either phage ES17 or HP3 (FIG. 5B). The dose of phage was also increased from $10^9$ PFU to $10^{10}$ PFU to also evaluate if giving more phage would improve HP3's ability to reduce ExPEC, especially in more proximal segments, as the phage slowly moves through the alimentary canal. Examination of the small and large intestines on day 6 showed phage levels were high across all groups ($10^6$ to $10^8$ PFU/g intestinal tissue) (FIG. 5C). Animals treated with phage HP3 had no detectable CFU in small intestinal tissue (FIG. 5D) but had indistinguishable levels from those of the untreated controls in the cecum. This reduction and improved phage levels in the gut may be due to a log increase in daily phage dose given to animals ($10^{10}$ PFU) compared to that used for FIG. 1 ($10^9$ PFU). In contrast, every animal treated with phage ES17, except one, had no detectable levels of ExPEC in either the small or large intestine, suggesting that this lytic phage possesses a unique ability to target ExPEC in complex mucosal environments such as the large intestine.

Materials and Methods

Bacterial strains and phages. ExPEC ST131 isolate JJ1901 was used in all ExPEC infections, except for JJ2528. Both isolates were previously obtained from Jim Johnson (University of Minnesota). Commensal *E. coli* ECN was isolated from a human fecal sample. Prior to infections, all strains were grown overnight at 37° C. from a single colony streaked on an LB agar plate.

Phages HP3, ES12, ES17, ES19, ES21, and ES26 were previously described and characterized. Phages 6914, 6915, and 6939 were recently isolated from sewage. All phages described were isolated by single plaque isolation from environmental sources as described previously.

Murine infections. Mixed ages (6 to 10 months) and sexes of BALB/c mice (Jackson Laboratories, Bar Harbor, ME) were used in mouse models of infection. Mice were kept in a specific-pathogen-free (SPF) environment at Baylor College of Medicine CCM (Center for Comparative Medicine) Taub facility. All methods performed on mice were approved and in accordance with relevant guidelines and regulations from the Guide for the Care and Use of Laboratory Animals (National Institutes of Health) and approved by Baylor College of Medicine's Institutional Animal Care and Use Committee (protocol AN-6372). For infections, mice were kept in a biohazard facility with sterile food and water. The mice were individually housed during colonization experiments, and bedding was replaced with autoclaved techboard liners for daily fecal collection. For colonization experiments, sample size was determined based on previous colonization experiments in mice. Mice received a $10^9$ CFU dose of ExPEC strain JJ1901 via oral gavage. Rodent health was monitored daily for indication of pain or disease. Bacterial colonization (fecal and intestinal) was determined after homogenization, selective plating for the chloramphenicol-resistant strain JJ1901 on LB agar plates containing chloramphenicol, and colony counting. A 6-day time course was established based on previous studies showing consistent colonization of ExPEC after 1 oral dose at $10^9$ CFU (87).

Purified phage in 3% (wt/vol) NaHCO3 was administered either via gavage or in water with 5% (wt/vol) sucrose ad libitum. All groups received sucrose and NaHCO3 in water for consistency. The antibiotic ampicillin (1 g/500 ml) was administered in water. Phage colonization was quantified after dilution of homogenates and serial plating on a double agar overlay assay of the ExPEC strain. Phage verification was determined by observation of plaque morphology compared to that of phage that was inoculated into mouse. Phage present in the native mouse microbiota did not plaque on the ExPEC strain.

Ex vivo cecal model. A modified cecal assay was used for experiments. Briefly, cecal contents from just-euthanized mice were pooled and homogenized in sterile 0.09% NaCl solution at a 1:5 dilution (milligrams per milliliter). The homogenate was centrifuged to remove large particulates (2,000×g for 30 s). The supernatant fluid was used for 4.5-h phage killing assays at a multiplicity of infection (MOI) of 10 at 37° C., shaking (255 rpm), as previously described. All cecal and mucin experiments were performed using independent bacterial cultures grown up from different colonies streaked on a plate. This was considered a biological replicate. For FS CM, cecal supernatant was centrifuged (6,000×g for 5 min.) and filtered through a 0.22-mm syringe filter. For HT CM, the supernatant was heated at 100° F. for 20 min in a hot water bath and then cooled to room temperature (RT) for infections. Insoluble CM and soluble CM (supernatant) were isolated post-high-speed centrifugation (9,000×g for 5 min) of CM. The insoluble pellet was resuspended in sterile 0.09% NaCl solution for infections (IN CM). For the mucin assays, porcine gastric mucin type II (PGM; Sigma-Aldrich) was used at various concentrations diluted in phosphate-buffered saline (PBS). The mucolytic drug N-acetyl cysteine (NAC; Sigma-Aldrich, 5 mg/ml) was diluted in PBS for demucolytic assays.

Mucin-coating adsorption and imaging. For the adsorption curves, assays were performed at an MOI of 1 using mid-log-phase cultures independently grown from different colonies on a plate (this was considered a biological replicate) as the inventors have done for previous publications to characterize phages ES17 and HP3. Prior to adsorption, PGM (0%, 0.5%, and 1.5% [wt/vol]) was added to the bacterial cultures for 10 min at RT with shaking (255 rpm). The cultures were centrifuged (6,000×g for 5 min) and gently washed with PBS. The adsorption rate constants (Ks) were determined from the natural log of the slope of the adsorption curve versus the bacterial concentration. Time points were taken every 5 min in order to accurately test simultaneously for the different conditions being assayed.

Mucin binding ELISA assay. Clear-walled Immulon 2 HB 96-well microtiter plates (Immunochemistry Technologies, no. 227) were used for the ELISAs. PGM (200 ml of 1 mg/ml) was added to a microtiter plate and incubated at 4° C. overnight. The next day, the mucin was removed and wells were washed twice with PBS. The phage was added to wells for 1 h and then washed three times in PBST (PBS with 0.1% Tween 20). The wells were blocked with bovine serum albumin (BSA) and then incubated with antibodies for the phage overnight at 4° C. Following washing steps, a horseradish peroxidase (HRP)-conjugated antibody was added for 1 h. To assess phage binding, 3,39,5,59-tetramethylbenzidine (TMB) solution was added until the wells turned light blue, and then a stop solution (2 M $H_2SO_4$) was added. The absorbance was read at 450 nm. Each well was considered a biological replicate for this experiment.

HIEM infection and imaging. Human enteroid monolayers (HIEMs) were differentiated for 5 days (0.90% confluence) as described previously (54). For experiments, each well containing a HIEM was considered a biological replicate. HIEMs were incubated with phage at 108 PFU/ml in culture differentiation medium for 1 h at 37° C. in the presence of 5% $CO_2$ in a humidified incubator and then washed in PBS. The HIEMs were fixed in Clark's solution for 10 min to preserve the mucus layer. The HIEMs were permeabilized and blocked with 5% BSA in 0.1% Triton X-100 in PBS for 30 min at RT. Mucus was detected using antibodies to Muc2 (1:200) (Abcam), and nuclei were stained with 49,69-diamidino-2-phenylindole (DAPI) (300 nM) for 5 min at RT. Antibodies against phages HP3 and ES17 were generated from whole-virus (phage) injection into rabbits performed by Pacific Immunology. A 13-week antibody production protocol consisted of 4 immunizations and antiserum collection.

To selectively removed HSPG from GAG chains, enteroid cultures were pretreated with heparinase III (Sigma, 2 U/ml) for 2 h, as described previously (89), followed by the addition of phage. Images were captured using a Zeiss LSM 510 confocal microscope. Represented images were adjusted equally for brightness and contrast using FIJI software version 2.0.0. The images were adjusted equally for brightness and contrast. Particle analysis was used to determine the number of particles per well.

Figure 3E:
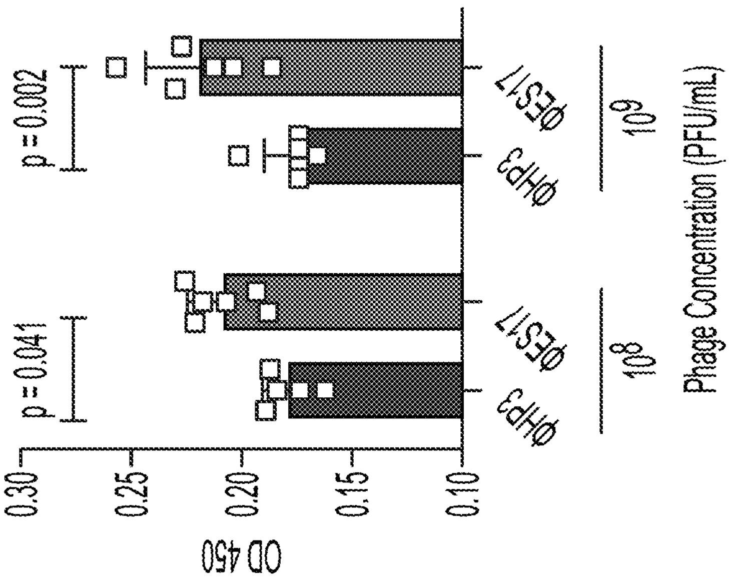

Statistics. Statistical analysis was performed using PRISM 8 software. Microbiome 16S data were analyzed using ATIMA (Agile Toolkit for Incisive Microbial Analyses). For figures with log-transformed data and groups of 0.2, significance was determined using a one-way analysis of variance (ANOVA) (FIGS. 1-5) or two-way ANOVA when necessary (FIG. 3E). For multiple-comparison analysis, the secondary test, Tukey, was used. For nontransformed data, a normality test (Shapiro-Wilk) was performed to determine normality before a one-way ANOVA analysis was performed. Significance was determined to be a P value of less than or equal to 0.05. Unless otherwise stated, all graphs show the means and standard deviations.

Example 2—Antiviral Resistance and Phage Counter Adaptation to Antibiotic-Resistant Extraintestinal Pathogenic *Escherichia coli*

Selection of phage-resistant bacterial isolates. 0HP3 is an extensively characterized, lytic phage that is an effective therapeutic in a murine sepsis model. It has also, with single-use INDs, been successfully used in two patients with *E. coli* infections. Three clinically-derived ExPEC strains, JJ2050, JJ2528, and JJ2547, were selected as MDR pathogens capable of causing illness in this model. These strains are all of sequence type (ST) 131 and were isolated from different patients. When treating mice for ExPEC-derived sepsis, the inventors found that although phage reduced bacterial burden in most animals, some subjects maintained relatively high bacterial levels. The inventors hypothesized that, in these cases, phage-resistant isolates ("resisters") had arisen during treatment. To test this hypothesis, the inventors isolated phage-resisters by challenging them with ϕHP3 using two different methods (FIG. 7A). The first method, culture-based selection, consisted of streaking an overnight bacterial culture on an LB plate coated with phage. The second, animal-based selection, used the inventors' murine sepsis model to recover resisters from phage-treated animals. Briefly, mice were given an intraperitoneal (IP) injection of each ST131 strain followed by IP injection of phage one hour later. Bacterial isolates were then recovered from the livers and spleens of the euthanized mice the next day.

Isolates from both strategies were tested for phage-resistance by two methods: co-incubation in liquid culture (1), and phage spot assay (2). For the co-incubation assay, isolates were grown for 4.5 hours in LB with or without phage. The three parental ST131 strains were readily killed by ϕHP3 (FIG. 7B). Isolates that survived the co-incubation selection, however, were refractory to any killing by phage (FIG. 7B). Further, parental isolates yielded a high phage titer by spot assay, but the resisters produced no observable phage progeny. These findings indicate the isolates have acquired full resistance to HP3. Between the two isolation strategies, a total of 21 independent resisters were isolated, summarized in FIG. 15. The majority of resisters had smaller colonies compared to their WT progenitors.

Resistance is associated with loss of fitness in host microenvironments. Resistance to phage may accompany a loss of fitness under certain environmental contexts; of particular interest are findings of loss of virulence in the hosts. Such a loss has been observed for bacterial pathogens of fish and moths, has been modeled in *A. baumannii*, and has been inferred with *V. cholera* in humans. To assess virulence in their isolated resisters, the inventors tested their growth ability in mediums which simulated the host microenvironment. Since ExPEC strains cause UTIs and bacteremia, human urine and blood were used here. In urine, most of the resisters demonstrated comparable growth relative to Luria broth (LB); these same resisters likewise had comparable growth to their wild-type (WT) progenitors (FIG. 8). Interestingly, all resisters with attenuated growth in urine (six of nine) were isolated from the murine model. Further, ϕHP3 retained effectiveness against WT isolates, but was ineffective against resisters. Strikingly, and for reasons currently unknown, the six attenuated animal-derived resisters showed enhanced growth in the presence of HP3 (FIG. 8; yellow bars, +). This growth enhancement was not replicated by the phage buffer alone (data not shown). Overall, this data suggested most of the animal-derived resisters, though none of the culture-derived ones, had undergone a fitness trade off that compromises their ability to grow well in human urine.

To assess if the ExPEC resistors demonstrated any fitness losses in blood, isolates were first assessed for growth and survival in unaltered human whole blood (WB; FIG. 9A). Whereas WT JJ2547 thrived in WB after 24 hours, the resistor strains, regardless of isolation method, had significant drop in viability (FIG. 9B). The inventors hypothesized the resisters' fitness loss was due to the complement system in serum, a potent antibacterial mechanism. To disable complement, the inventors heat treated the plasma fraction and recombined it with the blood cell fraction, a mixture termed heat-inactivated plasma blood (HIPB; FIG. 9A). The resistor strains remained substantially attenuated, with an average 7-log drop in viability (FIG. 9B). The inventors next hypothesized a loss in nutrient uptake may cause the resisters' loss of fitness. To replicate the nutritional environment of blood in a more readily accessible form, the inventors used a defined medium called blood serum mimic (BSM). Resister survival was improved when HIPB was mixed with BSM 1:1 (HIPB/BSM; FIG. 9B); interestingly, however, resister survival was poor when the blood cell fraction was suspended in BSM (BSM+; FIG. 9B). When grown in BSM alone, resister growth was comparable to the parental strain (FIG. 9B). This suggested something in both the blood cell and plasma fractions was unfavorable for resister survival. The other WT and resister strains reproduced this general trend. Interestingly, parental JJ2528 demonstrated a marked deficit in growth in blood; this was somewhat surprising due to the strain's high virulence in a murine model of bacteremia. Overall, this data suggested that in order for the resisters to overcome phage infection, they have acquired a dramatic loss of fitness in human blood that is not driven by complement or nutrient uptake.

Figure 10A:
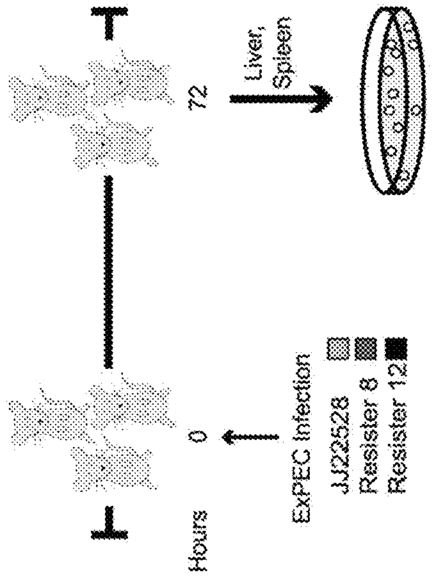
Figure 10B:
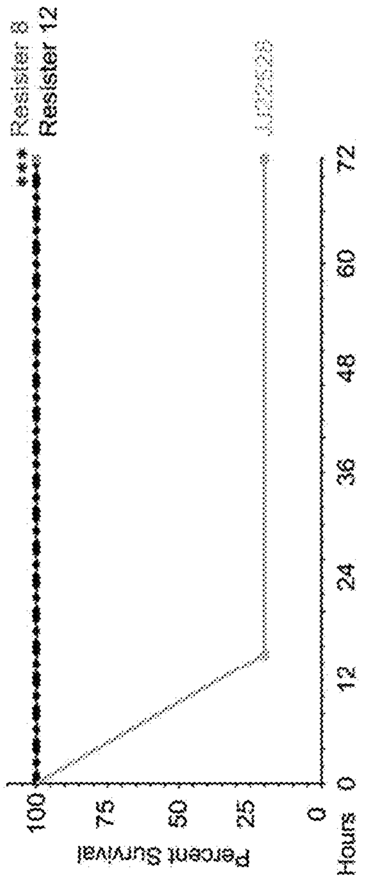
Figure 10C:
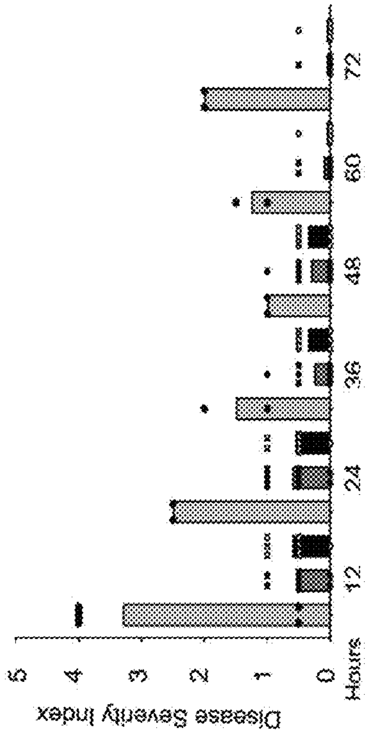
Figure 10D:
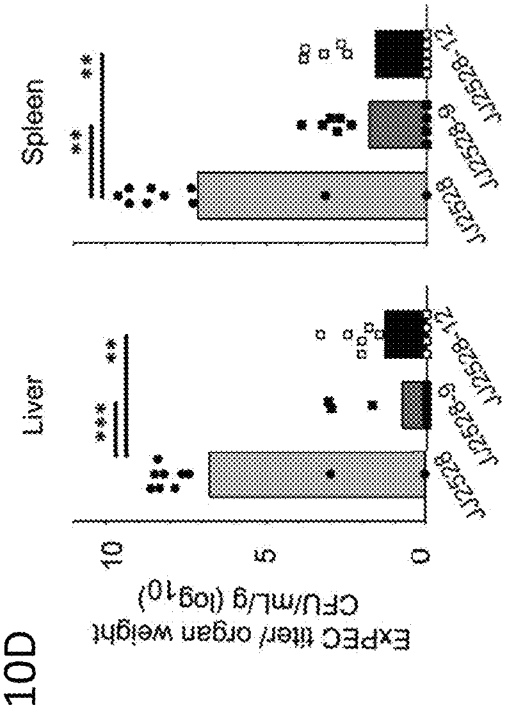

Phage resistors are attenuated during systemic infection. The resisters' loss of fitness in human blood and, in several of the animal-derived resisters, urine prompted us to assess resister pathogenicity in a murine model of bacteremia (FIG. 10A). For this study, the inventors selected two representative isolates from their resister list (both animal-derived, based on colony morphology) and compared their virulence and bacterial levels to the parental strain after infection. Surprisingly, every animal infected with the resister strains survived for the duration of the experiment, compared to 20% survival with the parental strain (FIG. 10B). Further, animals infected with the resisters had lower disease severity scores at every time point of the study (FIG. 10C) and displayed, on average, an approximately 4.5 log reduction in organ bacterial burden (FIG. 10D). This data suggested that these resisters sustained a loss of fitness in a murine model of systemic infection, and was consistent with the observed loss of survival in simulated host microenvironments.

Mechanism of resistance relates to mutations in bacterial surface components. To understand the mechanism driving ExPEC resistance to ϕHP3, as well as give insight into the reasons for reduced virulence, whole genome sequencing was performed on all 21 resisters, followed by an alignment of the assembled genomes to the parental strains (FIG. 11A). Remarkably, 15 of 21 resisters, regardless of the parental strain or isolation strategy, harbored truncations of varying degree in a single operon: the waa (or rfa) system, which is responsible for the assembly of lipopolysaccharide (LPS). Of these 15, one gene, waaC, was truncated or missing in every mutant. WaaC is responsible for the attachment of the second saccharide (L-glycero-D-manno-heptulose, LD-Hep) to the first (1-deoxy-D-manno-oct-2-ulsonic acid, KDO), forming the inner core of LPS (FIG. 11B). This mutation likely results in loss of most of the inner and outer core as well as O-antigen. Four of the remaining six resisters had truncations in hldE, responsible for two steps in the synthesis of LD-Hep (FIG. 10B). This mutation, phenotypically, is likely to produce an identical, truncated LPS molecule to the waaC truncation. This is consistent with the findings of Mutalik et al. who found a tendency for *E. coli* strains to develop mutations in the waa operon, or in the construction of LD-Hep when developing resistance to coliphages. This was similarly found for isolates of *Pseudomonas aeuruginosa*. This pointed to a conserved mechanism of resistance for ST131 *E. coli* to ϕHP3 via the truncation of surface LPS.

Of the final two resisters, one had a truncation in ompA, which expresses outer membrane protein (OMP) A, which forms pores in the bacterial outer membrane to import nutrients. Both of the two remaining mutant strains had a single nucleotide polymorphism (SNP) shortly downstream from the gene of ompA, which the inventors hypothesize to be a rho-independent terminator region; this modification may affect transcript polyadenylation, thus decreasing transcript stability. These two resisters also had truncations in the wzy O-antigen polymerase gene, though this may be unrelated to phage resistance in this case. A summary of the mutations in each of the 21 resisters, and a structural representation of their location in the LPS molecule, is shown in FIG. 11C. These findings suggested that the ST131 resister isolates attained resistance to ϕHP3 through loss of either LPS (19/21 cases) or OmpA (2/21 cases). Since both of these components are located on the surface of *E. coli*, the data suggested these two features may constitute primary and/or secondary receptors for phage HP3. An alternative hypothesis is that the loss of these genes disrupts *E. coli*'s surface integrity in a way that prevents proper attachment or adsorption of HP3.

Directed evolution guides the emergence of anti-resister phages. A somewhat unexpected finding from these studies was the frequency by which ST131 resisters arose in vitro and during infection, and their convergence in all 21 independent cases towards one or two key mutations in LPS or OmpA. Though there was clear reduction in virulence in the two mutants tested by murine sepsis model (one mutant in LPS and one in OmpA, FIGS. 10A-10D), it is worth noting that they were isolated during phage challenge of parental strains in infected animals, and were at high enough levels to be isolated (FIG. 13). The consistency of these findings suggested that a highly effective, "two-hit" phage cocktail could be developed; specifically formulated with phages to drive development of resisters that are less virulent in their host, and phages (developed to "predict" resistance mechanisms) which target those resisters.

To test this, the inventors first screened two well-characterized phages (ϕES17 and ϕEC1) for their ability kill the ST131 resister strains. Surprisingly, although these phages effectively kill all three parental strains, every resister was refractory to killing by these phages (FIG. 16). Since these phages are distinct from HP3 (genetically and morphologically), it may suggest there are common mechanisms of resistance in ST131 to coliphages. A screen of sewage samples for plaque formation on resister lawns also did not reveal any candidate lytic phages against the resisters. The inventors hypothesized the original phage, ϕHP3, could undergo adaptation in order to reinfect the resisters. To test this, the inventors generated an automated bacteria-phage bioreactor that continuously cycled fresh phage grown on its original bacterial host (parental strains) into a chamber that contains the target bacterium (resistant isolates) (FIG. 12A).

To determine if this approach would yield a phage derivative capable of infecting the resisters, parental JJ2528 was co-cultured with phage ϕHP3, and phage progeny then cycled to the chamber containing the resister isolate JJ2528-12. Samples were taken from the chamber at 5, 21, 24, and 37 hours and tested by spot assay on both the host and target isolates. Unexpectedly, a sample taken at five hours yielded noticeable clearing on JJ2528-12, as well as the parental host, which increased with time. A plaque from these was isolated, expanded in its new host, and purified. The new phage, designated ϕHP3.1, showed bacterial killing in the liquid culture assay (and plaque formation in the spot assay) for most of the resisters (either animal- or culture-derived) of JJ2528 (FIG. 12B). In addition, ϕHP3.1 was able to infect not just the target resister used in the directed evolution experiment, but every LPS-truncated resister as well, while retaining effectiveness against all three parental isolates (FIG. 12B; FIG. 16). Interestingly, the two ompA resisters retained partial (SNP only, JJ2528-9) or full (SNP and truncation, JJ2050-3) immunity to the evolved phage.

To verify ϕHP3.1 was a derivative of PHP3, and to identify genetic changes associated with its broad activity against the resisters, the inventors subjected the purified phage to whole genome sequencing. Bioinformatic comparison of ϕHP3.1 to ϕHP3 indicated just two SNPs along the length of all 176,000 base pairs. The first of these changes, a LysTyr464 to ArgHis464, was located in the gene encoding the spike protein (FIG. 13A), potentially at its binding site with the bacterial host (FIG. 13B). The second SNP coded a missense mutation in the long tail fiber gene, Gln9 to Arg9. Both instances result in substitution of residues with non-polar side groups to ones with positive charges at the extreme tip of the spike gene. This suggests that phage ϕHP3.1 may be able to reinfect ST131 resisters trough compensatory mutations which enhance the phage's interaction with the host surface, possibly via electrostatic charge modifications that promote binding or adsorption.

Compensatory ST131 ExPEC mutations allow resister re-resistance to the evolved ϕHP3.1. Phage and their bacterial hosts engage in cycles of coevolution. The inventors wondered if the resister strains had the ability to once again evolve resistance against the new phage, ϕHP3.1. Using the culture-derived selection method shown in FIG. 7A, the inventors identified three ExPEC isolates that grew in the presence of ϕHP3.1: two from JJ2528-5 (JJ2528-5.1 and JJ2528-5.2), and one from JJ2528-12 (JJ2528-12.1). It was not possible to derive animal-derived resisters to HP3.1 due to their poor virulence in infection challenge models (FIG. 10). The new resister strains were refractory to killing in both phage spot assays (FIG. 14A) and liquid culture assays (FIGS. 14B), confirming their resistance. These secondary resisters maintained their ability to grow in human urine (FIG. 14B). Whole genome sequencing of these resisters showed they maintained their parental truncations in hldE and waaC, respectively. Rather excitingly, and consistent with the above results, all three acquired new truncations in their ompA genes, similar to JJ2025-3 (FIG. 14C). This finding strongly suggests that OmpA is a partial receptor for phage ϕHP3 and a primary receptor for its evolved progeny, ϕHP3.1. That the ompA modification was observed in two of the 21 original resisters may reflect phage-ST131 evolution dynamics occurring at this second step during the first screen, possibly due to added selective pressure from the murine system.

Example 3—Activity of Phage Cocktail Comprising HP3, HP3.1, and HP3.2

*E. coli* were grown with a cocktail comprising phage ES17 and HP3. As shown in FIG. 17A, the phage cocktail initially suppressed the bacterial growth but was overcome by resistant strains (shown by an increase in OD600 in certain experiments within 24 hours after treatment). *E. coli* were then grown with a cocktail comprising phage HP3, HP3.1, and HP3.2. As shown in FIG. 17B, outgrowth of *E. coli* was not observed under these conditions past 8 hours up to 24 hours after treatment.

Next, *E. coli* biofilms were formed on human catheters, followed by treatment of the catheters with a cocktail comprising ES17, HP3, HP3.1, and HP3.2 (@Cocktail-R). As shown in FIG. 18, treatment with φCocktail-R disrupted biofilm formation and prevented resistance after 24 hours of treatment.

Example 4—Activity of Phage Cocktail Comprising HP3, HP3.1, and ES17

Mice (Swiss Webster; female; 6-8 weeks old) were infected with $10^8$ CFU of *E. coli* clinical isolate JJ2528 via IP (intraperitoneal) route. One hour later mice were injected (IP) with purified phage (HP3) or a cocktail of phages (HP3, HP3.1 and ES17) at a dose of $10^9$ PFU/phage. After an overnight infection mice were euthanized and major organs homogenized and plated for remaining CFU.

As shown in FIG. 20, mice treated with phage cocktail comprising HP3, HP3.1, and ES17 had significantly reduced *E. coli* CFU in the lungs, spleen, kidneys, and liver.

Example 5—Bacteremia Cocktail Efficacy

The subject matter was evaluated for cocktail performance relative to the prototype phage HP3. The first study (FIG. 20) assessed the effect of a cocktail of three phages (3, the anti-resistor phage 3.1, and the biofilm and mucosal binding phage ES17) at reducing bacterial levels in a murine model of bacteremia versus the parent and prototype phage HP3. The murine host was infected with ExPEC strain 2050 at 1×10^8 and 24 hrs later the cocktail was administered SC. The cocktail was superior to the HP3 only phage group at reducing bacterial levels in all four organs assessed. In FIG. 21, the disease index was assessed of the cocktail relative to no treatment, as above, showing substantial reduction in disease in cocktail treated animals. This extended to bacterial levels in organs.

All of the methods disclosed and claimed herein can be made and executed without undue experimentation in light of the present disclosure. While the compositions and methods of this invention have been described in terms of certain embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alavidze, Z. et al. Silk route to the acceptance and re-implementation of bacteriophage therapy. *Biotechnol. J.* 11, 595-600 (2016).

Altamirano, F. G. et al. Bacteriophage-resistant *Acinetobacter baumannii* are resensitized to antimicrobials. *Nat. Microbiol.* (2021) doi: 10.1038/s41564-020-00830-7.

Aslam, S. et al. Lessons Learned From the First 10 Consecutive Cases of Intravenous Bacteriophage Therapy to Treat Multidrug-Resistant Bacterial Infections at a Single Center in the United States. *Open Forum Infect. Dis.* 7, (2020).

Blanquart, F. & Gandon, S. Time-shift experiments and patterns of adaptation across time and space. *Ecol. Lett.* 16, 31-38 (2013).

Brockhurst, M. A. & Koskella, B. Experimental coevolution of species interactions. *Trends Ecol. Evol.* 28, 367-375 (2013).

Brüssow, H. Phage therapy: The *Escherichia coli* experience. *Microbiology* 151, 2133-2140 (2005).

Buckling, A. & Rainey, P. B. Antagonistic coevolution between a bacterium and a bacteriophage. *Proc. R. Soc. B Biol. Sci.* 269, 931-936 (2002).

Capparelli, R. et al. Bacteriophage-resistant *Staphylococcus aureus* mutant confers broad immunity against staphylococcal infection in mice. *PLOS One* 5, 1-13 (2010).

Chan, B. K. et al. Phage selection restores antibiotic sensitivity in MDR *Pseudomonas aeruginosa. Sci. Rep.* 6, 26717 (2016).

Conly, J. M. & Johnston, B. L. Where are all the new antibiotics? The new antibiotic paradox. *Can. J. Infect. Dis. Med. Microbiol.* 16, 159-160 (2005).

Fish, F. Phage therapy for the treatment of human intestinal bacterial infections: soon to be a reality? *Expert Rev. Gastroenterol. Hepatol.* 00, 1-4 (2013).

Fish, R, Kutter, E, Wheat, G, Blasdel, B, Kutateladze, M, Kuhl, S. Journal of wound care: Bacteriophage treatment of intransigent diabetic toe ulcers: a case series. 7, 27-33.

Gaba, S. & Ebert, D. Time-shift experiments as a tool to study antagonistic coevolution. *Trends Ecol. Evol.* 24, 226-232 (2009).

Gandon, S., Buckling, A., Decaestecker, E. & Day, T. Host-parasite coevolution and patterns of adaptation across time and space. *J. Evol. Biol.* 21, 1861-1866 (2008).

Green, S. I. et al. Bacteriophages from ExPEC Reservoirs Kill Pandemic Multidrug-Resistant Strains of Clonal Group ST131 in Animal Models of Bacteremia. *Sci. Rep.* 7, 46151 (2017).

Green, S. I. et al. Bacteriophages from ExPEC Reservoirs Kill Pandemic Multidrug-Resistant Strains of Clonal Group ST131 in Animal Models of Bacteremia. *Sci. Rep.* 7, 46151 (2017).

Green, S. I. et al. Murine model of chemotherapy-induced extraintestinal pathogenic *Escherichia coli* translocation. *Infect. Immun.* 83, 3243-3256 (2015).

Johnson, J. R. & Russo, T. A. Extraintestinal pathogenic *Escherichia coli*: 'The other bad *E. coli'*. *J. Lab. Clin. Med.* 139, 155-162 (2002).

Johnson, J. R., Johnston, B., Clabots, C., Kuskowski, M. A. & Castanheira, M. *Escherichia coli* Sequence Type ST131 as the Major Cause of Serious Multidrug-Resistant *E. coli* Infections in the United States. 55417, 286-294 (2010).

Leon, M. & Bastias, R. Virulence reduction in bacteriophage resistant bacteria. *Front. Microbiol.* 6, 1-7 (2015).

Levin, B. R. Nasty viruses, costly plasmids, population dynamics, and the conditions for establishing and maintaining CRISPR-mediated adaptive immunity in bacteria. *PLOS Genet.* 6, 1-12 (2010).

Ma, L., Green, S. I., Trautner, B. W., Ramig, R. F. & Maresso, A. W. Metals Enhance the Killing of Bacteria by Bacteriophage in Human Blood. *Sci. Rep.* 8, 1-11 (2018).

Poullain, V., Gandon, S., Brockhurst, M. A., Buckling, A. & Hochberg, M. E. The evolution of specificity in evolving and coevolving antagonistic interactions between a bacteria and its phage. *Evolution* (N.Y). 62, 1-11 (2008).

Rhoads, D. D. et al. Bacteriophage therapy of venous leg ulcers in humans: results of a phase I safety trial. *J. Wound Care* 18, 237-243 (2009).

Schooley, R. T. et al. Development and use of personalized bacteriophage-based therapeutic cocktails to treat a patient with a disseminated resistant *Acinetobacter baumannii* infection. *Antimicrob. Agents Chemother.* 61, 1-14 (2017).

Seed, K. D. et al. Evolutionary consequences of intra-patient phage predation on microbial populations. *Elife* 3, e03497 (2014).

Shabbir, M. A. B. et al. Bacteria vs. bacteriophages: Parallel evolution of immune arsenals. *Front. Microbiol.* 7, 1-8 (2016).

Wright A, Hawkins C H, Anggard E E, Harper, D. A controlled clinical trial of a therapeutic bacteriophage preparation in chronic otitis due to antibiotic resistant *Pseudomonas aeruginosa*: a preliminary report of efficacy. *Clin Otolaryngol* 34, 349-357 (2009).

Yen, M., Cairns, L. S. & Camilli, A. A cocktail of three virulent bacteriophages prevents *Vibrio cholerae* infection in animal models. *Nat. Commun.* 8, 14187 (2017).

What is claimed is:

1. A method of treating an *Escherichia coli* (*E. coli*) infection in an individual, comprising administering to the individual a therapeutically effective amount of a composition, wherein the composition comprises bacteriophage ES19, bacteriophage HP3.1, and bacteriophage HP3, wherein the composition is administered to the individual intravenously, orally, and/or upon a device, wherein the *E. coli* infection is in the urinary tract or in the blood, and wherein the *E. coli* infection comprises a multidrug-resistant *E. coli* strain.

2. The method of claim 1, wherein the *E. coli* infection is in the urinary tract.

3. The method of claim 1, wherein the *E. coli* infection is in the blood.

4. The method of claim 1, wherein the composition is administered to the individual intravenously.

5. The method of claim 1, wherein the composition is administered to the individual orally.

6. The method of claim 1, wherein the composition does not include bacteriophage ES17.

7. A method of treating an *Escherichia coli* (*E. coli*) infection in an individual, comprising administering to the individual a therapeutically effective amount of a composition, wherein the composition comprises bacteriophage ES19, bacteriophage HP3.1, and bacteriophage HP3, wherein the composition is administered to the individual intravenously, orally, and/or upon a device, wherein the *E. coli* infection is in the urinary tract or in the blood, and wherein the *E. coli* comprises an extraintestinal pathogenic *E. coli* strain.

8. The method of claim 7, wherein the *E. coli* infection is in the urinary tract.

9. The method of claim 7, wherein the *E. coli* infection is in the blood.

10. The method of claim 7, wherein the composition is administered to the individual intravenously.

11. The method of claim 7, wherein the composition is administered to the individual orally.

12. The method of claim 7, wherein the composition does not include bacteriophage ES17.

* * * * *

SEQUENCE LISTING

```
Sequence total quantity: 7
SEQ ID NO: 1            moltype = AA  length = 516
FEATURE                 Location/Qualifiers
source                  1..516
                        mol_type = protein
                        organism = Escherichia phage HP3
SEQUENCE: 1
MSNNTYQHVS NESKYVKFDP TGSNFPGTVT TVQSALSKIS NIGVNGIPDA TMEVKGIAMI  60
ASEQEVLDGT NNSKIVTPAT LATRLLYPNA TETKYGLTRY STNEETLKGS DNNSSITPQK  120
LKYHTDDVFK NRYSSESSNG VIKISSTPAA LAGVDDTTAM TPLKTQKLAI KLISQIAPSE  180
```

-continued

```
DTATESVRGV VQLSTVAQIR QGTLREGYAI SPYTFMNSVA THEYKGVIRL GTQTEINNNL  240
GGVAVTGETL NGRGATGSMR GVVKLTTQAG IAPEGDSSGA LAWNADVINT RGGQTINGSL  300
NLDHLTANGI WSRGGMWKNG DQPVATERYA SERVPVGTIM MFAGDSAPPG WIMCHGGTVS  360
GDQFPDYRNV VGTRFGGDWN NPGVPDMRGL FVRGAGTGGH ILNQRGQDGY GKDRLGVGCD  420
GMHVGGVQAQ QMSYHKHAGG WGEYNRSEGP FGASVYQGYL GTRKYSDWDN ASYFTNDGFE  480
LGGPRDAHGT LNREGLIGYE TRPWNISLNY IIKVHY                           516

SEQ ID NO: 2           moltype = AA  length = 516
FEATURE                Location/Qualifiers
source                 1..516
                       mol_type = protein
                       organism = Escherichia phage HP3.1
SEQUENCE: 2
MSNNTYQHVS NESKYVKFDP TGSNFPGTVT TVQSALSKIS NIGVNGIPDA TMEVKGIAMI  60
ASEQEVLDGT NNSKIVTPAT LATRLLYPNA TETKYGLTRY STNEETLKGS DNNSSITPQK  120
LKYHTDDVFK NRYSSESSNG VIKISSTPAA LAGVDDTTAM TPLKTQKLAI KLISQIAPSE  180
DTATESVRGV VQLSTVAQIR QGTLREGYAI SPYTFMNSVA THEYKGVIRL GTQTEINNNL  240
GGVAVTGETL NGRGATGSMR GVVKLTTQAG IAPEGDSSGA LAWNADVINT RGGQTINGSL  300
NLDHLTANGI WSRGGMWKNG DQPVATERYA SERVPVGTIM MFAGDSAPPG WIMCHGGTVS  360
GDQFPDYRNV VGTRFGGDWN NPGVPDMRGL FVRGAGTGGH ILNQRGQDGY GKDRLGVGCD  420
GMHVGGVQAQ QMSYHKHAGG WGEYNRSEGP FGASVYQGYL GTRRHSDWDN ASYFTNDGFE  480
LGGPRDAHGT LNREGLIGYE TRPWNISLNY IIKVHY                           516

SEQ ID NO: 3           moltype = DNA  length = 32767
FEATURE                Location/Qualifiers
source                 1..32767
                       mol_type = genomic DNA
                       organism = Escherichia phage ES17
SEQUENCE: 3
acttgagcta atcgcccacg gttaagggta gcggcggtca ttgctaacac ggtgctacag  60
tgaaagaagt taatcagggt aggcaagtcc gacgaattaa cgctcaattg agagcggcgg  120
ggagtggtta aaaagtggca aattgctatt taacaataag gtttaatgcg aacgtttacg  180
atgtgaacgg cttgagattc atcataggat gaaagtacat agccgggtta tgtagtaaac  240
ctgctgaaag atataaaacg ccggaatatt aggcggttag tgactctttc gcaatagtat  300
cccgtagtgg gcgatgacta gcgatagaga gctgatacaa aaggataagc gggagcgaaa  360
acaaagtaga cgatattgcc gacggttaca gcaatgtaat taaatagagt cggacgcata  420
gccttattgt gatgattgat catcgctatc aggtcggctt cgtttatagc gactaattaa  480
agataccaga tgaaacatca cggataaggg ggcggcaagg ttaactcctg ataagaccgc  540
cccgcttacc tataactact taacaacgag tggttatagt taagttaata gtgacttaaa  600
caagctcata gagagcgggg caatagcgcc cttacaattg aaaggtgaat attatggcta  660
aaatctttac tctggttaac gaatccggtt ttaatgctct ggctaacaac attcgcagta  720
ataacgcggc gatcaaacaa gatgtttcta acttcctgtt agggcatttg cagcactttc  780
gtagcaacgg taagaagtta gatgtattgc aggcggcggt tgacttcctg ttaactgaac  840
gtttccgtga tatggatgtt atcgctaccg caattacttt cttaactcct atcaagttta  900
acaccgatgc ggcaaatggt cgtaaaaagt ggattaatct ggaaggtgag gcgaaagcta  960
aagaagatgc gaaagaagcg caaattaaaa ccaaaatgga acaaaaccgc gctcgctggt  1020
caaatgcttt cgaaaacttt gcattaggtc gtgcaattga agtggataat cctaacttct  1080
acaaaggttg caatgacaac gtggcggcac acctgcaaat tccggcgaaa aacaaggaag  1140
attttaatca ggatatttat gctttggttg aacgcttgaa tgcaatccgt attgaagcca  1200
aattactggc tgatgagcgc aacggcgcaa ccagcgataa cactatcgcc ctgagtgaag  1260
aagttgggaa ggttaaaaag tcctttgatt cactcatcaa gaaaatcacg gcctcgacgg  1320
tagcgatctc ggatgattat ctgatgaacg catcaagcaa ggaattagaa tcactcgatt  1380
catacgctga tgaaatggaa aagactgttg cagctatgca ggagaagtta gaaagtctgc  1440
gcggtcgtat ctcttcaacg gttgctaccc gtagcgaaca agcggcgaaa gcagaagagg  1500
aagaagtatt gcgtaaagcg gctgaaatta tggcggcacg tcaagcggca taagtaatac  1560
aatttaaata aacataaggc gctatcttaa cgggtagcgc cttttctttt atcagtgcat  1620
tgattcagtg cattaatcaa agaatctaat taaaggtgac gatcatgtta attacacata  1680
ccacgatcta taggaatctt gtcaacggtc aacattaccg actatctaaa aagtatggcg  1740
ttgaatgtaa atgtgttatt accggtgaat ggtatccgtc gccaatgaag attgaaacgc  1800
tggaacgtga agcgatcagt tatattatca cgcaagaaac aacgttaggc cgtatcttaa  1860
gaaagctggg attgagaaaa tgatattcag tagtaatttt ggcaagtgtc ctatttgtga  1920
gaaacatcgc agcacgggaa accatcgcaa atgtagtaag atattacagc gccaacgtga  1980
taacaatcat tgggatactg tacacactaa ccagcgtaaa gaagaagtta ggaaaatggc  2040
tgttaaagcg tcatttgctc aatcaacccg tattgaacac attcaaaggt atcaagcatc  2100
atgatcacta acatttcaga gtttaagaaa gcaccttccc gcttgttagg ccgtcgtgtt  2160
gtatatcttt atagcaataa aggtaaatgt acaaccggac gaattacaac ggtgagtagt  2220
gccaataaga aactactaaa attatgtgta actatggatg acggtacaat ccttctacgt  2280
agttggaaat cgtttagttt acttgattaa gttatttgtt caagcctatc gccttgatgg  2340
gcttgcccga tataacttat cactgaaagg aataagattg tggctaaatc taaaatcagc  2400
atgaagggcg gtcgttgttt tgctatctct gaactagaga aagagaaacc gaaggcaact  2460
aatcacgtta gtaagcgtag tttaaaacgt cgtgctgcaa aggctgaggc tgaatcccat  2520
gttccttcca gtgtggcaaa gcgtgtaggc catcgtgtcc atcgggctga tgcgttgttg  2580
ttggctgatc ataaacgttc tttgttacag agcgggggag ctaaaacaga agaagagaag  2640
aagttagaaa tcttctgtaa tggtcgcact cgaggtaaac agaagtttaa ggggagcacg  2700
aaagacccgc aagccttccc taaaacaagc caatgtgcac ctgatgtttt ctacgcagat  2760
agtaaacaca agtggggcgt tgaaaaatac attgacccca tcaaagaggc aagggttaag  2820
tagtaggaat atagcccccct cttttagtac tatgacgctc tttctgtagc gtcgtgccct  2880
ctccccattt gaagcttccg catagccgcc tttgagcggc tttttgcgtt gctgtaagtg  2940
catttgcgag tgtatttata gcaacggtca tgtgttgctt tcaggtttgc cccggctacg  3000
```

-continued

```
gctggggctt ttttatgccc gtaaaacagg aggtatcaag ttctgataac aacggcacag  3060
ctaatgttga cattgactat ttattatgag gcagggaatc agccaaccgc atgtaaggcg  3120
ttagttgcgg ataccgtgat aaatagaatg gcccaacgaa aactgaccgc tgaacaggtg  3180
ataagacaaa agaaccagtt tgagtggatt ccggtactat taaaacagga gaaaccttat  3240
aagcgttatg taaagctgat tcgtgataaa aatccgatga ctaagcaagc cattggagaa  3300
agcgagcggc tagctaaacg tgcccttaag aagaattatg ttccgctgta tagtgggact  3360
tactttcaga gtaagagcga aggggtgcca aaatggtatg ccaatcctat gtattgtggt  3420
gatttagtgt tcgataacag ctctagggaa taatcactag tgccagattt gacaaactaa  3480
attcctttat aaaccaacca cttagtaaat ttattgaaaa agatggtagt attctgggac  3540
tatgggtaat gctctgtata tagacccttt gaaaatttct tagaaaataa gtttactaaa  3600
tataacttac ttaaataata ttacttttaa tctctgataa agggtaaata atatgacttt  3660
agaagtatat aaattccttt ttgtaagctg tttaactatc agtgttctag gatttattgt  3720
tctcagaaac aaagcagcaa gctgggaaag aatgtataaa tccctagttc gagtggatga  3780
gatgtataat gagaaagtta aagtaacact taacgatctt attatgcaag tagaggacag  3840
aaacaagcgt cttcagaacc tcaaccacga agtgttacgc cttgctcgtg ctaatgaaga  3900
cttgcgagtg gctattgcta aacagcagga gattaacaat gaagcatgat attaatacag  3960
cccctgtagt caagcaactg aaagacctga aggtggggag tgtttttgaa actgttccac  4020
ctaaaaataa aatatatctt acagtaaagc tagattcctc aaccgtttat tcagctagtt  4080
ggaagcctga cgaaagagta gtagtagatc tcacttcgga tagaataaca atgttgagaa  4140
aagatactgt tgttcaggta gttgataatg ctcgacttac caataaggtg gattaaagat  4200
gaaagttaat attaaatccg atcgtacaat gcttcgctta aataacatga agccgggggt  4260
tctgtttgag cgtaaagaat ccctttacat cagaaccgac acattgtacg cagacaatta  4320
tgtcaactgt gttgatgtgg taactggaaa gctcatgcct tttaaacggg atgaagtctg  4380
ccaagtacgt agtgatcttc acataaccaa catagaggct aaagatgaag attgatcttg  4440
agatgaaaga cccagatctt acagtgggtg atttaaagct tggagatgta ttccaagtta  4500
aatctacatg cgtcgatcac tatttggttg ttagtttatt cactccacac gtaaccgagt  4560
cgaacaggaa agattctgga acagttgtgc ttggtttaag aactaatcag gttatgaagc  4620
ttaattcaaa tcttcctgta atccttatcc cagatgcagt aattactaat aaaggtaagt  4680
gaatggaaat taaagtagtt gattatccta aatatgcaaa tgcagaagat gttaagggcg  4740
gtgatgtttt ctcttacgat aaacgtttct ggctgatgct agaagataag acctctgacg  4800
gtttgcgtaa ggctgctaac ttgagcagcg gttatgttga agtcttcggt ctatcaacca  4860
ctgttatgcc acgtcccgat ctgtgtttga ctcaaaagta acatcgactt atagcccttg  4920
tgtttatcag agggctatgt gagggtgttc ctcattaact tattaattca ggcatatgcc  4980
acaccgctag ggagagcttg ctcgaacatc cggtgctaga ctaaaacctg ttaattttcg  5040
aaagactttc tgatatgtag ggtacgtat tagtttggga ttcaggagac ttcctagggg  5100
tagggagtct tcaccagttg gaataagaga tagctctaga acctgaactc ttaggcagag  5160
aaggtcggca atgagtacgc ggtcaggatt agtctactga ctagggctat cccttatatc  5220
aactggcaat aatgcctcca ctaacaaaga gagataggta tgaaagtatc aaccaaacgt  5280
atgaaccgcc ctgaacgtat ggatgcagta gctaatggtg ctctgaaact ggaaggcttt  5340
tggattcatg caatgtcagc catccgtaac aagcaaggtg gttggacgta taacagttaa  5400
taaataaaag gctgccttcg ggtggccttt gttgttttag gtaaatcacc tttaattact  5460
tttcccatct gcattccaca tgaatgagtg cagcagtgat tggggtggtt tacctaaact  5520
aacaagagga agctcaaatg tctaagcaaa caatcaagaa tacacaagct ggttactctt  5580
atgtcaactc tccttgctgt ggtgctcgtg ttaatctggt taaggaagag gtccgtatcg  5640
ttcagcgtgg cgctactgtt gttcgttcat gctgtgtctg tggtaatgac atttttatca  5700
aaggtaaagt atgaaaaact tccaagctgc accaatcact aaagtgatcg aagttgatgg  5760
tataatgatg actgttcctc tgaacactcg ttacattgca attgacaaga tgggttatgt  5820
atgggcttgg aagatcaagc ctagttataa cgcattgttt gatgagtttg tttgtactgg  5880
tacttacagt cctacattct tgggtttatt tggagagttt gaaggcaagt ataaaatcat  5940
cactctccct gcttgcgctt gaggttatta tgttcaagtg gtttaaacgt ctattccatc  6000
tgcatgattg ggtaattctt gagaagtata cactaaagat cactgatgat tatggtggta  6060
cgaaacataa aggtgtacgc tatatcatgc agtgcaaaac atgtggtcat atcaccaagc  6120
gagatatgat ctaaataatt ccgcgccctt agttcaattg gacagaacat cggatttcta  6180
atccgtcggt tacaggttcg aatcctgtag ggtgcgccaa atcaaatagg aggtagccat  6240
gagttggggt ggtgtaatat ccttaatctg tatcttcctt gtctgtgtgg cccttacagg  6300
ctgcgtacag agccgtcctg atggatggtg tgcagtagca gtggaaggtg tttgtgtttc  6360
tcgctggcat aaaggtgaga aggttccttc tggtgaaatt gatatgcgtt acaatggtat  6420
ctcatgtctg aatggtgcag cagtagatga ggagactaaa accttatccg atgcgcagtg  6480
gtgtggtggc tctgtaacaa caaccggtaa ggagtggtaa tatggcagct cattattgga  6540
atacaaagaa gcttcttgaa gagatggctg gggtagtag agtacagtta atctctatgc  6600
ttcgaatgga tgctcgctcc ttacgcttcc aagtaaagat tggtaacttc agtgatggcc  6660
tttattacac gctgaaggaa aggattaaga agactcactt catcatgtac ggaatcaaac  6720
cgagaacgta cgttaactac atgtattgga atacatgcta cgataattga ggttattatg  6780
aaactagact ctaagcagtc ccttaaaacc gttgagctgt ccacgctgcc aaacggaagt  6840
atttttggtc atgataaaca cttctggatt aaaacagaca tcatagacga tggatatatc  6900
acctgtgtca atctttggaa cggttcagtg gatggttatc gccctagcgc aaaggtagtc  6960
cctcaacctg atgcaaaggc tgtaggttta gtttattagg gagtctgtat gagttgtttt  7020
ggtggcggtg aagtagatga cgatgatgac atggaatcca acggtacatg tcctgattgt  7080
ggatgtgaga cgtttgatgg ggtgtcagta tatcctgcct gtagttactc accagtgatc  7140
tgtaaaacat gtggagatca gccttgtgat cagtcttgtt agtatgttaa taacctacct  7200
gataggtatg gtgttatcag gagtacttat taaggttata gatgttaaag gtgatgaatg  7260
ctttagaaac tggaggggtg aagcagacct tgcaaagata gcagccatgg ttttcctatg  7320
gcctatcatt gctgtactgt ttatatctct cgcagtatgg gctgctcttt gggatttcat  7380
ccttcctaac aaaaagtatg aggactcatg actaaagaat ttttaaagtg gtttggtgat  7440
accttcaaag agtatctatt ctctccagaa gactttgaag aactgaaaac ctacacttgg  7500
ttggcttgga gagatagccg acgagagatg aataagtaat atcgtgaagg attcttacga  7560
gagtcctttg agataggact tcagatctcc tatcaaacta acattcatgt aactagccca  7620
taagggcgtt accctttaat aacccagccc actaaggggg cgggagttta gtgctggatt  7680
ggctttacgc ttattcctac aaaggcaacc gattgttaga tcttacatgc aatattaact  7740
```

```
aataggataa gggaggattc gtcccctccc cctattcata aactattagg ggagtatatt  7800
agctgattag ctgtggaagg taggccgata tctacagcgt ggcccagagc tagtgttctc  7860
ccctgatagt tttaacaatt aattggagga tgtatgaaag cacgaagaac tatatggact  7920
ccgatgcaga ttgaaaatct tcggagacta atcaaagagt actcggttca agaagtagct  7980
cagattatga atgtaacgga gaatgctgtt aacacagctt gcactaaatt cggcatatca  8040
agagcttcaa tccgagttaa atggtctgaa gaagaggacc agttccttat ccgtaatgct  8100
gggttcatgt ctattcagag aatggctgac atgctcggta gaagttatgc tgctgtacag  8160
aacagagcat gtatgcacct taacattagc ctcaaactta aataggaatc aagatgaatt  8220
ttgagctagt accaaaaagc aaaacaccct ccaagacttt ctctgacttg gagaatggag  8280
atgtttttcg ttttactggt gacgatgtag tccctaaatt ctggataaaa acaggggagc  8340
attctgcaat gtgtgttcgg aaccctaaag atattttctt tcctgtccct ttgtccaata  8400
ctgttgatct gttcgaatct aaacttatta ttcagggtaa ataatatgaa gattactcac  8460
aagaaagaag aagtgactac agttgacctc aactcacttc ccagcggagc tgtgtttaag  8520
tttcctgaca atgcaaccct gtatgtcaaa gggtctgtgt ctgcaagtcc aaacgttact  8580
atcaactctg acagatcaat cactcttcgt ctgtctgatg gcaatgtaac agcaccttct  8640
atttattgtc gagttattcc tgtgtcggca gaacttttgg tggataatac ataatgaaaa  8700
tcatcccaaa gaaaaaggat aatacggttc gattggaaac aatcattccc ggaaacccct  8760
tcatggttca gcacggaagt gcctctcctc agtattatat gagggttgaa aatgcttctg  8820
gtaacatccg tatagccagt ggctgggttc ctgtagtgaa tctatccaca ggtgtactat  8880
ctgttaaagg tcttgatgat caggtagaaa tgattcgtat gtctgtggtt caggagtgag  8940
aatgagcacg atacatatta aggttcacaa caaagaaaaa aagaaactct ttgttaaaga  9000
tctgtcaacc gctgacatct ttactttaaa agatgatgac agtcaggtca tttatttgat  9060
gatgcctcta tctggtggat atcgcagagc agttaattta ggtacaggcg aacctcgtcc  9120
tgtttctgac actcttgaag ttggcgagaa gtttgccaaa gcagagatca tcttaactcc  9180
gatgtaaggg taagtaagtg aaaacaaaag catattctta tgatgatatg atcaaccaga  9240
aaggcttcgg tcaacgccag cctgacggtt caattatctg gtttgtaaac ggacagaaaa  9300
aggtagctaa ataagccctc ttctctcctc cttttagtac tatgacgcct ctctgtgggc  9360
ggcccaattt gcgtagggaa ttccctctac gcagccatga ctttttaagg aatttcccct  9420
atgtctaaag taagtgcaat tgatgcaatc cgtcaaccgt tccagttcca atccaaatca  9480
acccaaacct tcagcgaacc taagcaaatt cgcttgggtg gcacagagaa aactgtgttc  9540
gatctggcta aaaacaagag cgttaccgta gttgatggtg gcactctggt taacgtttct  9600
catcgcatcc gcactggcaa aactgccaaa gatcgtgcta agaaaggcga gtaatgataa  9660
cacttgtgtc gatcgtttac agaatacact accgtctaga caaaggtaag acctataagt  9720
gcaagagtaa gacaggcaat agatgctctg tagaaaacaa ctctggtcaa tgggtggatg  9780
taccttgttg ttggttcagg aaagacttga ctaacaaaga aattgacgaa atccttagtg  9840
atgattttgt aaaatcaagt gatttttagt tgtagtaacg cctatagcct tcttcggagg  9900
gctatgtgag ttattctgac tcaactaacc taatcttaat atatttcccg tatggggccg  9960
atgctaggga gaggaacatt cctcgaacat ccgtcggata gatattttaa gagcaggtta  10020
tccacagata ttgggtaata tctttttgta tttaaagctt gactcttttc ggagagtcct  10080
tttttaaatt caacgagagg aaatatgtct aaattagatt taaaactgct agcagcagcg  10140
gtagtgattt gtgcactagc actggtaacg cagagaacat ctggatttat tcagtgtttc  10200
ttttctgggc aatccactta tcagtgggtt attgacgagt gtaaacaaca ggagtaagta  10260
tgaatacacg tcccatcaag ggcaacgtta atattgaaac tctgaacaag gttgcatcaa  10320
acctcggtgg tatgtccaac gaagagcttg agcaagaact tgcttggatt gcaaatggta  10380
tcaaggttgc taaaggtaag attgctcgtg agcaaagtaa catgaaagct cataagtatc  10440
taatccatcg tgcaaacgtg ttaccggagc gggttgtaca tcttgcccgt aaaaactacg  10500
cagaagcaaa gaaagctctg gaagaagctg agttccagaa gcatcaattt atgaacaact  10560
atcgaaactt ccgagatatt ctttatattc gtaagtcgat tgagttgatt aaaaaccaat  10620
agaggttggt ataatgtttc cagtaacatt agaagatact gaaggtaatg ttttaacagt  10680
caaccctcct tgttatgggt tccttcagct tcgcaactat aacggtggcg ttgatgaaga  10740
cgatgaagag tacgatgact acttcgaccc taacatgtat gaggcaactc atggatggaa  10800
tatgcacgtt cgagtgtggc atgaagaagc taacgttcgt agtgctgatg gggaagagtt  10860
cctgttaagc cgagagatgg atatgtgtaa aatcaagcat atctggaact ctggaactca  10920
tatgaagatg ttaggtttta gacgttggcg tgatgaaaag catgtagctg aagctttaag  10980
ttggtgttcg tatgaagatg aagacacgcc acctaagaac aacatcgaac gttggaacga  11040
caaaaaccct gagcatcgaa ccacacctcg tgctgtactg gaagctatgg aagcatttgt  11100
ggacaaagat cgtccctcct gtttacgctg gcacgataaa ggttttatgg gggtagcaac  11160
tgagaatatc cctgctgatc gttgtctgtt ctatttgatg ttagaccgaa ccttctattg  11220
tgaagatgaa gagagccaag tggaaacctt ccttcataaa tggttggttg aaggctggac  11280
aatccttcag gcttacgttt actcacgaat ggttagcacc tacaccaacc tcttgggcga  11340
aacgaaagca actctggtcg gtaatgattg ggatgcttgt atcttcccag cgtcactgtt  11400
tacagttggt atggctgata aatatgctga agcatttcaa gtgccttggc gtcaacagtc  11460
gtatagggat ggatgcggtc atttccgtga tgaagatttt aagtggattc attatgagaa  11520
tgatgaaaca gcagaattac gagttaataa ctcgatgttc ttgccggtga tgcaccccga  11580
cttagtagag agtgaatcgg aaatcctgaa atgtgacaac cttctgatta actttacccg  11640
tcgcgtgtct aaaaatgaga gaacagctaa caggttaatc tacggcattc gtgccgaggc  11700
taaagacctg ttcaacatct acaacattat tcagcgattt agtagtggga ctctggacca  11760
aagttcggag tattcagtga ttccatcctc tgagtgggat ggtgttatga gcggattatt  11820
tttaggaaaa taaaaggtta gttatgtcaa tctccacaac gatcgtacct ctgaatcttc  11880
aacaggattt aggggaacag aagttcttag gtcgtgggtg cttcggtatc cacaaccaca  11940
tgcaaggcca gtgggtaaat gacattaatg gtgaagttat cacggaagaa gggcgctatc  12000
gtagcttcaa ccgtgatatc aacttgcaac tggagatgtt gaattactgg actcactctt  12060
ttcacggtca tgttacatct gatatcgaaa agaacttagt tgaaacagca gacattatga  12120
actccatgtc ttgctatcgt gacgtattta cgatcacttc agcgaatagt gttgctgtca  12180
accttcgtga gcatccagca gatcagatct tcacaggact tatgctcttc cgtagcattc  12240
tggaagggca gtatcgtgga atggatttcc tagcagaagg aattgaagac agggaagagt  12300
ggctgaagcg taaacgcatc ggcatcgctc tagtgttagc tgggttgggt cgtgacttct  12360
ttggagggtg gactcaacaa ggaagatcca atgggagcag tgagagcaca tctattgtta  12420
ttaactacaa tatgccagca tcagcattcc ttcctttggt tgtagactct gatgaataca  12480
```

```
cgaatcaagt atgggttcaa aacccttttg gtgttggtta caatgagaac ggctatgttc  12540
gtaaccataa cccagagacc ttacgaagat ttgctcttgc taaagatcaa gacccagctg  12600
aatatgcaac aatgtcagag tggctaagac tctggtccac ttgtcatggt cataaacgtg  12660
aaaccataga cgacaagttg ggaaacatta cagtacaaaa ctttatagcc cgactgattc  12720
aaagaactgg agaagattcc ggtcttactc ctgaagaagt tggtaacaca atctcatctc  12780
tcttttctga actagtggag tattacaatg actaagcgca aattccttat cggctctgac  12840
cctgaaatgt tcgttcgtac cagtaatggt atcatcacct ctgtagctgg tctattaggc  12900
tgttctaagg acgataagat cactctggct aaagatgttc gtcttcaaga ggacaacgta  12960
ctggctgagt ttgatatcga cccacagagc ggttttgaag cgtttaacga taacatgcaa  13020
cgtggtatcg atcttaccaa taatgtcctg aacaaactgg acatggaaac agctccgggt  13080
gttagctctc acatcttcac cgaagaagaa atgaagacct ttaatgaatc agcgttcatc  13140
ttcgggtgca ctcctgattt caacgccttc actggtcaga aaaacccatc cccgacttct  13200
cagaataagg gacttcgtac tgccggtggt cacgtacatc ttggcgtagt tggtgctttg  13260
gatatcactc tgcaaactca gatgatgctg ggtgtgttgt gtgactactt cctgtctctc  13320
ccagcagtaa ttatggacaa agatactcgc cgtaaagaac tctacggtaa agcatctgca  13380
atccgttata aagactatgg tattgaatac cgttctctgt ctaacttctg gattagtgat  13440
cgtgaaaacc gtaagtttgt ttacgatcag gttgacaagg ttgttcagca gtgtgatatg  13500
tccaccctga tggcattgca ctctcgcctt ccgattgaga agcttcatga aatcattaac  13560
gggaacaacg ttaaagaagc tgaccagcag atcaaactcc ttcaggtagc ataagaggtt  13620
atcgtgagct tagtagctga tttttctcat tactataatg gtacatggat tgctaaacga  13680
gcaggcaata tcaaccttcc gtgttttgtg attggtgttg agcagagcgg taacttccgc  13740
agcgatgact tctcgcatga agcagaacag gctctgtatt ttgttgtaga gcagtggtac  13800
aagaacgagc atgggaatct ccgaaacact acgatgaata ttccagtgtt cgacccaacc  13860
ttgattcttg aatcacctga tgttggttat ctgttccata acggtaacac tgtaagctgg  13920
actcatatca accctgttcg tcagagagcg aagggtttga tgggtaacaa gattcgaaac  13980
gctcctggaa ttggtcgttc gatctctggt gaaatggttt acagtctgtt caatcctgaa  14040
tttgatggat tggttactcg ttatatttac atcaatccta cagatggtaa agtgcattat  14100
aaaggtgcac tggtaggtca ggtagatctg gaagcacctc gtgactctta tggtcaacaa  14160
ccgatgcgac ttctggagca ttttcatcac atctctgaaa accttagcaa ttataatatt  14220
acgttggtgg attcgttatg acaactgtag cgcaaacttt tggatatcga gaaggtcgtt  14280
taactgaggc gcatagttca attgcacttc agtgcggtgt cggtattgaa cttgaactcg  14340
aaggttctga acatatcgaa gcagatatgt gggattgcac agaggatggt tccctgcgta  14400
acggttgtga aatggtatgt tcacgacctt acaacggaca ggagttgtta gacgctatca  14460
acaacctgag tgaagcagta gctgaatcgc acgccgaggg gacttggcgt tgctctactc  14520
acgttcatat ggatatgagg gatgctgata gtaatatcct caagaagacc atccttgctt  14580
ggaccttcta tgaaaagatg ctgttcaagt gttcaggcta ccatcgttac cgtagcaatt  14640
tctgccctgc gtttgcagtg gtacaagcac aggtaatgaa tgcctctgac gcatttaact  14700
acgatggtga agaattcttc aaccgtctgg ttcgttcatg ggataaatat acatctctga  14760
accttctgcc acttgcccaa tacggttcaa ttgagttccg tatcagtgag cctaagtgga  14820
aacgtggtca acttctcaat ctggttaacc gcttcttgat gttgaagaag ctggctttag  14880
ataacgcaga tatgagcaat gatcagttta ttgagcactt aaatactgta cgatttgccc  14940
caatgcttcc ttaccttcct ctggattaca atctggatga atctgatttg cattcaggat  15000
attgtatggc ccgtgatgtt ttgtattgcc gttctcatga agtagaacag tctggtcgta  15060
ttcgtttacg tcgaaccaac tccaacggag aggctcttgt tgacttacgt cttatgtcag  15120
acttctatgg cttccttggg tatgtccgag ggaacgctaa caacttgtac caagagattt  15180
tggttatgct tcgtacagca gacctatctc aagtaagaca cgctccagaa cagcgtatcc  15240
gtgctatttt tgacttacta cgtgagtcag gtcacagtga tagcaatatc acagggtaca  15300
ttccagacca tctggaaaat cagttagagc aagcgctgta atcaatgggt gcctctgata  15360
aaggggcaca atttaaaggt taattagatg aaagggttta cccttcaggt ggattagaaa  15420
atttgtggca tcgtattagc tggcggtaat ctgtcaagca ctgatttaga cgtatttaac  15480
caactctttt atgctggagt attccgagga caacattcct ccggtatctt tggtcagcgt  15540
aaaagtacta aggaagtctt cacttataaa gaagctcttc cttctttcgc attcatccta  15600
caagatgagt acaagaagca caccactggt gaaacagctt acactgtagc accttcatgg  15660
attgttggtc acagccgtca tgcaacgaaa ggtgcagtta acgccaagaa cgcccatcct  15720
ttccaacatg gtaacatcac tctggttcat aatggaacct tgatggacca agacctgtta  15780
cctgacagta aaaacttcga ggtagatagt gagaacatct gccactctat taacactatt  15840
ggtgcagcag agactattca aaagctggat ggtgctttca ccttaatctg gcatgatgct  15900
tctgataacc gccttcatat cattcgtaac gaagagcgtc ctttccatct cgcacgttgt  15960
aacagagatt ggtttggcgc ttctgaagaa gatatgctga tgtggattct gaagcgttcg  16020
aagtctcaca agaaccgtat tgatgagcat tttgagtgta aagttggtac agagtatatc  16080
tttgacatgt ctaataacag catgacactg gttgaagagg tcgcccacga gcttccggtt  16140
tttacggtag tcaatcgttg gggcaattac tactcgaaca attacagcca aagcaactat  16200
caaagttcct caaaaagcag tacaagcaat ccttacgaca cgaagccggg tgtgacagcg  16260
gcagacgttc gtcgaagaaa cgcagtggta agtcaaaaca aaatcgcaag cgatcgaaac  16320
attgatattc gccgcgatat gactgtggaa atcactccgc atgagtttgt tccttatgca  16380
actgccggtg ctgttccttc tcgtggtaag atgattggtt atatctacga tgagaaatct  16440
caagagtata tcgaaggtga tgttcataac gtagacatta aggcttatca ggatgccctg  16500
aaagacccta aaattgttta ccgtgggaca gtatcctgca tctccgaagt caatgctatg  16560
gtccgtttag tgatcacagc aggtcgtttt gttgacccat ctctggagaa aaaggagcct  16620
gagtcaacta ctgctgactt cgatgatgat atcccttttg atatgaatga tagtttcgtc  16680
aacaagaatg gtgttactat cactcgtaaa ttctgggaag cgcactctca tggtgattgt  16740
ggtggttgtg ataagcacat tgattggaag gatgcaccta aagcagtctt cgcatatcag  16800
tgctattggc atcctgaatg tctggaaggt ttgactaaac ctaaagagga agaagaggag  16860
gaaactccta ttggtgtttg tgaaatctgc ggtgaagtta aaacagagaa tgagttcgat  16920
gatgaactta gtcgtcttcg tggtgaagat atctgtaaag tctgcgctgt agaagtaaag  16980
aagaaagtgt ctaatgctac gatcaaagat ggttatgtct ggattaaagc aacagataca  17040
acaaacgccc gtcgtcctga attcgcttta cgtgtaactg aagatatgat cggtcgtatg  17100
actgtattac cttcctcagc gaaacagaca ggcatcactc tggaggatgt tgttgatgct  17160
tatgttgaga aacgtagcaa cagtattttt gcaatctcaa ctaagccaaa aaaggaggaa  17220
```

```
cctgctgaga aagcaggtgt gtttcctgaa tcacgaacag ctctccgcaa aactgtcgtc  17280
agcttcgacg gaaaccgaag cactgacttc accaaagcaa tgtggtcaac cctcggatac  17340
tgctcagagt gttttaagca gattccgtgg cgcgatgctg aaagttgtac gcttggttct  17400
atgaatcaag tttattgtaa ttctcctaaa tgttcattga atagaggtta agtatggaaa  17460
ttcgtaagat gatgctggat aacgttgtaa ctactcgacg tatcccgatg acgagcacag  17520
gatgtgataa ccttcgtgca atccagaagt ggatgcaagc tggtattggt caagtacttg  17580
aaacacaggt tgaggttcct ttcccaacgg tgatcaacaa cgtgcttgct gattatgtaa  17640
aaatcaaagg cattaaggta gaacctcatg tcaaatctgg ttcctaagaa accgaagatt  17700
actctcctac agtattacat aggagttcat atcgaattgg taacggagca gcgaaagctg  17760
tatccgttcg ctttcggtct gattgatgca ccatccgatg aagtagagaa cgatgcgttc  17820
aatgactact tcgaaattga agctcagatt caaaaaactc gtaacgaaat tcttaaactt  17880
aaaggtatct aacaatgact actcgtatcc gtgttcttcc ttatggccct tctgattcag  17940
ttcgtgaact tacttctgca attaacacta agattcagga acttcgacta aatgctaacg  18000
taatgtctct ggtatcagag ggttctcgtt atcgttctcg agttggtgat attgttgtca  18060
actacggaaa ccgtcgatat aatgattctt tctttggcgg tgcaactgta ttgaactctg  18120
tggttgcctt gaaccgagcc gctaacaaag ttgcagcatt taacgcactg cgtttagctg  18180
aagtcaaaac tgttgaatac accgtagatc gtgaagtagc tcagaactgg aaccggaatg  18240
aaattgttta tgaacgtgca accttgactg gtcactctgg tgaggggatc actgttcgtc  18300
ttccgcgaga aggtgttgcg gatgctcctc tgtacaccaa aggcatccaa ggcccacgtc  18360
gtgaatggcg tgttcatgtg ttcgaaggtg ttatcactta cgttcagaag aagattcgtc  18420
gtaatggtta tcgtgaactg gaaagctatc gtgaagatat tcgtaaccat catactggtt  18480
gggtttattc taactccttc actgaagcgc ctcctgatca agttctgatt caagctcaca  18540
aagctgtatc tgctctgggt ttgaacttcg gtgctgttga cctgattagc aaaggtacta  18600
acgcttgggt tctggaagtt aatacagctc cgggcctgac tggcacaact ctggaaacct  18660
acactcacaa catcgttgag tttgttaaga gcttctctgg tgttgagcct gactaccgtg  18720
ttgcatacga acttcccgtg gaagaagtgg aagaaacatt ttcaccagca ggtgatgagg  18780
attacgcact atcagcggaa agctccgagc cagttgttga agagtcttcg gagcctgtcc  18840
ctgaaataat gcaggttgaa gagcaagggt tagagatcaa ccctgtaacc cgtcgtaatc  18900
tgcgtcgtgg ttattatatc gctaacatca agcatcctga aaatggttca actgtagcaa  18960
gtaatgtgat cttgttcttc tgtggtcgta acttctaccg ctctggatgg aacgcaccaa  19020
ttagtgatcg tcagcttggt cgtgtgttgc agattaataa ccttaccctg aatgatggca  19080
ctgttgtaaa ctactaagga tatatggata tgttttcatt ggaagatcta gtacaaaatg  19140
gaatgatgga acaaaaagag cctcttattg taggctctcg taaagagttg cgtaaattgt  19200
gtgaggagtt gggtattact aatcagcgaa tgattggtaa tcaattctct gcaattgtaa  19260
ctttcctaaa acgtggtgat aagtactcta tggaatgtgt agagcgtatc atcactgaag  19320
cacaacaaga caagggagta acatatctgt gaataagtat aaagttctgt ttaaagatac  19380
caatgcagct ggtgagatgc gagcaatgga cctcgatgct gacatgttta acttctctga  19440
tggcaaagtg gccttctttc aaggaagtga agctgttgca gtgtttgaaa gtgcagcaat  19500
ctgcggtgta atcaaaatct ttattacaga gtaatctgct ttagcctctt cgaaagatga  19560
ggctagttcg gataaactaa acaaaccaac aaaggtatag ataatgtcag aagtaattta  19620
cgtagcaact tatggttctc ttcgtcgtgg tcaagctaac tatttagtta atgaccgagc  19680
tggtgctaag tcaattggtg aaggttggac tgaagacaac ttcgatctgt tccgttacgg  19740
tggttcctac ttcccgagca tctctctcgc acacagcaat aacaataagc ctgttcgtgt  19800
agaagtgttt gctactgaca aagcaggtct ggaaggtccg tatgaccgtc tggaaggtta  19860
caacaaacgt agccctgaag acagcttcta tcagcgtact cagattgctg ttaagatgga  19920
ctcaggtgaa actgttatcg cttggattta tcatatcgac gaagaacaag atattctggt  19980
tgaatctggc gactggtcag agtatctgaa aagtgaatct tgagaaaagg caggctcttc  20040
ggagacttga agccaagtat ttaatgctac ggtgcaaaat caaccgacat gaacgtttcg  20100
ttgaagctgc acaaaccaaa aactttgaat catcagtgga gatgttcaag acccaacttt  20160
ctttttatag gaaagaacag gaacaagtgt gggatgaaat tcgttcgttc tactaagctc  20220
aaggattcca aggaggaaga gcatgtcaaa gatcattttg ggagacacag gttgtaagga  20280
atgtatctct catggtcgtg ataaaaccca caaccacatg attctcttcc gtaacgaaga  20340
gactggtgag gagtggggaa gttgtaaccg ttgtgggaat tacgaagtgt tcgaaaaggg  20400
cactacacct actccaaacg agaagaaaga gttatcccct gaagagttga gagaagtctt  20460
agatgattgc ttagagcttc ctcagggtga actcactcgc cgtttaatcc ctaaagctgt  20520
atcagagcgg tttgagtgtc gtattggtct cagtcaaact gatggtcaga caccagacag  20580
ctacttcttt cctcgtgaac gtgatggaaa catcgttggt tatgaggtta agctgctaga  20640
tagtaagaag ttctattacg tcggcagtgt gaaagaagca gatttgtttg gtatggcaca  20700
agctcaacgt ggagatgtgt acaacaagaa gctgttcatt tttgaagacc cgctatcctg  20760
tatgtcaggt ttccatgtcc ttacagcttt tacaaatgca acaaacatca aaccagcatg  20820
tgtttcttta ccgttcggtg caggttcaat ctcttctgtg ttgtctcgta atcgagactt  20880
cgtaaatggt tttgaggagg ttgtgctctg catggacaac gatgatgcag gtgagatagc  20940
tttaacaaaa ggtcgttctt tattccctca tgttaagttt gctcgtattc ctaaaggaac  21000
tttcccatac aacggtgtgg agaaagagat taaggatgcg aatgacatgc ttctgtctgg  21060
tcgtggtcaa gagttattca acattctcaa gtactcagca aagcgggaat ctcctgctgg  21120
tgctgtaaca atctttgatt gccttgatga tgctctgaag aaagcggagt ggggtatccc  21180
atatccgtgg aagactctga atgagatgac cttcggtatt cgatggggag aggtggtagc  21240
aattggtggt ggagtaggga gtggtaaaac actcattgct catgagctgg ttgctcatct  21300
gtgcttagaa catggtttta atggaggtgg cttcttcttg gaagagaagg taggcatgtc  21360
tgttaagaac attgctggta agtcggcatc aattcctttc caccgacctg atgttgaata  21420
tgatgaggag gatttgcgta atgaagcact tcgttatgca gacaaattct tcttgtatga  21480
caacttcgga cagaatgaat gggaagacat taaacagtgt atccgtttct gggtagttga  21540
aaaccagtgt aagttcatca tccttgataa cattaccgct ctggtgtccc atttaacacc  21600
ttcagagatt aacactgaaa tcagtaagat tgcttccgag cttgctggta tgtgcaaaga  21660
attagacttt accgctttcg tgctatctca ccttaatgct ccggcaggtg gtgctcctca  21720
tgaagaaggt ggacaggtac gtgaagtgca gttcactggc tctcgttctc ttatgcgttg  21780
gtgtcagtgt atcattggct ttgagcgtga caagcaagct gatggcttag ctaagaacct  21840
ctcagtcatt cgattactga aagaacgtaa ctacggtcag acaggtgtct gctatactaa  21900
gtatatcagt gaaaccggga gacttgtaga aagggaagac tttgaagttg atgaagataa  21960
```

-continued

```
tccattcgtt ttaactaacg gagaggatgc agcttctctc gtcaaccaag cagatggagc  22020
ttcaccgtgg taaagaaaaa gaagaaagtg tttgcattcg atatcgagag taatgcactg  22080
tacgatgaca taactaaagt atggtgtatt tatatcttcg atgttgaaac tggtgaaagg  22140
tggggctatc ggcctcacca aattgaagat gggattcgta aacttacaga agcagatgta  22200
ctggtgggtc acaatattat tgacttcgac ctttgtgctc tgaagaagat gtatcccaat  22260
ctgattaact atcgttttaa cgtcttcgac actttatgtc ttagtcgata tcttaaacct  22320
gaccgtattg gtgacagtcc tgagtatccg aaaggcgacc ctagacgtgg cccaaggggt  22380
catggtttga agcagtgggg tgagttctta ggagaactta agggcgatta tggtgagcaa  22440
gaggaagcat gggatgcttt cactgaagat atgtttactt attgtgaaca ggacgttaac  22500
ttaactgtta aggtttatct tttcttgtgt gaactcacgg gatttgaccc ttacgaccca  22560
ccttcattat attggaaaat gtaaaatgat tgttatcccg attaaccaaa ttgaagataa  22620
ggttgctcaa caacctgata tcactgttgg tcgtcacttc attgaacagt tgattaacaa  22680
caacttgatt ccagatggta tctgtcccat cattactggt ggggctgttc gtgatgctgt  22740
ccttaataac atagctccac atgacattga tatctttatt gtcagaggac aaacaccaag  22800
aactcaaaac actttcatcc caactgatcg ttggcaagag cttggacggg agattgaaag  22860
taatgtgaag gaatggctag agtcacaaga tattgaatat gcatcacttc ttgctgaagc  22920
tacaaacgaa tcctatgctg ggggttctca attaacattc actgatatta ttgagtttca  22980
gtggaatggg gttcgtatcc aattcatgtt taattatcct acttctattg aagaggtatt  23040
ggataatttt cctatgatgt gccgtggtgc gatgactctt gacaacttat tcatgacttc  23100
tcacggatat ttggctatga cttcccettg tccagtggtt gtctctagtc gtgaaatcag  23160
gtatgttcac aagaagtggc ctaactcaca agtgttgaga ttttcctctc cagcagttgc  23220
gcatcaatac atggcccaaa ctcgatatct tcccacacct cagccagtta gtcatctagt  23280
caatggatta ggtcaggttt ctcttattga agatacaaca agtgctctat attgtgttaa  23340
ccgagacatg agtcgattct ttggaatccc ttatgaagag attcagatta tgtctagtct  23400
tcacggttct ggtcagattc atgcgtattg gtctgagggg ttgacaaatt taacgactaa  23460
cacgggtggt gatctgcttg gtcgagaaga ggaacctaac cgacacaatg caattgaagg  23520
ggtgtttgta gcccctgcaa tgcgtcgagc acaagagtca cgaagagaaa gccctactcg  23580
tagaacatct tttgaagaag ctcttggtat tacaagtgat tctatggagc gatggatggc  23640
tagaccctct cgtggtcgac caaacggctt aactgttagc gcacgtcagt tctctggtca  23700
gggtttcgct gttggtgata tcaacgcccc ttctcgtgtt atctggactg atgaaggtat  23760
ggaacaagat ttgggagata gtctcgctga tcgctttatt gctaacaacc ctgaagtatt  23820
agaacctcaa acccgtacag ttcggtttgc cgatgaagcg ggtcgtggaa tctcttttga  23880
catggaaaca aataactaag gaataagaat gagtttacta ggaagtccag agttacataa  23940
attaattgat gatggtgtta ttgatgcacc acactcagct gttaattcct ccagcattga  24000
tgttcgtatt ggagatcgcg ttctaatgga aggtgcagct aacggggttg ttgatatctc  24060
tgctaaagaa tctcctaact tcaatgaggt tatgattcca gaggaagggt tagtgatcaa  24120
accgggtgag tgtttcttgg ctcatacaat ggagacattc aatctgccag ataatattag  24180
ctgcgatttc atgctacggt ccactgttgg tcgttgtttc ttagagcaca tgcacgctgg  24240
tcatgctgac ggcggttggc atggtagcca gttaactatg gaattcaaga atgttctaca  24300
gcatcactct ctgctgatca aaccgggaat gcgtattggt caaatggaat tctttaaaca  24360
ctcttcatcc gaagaggaca gctacgcaac gaaaggttca tataataacc aacaagggcc  24420
aacaaaagct tttggtggaa caaatcatgc tgatatgcta tgatgaagta gttgatctct  24480
ttaacataga catgtcatca ccttcagggc tttcttggaa aaggaagcct agtaagtttg  24540
ctaatgatat agtaggtaaa cctgctggca agctcacaaa agatggatat tatcaaattc  24600
ccttaggagg agttcatgtc cacaatcata ggattctttt tgttctttat actggtgagg  24660
atttatcgga tgaatatcaa atagatcatg ccgatggtaa cagagaaaac ctagaagaaa  24720
ctaacctgag aaagtgctat cactctgaga acagtcagaa tgctaagaca agggttgata  24780
acaaactagg agttaagaat gtctaccaag agaagggcgg gacattctgt gtatctattc  24840
aaaaagatgg taaacgtgag tctgtatatg gagtgaaaac tcttgaagag gcaaaactcc  24900
tagcgaagtc tatgagaagt aggcttcacc tatcctttaa tgtggatgaa agatagatga  24960
ctaatgaaaa aatgaccgag cttctgtgaa gtgtttataa caacaactta gaagaaggag  25020
agaagtctgt atcagaattt gatgtggggt tgattgttaa acaaacccaa cttgacagta  25080
atcatactaa ggagctgaaa ggtgaattca aacatcacag cctagtttgg tcaaacgata  25140
gtgaaatgga gcagtgaggt atgcataaaa cagtagatct ttatgttata gtcccctaca  25200
aaagaggtga agtgtatccg atacaattct ccactgaaaa agataaggca gttgaaatct  25260
tccacgaagt tcacggctct gggaaatatg atattgttat tgcttgtcga gggactgctc  25320
ctgagaataa tctaatatct ccgtatgtcg gttatgatac tagtcgcctt atcgagacct  25380
aatgttataa tccatagtaa taatatttaa agagtttagt aaaatgagac caatcactat  25440
gagacaattt tggttagcaa agattaagtg ggcatcaggt ggcatgacta tgactgcact  25500
acccactcgc caacaagctc gagattttaa aaagtctatg ttcaatgtag acttaactaa  25560
gagcatcagt attcataagg ccaaggagta ttcttctggt cgtgtttata tcagcggaaa  25620
ggtgcattac taatgaaaaa gatgtgggct attcatgttg tttgggatct tgagcaacac  25680
atgagaaaag atagcatcaa attgtttgac actcgcaaag aggctcgtat tgctaagaaa  25740
cagttgaaga ctctgggcac aatagtaaaa agcgctgaca tacatcgctg gcatgaagac  25800
cctaacactg gttcttttat gtctaaagta atttactact gattggtagt agatatggta  25860
actctcaaat gtatatagag tacaataaga atttgtattt tacaggagag agttatgtta  25920
gatttgagta aagtggcccc gcccactgaa gagattacaa aatccaaggt gatgcaacag  25980
ttttatcatc gtgatatgct tggtcgcttt atcaagaatc gtgatgttgt tgcttggtct  26040
atcggtaatc agggatatct gttgaaggtt cttcaggtta caggttcaac tgctaagcga  26100
gttaaggtgt atgaccctga aatggggcgt tctaagtcag tagatccaca gaactgcatc  26160
gtaattaccc agcaggtaat ggataatatt gcacgtaatg ttgctaattc agttgaactt  26220
gatggagaaa acccaaatgc ataagaatgt ctttgattta cctgagattg gtcgtgacag  26280
ttatagtatg ttagaccggt ctgagctttc aatctctcgc cttgaaacaa tgcaaggcat  26340
gattagtgca aacagcctag aacacatcct gagctgctta caagctaaca tggaactctt  26400
gcatatcaaa gctaaaaact accactggaa cgtctctggt gcaggatttc agggtgttca  26460
tggtatgttt gatgagctgg aagattacgc acgacaggta ggagatcgta ttgctgaacg  26520
tatgcgttac cactgtgtta aagtggatgc tacagcagct aactacctct ctcatgcttg  26580
gttctcagag ggtaacgctg atctagacat ggacggtatg ctctctgata tgtgcatgac  26640
cttgatgtgt attattgaga agatggatga gtttgatggt gatttagcca cctaccctgt  26700
```

```
cgatcagagt atgcttcaag aaattaatga aggtcttggc aagtattgct acttcgtcaa  26760
gagcaacatg tcccattcaa gtggtgacgt gtcttactaa aaacctccgc cctgtctcct  26820
aacccgaggt ggggcgaact tatttataag gatatagata tatgttatca gcaatcgtat  26880
ggggtatttg ggctatcttt attggtggtg gtatttattg ggcttctggt aagcttattg  26940
aagaaactcc tgataagaaa ggtgagattc aaacagcatc aactatcatg gttatcgtag  27000
ctgttgttat cccattcctg cttcacctcc tgactgcata aggatttaca tgcctaaagt  27060
aattaagttt tatagtgatc agtgtgctcc atgtaaagca atggctccta cctttgagaa  27120
ggttgttaag gagtttgatg tagaagtgga agagattaac atccttgaag gtgatggtcg  27180
tgaacaagct gttaagtatg gtgtacgaag tatccctgct ttcgttgtgc ctgaccgtaa  27240
cagtggtgca cactacagcc tctctggtat gcagactgaa gcaaacctga aagcattttt  27300
agatacagct ctgaatgtta atcgatgatt tagagtatat ccctgagact ggagagttct  27360
ttcgaaaagg taagaaatta ggaggaactc gaagtaagta cataaccctg cggtttaaag  27420
ggaaagtaca caaagctcat aaagtggcat ggttctttta ctatggagag tggccttctt  27480
ctcagataga ccatatcgat agaaataaga agaacaactc aatacagaac ttgagattgg  27540
tggacacctc gacaaactgc cacaaccagt tcggggctag ggtatcaaac aaggaaacag  27600
ggcttcaagg tgttaaggtt gtcaaatata aatcagggac tattagatat agggctgtta  27660
tttgtattga taaagtagat atacatctag gtatgtatgg aactgccgaa gaagctcatc  27720
aagtttacat gaatcgaaaa aaggaacttt taattgaacg aacaactaca agcaacactg  27780
attgaagcaa tgggtagtga caaatctgta gtcaatgcag ctagagtatc tttcggtgtt  27840
gttcgagaag gtgacttaaa tgagagagac acaaaactta tcaacttcct tgcacgggaa  27900
aaacactgta ctccattccg acacccgcaa gtcagtttcc gatgcaaagc acctatcgca  27960
attgcgagac agttgggcaa gcatcaggtt ggattctcgt ggaacgaaat gtcccggcgg  28020
tataaagatg gagcagttga agtcttcatc cctaaagaga tttttgcgag accttcggac  28080
ctccatgcag gttcagggat tcaactcatc gacggagagc gagctgaagc attaatgtta  28140
attaacgatg catatgaagc ttctctagca acatatgaca agttgattga atttattgca  28200
ccagagcaag ctcgatttgt tcttcctcag gggatgatca ctgagtgggt gtggactggt  28260
tctttgtatg gctggtttga gttgtgtcgt cagcgactct catctcacgc tcaatatgaa  28320
gttcgagtgt ttgctaaatc cgtagatgaa gagatggcta agctctaccc aatctcatgg  28380
gcagctctga agaaaacttt ggagagttaa tatcagaggc tttctgatga aaatcaaaca  28440
tattacagat attcaggagg catttaggat gcttcctcga agagagaagg ataagattaa  28500
aaagcttatt caagtttatg gtcatacatc taaagatgat gtagactata tgccttctac  28560
tttcgtagag tgtgggattg ctcgtggttt cacattcgac cataaggtgt ttcagcaatt  28620
cgttgaccac tggagaaaag atggaaaaga aagtctgtag cttctgtaag aaagagaagc  28680
ctgtcgccaa cttcaaacct aaccctgtaa ctggtctgac ccatgtcatg tgccactctt  28740
gcaggatata tctcgaaaca aagcacacta tcaataggtt gcattattat cacccaacaa  28800
cattcaaatt taaggttgtg aaatgattga cagtaataca tttaggactt caaatggaag  28860
tgagataagt cccgctgaag taatcaatcg gcatagaaag caattgatca tccattccta  28920
tttgtattac tggttggatg accctatctg gtctgatgat aaatggcaac aagttgctaa  28980
tgatctagtg gagctgcaag ctctatatcc agagcctacc ggagtctttg acaatgagtt  29040
caaagattgg gatggttcta cagggatgca cctcccacac aacgaggctg ttgcttgtat  29100
ggcgacagct gtttacagga ttcataaaga tatgaaccat gaagtgctct aaatgtgaag  29160
gaacaaacct tcatttaagt aacaaggtta tcagagagct tgccaaaggc tctccaacca  29220
aaggggagaa caaacgattt actaacgtca gggtttatac agcaatctgt aaagactgct  29280
taactactga gtgtcattac gaagaaattg gagagcgtaa atgagtcgtc gtcaatcacg  29340
gaaagaatca cggaaagacc ttcgtcggga agcacttgtt actcgtaaag gtaagcgaga  29400
gtatgaagag gtggttttag caaagcctgt agtccctcag aaccagtttc agtctgagct  29460
actcaatgct attaagacta aacaagttgt gttcacagac gctcctgcgg gctgtggtaa  29520
gacctttgta atcacttcca cagttattga tgcactgaag agcggtaaga ttcagaagat  29580
cattctgagt cgcccttctg tcggcatggg caactctctt gggttacttc cgggaggaat  29640
gcgtgagaag tttgaacctt acctgatgcc tatcattgat gttattactc agcgatatgg  29700
taaggggttc tatgaatgcc agctcggtaa cagtaacatc gagttcgtac ctctggaata  29760
tctccgtggt cgttctttca atgatgctat tgttattgtt gatgagttcc agaacaccac  29820
taaagatgaa gccttctcaa tcatgactcg attgggagaa acctctcagc tgttctgcat  29880
gggtgatact aaccagcatg atatgcgtgg tcgtgagagc ggtcttactt gggctactaa  29940
ctttattgat gaacatgatc tgtatgagtt cgctgagatt gtagacggcg aatcggatga  30000
cattgttcgt tctggtttct gtaaagctat tgttaaagct atggaaaagg taaacagtta  30060
atgctttata gtgaaaagat tttgaagtgt atagatagtc tagaatacat tcgagagggg  30120
ccgatgtttt tcaccaaaag ggaacctcta atccctttca catctaagtg gtataatttt  30180
agcttacagc ctaatatcct atacatagga ctaccatgtg gcattgttga attgaagaaa  30240
gccgtatggt ataaagagac aggccagtgg cctcaatctt atttacacca tctggatggg  30300
cgcactgata attgtcatat tgataattta tcccgacata acccagcatg gggcgagca  30360
gtcaaagcaa ataataaaga tgttcacgta tctctgatat tcaaagaagg tgattggttc  30420
atcagaaaag atagtgaggt gcttggtcca tatgtagata tgaaagatgc tcaggaagca  30480
atgtacagga ttatactaga agagagttga ttcttatagt tcacacaagg gggtccaaat  30540
agcaacatac cacaaggaat gtgaaacctg taaggtacca tttgtaacga agtatataat  30600
gcagaggttt tgcaatgact cgtgtagatg ggccgaccca ggaaatagag ataagagaaa  30660
ggcagataac gagaaaagaa gagttaggca actagctttt atccgtagag ttaaaacatt  30720
ctatggatgc tctgagtgtg gctttaaggg ccacgcatct gctcttcagt ttgatcattt  30780
aaatccatta actaagtcat tcgaactctc caaagggcac accagatctt tatctcaagt  30840
aaaagaagag atgaggaagt gcaggatatt gtgtgctaat tgccacgcca tccacacctt  30900
taatcaaaga gaatcaggag aaatctaatg gcagatcatg taggaaaaag agactatgca  30960
caagaaagaa ggactgcgat caagcgcggt gaaacgggaa ttgggagcaa gagcggagat  31020
gctcagcgcc accgtgcacg tcgcatcgtt gaaaagcgcg atggaaaagc tgctgtcaga  31080
ggtaaagacg ttggacacaa acgagctgtc aagtctggag gctctaatgc gtcaagcaac  31140
ttacgtgttg aatcagtcag ctcaaaccgt tcaaacggcg gcaaaagtgg tgatcgagct  31200
ggaaaagcag ctggagcacg caaaggagct ttaagctcat aaagaggtta tagtgtcagc  31260
agaaacaaaa agatgtacaa ttcacactta ttgtaaattc tgtaaagcag agggtgtaaa  31320
aagagttgca actttaatga ccaagtattc tccaagtaga ggatacaggg accactataa  31380
gcactactct tgtagtgatc actcccatct attagaagat acagacccga atagaacaag  31440
```

```
gagagagcat aacattgacc tgagagctac tctcaaggaa atgaaaaaca actctcgaaa  31500
caaccattac actgaagctg actatcaaac ttggcttcgt ctctagaaca aaggctgcct  31560
aatcaggtgg ccttttcttt tatataaacc aaattaaact tcttaggtaa taaatatgtc  31620
tattgtaaaa atcgtaaata tcattgatgt aactcgtacc ggtaaaacta tcagttggaa  31680
attcaccaat aagcatagag gttcagagaa catcattcgt tctatgattc aacaaaaccc  31740
aaatacagct cgcactaacg tactccttcg aggagctgat ggaaaattta tctcttataa  31800
gaataagaac gtagaaaaat ctttccgtgt tgcagtagaa aatctcatcc cattccctaa  31860
aggagtttaa tatgaataag ttagctatgg ttcaaattcg ggacacatac cctaaccgcc  31920
cggagcagaa accgcgtact tggtcttatc tgttggctga aagtaagact attgacaaat  31980
acgctgtagg gattgatgct attccaacta gtatcacatt gctccctcac aaaacagcca  32040
gaacccatgt gatgttacgt gatagcaaag gtaagtttat ctcttatcgt gattcacgaa  32100
tcaataatga gattaaatct gctatggaat ttttgatgcc actcccaaaa ggttgagtaa  32160
tgaaagaata catttacgta ggacagcgct ggttcggtga tgaatgggaa ggtggttaca  32220
gcgttgtgaa agcttttaag tctgaagaag atgccaagtc atgggtctta aaagatgacg  32280
tcggtgagag aacttacatt gaagtagagg tggagtagga tgccattacc agctagacac  32340
caaaaccgtt tcttagttct caagtgggat gatatcgaaa tgaatctcac tgaacatgaa  32400
ctagatttgt tccatgaatt attatcagag attcgctctg gtattcctga acgtcagtat  32460
gtggttatca gcgataaaca ccctcaagag tttgaagaag cttggggtat gaagctggcc  32520
tacattcaga gagctattag agaaagagaa gaagttgcta atcagagggt tgtggctcat  32580
ctggtacgag aacagcctcg tgaagttagg tcttcttatt ctcaatctac ttgggcacaa  32640
acaaatgcag caatgagaac atatgctgtt gattccacat ccttggatgt agtagaagat  32700
aaccaagcat ttacagattt actttaccaa taatttaaag gagtataaag tgagcaaccc  32760
ggacgct                                                            32767

SEQ ID NO: 4            moltype = DNA  length = 32767
FEATURE                 Location/Qualifiers
source                  1..32767
                        mol_type = genomic DNA
                        organism = Escherichia phage HP3
SEQUENCE: 4
ccgccgccgc cgccaccgcc gcctgcaata gctccgccat tattaattct tagtctccca  60
ccaatatcgt tttgaataca atgacctcca gctgaaccag gactattgct accgccatta  120
ccgccacgtc catacatcgt tacgccgtgt atattcaact gaacatattc attcggtgta  180
tctccgtaca tgaagaataa aggaacatct ttagaatatg atactaaatc acctgtaata  240
ttaaacacta taggtgcact acctgcctca aaacatctat ctcggaacca ttgaccattg  300
aagttatggt ctgctccaag cgtgtgaata atttctcgtg agcgacctgc aaattgactc  360
atccagcaag gaacacccaa tcttaattga ccagccgctt gactcatcca gcgctgtcct  420
gtttcatttg cggctgaact tccaatccaa ccaggaacac caactactgc cataatttat  480
actccaaagg gggcatttcc cccttgttgt tagaatttaa aatatttact aattttgcga  540
gcaattttag taaagaaagg agttttcaat tctttaattt cttcactcat ttcctgaata  600
gccttaatta aaagagcatt cacagcagag ttagaaattg tcagaacatc agatccatca  660
acttcaactt tagatacagc ttccggtaat tccttttcaa ggtcctgagc aataatacca  720
acttcacgtt taataacact acggtcttta atagacttaa ctttatcgta aatataaact  780
ttcagtcgac atactttttc aagtgctccg ttttctagct ctttttttatt aatcttaaga  840
cgaccatcgg aacgaatata cacatcgtta aagttaccat taccaggaga atagaaagta  900
ccgtcgtaat gaaattcaaa taccgcgtta gggtgtccag ccgctggcga tgcctccgca  960
gatccaacac gaataattgc ttgcccccaa ttgttaggga cacgacgaat accaagatcg  1020
acggcagtta caaacccttg attggtgatt acacttcttc ctttgagaat cggataataa  1080
caatcctgtg aaacataacc atgatcgacg aatattggtg cttctactcg ccattggttg  1140
ccccaatcac ccggttgtct agcaatccat ccagaaccgt taatgtgtac acgatcgcgg  1200
ttaacgttaa ccattgcgat attttgtgga tttagcgaaa tctcaccatt gtttgtgata  1260
tgtactgccg cctgagtagc atagctataa aatgctagcg aattatcagc accaccctta  1320
ccaatatacc agttaccact cccgtctacg tcaccacgaa tatgcaaagc attaccagca  1380
gttgttgata atacaataga atcacccgga cgtttaataa tcaatctacc ttcggattca  1440
atttcaccaa aaaatttagt cttaattgca ccagtcgcta aagtacgttc agtggaaaaa  1500
tgaacgcctt tgctgtcttc taactgaata atgttatcgc gcgcattatt actatcaccc  1560
caatgattaa accggaaata atcacgtgat tgcttaccac ccgcttcaaa cgtcagcgta  1620
cctttactta aattaacatc accgctaaag gtagcagcaa gagaatcacg ttctaatttt  1680
aaaacgttag caccactagt accacctaaa gtaacatcac cagttctcaa ttcataacgg  1740
aaaggtctat ttgtattata gtttccattt tgatcatctt cgttggtgga aagaatataa  1800
agattctctc cataagtacg gaaaattgta ccaaaatttc cggcatacat acggaatgca  1860
ttagatgagc gaaatttaac ttctgtttta aaagtggtag tgttattaag gttaacagta  1920
gagttaaaat tggtaggagc accgaagtta actgcgccat taaaatcttg ttgagctgtc  1980
catgtgtggc gaccatcttc aagaacaaca cggcggactg tgcaagttct atttccagaa  2040
ttaccgaaca cacgaacgac aaaataacgg tagtttgtct gggatacagt accgcgccaa  2100
acctgaacag tacgccctgt gctagtgtgt tcgctaggac caacggaaaa cataaccagg  2160
tttccgtcaa tcgtccccca atccatattt gctggcatat tctttatttt gttcaaagga  2220
acactaaaca tactaccagg gacaaaatca aaggtttgcc aatctagctc cgctaattga  2280
gttttaatac cacccatacc caaagtaatt ggcaaagagt aagatgtata tacttcgttc  2340
catgtacccc acgcgccacc ggtatatgca cgctcaaaaa tacgatcgcg agtagttgca  2400
cccgttccgg cagtagtaaa tttttggaaa atagcaccac cagaagcacg ctgtttaact  2460
tccagcaaac caacaataac ggctggtaaa ccttcaccag taggacagtt aataacggca  2520
tcagtgccta aaatgttata taacccagga gttttaaaat cattcagatc tccatcatag  2580
aaagtcgctg gtgtgccatg accaacctgc ttccattcct cccacttagg tgcactagca  2640
tcccatgcag cagcgagaca acgagtataa accataccca tgcgggtagt ataacgctga  2700
gttctcgtgt ataaaccacc ttcaaatatt tctaaaaatc cttgtgcggc tgatccttct  2760
tctggataat ggcgatcaaa tgatgcgatt gcgcttgaac tgtttcgcca taagccacaa  2820
tgttctaatt ctcccaagct atcaaggtca atcgtttgtg aaagtggacg agttgacgct  2880
tgaacattac gccacacacc ccatggacca ttgacgccat tccatttagc agataaggaa  2940
```

-continued

```
cgaatataga cgttaccaga tcttacagta taacgctgag tgccagcaaa ttggccggcc  3000
acaaacactt ctagtacacc tacggcattt tcttctggga atttatttgc tggttgcgca  3060
tttgttgaag tagatttcga ccaaacacca agatattctt caatgggccc atacgtatct  3120
aaattagcat cagtaggtaa ttcgccatta tttttataa atgttgtgct attgacattt  3180
atgtcagatg gagttaaggt aatgtccttt gacccatcaa aagatatacc attaattttc  3240
ctaggtgttt gcaatttagt agctgtgcta gaatttccaa ttaaagttcc agttatattt  3300
tctgtaacct ctaaagaccc atttatagtt cctccatatt ttaaacctaa ttctataaca  3360
ctacctgagt catcttttgt gaaaattgtt ttatctttta agtttatagc caattcacct  3420
tcggctaata ctgaagcagc aggacgttga cctgcagttt tgcttctttt aaattgtatt  3480
tgttttaaag tagccataag tcctcttaat aatagccgaa atcttgaaca gaatccttaa  3540
ttacgatttg gtcaaatcgt ggaacgtgtg aaggttgaga tgcaggattc tgtgaaaaaa  3600
ggtttggcgc agttaaattt cctgtcatag tgtctccaga gcgtaatacc ctagagtttg  3660
catttgctgt aacagtattt attgctccat caacataatc tttgcgagta acatcagatg  3720
ctgcggaagg agtagatgta acagttaccg atggagccgt tacagccctg gtaaatgttg  3780
tcaaaccttc tggcgtaata gtaatttgtc cagtagtgat ttcactacct gctggtctaa  3840
aactaatacc gccagaagag ccaccaacta caagagtatt accagtgccg ccaccagaac  3900
gaattcggat gggggtttca ttattactta attgaagata actatttacc ccgtaattaa  3960
tagtaattgg accggtgtaa gtaccaccat tagctttaga aacgaaatcg ttatcagctg  4020
cctgcggttt attatattct gaatatattt taaatgattt gtagagtaca tcgtcaccgg  4080
ctgaattcaa tggaaaattt ccttgatgcc aaatgacaga tccacctaca gttgaaccta  4140
cttttaaatc agccattata tgccccttta ttttaatatt atttataaag aaaaagggaa  4200
cccgaaggct ccctcagttt aaacttctct aaattcttgc ccaaacactt tgccagtttt  4260
agaagaggct tgtgtaggaa gtaccattat atctggaggt gaagccgatt cgcagacata  4320
attaacgcga ataccgttga cgccaaattc ggcaggtttt gaaatgccgc catttcttga  4380
tacttcagaa aagcttaaat ttctcatgcc gccttgacct gcttgggcag ttctttgtgc  4440
atatatcgta aatcctactg cattttcagg aacaactaca taatcttctt ttaattccca  4500
agacccagct tgcccagtaa actcagcttg ggtcgaggaa atatatccat ttgatgcatc  4560
ataaaaacga atagatatat ttgtagttcc aagatcaagt aaatcagcat cagcatatag  4620
ttgtgcttta agataaagaa catcaccagg aattaaattg tagtcagaaa gtttacttat  4680
agcagctgaa gttggcaatc gcgcaatttc attattagtt cctccaaccg cagacataaa  4740
ttgctcaacg ctttcgtatg ttcttttagg aaatcctgta gctccgacgt cttctaaact  4800
atcaaataca acatctaaaa tagtttgata atcatctgtg ctttttctat tacttagttt  4860
aacatgctct aatgcaatag ctcttttaga agaagtataa aaagcagcat atgatacgtc  4920
aaatcttgac aatactgaat ctgatggaaa aactgaagtt cctgctcccc ttaaccaaga  4980
taccacttca ggaggaaaat taacctttcc gctagttaat atagcagcaa gtctattgtt  5040
tgacaaagaa ttcatgaaac tgacaaaagc agctgatgta gtattatttg aagcagaaaa  5100
agcatatgac ttgctatcaa ctaatgctcc cgtagaaggg tcaaaaactc ttaaatgaag  5160
acctgcacta aatgtttgat ttccaacggg attatcctga aatttaacat atggccccgc  5220
agtagaaagc gggcaagaac ccgctatgct tattttatat cttactgaat tgctttccga  5280
taaaaatggc gtttggacat atccttgtcc aaactctgcc ataaattttt ccataatacc  5340
tcttattcaa cccattcaaa tttaacagtt ttattcactg ggtcaggaat aatgcgaaca  5400
ttaccaattc gtaagaaatc acgaatagta agattaccta ttattccatt atcagatggg  5460
atcgctccta tatctgaagg ttgaggaggg ttacctccgt caaatacctg aacaaaactt  5520
gaccaagagt tttggtttt ctgccatgta cgtgtccagc gagtggtacg tgcttctggg  5580
gtcgttggat aagtaatcca atcttggtaa agcgaatcaa gtgtgttacc aaactgagtc  5640
aatgtaccag gagatttaac ttcttcgcca cgttctaagt atggaagccc agtcacttca  5700
ttagtttttt caaccatttt aaaataaccc gggaactggt tataagtggc tgaatcatta  5760
atatcgattg accagaatcc tacagtatca gatgtcggcg cgcgggtata taaatcagag  5820
gttttagtac cctgagaacg aattctcgag ttaacagtca aaccacccga acttatagta  5880
gcaccttttg caatgattaa gctttcacca atcgttactt ggccagatgc attattaata  5940
gctaaaggac gcaatccatt aaatacgcca gtttgatcac ccgatgcagt aagcataaaa  6000
ttcgttactg atccatcatt gcgaacaatg aaaccataat ttccgttaat agcacggaaa  6060
gcatttgcgc ttcgagaaat aatttcacca gttgcagtga ctgaattacc aaatgttgct  6120
acaccatttg cattcaatgt tcctgaagca ttaacattta tcggtgttac tgtaccgttg  6180
atattaaatg ttatatttcc agctttatta cgctgagaat aaaaatgact agacgtttca  6240
tcactaactt caaatacggt agaacgtgtt gtgtctgatt ccccactaaa ttgatttccc  6300
cacactctga ctgtcatcgt ttgagccggg tttgttccag tttgaggtcc tttctcaaaa  6360
atcagacgag ttgccgttcc agtattagaa atagttaatg tactatttgc tgaaactgat  6420
ccaccgaatg tagcagtact agatgataca agaggggcac tcagattcgt ttgttgggtt  6480
aaggttagtg aaccattaac tgtttgtgca atgtccctac gaatgaactg gagcgaatct  6540
agaccatcta ataaattact atctacggct tttgctttta atggcaaata atttgctaat  6600
acgcgattta attcatatgg tgatactgca taaccatttt tctcatatga ttctaatggc  6660
tgtgttgaac cagctgtatc attaccaacg aatgtaattg aaccagacga agttttaaca  6720
aaacctctta tcgcagtagt cgctgcccaa gtaggttcac tctgcacaat ccattttaaa  6780
tttttggag atacagcagt atttgctgac gttccagcta cagtttcaga ccgagttgca  6840
actttaataa cgccttcctg tgcttcagta gatttagtac ctaaaagctt tttaggagtt  6900
attaaaacat tatctaatgt tcctgcagca gcttcaactt gtgtagctac acgaagtgta  6960
ccacgctgtg tctcatttgc ttcaagaata ttaagggtat aatggtccca gagagttcct  7020
gattcaacta atccagatag agcaacaaca gaagtacgat cagtactatt aaatctggtt  7080
ttaattttta atggtgtaga gatacgagta tcgtcgacgc ctgcgtcgaa ttcaacctgt  7140
gtagcaattt cagctatacc acttaaactt tcagttgctc tacggtcatt taaagtttta  7200
ggagtgactg cacgagtata atcagttcct gtattaactt cactttgcgt agcaatttca  7260
attaaaccaa ttcttccatc agttgatgtc tttttatgta acgtttctgg tgttacaacc  7320
gcatttgccc atccttcttg gctttgtcca gcaattactt cactttcaac tgctaaaatt  7380
actgcgcctt gttgcgttgg agtagcttta tactgatcca aagctttagg tgaaacaact  7440
aaattattag tgttttatt ataaacattc gtaccattta attcacgact agaagctgga  7500
gtagctcctg cagtagatac aaaagttaca atacccgata atgtttcaga accttgacga  7560
gcttgaagct tttaggagt gatgattgta gtatcatcga tacctgtatt agtttcctgc  7620
tgcgtagcaa tttcagcaac acctctgcga gtttctgtag cagttctttc attcagcttt  7680
```

-continued

```
ttaggagtga tgataaggtc atctgcaaaa gagaatgtag tgttctgatt tacttgagca  7740
gtagttgcta ttcttgcaat acctctgcga gtttcagtag cagtacgatt agctaacgtt  7800
tctggagtaa ttgctaattc tttttgtgga gaattttcta aatcagcatt tgcttgagct  7860
tgcgtagcta aagcaattac gcctaatctt gctctagtag aagcatttaa agagtctact  7920
ctttctacag ttggaacgtt ttgctgtaca acccagtatt ttccatcaga atcttctata  7980
taagcaagtt gcaaaactgg tacataatta gtttcaccat taaaaactaa ttcttgaact  8040
gttacccatt cagcttcagg cggatattct gaacgttttg ggaattgcag caattgaact  8100
gaagaagcaa ttttatcttc accagcagct ttgattttaa ctgtttgtcc ttttctcatg  8160
taattcatgg aaattttaac agtatcacca acagaaatat cagtcggaag ctgaagttca  8220
attgtttggg ttgttccatt attcgcgcca aataccatga cttcttcatt tggacgaata  8280
tttgaattag ttgttataat gcgtaaacgt gctttactat ccccgtcaaa caatctccac  8340
aatttctcat tatcgtcaaa catcaagaaa ccgtcaatcg atgtacggcc ttcaatggaa  8400
tgagttccaa cttcttgtac tgaagtcgtt tcatcgtatg tagtaacaat tgtatgataa  8460
agtggattca gtttatctaa atcaacgaaa ttaataatat cgccatgatt agcaaatctc  8520
ggaagtttaa cattaattgg tgcagcagaa gtaaatctac gtacgataaa atcattagat  8580
tgtgcttgat acgcagtcga tggagtaaca atcgcagctt ctctgctata atcagcaaca  8640
tacatttgcc acaaacgatt attaaaaatg aatatcatct gtgactttgg atgagtcatt  8700
aaaactgaac gtacctgttc acctctaaaa ttgacaatac tctgatttga agaatttatt  8760
ttaacctgat ttatgccagg ttttccaccg atatcttgaa ttattacggt ttctccatca  8820
agcggagaag gtggtaaagt aaactcaatg tcattgccaa ctgatgtatc tactgaaatt  8880
gcttctccgg attttaattg atatggtcca gatgatacgg ttgtatatac ggcatcagta  8940
cgtaatgctt tccaacgaat tctattaaaa tttccagcag gttttggaat attatccgtt  9000
gctgcccaaa aacgattatt ataaatgatt acaaaatctt ttaaatatcc acgagttggg  9060
tcatattgct gaactgtgtt ttcttgaatt aagtaatcaa cgttaacacc gtcagttcct  9120
acggtacgat cagctaaagc tacgttgatt attttatcgc cacctgcgtc cagaccatct  9180
tctgctctga actttctttt aatctcggcc attctcccgg gctcctattg tgttttcaat  9240
aataagtatt tatacctgtt tactttaaga tttagatagt atataataga aatctcacta  9300
attgaacgag gttcatatgg atttagaaat gatgctggat gaagattaca aagaaggaat  9360
ttgctttatt gactttagtc aaattgctct ttcaactgct ctggtaaact tcccagataa  9420
agaaaaaatt aatttatcaa tggttcgtca tttgatattg aactcaatta agtttaatgt  9480
caaaaaagca aaaacgcttg gatacactaa aattgtactg tgtattgata acgcgaaatc  9540
tggatactgg cgtcgtgatt tcgcttatta ttataagaaa aaccgtggaa aagcacgaga  9600
agaatctact tgggactggg aaggttattt tgaatccagt cataaagtta tagatgaatt  9660
gaaagcttat atgccataca ttgttatgga tattgataag tatgaagcag atgaccacat  9720
tgctgttctt gttaaaaagt tctctttaga aggacataag attttaatca tttcatcgga  9780
cggtgacttt actcaacttc acaaatatcc aaatgttaag caatggtcac cgatgcacaa  9840
gaaatgggtt aaaattaaaa gcggttctgc tgaaattgat tgtatgacta aaattcttaa  9900
gggtgacaaa aaggataacg ttgcttcagt taaagtacga tctgactttt ggtttaccag  9960
agttgaaggt gaacgaactc cttcaatgaa aacttcaatc gttgaagcta ttgctaatga  10020
ccgtgagcaa gctaaggtgc ttctcacaga atctgaatat aatcgttata aagaaaattt  10080
agttctaatt gattttgatt atattcctga taatattgct tcaaacattg tgaattacta  10140
taattcatat aaattaccac cgcgtggcaa aatttattca tattttgtaa aagcgggtct  10200
ttctaaatta actaatagca ttaatgaatt ttgaggtgaa taatggctaa aaaagaaatg  10260
gttgaatttg atgaagctat ccatggcgaa gacttggcta aatttattaa agaagcatct  10320
gatcataaac tgaaaatttc cggttataat gaactgatta aagatattcg aattcgtgcc  10380
aaagatgaac ttggcgttga tggtaagatg tttaatcgtc tattagcttt gtatcataaa  10440
gataaccgtg atgtgtttga agctgaaact gaagaggtag ttgaacttta tgacacagtt  10500
ttctctaaat gatattcgtc cggtcgatga gaccgggctt tcagaaaaag aactttcaat  10560
taagaaagaa aaggatgaaa ttgcaaagct tcttgaccgc caagaaaatg gatttattat  10620
tgaaaaaatg gtagaagagt ttggaatgag ttatcttgaa gctacaacag cattcttaga  10680
agaaaattct attcctgaaa ctcaatttgc taaatttatt ccttcgggta taattgaaaa  10740
aattcagtca gaagccattg acgaaaatct tttacgtcct tctgttgttc gttgtgaaaa  10800
aactaataca ttagattttc tactatgatt aaactccgca tgcctgctgg tggtgaaaga  10860
tacattgatg gtaaatcagt ttataaatta tacttaatga taaaacaaca tatgaatgga  10920
aagtatgatg ttattaagta taattggtgc atgcgggtgt ctgatgccgc ttatcaaaag  10980
cgaagggata agtatttttt ccagaagtta tcagaaaaat ataaattaaa ggaacttgct  11040
ttaatcttta taagcaatct tgttgctaac caggatgctt ggattggcga catctctgac  11100
gctgatgcac ttgtgtttta tcgtgaatat atcggacgct taaagcaaat taaatttaag  11160
tttgaagaag atattcgcaa catttattat tttagtaaaa aagttgaagt ttctgctttt  11220
aaagaaatct ttgagtataa tccaaaagtt caatcaagtt atattttttaa actacttcaa  11280
tcgaatataa tttcgtttga aacgtttatc ttgcttgatt cgtttttaaa tataattgat  11340
aaacatgatg aacagactga taatttagtc tggaataatt attctataaa gttaaaggct  11400
tatagaaaaa ttttaaatat tgattcacag aaagctaaaa gtgtttttat tgaaactgtg  11460
aaatcttgca agtattgata tgaatatagt atattggttt acatttgaag accgtgtcaa  11520
aaataagact ccaccgtact actatatcgg tagtaaatta aattgctcat ttgagaacgg  11580
aataatatat gactcttccg gaaaggaata ctggagctca tgtaaacaaa aaagattttt  11640
gaatgcgcta atgcttcaaa aaccgagcgt taaaataatt caaattgatg atgacttgga  11700
tgttattgaa gcagaacgaa aataccaact tgaagtaaat gcaagagata atccagacta  11760
ttttaatctg gtatatgctg gtggtggatt tggtgtgagt ggtgaaactc atccagccaa  11820
agacccggaa gttagagagc atatgagatt ggctaattat atgaaccgtg acgattttag  11880
accttggaaa acatcacgag ctaatataga gtcttggaaa ttatctcata ttgcttacga  11940
gaattatgtg ttattattat cctctaatct gtacggtaaa actcctggat ggcgaagagt  12000
taaaggtaat ataaatataa ctgatacaac tgctaaatcg atggtaaagt atttcaactt  12060
aggttggata cctctcgaag acccagagta ttgcgaatta tgccagctat gaggtaaagt  12120
gtcatagcac caactgttaa ttaaattaaa ttaaaaagga aataaaatgt ttaaacgtaa  12180
atctactgct gaacttgctg cacaaatggc taaactgaat ggcaataaag gtttttcttc  12240
tgaagataaa ggcgagtgga aactgaaact cgataatgcg ggtaacggtc aagcagtaat  12300
tcgttttctt ccgtctaaaa atgatgaaca agcaccattc gcaattcttg taaatcacgg  12360
tttcaagaaa aatggtaaat ggtatattga aacatgttca tctacccatg gtgattacga  12420
```

```
ttcttgccca gtatgtcaat acatcagtaa aaatgatctg tacaacactg acaataaaga  12480
gtacagtctt gttaaacgta aaacttctta ctgggctaat attcttgttg taaaagaccc  12540
agctgctcca gaaaatgaag gtaaagtatt taaatatcgt ttcggtaaga aaatctggga  12600
taaaatcaat gcaatgattg cggttgatgt tgaaatgggt gaaactccgg ttgatgtaac  12660
ttgtccgtgg gaaggtgcta actttgtact gaaagttaaa caagtttccg gatttagtaa  12720
ctacgatgaa tctaaattcc tgaatcaatc tgcgattcca aacattgatg atgaatcttt  12780
ccagaaagaa ctgttcgaac aaatggttga cctttcgaac atgacttcta aagataaatt  12840
caaatcgttt gaagaactga gcactaagtt cagtcaagtt atgggaactg ctgctatggg  12900
tggtgccgct gcaactgctg ctaagaaagc tgataaagtt gctgatgatt tggatgcatt  12960
caatgttgat gacttcaata caaaaactga agatgatttt atgagctcaa gctctggcag  13020
ttcatctagt gctgatgaca cagacctgga tgaccttttg aatgaccttt aatagattat  13080
attactaatt aattggggac cctagaggtc cccttttta tttcaaaaat ttttcataaa  13140
acggtttaca tccttgtcct tccatggtac tatacaacta tcggcaatac tgctgataat  13200
taaagaggaa aataatatgg ctaaagttga tattgacatc gttgattttg aatatattga  13260
agaaattatt cgtaatcgtt atcctgaact tagtatcaca agtgtacaag attctaagtt  13320
ttggagtatt caaatcgtta ttgaaggtcc tttagaagtt cttgagcggt ttatggctaa  13380
tgaatactgc gatggtatgg atgctgaaga cgtagaattt tacatgggac tgattgaaca  13440
ataattatca aggggctatt aagcccctat taaaatgagg aaaatcaaaa tggaaatcgg  13500
caaaaaatac gagttaaatc cacatcgtat taaatctttc attgatatta gttcatcaaa  13560
tgctagtatg gtcggcatca ttcaagaaaa tggcggttgg tttgaagtta aatcaatatc  13620
aagtttagat ggctttgatt atgtaaccga aatcatttgt gctaatggtg aaatctataa  13680
tgatgatggt atgggtgatg attattttga acttagtgaa gaagagtttt attgtttccg  13740
cgaatataaa gaaccgactt ctgaagagga tgaagtcaaa gacaaggttt ctggcgtaac  13800
aaaaattcac tgcattgttg acgaaaacaa tgcagatgaa atcattgaac ttttgcgaaa  13860
aactttcaaa aagtagttta catcagggta gtagtgtgat actattaccc tatcaaaact  13920
aatggagaaa agaaaatgtt cgcaccttat attatggcag cagttatgtt ggtctgttta  13980
tatcttttga ttaaagcttg ctaaggagaa taaaatgaga ttacaacgtc agagtatcaa  14040
agattcagaa gttagaggta aatggtattt taatatcatc ggtaaagatt ctgaacttgt  14100
tgaaaaagct gaacatcttt tacgtgatat gggatgggaa gatgaatgcg atggatgtcc  14160
tctttatgaa gatggagaaa gcgcgggatt ttggatttac tattctgacg ttgaacagtt  14220
taaagctgat tggaaaattg tgaaaaagtc tgtttaagga aaataatatg atttttgtat  14280
ttgaatttat gaatgatgaa ttcgattatg caatttttaa cgcattgcat aatcctgatt  14340
taagtgaatt taatgaaatg ttttctgatg ctttgagtat gtcagaagaa tactgtggag  14400
aatgtcaacg tgtttgtgtg acagtttttg aaaacaaaga aaagacgtat gaagaattat  14460
tctttgatgc taataaagcc actgaatggt ttatcgaaag aggatttgcg taatgattaa  14520
attggtattc gcttattctc caactaaaac agttgaaggc tttgacgaat tagcatttgg  14580
tttaggtgat ggtttaccat ggggacgagt taaaaaggac cttcagaatt ttaaagctcg  14640
tactgaaggt acaattatga ttatgggtgc taaaacgttc cagtcattat ctacattact  14700
tcccggtcgt agccatattg tggtgtgtga ccttgagcgt gattatcctg taactaaaga  14760
cggcgattta gcacatttct atattacttg ggagcaatat ataacttaca tttctggcgg  14820
cgaaattcaa gtgtcaagcc ctaatgtacc attcgagact atgcttgatc agaattccaa  14880
agtaagtgta attggcgggc ctgctctgtt atatgctgcg ttaccttatg cggatgaagt  14940
agttgtttcc cgcattgtta aaaggcatcg tgttaattca acggttcaat tagacgcaag  15000
ttttcttgat gatataagca agcgtgaaat ggttgaaacg cattggtata aaatagatga  15060
agtaacaacc cttacggaat cagtatataa atgaaataac acgtggcgga aaatatgaat  15120
tttaattatt accctattct attagaagaa gacgcgaaac agccaaagtg gcagggtcct  15180
cagtttatta aaggtgtcta tcaattagta gttcctaaag acaagattta tagcagttgt  15240
ttcactgaat ccgcttgcag tattttcggt aatagttctc cgtattggaa ttttgacata  15300
aagctggata gaaatatcga tatttggttg aaagctatgg atattggtaa tatcacgttt  15360
gatgagaata attatcatat tattggtcgc ttttccaaac gcggtaaaga attatatttc  15420
acgcctgaaa ttgagagaaa atttgatgct aaaccgtatt gattatttag cttcataaaa  15480
tgtattataa tttatataag gtactaaatg aaacaatacc aagatttaat taaagacatt  15540
tttgaaaatg gctatgaaac tgatgaccga acgggcacag gaacaattgc tttgttcggt  15600
actaaattac gctgggattt aactaaaggt tttcctgcag taacaactaa gaagctcgcc  15660
tggaaagctt gcattgctga gctactttgg tttttatcag gaagcacaaa tgtcaatgat  15720
ttacgattaa ttcagcatga ttcgttaatc caaggcaaaa cagtttggga tgaaaattac  15780
gaaaatcagg caaaagattt aggataccat agtggtgaac ttggcccaat ttatggaaaa  15840
cagtggcgcg attttggcgg tgtagaccaa attatagaag ttattgatcg tattaaaaaa  15900
ctaccaagtg ataggcgtca aattgtttct gcgtggaatc cagctgaact taaatatatg  15960
gcattaccac cttgtcatat gttctatcag tttaatgtgc gtaatggtta tcttgattta  16020
caatggtatc aacgcagtgt agatgttttc ttgggttaat tgaggcctag gtataaggtg  16080
acttatactt gtaatctatc taaacggggg acctctctag tagacaatcc cgtgctaaat  16140
tgtaggacta ccctttaata atttcatcag gattagttac ttaccgtgta aaatctgata  16200
aatggaattg gttctacata aatgcctaac gactatccct ttggggagta gggtcaagtg  16260
actcgaaacg atagacaact tgctttaaca agttgaagat atagtctgat ctgcatggtg  16320
acatgcagct ggatataatt ccggggtaag attaacgacc ttatctgaac ataatgcttc  16380
catttaatat tgcatcatat gctacgttag ttcatattgt agctaagatg tgtaatctta  16440
ttccgggaga tttgatattt tccggtggta atactcatat ctatatgaat cacgtagaac  16500
aatgtaaaga aattttgcgt cgtgaaccta aagagctttg tgaactggta ataggcggat  16560
tgccttataa attccgctat ctttctacta aagaacaatt ggaatacatt cttaaactca  16620
ggcctaaaga tttcgttctc aaagattatc agtcccacgg cgtcttgaaa ggaaaaatgg  16680
cggtgtaatt tcaatttaat tgcgaggata tatgatttta cgatttaaag atacttctgg  16740
tgcagttctt tttacacttc ctaatccaag tgagctagaa gttccaggac caaatcagcc  16800
tattatcatt tatggcaaaa aatattatac tcataaaatg actcgtgagt attttgataa  16860
taaaatttct acagttaaaa cttcttctga ttgttactat gatattactg ttttaacgga  16920
aaaacaatat gacgaattat caccgcgcgg gccgtctatg tcgggtagtg aataaatata  16980
aatccgactt tgatgtcaat attcaccgcg gtacattttg ggaaaattac gtcggtaaag  17040
atgctggcag ccgggaggct gccattgaat tattcaaaaa agattttata cgtcgaatta  17100
aatccggaga aataactaaa gcacatttag agcctttacg tggaatgagg ctaggatgca  17160
```

-continued

```
catgtaaacc aaagccgtgt catggtgata taatagctca tatagttaac cgattgttta  17220
aagacgattt tcaagttgag gacttatgca attaattaat gttatcaaaa gtagtggtgt  17280
ttctcagagc tttgacccgc aaaaaattat taaagtttta tcttgggcag ctgagggaac  17340
atcagtagat ccttatgaat tatatgaaaa tattaaatca tatctccgtg atggaatgac  17400
aactgatgac attcagacta ttgtcattaa ggctgctgcg aattctattt cggttgaaga  17460
acctgattat caatatgtag ctgcacgttg tttaatgttt gctcttcgta agcatgttta  17520
tgggcagtat gaaccacgtt catttattga ccatatttct tactgtgtaa atgaaggtaa  17580
atatgacccc gaattattgt caaaatattc agcagaagaa attacatttt tagaatcaaa  17640
aattaagcac gaacgggata tggaatttac ttattccggg gcgatgcaat taaaagaaaa  17700
atatctagtt aaagataaaa ccactggtca aatttatgaa actccacagt ttgcatttat  17760
gactattgga atggcattgc atcaagatga acctgttgat agattaaaac atgttattcg  17820
tttttatgaa gcagtatcta ctcgacagat ttcattacca actcctatta tggctggttg  17880
ccgtactccg actcgacagt tcagttcatg cgttgttatt gaggcaggag attcattgaa  17940
gtctatcaat aaggcttccg cttcgattgt tgaatatatc tctaaacgcg ctggaattgg  18000
tattaacgtt ggtatgattc gtgctgaagg ttctaagatt ggcatgggtg aagtacgcca  18060
tactggtgtt attccttttt ggaaacattt tcagactgct gttaaatcat gttcacaggg  18120
tggaattcgt ggcggcgctg ctactgctta ttatcctatt tggcatttgg aagttgaaaa  18180
tcttctcgtt ttgaaaaata acaaaggcgt agaagaaaac cgcattcgtc atatggatta  18240
tggtgttcaa ctgaatgatt tgatgatgga acgattcgga aagaacgatt acattacttt  18300
gttcagtccg catgaaatgg gtggagagct ttattattct tattttaaag acaaagaccg  18360
tttccgtgaa ttatacgaag cagcagaaaa agaccctaat attcgtaaaa agcgtattaa  18420
agcccgtgaa ctatttgaat tgctcatgac tgaacgttca ggaacagcaa ggatttatgt  18480
acagttcatt gataatacga ataactatac tccgtttatt cgtgaaaagg cacctattcg  18540
tcagagtaac ttgtgctgtg aaattgctat tccaacaaat gatgtgaata gtcctgatgc  18600
tgaaattgga ttgtgtactc tctctgcatt cgtactagat aattttgact ggcaagacca  18660
agataaaatt aatgaattgg cagaagttca agttcgtgct cttgataatc tgttggatta  18720
ccaaggatat ccagttcctg aagcagaaaa agctaaaaag cgtcgaaatc ttggcgtagg  18780
tgttaccaac tatgcagctt ggctggcaag taactttgct tcttatgaag atgctaacga  18840
tttaacgcat gaactatttg agagattaca gtatggactc attaaagcat ccattaagct  18900
cgccaaagaa aaaggacctt gcgaatatta ttcagacact cgttggtctc gaggcgaatt  18960
acctatcgac tggtacaata aaaagattga ccaaatcgca gctccaaaat acgtttgtga  19020
ctggtcgtcg ctgcgggaag accttaagct ctttggcatc cgtaatagca cattatcagc  19080
acttatgcca tgtgagtcat cttcccaagt ttctaacagt acaaacggta tcgagcctcc  19140
acgtggacca gtctctgtta aagaatcaaa agagggctcc tttaatcaag tcgtgcccaa  19200
tattgagcat aacatagacc tttacgacta tacatggaaa ttagctaaga aaggtaataa  19260
accttatctt acgcaggtag ctattatgct gaaatgggta tgtcaatcag cttcagcgaa  19320
tacatattat gacccgcaga tttttccaaa aggaaaggtt ccaatgtcaa taatgattga  19380
tgacatgcta tacgggtggt attatggcat taaaaatttc tattatcata atacccgtga  19440
tggttctggt actgatgatt atgaaataga aactccaaaa gctgaagatt gttcatcctg  19500
taaattatga tataatttga ctcacggacg agtcaccaac tattaactaa gtggaaaatt  19560
tatgagcaca gtttttaata caaacccagt tgatgtttta aaagaaccta tgtttttttgg  19620
ttcaggtctt ggtattgcgc gttatgatat tcaacggcat cgagtatttg aagaacttac  19680
agagaagtcc ttatcatttt tctggcgccc ggaagaagta aacttaatga tggatgctgc  19740
acagtttaat aagcttcctc agtatcagca aaatattttt actaacaact tgaagtatca  19800
atcacttttg gatagcattc agggtcgtgc gccgtctgct gtacttatgt cattaatttc  19860
agacccaagc cttgatacgt ggattgctac atggactttt agtgaaacta ttcacagtcg  19920
ttcatataca catatcatgc gaaatcttta tactgatcca tcgaaggtat ttgatgagat  19980
tgtattagat gaagctatta tgaaacgtgc tgaatccatt ggacgttatt atgatgatgt  20040
tctgattaaa actcgtgaat gggaaaatgc taaagaattt gtagaactat ctaaagaatc  20100
tcctgatgcc gactttcgtt taaaccgagc tattaaacaa gaagccgaag ctaaacgtgc  20160
tttaatgaaa tctctttacc tctgtttgca cgttattaat gcattagaag ctattcgttt  20220
ttatgtatcc tttgcgtgta cctttaactt ccataagaac atggaaatca tggaaggtaa  20280
tgccaagatt atgaagttca ttgcgcgtga tgagcagctt catcttaaag gcacccaata  20340
tattattcgt caacttcaac ttggcactga tggcgatgaa tgggttaaaa ttgctcaaga  20400
gtgtgaacaa gaagcagttg atattttcat ggaagttaac cgccaagaaa aagattgggc  20460
agttcattta tttaaagatg gagatgttcc tggattaaat acaaatagca tgtggagctt  20520
tattgattac ttaactgtat ctcgtatgaa gcagtgtggt cttccatgcc caattaccga  20580
tgctccggtt aaacatccat atccttggat tcgtgaatat cttaattctg ataatgttca  20640
atctgcacca caagaagtag aattgtcatc ttaccttgtt gcacagattg ataatgatgt  20700
tgatgataaa gttatgatga gttttaaaaa atacttttaa ggagtgggcc gcaaggccca  20760
ttttattatg aaagaaattg caacagaata ttcatttatt aaatatactg agctagaatt  20820
agacgacaac ggaagtataa aacaattatc tattccaaac aagtataacg taatttatgc  20880
tattgctata aatgatgagc ttgtttatat tggaaaaact aaaaatttac gtaaaagaat  20940
aaattattat agaactgcta ttaaccgtaa agacaaaacg tctgattcta ctaaatctgc  21000
attaattcat tctgcgctaa aggaaggaag caaagttgaa ttttacgccc gccaatgttt  21060
taatctttct atgacaaatg agttaggtac aatgacaatc gcaacgattg acctagagga  21120
gccgctattc attaaactgt ttaacccgcc ttggaatatt caacacaaga aaaaatgatg  21180
cttccacatg gagtgtggta ctatattcaa aacacaaaag aggatacaca atgcaagaac  21240
tttttaacaa tttaatggaa ctatgtaagg attcacagcg taagtttttt tactcggatg  21300
atgtaagtgc atctggaaga acttatagaa ttttctcata taattatgca tcttattctg  21360
attggttact tccagatgca ctggaatgtc gtggaattat gtttgaaatg gatggagaaa  21420
aaccggtaag aattgcctct cgtcccatgg aaaagttttt taacttgaat gaaaatccat  21480
tcacgatgaa tatcgattta aatgatgttg attacattct aacaaaagaa gacgggtctt  21540
tggtatcaac ttatttagat ggtgatgaaa ttctgttcaa atcaaagggt tcaatcaaat  21600
ctgagcaggc tttaatggct aatgggattt tgatgaatat taatcatcat cggttgcgcg  21660
atagacttaa agaattagct gaagatggat ttactgctaa cttcgaattc gttgctccga  21720
cgaatagaat cgttcttgct taccaagaaa tgaaaattat tttactgaat gttcgtgaaa  21780
acgaaacggg tgaatacatt tcatacgatg atatttataa agatgctgct cttcgtccat  21840
atctagttga acgattcgaa atcgatagcc ctaaatgggt agaagaagct aaaaatgcag  21900
```

```
aaaacatcga aggctatgtt gctgtgatga aagatggttc tcattttaaa attaagtctg  21960
actggtacgt gtctcttcat agtacaaaaa gttcattaga taatccagaa aaattgttta  22020
agactattat tgacggtgca tcagatgatc ttaaagcaat gtacgctgac gatgaatatt  22080
catacagaaa aattgaggcg tttgaaacga cttatctgaa gtacttagac cgagctctgt  22140
ttttagttct tgactgtcac aataagcatt gtggtaaaga tagaaagact tatgcaatgg  22200
aagcgcaagg tgttgctaaa ggtgctggaa tggatcactt gttcggtatc attatgagtc  22260
tataccaggg gtatgatagt caagagaagg ttatgtgcga aatcgaacag aattttttga  22320
aaaattataa aaaatttatc ccagaaggat actaagctgt ttacaagtcc ctcgtgttgt  22380
gttatagtag tcttactgac ataacatgag gactttatga tggatttgca gcttattact  22440
actgaaatgg tcgttaaagc atacggtgat actacagatg ggatttctgt atttaaagga  22500
aatcgtcgag ttggatatat caccgatctt aagaaagatt tagctaagca agtcaagcgg  22560
aaaacgacca ttaaagaata tcgaaatcgt cgtcttgagc aagcccgtga tatgcttcct  22620
gatgcggttg aggagatgaa agtcttttta gaaaatcagc ttgcgaaata tgattgcgat  22680
gtgttcatta atcagactca acctaatgtt catattaaca actgtaaatg ctatatcatc  22740
gttaatcctt taacgggaaa acatcgtctt ggaattagta atccaaatcg tagcgcatcg  22800
gatatggcag aagatgttga ggcatgcttt aaaatttcta aatctccggc tgaacatcat  22860
attttaatta acggtctttc tcaagacgat attatagagg ttattaaaac tttatgcaat  22920
taagtaatac gacagcaggt ttgctattaa ttgtaattgc attaggcgga acttctttaa  22980
ttttaaaaaa taaaattgaa agattagaaa cgtctgttgt agaaattaca aaaacggcca  23040
atgaaaacgc cttagcatta aataatttgc gaattcagta taattatatt gatgcgatga  23100
ataataaaaa tcgtgaggcg attgctgcta ttgagcgtga aaatgaaaaa ctgcgcaaag  23160
atgcaaagaa ggcggatgtg gtggctcgta agccaggatt ggttgaaaaa caaatcaaca  23220
actccttcaa caagttcgca gaagacatcc aggacctttc taaatgatta gactatcagc  23280
agtaatatta tctatcggtc ttctagctgg ttgttcgaca aagcctctag aagtaaagaa  23340
agaaacagtt catcctaatt ggcctgtaca aataaagtca tatgacgaag ctaaattatc  23400
ttggcaagtt aaagttattg atggcaaagc ttgggtcggt atgccatttg aagattctca  23460
ggaatttcgt atttggctta atgatgtaaa acgatatgta catgaccaga aaactatgat  23520
atgttattat cgtcaagagt taaaagagga taaatgtaaa tgatttcatg gcatcaattt  23580
gaacatctca aaggattgat ttatgaatcc gagatggctg caatgattta tggacgccag  23640
attcagcgat tagaatcttt acctccaact aatgatgttt tattagctca atcacgtgct  23700
aatcttaaaa atgaatacca aaataagtgg ggcaaagcat ctaaagacct gcatgattat  23760
attcaatcat tagttgagaa aaataaatga aaactctgct agaacgttat attgaatgct  23820
cagaccgtta cattgatgca tgtcatggtg cagtatacat ggatttggat cgtggaatag  23880
tattaaatga tgaagaccct gctaaagctt tagatgatgc tggtaaagcc ctgcgaaaag  23940
aagcgaaagc tcgtgggctt gatatgtatc agcttaaaaa tcacatgata aaatttattt  24000
catccaatgt tcagagtaaa tcagcgaatc aatcaacagc tgaattgtac aaaggacggt  24060
gtgagcacaa tattcgtatt cttgaagttt tcttaggaat taaatgatga aaaagattat  24120
tttgactatt ggctgtcctg gttctggtaa gagtacttgg gctcgcgaat ttattgctaa  24180
aaatccaggg ttttataata ttaatcgtga tgattatcgt caatccatca tgggtcatga  24240
agaacgcgac gagtataagt ataccaaaaa gaaagaaggt atcgtaactt acatgcagca  24300
tgatgttgct aacatgattc tctgccaaga cgcaacgaag ggtgtaattg tttcagatac  24360
taatctgaat cctgaacgac gtaaggtctg ggaagagttt gccaaagagc ttgggcatca  24420
aattgaatat aaagtgtttg atgttccttg gactgaattg gttaaacgca actcaaaacg  24480
cggaactaaa gcagtaccaa ttgatgtttt acgttcaatg tataaaagca tgcgagagta  24540
tctcggtctt ccggtatata aagggactcc tggtaaacca aaagcagtta tttttgatgt  24600
tgatggcgcg ttagcaaaaa tgaatggtcg tggtccttat gaccttgaaa aatgcgatac  24660
cgatattatt aatccaatgg tcgttgaact atccaagatg tatgctctta tgggttatca  24720
aatcgtagtc gtttcaggcc gtgaaagtgg aaccgaagaa gatccaacga aatattatcg  24780
tatgaccccgt aaatgggttg aggacattgc tggtgttcca ttagtcatgc agtgtcaacg  24840
cgaacaaggc gatacccgta aagatgatgt agttaaagaa gaaattttct ggaaacacat  24900
cgcaccacat tttgatgtga aattagctat tgatgaccga actcaagtag ttgaaatgtg  24960
gcgccgcatc ggtgttgaat gctggcaagt cgcttcggga gatttttaat ggcttggcac  25020
catgaaactt gggctattgt tattgtaaat agcggtttag ttggtactag taatgggcaa  25080
ttttgtgtat ttactagtga aaatagagca tgggaggaat gccttaaatt aagagaaaag  25140
aatcctgatg ttgaactagt agtaaagaaa actaaactgc ctttaccatg gaaaacgtat  25200
gaataaccta gaaaagattt atcgtctttg tgataaaatt gaaaaagaaa agaaatatct  25260
attttgtcta tggcctattg ttgacggaag agtaggccta gatgttcttg attatgaaac  25320
agaagacaaa gtagatggcg caacttttga taacgctttg gatgttattg attggctcga  25380
agaaaattat gtgaggtaaa tatgtttccg acttactcta aaatcgtaga agtagtgttt  25440
agccaaatta tcgctaataa tatgtttgaa aaacttgata acgcagctga gcttcgaatc  25500
cacgctcaag tgactcatgt attgaacact ttgcttccag accaggtgga ttctattgcc  25560
attacgttgt atccaggttc cgcgcatatc attgttgtat tcggtcttga tgctgagcta  25620
gttatcaaag gcgacattcg ctttgaatct caaactgcgg aattcaaagc gatttaatgg  25680
tttactttac ggtagagttg tgatattata gctctaccaa aacaaatgag gaaattgaaa  25740
tgagcgaatg gtttgaagaa gataaggttt atcgctttaa aactgggtat aaagatattt  25800
ttaatgaaac ttgcggggct aataaacgaa tcgcccagtt tattggggaa aattcattta  25860
aagtaaaaat tgaccctgca aagaatgtta ttagcattaa acgcgaaatt gatgattgtt  25920
ggtataaagc tgttgatgta atgggtgaat cctataaagt tagcccgtta ttttcaattg  25980
cttatatgtt agaatattct tttttcgaag aagttcaaaa agatgattct gtcagtaaat  26040
ttgaaattaa aactgataaa gaaattaagt ggaaagtagt aggtattact ggttgcatgt  26100
tttatatcta tgctcaaact gatacaaagg aagaagctaa aaagaaagct ctagaatatc  26160
ttgaagagta tgaagaaggc ccggtaatga ttacccaaga tgctgaatta gtttctgtca  26220
aattagttaa aaacgttgaa agtaaggagc tgggatcaac atgctaagcg aaaaaccaat  26280
tactgttaaa gaattccaag aaaaagttaa actatttgct caagaattgg taaataaggt  26340
ttctgaacga tttcctgaaa cgtcggttcg tgttattacc gaaactcctc gttcggtatt  26400
agtaattgtg aatccaggtg atggtgacca aataacacat ctcaaattgg attttgatgg  26460
attagttgaa gcacaaaggg tgtatggcgt actatgatga atttaactga tataattgat  26520
aattgtcttg aaaatgatac tggcgatcat agagcgcttg actctgaaac agcaaagttc  26580
attagaataa ctttaatgaa tgatactctg gtgaatagta ttcatccttc tgtgtatgat  26640
```

gctattattg tgacgaagta tccagttgag cttcacaaaa agatggttgg cgcaattttt 26700
attgataaga aaaaccgctt taaagatggg cagaatataa ttagttctgt tattaaaagt 26760
ataactaaac ttcgtcacga aatttatcgt gttgaaactg ctaaatctgc ttatctggtg 26820
attatgaaat gaaagcgagt acagtacttc aaattgcata tttagtatca caagaatcaa 26880
aatgttgctc ctggaaagta ggagcagtaa ttgaaaagaa tggacgtatt atttctactg 26940
gatataatgg ttcacctgca ggtggtgtga actgctgtga ttatgctgct gagcaaggtt 27000
ggttgctgaa taagcctaaa catactatca ttcaaggtca taagcctgaa tgtgtatcgt 27060
ttggttcaac tgatcgtttt gtattggcga aagaacatcg tagcgcgcac tctgaatggt 27120
cgtctaaaaa tgaaattcat gctgaactaa atgcgatttt gtttgctgca cgaaacggtt 27180
cttcaattga aggtgctact atgtatgtaa cactttctcc ttgcccagat tgtgcaaaag 27240
caatagctca atctggaatt aaaaagctgg tttattgtga aacatacgat aaaaataaac 27300
ctggctggga tgatattctg cgaaatgcag gtattgaagt gtttaatgtt cctaagaaaa 27360
acttaaataa gttaaactgg gaaaatatca acgaattctg tggtgaataa tgaaatttcg 27420
tttggtacag ctcacagcaa ttagttctta ttccaacgag aacatttcat ttgctgtaga 27480
gtataagaag tattttttct ctaaatggaa gcagtattat aagtcaaact gggtttgtat 27540
tgatagacca catagttgga aatctgattt agaaaaatgc caaaaattac tttccactct 27600
taaagaacgt ggaacaactc atattaaaac tgtaataggt aaataaatga aactgacgac 27660
tgaacaaaaa gtagcaattc gtgaaatttt gaaaactaaa ttgtccatgg gtgtttcaaa 27720
cgtagttttt gaaaagtctg atggtactat tcgtgttatg aaaggtactc gcgatgctga 27780
ctttatgcca accatgcaaa ctggtaaatt gactgaatct acccggaaag aatctactga 27840
tatgattcca gtatttgatg ttgaacttgg tgcatggcga ggtttttcta ttgacaaatt 27900
gatttccgtt aatggtatga aagttgagca tttgctccaa tttattggta aataaatgct 27960
ttaagaatta tttgttatta ttaattcatc tgttaacaaa aaggaaaaac gatgtctgaa 28020
gtacaacagc taccaattcg tgctgtcggt gaatatgtta ttttagtttc tgaacctgca 28080
caagccggtg atgaagaagt tacagaatca ggacttatta tcggtaaacg tgttcaaggt 28140
gaagttcctg aactgtgtgt agttcactct gtcggtcctg atgttcctga aggtttctgt 28200
gaagttggtg atttgacttc tcttccagtt ggtcaaattc gaaacgttcc acaccctttt 28260
gtagctctgg gtcttaagca gccaaaagaa attaaacaaa aattcgttac ctgtcactat 28320
aaagctattc cgtgtcttta taagtgatat aaataataat atgaattggg tgtcggaata 28380
ataagttaac cgaacaattc tatgtggtag tctacaactg agagatctgt cgaaagaaga 28440
tgaaattcag aagaacgtga ctaccgagtt ttaatctcta acgagaattt ttaaatgatt 28500
aaacaattac aacacgctct tgaactgcaa cgaaacgcat ggaataatgg tcacgaaaac 28560
tatggcgcat ctattgatgt tgaagccgaa gctcttgaaa tcctgcgtta tttcaaacat 28620
ctgaatcctg ctcaaactgc attagctgct gagcttcagg aaaaagatga acttaaatat 28680
gctaagcctc tggcttctgc tgcacgaaaa gcagttcgtc actttgtggt aacattgaag 28740
taatttattg gagattcact gccttagtgt gagctaaatc gaggagccgt cgaactgtct 28800
gattaatgat ttgcgaatca ttatagtttt aagaccccgg cagttttacg gtgtacctct 28860
tgaatgtgaa tgatgacggg tttatggtta tcctggtcgt taaatatcca aaaacctatg 28920
ttccccttga gggcttgcgc aggcaatgcc aataagtcct gcattttcat ttaaaagaga 28980
atttataatg gcaaaacaag ctaaagcaaa gaaagcagtt gaaaagaaag ttggtgattc 29040
taaacgcgct ggctacaagc gtgggtcgaa ctctcgtatc aatcaaactg ttgagaagat 29100
catgcgccga gcacgtgcgg ttcttcgaga tgatgcttct cgttttggta agcagaaagc 29160
ataagttgag gactccttcg ggagtccttt tttattttcc aaagattgca taaagttgtt 29220
tacagtatgg ttcctttgtg atagtattat cttacacaaa caaaggagaa taaaatgaaa 29280
acgattaatc tgaacgctgc agttaaaact aaatgcttca atggtaaata tgatgaaact 29340
atgtggttct taatggcagt tgaaggtgat attattgaag tagaaacaac agaaggtatg 29400
ggaacagatt tcacctttac aattcaagtt cataatttct ttactggttg gatttatgaa 29460
ttgaatacag taatcgttgg aaaaattgaa caaaatgaat taggtgaatg gtattatgtt 29520
acagctcgcc aacgtgccga acgcttaatt gagaagatga aaaaagttgg taaacttgat 29580
atgcagcatt ggaaagtagt aaaataattg tttactttgg tacaggatat gatattatat 29640
acctgtaccg caattaaaca tcttggagaa taaaatgaac tacatcaact ttgaacgtaa 29700
atatgtttct aatggtatta caggttctat tgataccatc tgcctttgga aacatcaaaa 29760
tggatcagta tgcgaaattg aacagtacat gactcctaat tacgtttata tgcgatttga 29820
aaacggtatc acggtttcaa tcacgatgga aggttccaac tttaaaatcg ctctggatga 29880
tgatttccgt gaacgcgatt tagggactca tccttgctgg aatggcgtta atcgcaagct 29940
tttggttaaa acttggattc gtcatattct gagtaacaga gctaaacctg agcatcttga 30000
agcaatcttt gatgtagttc ttaacgaatt tgatatttaa aataaatgag gggctttggc 30060
cccttactga ggaaaatgtt atgtttatga ccacttattt tgatactcgt aaaaacttct 30120
gcgaagtagt tttctcaaag gcgcctaaag accttcctgc acatttgcag cctactagcg 30180
aatcgattaa aaactacgtt gatgtggttt gtcctttaga gtttcgtact gtaaatgggc 30240
gcgatacttt agctatcact aaactcaatc gtgaaattga cattgacccc tcaattgcac 30300
gtgaaattaa tagttctgat attaatggcg gtaatgttaa atcgcacggt tttcagatga 30360
ggttttaatg aaattctttt taggtcaaac tgttgaatta aagggagttg gtatacctgg 30420
attaatttct aaggttctac ctccgtttaa atggagtggt attcaaataa aagaggctta 30480
tattgttttc tgggtagatg gaaatgaaga ccttcgtatg ggtgatgaat tatctcctat 30540
ctacggatta aaggaaatag tatgaatata attaataaga tttttggaat tcagtacatt 30600
aaggtcacat ataaagtaac agataaaaat ccgtatactg atgaacatga agaaccgcaa 30660
gttgagtcta ttatattaga aaaggaccct aactggccag ttgaatttcg tcttccttgc 30720
tatggtcatt gggctgatgt tgaaattata agcattgaaa atgtctgagt tagagattag 30780
aagcaatttt aggtggccat catgtgcatt aagtaatttc gcccattggc ctttcgttat 30840
ggatggcatt caatttggag gtcttgaagg attcctccaa ggatgcaagg tgaaaaacgt 30900
tgaacaacaa cgtcgtatat ttgggttatc cgggcttgcc gctcaacaag ctggaaggtc 30960
ttatgcaaga gctcaggacc gtgggaccct cttctggctt ggagttccat tttcaagata 31020
ctccccggcg tggaaagaat tatacacaaa tgcatatttt gaagcagcga tccaaaacaa 31080
gggcttccgt gatgcattac aagcctcgaa aggaaaagtt ttgaagcaca gcatggctag 31140
tggtctaaca aaagatgata caatactaac cgaagctgaa tttattgatg tgttaaacct 31200
attaagagac tctctatgaa gcctactatt ttaactgata ttgatggagt atgtttaagc 31260
tggcaatcag gccttcctta ttttgctcag aaatataatc ttccgttaga acatatttta 31320
aaaatgatcc aggatgagaa atttatttct cctggtaaac tctttaattg tgacgaagaa 31380

```
cttggcgtta agctaattga aaaatacaat cgttcagatt ttattcgtta cttgtctcca  31440
tataaagatg ctctgtgtgt aattaacaaa ttaaaagaag attataattt tgtagctgtt  31500
acagcattgg gtgattctat tgacgctctg ctgaatcgtc aatttaattt gaacgctctt  31560
tttcctggtg ccttctcaga agtactgatg tgtggtcatg attcttcaaa agaagagttg  31620
ttcaaaaagg caaaagagaa atataacgta atttgttata ttgacgatct cgctcaccat  31680
tgcgatcatg cgagtgaaat attaaatgtt cctgtttatt ggatggctcg aggggagcgt  31740
gacaatattc caaaaactgc tcagcgagtt tatacatgga atgatgtaga gaataagatt  31800
ttttcgccga aggaaaataa agaaagtttt gatcgtgaaa aagctataaa agatgcaatc  31860
gagaagatga ttaaaaacga ttcttttcct tggaacacta cctggagaac gcctggattt  31920
aatccttata atcatctata tcatccatat cagacacatc cgtttcagac atggaactat  31980
attaaacctg gtggcataga gtatttgtat aatagaccta ctagtggtga taatattttc  32040
caaggagcat tctaatgttt gttgttcaca ctatttatga aaatgaaggt aatactacac  32100
gtgattacgg tcacgtaaat caattttttta gatgcaatcc agaattccga gctcaaaaag  32160
acgaacgaat ttttaaaaaa tgtgtagagc aaggtttcat ttacgtcaag cactggatgc  32220
aaggaaataa agttagaacc acatatcata agtctttgac tgagcttaat gatgaattga  32280
tttataatag agctgtaaac caaactctga aggatgaata atgattctta aaattctgaa  32340
cgaaatagca tctattggtt caactaagca gaagcaagca attcttgaaa agaataaaga  32400
taatgaattg cttaaacgag tatatcgtct gacttattct cgtgggttac agtattatat  32460
caagaaatgg cctaaaccgg gtattgctac ccagagtttt ggaatgttga ctcttaccga  32520
tatgcttgac ttcattgaat tcacgttagc tactcggaaa ttgactggaa atgctgcaat  32580
tgaggaatta actggatata ttactgacgg taaaaaagat gatgttgaag ttttgcgtcg  32640
ggtgatgatg cgagaccttg aatgcggtgc ttcagtatct attgcaaaca aagtttggcc  32700
aggtttaatt cctgaacaac ctcaaatgct tgcaagttct tatgatgaaa aaggcattaa  32760
taagaat                                                            32767
```

```
SEQ ID NO: 5            moltype = DNA  length = 32767
FEATURE                 Location/Qualifiers
source                  1..32767
                        mol_type = genomic DNA
                        organism = Escherichia phage HP3.1
SEQUENCE: 5
```

```
ccgccgccgc cgccaccgcc gcctgcaata gctccgccat tattaattct tagtctccca  60
ccaatatcgt tttgaataca atgacctcca gctgaaccag gactattgct accgccatta  120
ccgccacgtc catacatcgt tacgccgtgt atattcaact gaacatattc attcggtgta  180
tctccgtaca tgaagaataa aggaacatct ttagaatatg atactaaatc acctgtaata  240
ttaaacacta taggtgcact acctgcctca aaacatctat ctcggaacca ttgaccattg  300
aagttatggt ctgctccaag cgtgtgaata atttctcgtg agcgacctgc aaattgactc  360
atccagcaag gaacacccaa tcttaattga ccagccgctt gactcatcca gcgctgtcct  420
gtttcatttg cggctgaact tccaatccaa ccaggaacac caactactgc cataatttat  480
actccaaagg gggcatttcc cccttgttgt tagaatttaa aatatttact aattttgcga  540
gcaattttag taaagaaagg agttttcaat tctttaattt cttcactcat ttcctgaata  600
gccttaatta aaagagcatt cacagcagag ttagaaattg tcagaacatc agatccatca  660
acttcaactt tagatacagc ttccggtaat tccttttcaa ggtcctgagc aataatacca  720
acttcacgtt taataacact acggtcttta atagacttaa ctttatcgta aatataaact  780
ttcagtcgac atacttttc aagtgctccg ttttctagct cttttttatt aatcttaaga  840
cgaccatcgg aacgaatata cacatcgtta aagttaccat taccaggaga atagaaagta  900
ccgtcgtaat gaaattcaaa taccgcgtta gggtgtccag ccgctggcga tgcctccgca  960
gatccaacac gaataattgc ttgcccccaa ttgttaggga cacgacgaat accaagatcg  1020
acggcagtta caaacccttg attggtgatt acacttcttc ctttgagaat cggataataa  1080
caatcctgtg aaacataacc atgatcgacg aatattggtg cttctactcg ccattggttg  1140
ccccaatcac ccggttgtct agcaatccat ccagaaccgt taatgtgtac acgatcgcgg  1200
ttaacgttaa ccattgcgat attttgtgga tttagcgaaa tctcaccatt gtttgtgata  1260
tgtactgccg cctgagtagc atagctataa aatgctagcg aattatcagc accaccctta  1320
ccaatatacc agttaccact cccgtctacg tcaccacgaa tatgcaaagc attaccagca  1380
gttgttgata atacaataga atcacccgga cgtttaataa tcaatctacc ttcggattca  1440
atttcaccaa aaaatttagt cttaattgca ccagtcgcta aagtacgttc agtggaaaaa  1500
tgaacgcctt tgctgtcttc taactgaata atgttatcgc gcgcattatt actatcaccc  1560
caatgattaa accggaaata atcacgtgat tgcttaccac ccgcttcaaa cgtcagcgta  1620
cctttactta aattaacatc accgctaaag gtagcagcaa gagaatcacg ttctaatttt  1680
aaaacgttag caccactagt accacctaaa gtaacatcac cagttctcaa ttcataacgg  1740
aaaggtctat ttgtattata gtttccattt tgatcatctt cgttggtgga aagaatataa  1800
agattctctc cataagtacg gaaaattgta ccaaaatttc cggcatacat acggaatgca  1860
ttagatgagc gaaatttaac ttctgtttta aaagtggtag tgttattaag gttaacagta  1920
gagttaaaat tggtaggagc accgaagtta actgcgccat taaaatcttg ttgagctgtc  1980
catgtgtggc gaccatcttc aagaacaaca cggcggactg tgcaagttct atttccagaa  2040
ttaccgaaca cacgaacgac aaaataacgg tagtttgtct gggatacagt accgcgccaa  2100
acctgaacag tacgccctgt gctagtgtgt tcgctaggac caacggaaaa cataaccagg  2160
tttccgtcaa tcgtccccca atccatattt gctggcatat tctttatttt gttcaaagga  2220
acactaaaca tactaccagg gacaaaatca aaggtttgcc aatctagctc cgctaattga  2280
gttttaatac cacccatacc caaagtaatt ggcaaagagt aagatgtata tacttcgttc  2340
catgtacccc acgcgccacc ggtatatgca cgctcaaaaa tacgatcgcg agtagttgca  2400
cccgttccgg cagtagtaaa tttttggaaa atagcaccac cagaagcacg ctgtttaact  2460
tccagcaaac caacaataac ggctggtaaa ccttcaccag taggacagtt aataacggca  2520
tcagtgccta aaatgttata taacccagga gttttaaaat cattcagatc tccatcatag  2580
aaagtcgctg gtgtgccatg accaacctgc ttccattcct cccacttagg tgcactagca  2640
tcccatgcag cagcgagaca acgagtataa accatacca tgcgggtagt ataacgctga  2700
gttctcgtgt ataaaccacc ttcaaatatt tctaaaaatc cttgtgcggc tgatccttct  2760
tctggataat ggcgatcaaa tgatgcgatt gcgcttgaac tgtttcgcca taagccacaa  2820
tgttctaatt ctcccaagct atcaaggtca atcgtttgtg aaagtggacg agttgacgct  2880
```

```
tgaacattac gccacacacc ccatggacca ttgacgccat tccatttagc agataaggaa  2940
cgaatataga cgttaccaga tcttacagta taacgctgag tgccagcaaa ttggccggcc  3000
acaaacactt ctagtacacc tacggcattt tcttctggga atttatttgc tggttgcgca  3060
tttgttgaag tagatttcga ccaaacacca agatattctt caatgggccc atacgtatct  3120
aaattagcat cagtaggtaa ttcgccatta tttttataa atgttgtgct attgacattt  3180
atgtcagatg gagttaaggt aatgtccttt gacccatcaa aagatatacc attaattttc  3240
ctaggtgttt gcaatttagt agctgtgcta gaatttccaa ttaaagttcc agttatattt  3300
tctgtaacct ctaaagaccc atttatagtt cctccatatt ttaaacctaa ttctataaca  3360
ctacctgagt catcttttgt gaaaattgtt ttatctttta agtttatagc caattcacct  3420
tcggctaata ctgaagcagc aggacgttga cctgcagttt tgcttctttt aaattgtatt  3480
tgttttaaag tagccataag tcctcttaat aatagccgaa atcttgaaca gaatccttaa  3540
ttacgatttg gtcaaatcgt ggaacgtgtg aaggttgaga tgcaggattc tgtgaaaaaa  3600
ggtttggcgc agttaaattt cctgtcatag tgtctccaga gcgtaatacc ctagagtttg  3660
catttgctgt aacagtattt attgctccat caacataatc tttgcgagta acatcagatg  3720
ctgcggaagg agtagatgta acagttaccg atggagccgt tacagccctg gtaaatgttg  3780
tcaaaccttc tggcgtaata gtaatttgtc cagtagtgat ttcactacct gctggtctaa  3840
aactaatacc gccagaagag ccaccaacta caagagtatt accagtgccg ccaccagaac  3900
gaattcggat gggggtttca ttattactta attgaagata actatttacc ccgtaattaa  3960
tagtaattgg accggtgtaa gtaccaccat tagctttaga aacgaaatcg ttatcagctg  4020
cctgcggttt attatattct gaatatattt taaatgattt gtagagtaca tcgtcaccgg  4080
ctgaattcaa tggaaaattt ccttgatgcc aaatgacaga tccacctaca gttgaaccta  4140
cttttaaatc agccattata tgccccttta ttttaatatt atttataaag aaaaagggaa  4200
cccgaaggct ccctcagttt aaacttctct aaattcttgc ccaaacactt tgccagtttt  4260
agaagaggct tgtgtaggaa gtaccattat atctggaggt gaagccgatt cgcagacata  4320
attaacgcga ataccgttga cgccaaattc ggcaggtttt gaaatgccgc catttcttga  4380
tacttcagaa aagcttaaat ttctcatgcc gccttgacct gcttgggcag ttctttgtgc  4440
atatatcgta aatcctactg cattttcagg aacaactaca taatcttctt ttaattccca  4500
agacccagct tgcccagtaa actcagcttg ggtcgaggaa atatatccat ttgatgcatc  4560
ataaaaacga atagatatat ttgtagttcc aagatcaagt aaatcagcat cagcatatag  4620
ttgtgcttta agataaagaa catcaccagg aattaaattg tagtcagaaa gtttacttat  4680
agcagctgaa gttggcaatc gcgcaatttc attattagtt cctccaaccg cagacataaa  4740
ttgctcaacg ctttcgtatg ttcttttagg aaatcctgta gctccgacgt cttctaaact  4800
atcaaataca acatctaaaa tagtttgata atcatctgtg ctttttctat tacttagttt  4860
aacatgctct aatgcaatag ctcttttaga agaagtataa aaagcagcat atgatacgtc  4920
aaatcttgac aatactgaat ctgatggaaa aactgaagtt cctgctcccc ttaaccaaga  4980
taccacttca ggaggaaaat taacctttcc gctagttaat atagcagcaa gtctattgtt  5040
tgacaaagaa ttcatgaaac tgacaaaagc agctgatgta gtattatttg aagcagaaaa  5100
agcatatgac ttgctatcaa ctaatgctcc cgtagaaggg tcaaaaactc ttaaatgaag  5160
acctgcacta aatgtttgat ttccaacggg attatcctga aatttaacat atggccccgc  5220
agtagaaagc gggcaagaac ccgctatgct tattttatat cttactgaat tgctttccga  5280
taaaaatggc gtttggacat atccttgtcc aaactctgcc ataaattttt ccataatacc  5340
tcttattcaa cccattcaaa tttaacagtt ttattcactg ggtcaggaat aatgcgaaca  5400
ttaccaattc gtaagaaatc acgaatagta agattaccta ttattccatt atcagatggg  5460
atcgctccta tatctgaagg ttgaggaggg ttacctccgt caaatacctg aacaaaactt  5520
gaccaagagt ttttggtttt ctgccatgta cgtgtccagc gagtggtacg tgcttctggg  5580
gtcgttggat aagtaatcca atcttggtaa agcgaatcaa gtgtgttacc aaactgagtc  5640
aatgtaccag gagatttaac ttcttcgcca cgttctaagt atggaagccc agtcacttca  5700
ttagtttttt caaccatttt aaaataaccc gggaactggt tataagtggc tgaatcatta  5760
atatcgattg accagaatcc tacagtatca gatgtcggcg cgcgggtata taaatcagag  5820
gttttagtac cctgagaacg aattctcgag ttaacagtca aaccacccga acttatagta  5880
gcaccttttg caatgattaa gctttcacca atcgttactt ggccagatgc attattaata  5940
gctaaaggac gcaatccatt aaatacgcca gtttgatcac ccgatgcagt aagcataaaa  6000
ttcgttactg atccatcatt gcgaacaatg aaaccataat ttccgttaat agcacggaaa  6060
gcatttgcgc ttcgagaaat aatttcacca gttgcagtga ctgaattacc aaatgttgct  6120
acaccatttg cattcaatgt tcctgaagca ttaacattta tcggtgttac tgtaccgttg  6180
atattaaatg ttatatttcc agctttatta cgctgagaat aaaaatgact agacgtttca  6240
tcactaactt caaatacggt agaacgtgtt gtgtctgatt ccccactaaa ttgatttccc  6300
cacactctga ctgtcatcgt ttgagccggg tttgttccag tttgaggtcc tttctcaaaa  6360
atcagacgag ttgccgttcc agtattagaa atagttaatg tactatttgc tgaaactgat  6420
ccaccgaatg tagcagtact agatgataca agaggggcac tcagattcgt ttgttgggtt  6480
aaggttagtg aaccattaac tgtttgtgca atgtccctac gaatgaactg gagcgaatct  6540
agaccatcta ataaattact atctacggct tttgctttta atggcaaata atttgctaat  6600
acgcgattta attcatatgg tgatactgca taaccatttt tctcatatga ttctaatggc  6660
tgtgttgaac cagctgtatc attaccaacg aatgtaattg aaccagacga agttttaaca  6720
aaacctctta tcgcagtagt cgctgcccaa gtaggttcac tctgcacaat ccattttaaa  6780
tttttggag atacagcagt atttgctgac gttccagcta cagtttcaga ccgagttgca  6840
actttaataa cgccttcctg tgcttcagta gatttagtac ctaaaagctt tttaggagtt  6900
attaaaacat tatctaatgt tcctgcagca gcttcaactt gtgtagctac acgaagtgta  6960
ccacgctgtg tctcatttgc ttcaagaata ttaagggtat aatggtccca gagagttcct  7020
gattcaacta atccagatag agcaacaaca gaagtacgat cagtactatt aaatctggtt  7080
ttaattttta atggtgtaga gatacgagta tcgtcgacgc ctgcgtcgaa ttcaacctgt  7140
gtagcaattt cagctatacc acttaaactt tcagttgctc tacggtcatt taaagtttta  7200
ggagtgactg cacgagtata atcagttcct gtattaactt cactttgcgt agcaatttca  7260
attaaaccaa ttcttccatc agttgatgtc tttttatgta acgtttctgg tgttacaacc  7320
gcatttgccc atccttcttg gctttgtcca gcaattactt cactttcaac tgctaaaatt  7380
actgcgcctt gttgcgttgg agtagcttta tactgatcca aagctttagg tgaaacaact  7440
aaattattag tgtttttatt ataaacattc gtaccattta attcacgact agaagctgga  7500
gtagctcctg cagtagatac aaaagttaca atacccgata atgtttcaga accttgacga  7560
gcttgaagct ttttaggagt gatgattgta gtatcatcga tacctgtatt agtttcctgc  7620
```

-continued

```
tgcgtagcaa tttcagcaac acctctgcga gtttctgtag cagttctttc attcagcttt  7680
ttaggagtga tgataaggtc atctgcaaaa gagaatgtag tgttctgatt tacttgagca  7740
gtagttgcta ttcttgcaat acctctgcga gtttcagtag cagtacgatt agctaacgtt  7800
tctggagtaa ttgctaattc tttttgtgga gaattttcta aatcagcatt tgcttgagct  7860
tgcgtagcta aagcaattac gcctaatctt gctctagtag aagcatttaa agagtctact  7920
ctttctacag ttggaacgtt ttgctgtaca acccagtatt ttccatcaga atcttctata  7980
taagcaagtt gcaaaactgg tacataatta gtttcaccat taaaaactaa ttcttgaact  8040
gttacccatt cagcttcagg cggatattct gaacgttttg ggaattgcag caattgaact  8100
gaagaagcaa ttttatcttc accagcagct ttgattttaa ctgtttgtcc ttttctcatg  8160
taattcatgg aaattttaac agtatcacca acagaaatat cagtcggaag ctgaagttca  8220
attgtttggg ttgttccatt attcgcgcca aataccatga cttcttcatt tggacgaata  8280
tttgaattag ttgttataat gcgtaaacgt gctttactat ccccgtcaaa caatctccac  8340
aatttctcat tatcgtcaaa catcaagaaa ccgtcaatcg atgtacggcc ttcaatggaa  8400
tgagttccaa cttcttgtac tgaagtcgtt tcatcgtatg tagtaacaat tgtatgataa  8460
agtggattca gtttatctaa atcaacgaaa ttaataatat cgccatgatt agcaaatctc  8520
ggaagtttaa cattaattgg tgcagcagaa gtaaatctac gtacgataaa atcattagat  8580
tgtgcttgat acgcagtcga tggagtaaca atcgcagctt ctctgctata atcagcaaca  8640
tacatttgcc acaaacgatt attaaaaatg aatatcatct gtgactttgg atgagtcatt  8700
aaaactgaac gtacctgttc acctctaaaa ttgacaatac tctgatttga agaatttatt  8760
ttaacctgat ttatgccagg ttttccaccg atatcttgaa ttattacggt ttctccatca  8820
agcggagaag gtggtaaagt aaactcaatg tcattgccaa ctgatgtatc tactgaaatt  8880
gcttctccgg attttaattg atatggtcca gatgatacgg ttgtatatac ggcatcagta  8940
cgtaatgctt tccaacgaat tctattaaaa tttccagcag gttttggaat attatccgtt  9000
gctgcccaaa aacgattatt ataaatgatt acaaaatctt ttaaatatcc acgagttggg  9060
tcatattgct gaactgtgtt ttcttgaatt aagtaatcaa cgttaacacc gtcagttcct  9120
acggtacgat cagctaaagc tacgttgatt attttatcgc cacctgcgtc cagaccatct  9180
tctgctctga actttctttt aatctcggcc attctcccgg gctcctattg tgttttcaat  9240
aataagtatt tatacctgtt tactttaaga tttagatagt atataataga aatctcacta  9300
attgaacgag gttcatatgg atttagaaat gatgctggat gaagattaca aagaaggaat  9360
ttgctttatt gactttagtc aaattgctct ttcaactgct ctggtaaact tcccagataa  9420
agaaaaaatt aatttatcaa tggttcgtca tttgatattg aactcaatta agtttaatgt  9480
caaaaaagca aaaacgcttg gatacactaa aattgtactg tgtattgata acgcgaaatc  9540
tggatactgg cgtcgtgatt tcgcttatta ttataagaaa aaccgtggaa aagcacgaga  9600
agaatctact tgggactggg aaggttattt tgaatccagt cataaagtta tagatgaatt  9660
gaaagcttat atgccataca ttgttatgga tattgataag tatgaagcag atgaccacat  9720
tgctgttctt gttaaaaagt tctctttaga aggacataag attttaatca tttcatcgga  9780
cggtgacttt actcaacttc acaaatatcc aaatgttaag caatggtcac cgatgcacaa  9840
gaaatgggtt aaaattaaaa gcggttctgc tgaaattgat tgtatgacta aaattcttaa  9900
gggtgacaaa aaggataacg ttgcttcagt taaagtacga tctgactttt ggtttaccag  9960
agttgaaggt gaacgaactc cttcaatgaa aacttcaatc gttgaagcta ttgctaatga  10020
ccgtgagcaa gctaaggtgc ttctcacaga atctgaatat aatcgttata aagaaaattt  10080
agttctaatt gattttgatt atattcctga taatattgct tcaaacattg tgaattacta  10140
taattcatat aaattaccac cgcgtggcaa aatttattca tattttgtaa aagcgggtct  10200
ttctaaatta actaatagca ttaatgaatt ttgaggtgaa taatggctaa aaaagaaatg  10260
gttgaatttg atgaagctat ccatggcgaa gacttggcta aatttattaa agaagcatct  10320
gatcataaac tgaaaatttc cggttataat gaactgatta aagatattcg aattcgtgcc  10380
aaagatgaac ttggcgttga tggtaagatg tttaatcgtc tattagcttt gtatcataaa  10440
gataaccgtg atgtgtttga agctgaaact gaagaggtag ttgaacttta tgacacagtt  10500
ttctctaaat gatattcgtc cggtcgatga gaccgggctt tcagaaaaag aactttcaat  10560
taagaaagaa aaggatgaaa ttgcaaagct tcttgaccgc caagaaaatg gatttattat  10620
tgaaaaaatg gtagaagagt ttggaatgag ttatcttgaa gctacaacag cattcttaga  10680
agaaaattct attcctgaaa ctcaatttgc taaatttatt ccttcgggta taattgaaaa  10740
aattcagtca gaagccattg acgaaaatct tttacgtcct tctgttgttc gttgtgaaaa  10800
aactaataca ttagatttc tactatgatt aaactccgca tgcctgctgg tggtgaaaga  10860
tacattgatg gtaaatcagt ttataaatta tacttaatga taaaacaaca tatgaatgga  10920
aagtatgatg ttattaagta taattggtgc atgcgggtgt ctgatgccgc ttatcaaaag  10980
cgaagggata agtatttttt ccagaagtta tcagaaaaat ataaattaaa ggaacttgct  11040
ttaatcttta taagcaatct tgttgctaac caggatgctt ggattggcga catctctgac  11100
gctgatgcac ttgtgtttta tcgtgaatat atcggacgct taaagcaaat taaatttaag  11160
tttgaagaag atattcgcaa catttattat tttagtaaaa aagttgaagt ttctgctttt  11220
aaagaaatct ttgagtataa tccaaaagtt caatcaagtt atatttttaa actacttcaa  11280
tcgaatataa tttcgtttga aacgtttatc ttgcttgatt cgtttttaaa tataattgat  11340
aaacatgatg aacagactga taatttagtc tggaataatt attctataaa gttaaaggct  11400
tatagaaaaa ttttaaatat tgattcacag aaagctaaaa gtgtttttat tgaaactgtg  11460
aaatcttgca agtattgata tgaatatagt atattggttt acatttgaag accgtgtcaa  11520
aaataagact ccaccgtact actatatcgg tagtaaatta aattgctcat ttgagaacgg  11580
aataatatat gactcttccg gaaaggaata ctggagctca tgtaaacaaa aaagattttt  11640
gaatgcgcta atgcttcaaa aaccgagcgt taaaataatt caaattgatg atgacttgga  11700
tgttattgaa gcagaacgaa aataccaact tgaagtaaat gcaagagata atccagacta  11760
ttttaatctg gtatatgctg gtggtggatt tggtgtgagt ggtgaaactc atccagccaa  11820
agacccggaa gttagagagc atatgagatt ggctaattat atgaaccgtg acgattttag  11880
accttggaaa acatcacgag ctaatataga gtcttggaaa ttatctcata ttgcttacga  11940
gaattatgtg ttattattat cctctaatct gtacggtaaa actcctggat ggcgaagagt  12000
taaaggtaat ataaatataa ctgatacaac tgctaaatcg atggtaaagt atttcaactt  12060
aggttggata cctctcgaag acccagagta ttgcgaatta tgccagctat gaggtaaagt  12120
gtcatagcac caactgttaa ttaaattaaa ttaaaaagga aataaaatgt ttaaacgtaa  12180
atctactgct gaacttgctg cacaaatggc taaactgaat ggcaataaag gtttttcttc  12240
tgaagataaa ggcgagtgga aactgaaact cgataatgcg ggtaacggtc aagcagtaat  12300
tcgtttttctt ccgtctaaaa atgatgaaca agcaccattc gcaattcttg taaatcacgg  12360
```

```
tttcaagaaa aatggtaaat ggtatattga aacatgttca tctacccatg gtgattacga  12420
ttcttgccca gtatgtcaat acatcagtaa aaatgatctg tacaacactg acaataaaga  12480
gtacagtctt gttaaacgta aaacttctta ctgggctaat attcttgttg taaaagaccc  12540
agctgctcca gaaaatgaag gtaaagtatt taaatatcgt ttcggtaaga aaatctggga  12600
taaaatcaat gcaatgattg cggttgatgt tgaaatgggt gaaactccgg ttgatgtaac  12660
ttgtccgtgg gaaggtgcta actttgtact gaaagttaaa caagtttccg gatttagtaa  12720
ctacgatgaa tctaaattcc tgaatcaatc tgcgattcca aacattgatg atgaatcttt  12780
ccagaaagaa ctgttcgaac aaatggttga cctttctgaa atgacttcta aagataaatt  12840
caaatcgttt gaagaactga gcactaagtt cagtcaagtt atgggaactg ctgctatggg  12900
tggtgccgct gcaactgctg ctaagaaagc tgataaagtt gctgatgatt tggatgcatt  12960
caatgttgat gacttcaata caaaaactga agatgatttt atgagctcaa gctctggcag  13020
ttcatctagt gctgatgaca cagacctgga tgacctttg aatgaccttt aatagattat  13080
attactaatt aattggggac cctagaggtc cccttttta tttcaaaaat ttttcataaa  13140
acggtttaca tccttgtcct tccatggtac tatacaacta tcggcaatac tgctgataat  13200
taaagaggaa aataatatgg ctaaagttga tattgacatc gttgattttg aatatattga  13260
agaaattatt cgtaatcgtt atcctgaact tagtatcaca agtgtacaag attctaagtt  13320
ttggagtatt caaatcgtta ttgaaggtcc tttagaagtt cttgagcggt ttatggctaa  13380
tgaatactgc gatggtatgg atgctgaaga cgtagaattt tacatgggac tgattgaaca  13440
ataattatca aggggctatt aagcccctat taaaatgagg aaaatcaaaa tggaaatcgg  13500
caaaaaatac gagttaaatc cacatcgtat taaatctttc attgatatta gttcatcaaa  13560
tgctagtatg gtcggcatca ttcaagaaaa tggcggttgg tttgaagtta aatcaatatc  13620
aagtttagat ggctttgatt atgtaaccga aatcatttgt gctaatggtg aaatctataa  13680
tgatgatggt atgggtgatg attattttga acttagtgaa gaagagtttt attgtttccg  13740
cgaatataaa gaaccgactt ctgaagagga tgaagtcaaa gacaaggttt ctggcgtaac  13800
aaaaattcac tgcattgttg acgaaaacaa tgcagatgaa atcattgaac ttttgcgaaa  13860
aactttcaaa aagtagttta catcagggta gtagtgtgat actattaccc tatcaaaact  13920
aatggagaaa agaaaatgtt cgcaccttat attatggcag cagttatgtt ggtctgttta  13980
tatcttttga ttaaagcttg ctaaggagaa taaaatgaga ttacaacgtc agagtatcaa  14040
agattcagaa gttagaggta aatggtattt taatatcatc ggtaaagatt ctgaacttgt  14100
tgaaaaagct gaacatcttt tacgtgatat gggatgggaa gatgaatgcg atggatgtcc  14160
tctttatgaa gatggagaaa gcgcgggatt ttggatttac tattctgacg ttgaacagtt  14220
taaagctgat tggaaaattg tgaaaaagtc tgtttaagga aaataatatg atttttgtat  14280
ttgaatttat gaatgatgaa ttcgattatg caatttttaa cgcattgcat aatcctgatt  14340
taagtgaatt taatgaaatg ttttctgatg ctttgagtat gtcagaagaa tactgtggag  14400
aatgtcaacg tgtttgtgtg acagtttttg aaaacaaaga aaagacgtat gaagaattat  14460
tctttgatgc taataaagcc actgaatggt ttatcgaaag aggatttgcg taatgattaa  14520
attggtattc gcttattctc caactaaaac agttgaaggc tttgacgaat tagcatttgg  14580
tttaggtgat ggtttaccat ggggacgagt taaaaaggac cttcagaatt ttaaagctcg  14640
tactgaaggt acaattatga ttatgggtgc taaaacgttc cagtcattat ctacattact  14700
tcccggtcgt agccatattg tggtgtgtga ccttgagcgt gattatcctg taactaaaga  14760
cggcgattta gcacatttct atattacttg ggagcaatat ataacttaca tttctggcgg  14820
cgaaattcaa gtgtcaagcc ctaatgtacc attcgagact atgcttgatc agaattccaa  14880
agtaagtgta attggcgggc ctgctctgtt atatgctgcg ttaccttatg cggatgaagt  14940
agttgtttcc cgcattgtta aaaggcatcg tgttaattca acggttcaat tagacgcaag  15000
ttttcttgat gatataagca agcgtgaaat ggttgaaacg cattggtata aaatagatga  15060
agtaacaacc cttacggaat cagtatataa atgaaataac acgtggcgga aaatatgaat  15120
tttaattatt accctattct attagaagaa gacgcgaaac agccaaagtg gcagggtcct  15180
cagtttatta aaggtgtcta tcaattagta gttcctaaag acaagattta tagcagttgt  15240
ttcactgaat ccgcttgcag tattttcggt aatagttctc cgtattggaa ttttgacata  15300
aagctggata gaaatatcga tatttggttg aaagctatgg atattggtaa tatcacgttt  15360
gatgagaata attatcatat tattggtcgc ttttccaaac gcggtaaaga attatatttc  15420
acgcctgaaa ttgagagaaa atttgatgct aaaccgtatt gattatttag cttcataaaa  15480
tgtattataa tttatataag gtactaaatg aaacaatacc aagatttaat taaagacatt  15540
tttgaaaatg gctatgaaac tgatgaccga acgggcacag gaacaattgc tttgttcggt  15600
actaaattac gctgggattt aactaaaggt tttcctgcag taacaactaa gaagctcgcc  15660
tggaaagctt gcattgctga gctactttgg tttttatcag gaagcacaaa tgtcaatgat  15720
ttacgattaa ttcagcatga ttcgttaatc caaggcaaaa cagtttggga tgaaaattac  15780
gaaaatcagg caaaagattt aggataccat agtggtgaac ttggcccaat ttatggaaaa  15840
cagtggcgcg attttggcgg tgtagaccaa attatagaag ttattgatcg tattaaaaaa  15900
ctaccaagtg ataggcgtca aattgtttct gcgtggaatc cagctgaact taaatatatg  15960
gcattaccac cttgtcatat gttctatcag tttaatgtgc gtaatggtta tcttgattta  16020
caatggtatc aacgcagtgt agatgttttc ttgggttaat tgaggcctag gtataaggtg  16080
acttatactt gtaatctatc taaacggggg acctctctag tagacaatcc cgtgctaaat  16140
tgtaggacta ccctttaata atttcatcag gattagttac ttaccgtgta aaatctgata  16200
aatggaattg gttctacata aatgcctaac gactatccct ttggggagta gggtcaagtg  16260
actcgaaacg atagacaact tgctttaaca agttgaagat atagtctgat ctgcatggtg  16320
acatgcagct ggatataatt ccggggtaag attaacgacc ttatctgaac ataatgcttc  16380
catttaatat tgcatcatat gctacgttag ttcatattgt agctaagatg tgtaatctta  16440
ttccgggaga tttgatattt tccggtggta atactcatat ctatatgaat cacgtagaac  16500
aatgtaaaga aattttgcgt cgtgaaccta aagagctttg tgaactggta ataggcggat  16560
tgccttataa attccgctat ctttctacta aagaacaatt ggaatacatt cttaaactca  16620
ggcctaaaga tttcgttctc aaagattatc agtcccacgg cgtcttgaaa ggaaaaatgg  16680
cggtgtaatt tcaatttaat tgcgaggata tatgatttta cgatttaaag atacttctgg  16740
tgcagttctt tttacacttc ctaatccaag tgagctagaa gttccaggac caaatcagcc  16800
tattatcatt tatggcaaaa aatattatac tcataaaatg actcgtgagt attttgataa  16860
taaaatttct acagttaaaa cttcttctga ttgttactat gatattactg ttttaacgga  16920
aaaacaatat gacgaattat caccgcgcgg gccgtctatg tcgggtagtg aataaatata  16980
aatccgactt tgatgtcaat attcaccgcg gtacattttg ggaaattac gtcggtaaag  17040
atgctggcag ccgggaggct gccattgaat tattcaaaaa agattttata cgtcgaatta  17100
```

-continued

```
aatccggaga aataactaaa gcacatttag agcctttacg tggaatgagg ctaggatgca  17160
catgtaaacc aaagccgtgt catggtgata taatagctca tatagttaac cgattgttta  17220
aagacgattt tcaagttgag gacttatgca attaattaat gttatcaaaa gtagtggtgt  17280
ttctcagagc tttgacccgc aaaaaattat taaagtttta tcttgggcag ctgagggaac  17340
atcagtagat ccttatgaat tatatgaaaa tattaaatca tatctccgtg atggaatgac  17400
aactgatgac attcagacta ttgtcattaa ggctgctgcg aattctattt cggttgaaga  17460
acctgattat caatatgtag ctgcacgttg tttaatgttt gctcttcgta agcatgttta  17520
tgggcagtat gaaccacgtt catttattga ccatatttct tactgtgtaa atgaaggtaa  17580
atatgacccc gaattattgt caaaatattc agcagaagaa attacatttt tagaatcaaa  17640
aattaagcac gaacgggata tggaatttac ttattccggg gcgatgcaat taaaagaaaa  17700
atatctagtt aaagataaaa ccactggtca aatttatgaa actccacagt ttgcatttat  17760
gactattgga atggcattgc atcaagatga acctgttgat agattaaaac atgttattcg  17820
tttttatgaa gcagtatcta ctcgacagat ttcattacca actcctatta tggctggttg  17880
ccgtactccg actcgacagt tcagttcatg cgttgttatt gaggcaggag attcattgaa  17940
gtctatcaat aaggcttccg cttcgattgt tgaatatatc tctaaacgcg ctggaattgg  18000
tattaacgtt ggtatgattc gtgctgaagg ttctaagatt ggcatgggtg aagtacgcca  18060
tactggtgtt attccttttt ggaaacattt tcagactgct gttaaatcat gttcacaggg  18120
tggaattcgt ggcggcgctg ctactgctta ttatcctatt tggcatttgg aagttgaaaa  18180
tcttctcgtt ttgaaaaata acaaaggcgt agaagaaaac cgcattcgtc atatggatta  18240
tggtgttcaa ctgaatgatt tgatgatgga acgattcgga aagaacgatt acattacttt  18300
gttcagtccg catgaaatgg gtggagagct ttattattct tattttaaag acaaagaccg  18360
tttccgtgaa ttatacgaag cagcagaaaa agaccctaat attcgtaaaa agcgtattaa  18420
agcccgtgaa ctatttgaat tgctcatgac tgaacgttca ggaacagcaa ggatttatgt  18480
acagttcatt gataatacga ataactatac tccgtttatt cgtgaaaagg cacctattcg  18540
tcagagtaac ttgtgctgtg aaattgctat tccaacaaat gatgtgaata gtcctgatgc  18600
tgaaattgga ttgtgtactc tctctgcatt cgtactagat aattttgact ggcaagacca  18660
agataaaatt aatgaattgg cagaagttca agttcgtgct cttgataatc tgttggatta  18720
ccaaggatat ccagttcctg aagcagaaaa agctaaaaag cgtcgaaatc ttggcgtagg  18780
tgttaccaac tatgcagctt ggctggcaag taactttgct tcttatgaag atgctaacga  18840
tttaacgcat gaactatttg agagattaca gtatggactc attaaagcat ccattaagct  18900
cgccaaagaa aaaggacctt gcgaatatta ttcagacact cgttggtctc gaggcgaatt  18960
acctatcgac tggtacaata aaaagattga ccaaatcgca gctccaaaat acgtttgtga  19020
ctggtcgtcg ctgcgggaag accttaagct ctttggcatc cgtaatagca cattatcagc  19080
acttatgcca tgtgagtcat cttcccaagt ttctaacagt acaaacggta tcgagcctcc  19140
acgtggacca gtctctgtta aagaatcaaa agagggctcc tttaatcaag tcgtgcccaa  19200
tattgagcat aacatagacc tttacgacta tacatggaaa ttagctaaga aaggtaataa  19260
accttatctt acgcaggtag ctattatgct gaaatgggta tgtcaatcag cttcagcgaa  19320
tacatattat gacccgcaga tttttccaaa aggaaaggtt ccaatgtcaa taatgattga  19380
tgacatgcta tacgggtggt attatggcat taaaaatttc tattatcata atacccgtga  19440
tggttctggt actgatgatt atgaaataga aactccaaaa gctgaagatt gttcatcctg  19500
taaattatga tataatttga ctcacggacg agtcaccaac tattaactaa gtggaaaatt  19560
tatgagcaca gtttttaata caaacccagt tgatgtttta aaagaaccta tgttttttgg  19620
ttcaggtctt ggtattgcgc gttatgatat tcaacggcat cgagtatttg aagaacttac  19680
agagaagtcc ttatcatttt tctggcgccc ggaagaagta aacttaatga tggatgctgc  19740
acagtttaat aagcttcctc agtatcagca aaatattttt actaacaact tgaagtatca  19800
atcacttttg gatagcattc agggtcgtgc gccgtctgct gtacttatgt cattaatttc  19860
agacccaagc cttgatacgt ggattgctac atggactttt agtgaaacta ttcacagtcg  19920
ttcatataca catatcatgc gaaatcttta tactgatcca tcgaaggtat ttgatgagat  19980
tgtattagat gaagctatta tgaaacgtgc tgaatccatt ggacgttatt atgatgatgt  20040
tctgattaaa actcgtgaat gggaaaatgc taaagaattt gtagaactat ctaaagaatc  20100
tcctgatgcc gactttcgtt taaaccgagc tattaaacaa gaagccgaag ctaaacgtgc  20160
tttaatgaaa tctctttacc tctgtttgca cgttattaat gcattagaag ctattcgttt  20220
ttatgtatcc tttgcgtgta cctttaactt ccataagaac atggaaatca tggaaggtaa  20280
tgccaagatt atgaagttca ttgcgcgtga tgagcagctt catcttaaag gcacccaata  20340
tattattcgt caacttcaac ttggcactga tggcgatgaa tgggttaaaa ttgctcaaga  20400
gtgtgaacaa gaagcagttg atattttcat ggaagttaac cgccaagaaa aagattgggc  20460
agttcattta tttaaagatg gagatgttcc tggattaaat acaaatagca tgtggagctt  20520
tattgattac ttaactgtat ctcgtatgaa gcagtgtggt cttccatgcc caattaccga  20580
tgctccggtt aaacatccat atccttggat tcgtgaatat cttaattctg ataatgttca  20640
atctgcacca caagaagtag aattgtcatc ttaccttgtt gcacagattg ataatgatgt  20700
tgatgataaa gttatgatga gttttaaaaa atactttttaa ggagtgggcc gcaaggccca  20760
ttttattatg aaagaaattg caacagaata ttcatttatt aaatatactg agctagaatt  20820
agacgacaac ggaagtataa aacaattatc tattccaaac aagtataacg taatttatgc  20880
tattgctata aatgatgagc ttgtttatat tggaaaaact aaaaatttac gtaaaagaat  20940
aaattattat agaactgcta ttaaccgtaa agacaaaacg tctgattcta ctaaatctgc  21000
attaattcat tctgcgctaa aggaaggaag caaagttgaa ttttacgccc gccaatgttt  21060
taatctttct atgacaaatg agttaggtac aatgacaatc gcaacgattg acctagagga  21120
gccgctattc attaaactgt ttaacccgcc ttggaatatt caacacaaga aaaaatgatg  21180
cttccacatg gagtgtggta ctatattcaa aacacaaaag aggatacaca atgcaagaac  21240
tttttaacaa tttaatggaa ctatgtaagg attcacagcg taagtttttt tactcggatg  21300
atgtaagtgc atctggaaga acttatagaa ttttctcata taattatgca tcttattctg  21360
attggttact tccagatgca ctggaatgtc gtggaattat gtttgaaatg gatggagaaa  21420
aaccggtaag aattgcctct cgtcccatgg aaaagttttt taacttgaat gaaaatccat  21480
tcacgatgaa tatcgattta aatgatgttg attacattct aacaaaagaa gacgggtctt  21540
tggtatcaac ttatttagat ggtgatgaaa ttctgttcaa atcaaagggt tcaatcaaat  21600
ctgagcaggc tttaatggct aatgggattt tgatgaatat taatcatcat cggttgcgcg  21660
atagacttaa agaattagct gaagatggat ttactgctaa cttcgaattc gttgctccga  21720
cgaatagaat cgttcttgct taccaagaaa tgaaaattat tttactgaat gttcgtgaaa  21780
acgaaacggg tgaatacatt tcatacgatg atatttataa agatgctgct cttcgtccat  21840
```

```
atctagttga acgattcgaa atcgatagcc ctaaatgggt agaagaagct aaaaatgcag  21900
aaaacatcga aggctatgtt gctgtgatga aagatggttc tcattttaaa attaagtctg  21960
actggtacgt gtctcttcat agtacaaaaa gttcattaga taatccagaa aaattgttta  22020
agactattat tgacggtgca tcagatgatc ttaaagcaat gtacgctgac gatgaatatt  22080
catacagaaa aattgaggcg tttgaaacga cttatctgaa gtacttagac cgagctctgt  22140
ttttagttct tgactgtcac aataagcatt gtggtaaaga tagaaagact tatgcaatgg  22200
aagcgcaagg tgttgctaaa ggtgctggaa tggatcactt gttcggtatc attatgagtc  22260
tataccaggg gtatgatagt caagagaagg ttatgtgcga aatcgaacag aattttttga  22320
aaaattataa aaaatttatc ccagaaggat actaagctgt ttacaagtcc ctcgtgttgt  22380
gttatagtag tcttactgac ataacatgag gactttatga tggatttgca gcttattact  22440
actgaaatgg tcgttaaagc atacggtgat actacagatg ggatttctgt atttaaagga  22500
aatcgtcgag ttggatatat caccgatctt aagaaagatt tagctaagca agtcaagcgg  22560
aaaacgacca ttaaagaata tcgaaatcgt cgtcttgagc aagcccgtga tatgcttcct  22620
gatgcggttg aggagatgaa agtcttttta gaaaatcagc ttgcgaaata tgattgcgat  22680
gtgttcatta atcagactca acctaatgtt catattaaca actgtaaatg ctatatcatc  22740
gttaatcctt taacgggaaa acatcgtctt ggaattagta atccaaatcg tagcgcatcg  22800
gatatggcag aagatgttga ggcatgcttt aaaatttcta aatctccggc tgaacatcat  22860
attttaatta acggtctttc tcaagacgat attatagagg ttattaaaac tttatgcaat  22920
taagtaatac gacagcaggt ttgctattaa ttgtaattgc attaggcgga acttctttaa  22980
ttttaaaaaa taaaattgaa agattagaaa cgtctgttgt agaaattaca aaaacggcca  23040
atgaaaacgc cttagcatta aataatttgc gaattcagta taattatatt gatgcgatga  23100
ataataaaaa tcgtgaggcg attgctgcta ttgagcgtga aaatgaaaaa ctgcgcaaag  23160
atgcaaagaa ggcggatgtg gtggctcgta agccaggatt ggttgaaaaa caaatcaaca  23220
actccttcaa caagttcgca gaagacatcc aggacctttc taaatgatta gactatcagc  23280
agtaatatta tctatcggtc ttctagctgg ttgttcgaca aagcctctag aagtaaagaa  23340
agaaacagtt catcctaatt ggcctgtaca aataaagtca tatgacgaag ctaaattatc  23400
ttggcaagtt aaagttattg atggcaaagc ttgggtcggt atgccatttg aagattctca  23460
ggaatttcgt atttggctta atgatgtaaa acgatatgta catgaccaga aaactatgat  23520
atgttattat cgtcaagagt taaaagagga taaatgtaaa tgatttcatg gcatcaattt  23580
gaacatctca aaggattgat ttatgaatcc gagatggctg caatgattta tggacgccag  23640
attcagcgat tagaatcttt acctccaact aatgatgttt tattagctca atcacgtgct  23700
aatcttaaaa atgaatacca aaataagtgg ggcaaagcat ctaaagacct gcatgattat  23760
attcaatcat tagttgagaa aaataaatga aaactctgct agaacgttat attgaatgct  23820
cagaccgtta cattgatgca tgtcatggtg cagtatacat ggatttggat cgtggaatag  23880
tattaaatga tgaagaccct gctaaagctt tagatgatgc tggtaaagcc ctgcgaaaag  23940
aagcgaaagc tcgtgggctt gatatgtatc agcttaaaaa tcacatgata aaatttattt  24000
catccaatgt tcagagtaaa tcagcgaatc aatcaacagc tgaattgtac aaaggacggt  24060
gtgagcacaa tattcgtatt cttgaagttt tcttaggaat taaatgatga aaaagattat  24120
tttgactatt ggctgtcctg gttctggtaa gagtacttgg gctcgcgaat ttattgctaa  24180
aaatccaggg ttttataata ttaatcgtga tgattatcgt caatccatca tgggtcatga  24240
agaacgcgac gagtataagt ataccaaaaa gaaagaaggt atcgtaactt acatgcagca  24300
tgatgttgct aacatgattc tctgccaaga cgcaacgaag ggtgtaattg tttcagatac  24360
taatctgaat cctgaacgac gtaaggtctg ggaagagttt gccaaagagc ttgggcatca  24420
aattgaatat aaagtgtttg atgttccttg gactgaattg gttaaacgca actcaaaacg  24480
cggaactaaa gcagtaccaa ttgatgtttt acgttcaatg tataaaagca tgcgagagta  24540
tctcggtctt ccggtatata aagggactcc tggtaaacca aaagcagtta tttttgatgt  24600
tgatggcgcg ttagcaaaaa tgaatggtcg tggtccttat gaccttgaaa aatgcgatac  24660
cgatattatt aatccaatgg tcgttgaact atccaagatg tatgctctta tgggttatca  24720
aatcgtagtc gtttcaggcc gtgaaagtgg aaccgaagaa gatccaacga aatattatcg  24780
tatgacccgt aaatgggttg aggacattgc tggtgttcca ttagtcatgc agtgtcaacg  24840
cgaacaaggc gatacccgta aagatgatgt agttaaagaa gaaattttct ggaaacacat  24900
cgcaccacat tttgatgtga aattagctat tgatgaccga actcaagtag ttgaaatgtg  24960
gcgccgcatc ggtgttgaat gctggcaagt cgcttcggga gatttttaat ggcttggcac  25020
catgaaactt gggctattgt tattgtaaat agcggtttag ttggtactag taatgggcaa  25080
ttttgtgtat ttactagtga aaatagagca tgggaggaat gccttaaatt aagagaaaag  25140
aatcctgatg ttgaactagt agtaaagaaa actaaactgc ctttaccatg gaaaacgtat  25200
gaataaccta gaaaagattt atcgtctttg tgataaaatt gaaaaagaaa agaaatatct  25260
attttgtcta tggcctattg ttgacggaag agtaggccta gatgttcttg attatgaaac  25320
agaagacaaa gtagatggcg caacttttga taacgctttg gatgttattg attggctcga  25380
agaaaattat gtgaggtaaa tatgtttccg acttactcta aaatcgtaga agtagtgttt  25440
agccaaatta tcgctaataa tatgtttgaa aaacttgata acgcagctga gcttcgaatc  25500
cacgctcaag tgactcatgt attgaacact ttgcttccag accaggtgga ttctattgcc  25560
attacgttgt atccaggttc cgcgcatatc attgttgtat tcggtcttga tgctgagcta  25620
gttatcaaag gcgacattcg ctttgaatct caaactgcgg aattcaaagc gatttaatgg  25680
tttactttac ggtagagttg tgatattata gctctaccaa aacaaatgag gaaattgaaa  25740
tgagcgaatg gtttgaagaa gataaggttt atcgctttaa aactgggtat aaagatattt  25800
ttaatgaaac ttgcggggct aataaacgaa tcgcccagtt tattggggaa aattcattta  25860
aagtaaaaat tgaccctgca aagaatgtta ttagcattaa acgcgaaatt gatgattgtt  25920
ggtataaagc tgttgatgta atgggtgaat cctataaagt tagcccgtta ttttcaattg  25980
cttatatgtt agaatattct tttttcgaag aagttcaaaa agatgattct gtcagtaaat  26040
ttgaaattaa aactgataaa gaaattaagt ggaaagtagt aggtattact ggttgcatgt  26100
tttatatcta tgctcaaact gatacaaagg aagaagctaa aaagaaagct ctagaatatc  26160
ttgaagagta tgaagaaggc ccggtaatga ttacccaaga tgctgaatta gtttctgtca  26220
aattagttaa aaacgttgaa agtaaggagc tgggatcaac atgctaagcg aaaaaccaat  26280
tactgttaaa gaattccaag aaaaagttaa actatttgct caagaattgg taaataaggt  26340
ttctgaacga tttcctgaaa cgtcggttcg tgttattacc gaaactcctc gttcggtatt  26400
agtaattgtg aatccaggtg atggtgacca aataacacat ctcaaattgg attttgatgg  26460
attagttgaa gcacaaaggg tgtatggcgt actatgatga atttaactga tataattgat  26520
aattgtcttg aaaatgatac tggcgatcat agagcgcttg actctgaaac agcaaagttc  26580
```

```
attagaataa ctttaatgaa tgatactctg gtgaatagta ttcatccttc tgtgtatgat  26640
gctattattg tgacgaagta tccagttgag cttcacaaaa agatggttgg cgcaattttt  26700
attgataaga aaaaccgctt taaagatggg cagaatataa ttagttctgt tattaaaagt  26760
ataactaaac ttcgtcacga aatttatcgt gttgaaactg ctaaatctgc ttatctggtg  26820
attatgaaat gaaagcgagt acagtacttc aaattgcata tttagtatca caagaatcaa  26880
aatgttgctc ctggaaagta ggagcagtaa ttgaaaagaa tggacgtatt atttctactg  26940
gatataatgg ttcacctgca ggtggtgtga actgctgtga ttatgctgct gagcaaggtt  27000
ggttgctgaa taagcctaaa catactatca ttcaaggtca taagcctgaa tgtgtatcgt  27060
ttggttcaac tgatcgtttt gtattggcga aagaacatcg tagcgcgcac tctgaatggt  27120
cgtctaaaaa tgaaattcat gctgaactaa atgcgatttt gtttgctgca cgaaacggtt  27180
cttcaattga aggtgctact atgtatgtaa cactttctcc ttgcccagat tgtgcaaaag  27240
caatagctca atctggaatt aaaaagctgg tttattgtga aacatacgat aaaaataaac  27300
ctggctggga tgatattctg cgaaatgcag gtattgaagt gtttaatgtt cctaagaaaa  27360
acttaaataa gttaaactgg gaaaatatca acgaattctg tggtgaataa tgaaatttcg  27420
tttggtacag ctcacagcaa ttagttctta ttccaacgag aacatttcat ttgctgtaga  27480
gtataagaag tatttttctt ctaaatggaa gcagtattat aagtcaaact gggtttgtat  27540
tgatagacca catagttgga aatctgattt agaaaaatgc caaaaattac tttccactct  27600
taaagaacgt ggaacaactc atattaaaac tgtaataggt aaataaatga aactgacgac  27660
tgaacaaaaa gtagcaattc gtgaaatttt gaaaactaaa ttgtccatgg gtgtttcaaa  27720
cgtagttttt gaaaagtctg atggtactat tcgtgttatg aaaggtactc gcgatgctga  27780
ctttatgcca accatgcaaa ctggtaaatt gactgaatct acccggaaag aatctactga  27840
tatgattcca gtatttgatg ttgaacttgg tgcatggcga ggtttttcta ttgacaaatt  27900
gatttccgtt aatggtatga aagttgagca tttgctccaa tttattggta aataaatgct  27960
ttaagaatta tttgttatta ttaattcatc tgttaacaaa aaggaaaaac gatgtctgaa  28020
gtacaacagc taccaattcg tgctgtcggt gaatatgtta ttttagtttc tgaacctgca  28080
caagccggtg atgaagaagt tacagaatca ggacttatta tcggtaaacg tgttcaaggt  28140
gaagttcctg aactgtgtgt agttcactct gtcggtcctg atgttcctga aggtttctgt  28200
gaagttggtg atttgacttc tcttccagtt ggtcaaattc gaaacgttcc acaccctttt  28260
gtagctctgg gtcttaagca gccaaaagaa attaaacaaa aattcgttac ctgtcactat  28320
aaagctattc cgtgtcttta taagtgatat aaataataat atgaattggg tgtcggaata  28380
ataagttaac cgaacaattc tatgtggtag tctacaactg agagatctgt cgaaagaaga  28440
tgaaattcag aagaacgtga ctaccgagtt ttaatctcta acgagaattt ttaaatgatt  28500
aaacaattac aacacgctct tgaactgcaa cgaaacgcat ggaataatgg tcacgaaaac  28560
tatggcgcat ctattgatgt tgaagccgaa gctcttgaaa tcctgcgtta tttcaaacat  28620
ctgaatcctg ctcaaactgc attagctgct gagcttcagg aaaaagatga acttaaatat  28680
gctaagcctc tggcttctgc tgcacgaaaa gcagttcgtc actttgtggt aacattgaag  28740
taatttattg gagattcact gccttagtgt gagctaaatc gaggagccgt cgaactgtct  28800
gattaatgat ttgcgaatca ttatagtttt aagaccccgg cagttttacg gtgtacctct  28860
tgaatgtgaa tgatgacggg tttatggtta tcctggtcgt taaatatcca aaaacctatg  28920
ttccccttga gggcttgcgc aggcaatgcc aataagtcct gcattttcat ttaaaagaga  28980
atttataatg gcaaaacaag ctaaagcaaa gaaagcagtt gaaaagaaag ttggtgattc  29040
taaacgcgct ggctacaagc gtgggtcgaa ctctcgtatc aatcaaactg ttgagaagat  29100
catgcgccga gcacgtgcgg ttcttcgaga tgatgcttct cgttttggta agcagaaagc  29160
ataagttgag gactccttcg ggagtccttt tttattttcc aaagattgca taaagttgtt  29220
tacagtatgg ttcctttgtg atagtattat cttacacaaa caaaggagaa taaaatgaaa  29280
acgattaatc tgaacgctgc agttaaaact aaatgcttca atggtaaata tgatgaaact  29340
atgtggttct taatggcagt tgaaggtgat attattgaag tagaaacaac agaaggtatg  29400
ggaacagatt tcacctttac aattcaagtt cataatttct ttactggttg gatttatgaa  29460
ttgaatacag taatcgttgg aaaaattgaa caaaatgaat taggtgaatg gtattatgtt  29520
acagctcgcc aacgtgccga acgcttaatt gagaagatga aaaaagttgg taaacttgat  29580
atgcagcatt ggaaagtagt aaaataattg tttactttgg tacaggatat gatattatat  29640
acctgtaccg caattaaaca tcttggagaa taaaatgaac tacatcaact ttgaacgtaa  29700
atatgtttct aatggtatta caggttctat tgataccatc tgcctttgga aacatcaaaa  29760
tggatcagta tgcgaaattg aacagtacat gactcctaat tacgtttata tgcgatttga  29820
aaacggtatc acggtttcaa tcacgatgga aggttccaac tttaaaatcg ctctggatga  29880
tgatttccgt gaacgcgatt tagggactca tccttgctgg aatggcgtta atcgcaagct  29940
tttggttaaa acttggattc gtcatattct gagtaacaga gctaaacctg agcatcttga  30000
agcaatcttt gatgtagttc ttaacgaatt tgatatttaa aataaatgag ggctttggc   30060
cccttactga ggaaaatgtt atgtttatga ccacttattt tgatactcgt aaaaacttct  30120
gcgaagtagt tttctcaaag gcgcctaaag accttcctgc acatttgcag cctactagcg  30180
aatcgattaa aaactacgtt gatgtggttt gtcctttaga gtttcgtact gtaaatgggc  30240
gcgatacttt agctatcact aaactcaatc gtgaaattga cattgacccc tcaattgcac  30300
gtgaaattaa tagttctgat attaatggcg gtaatgttaa atcgcacggt tttcagatga  30360
ggttttaatg aaattctttt taggtcaaac tgttgaatta aagggagttg gtatacctgg  30420
attaatttct aaggttctac ctccgtttaa atggagtggt attcaaataa aagaggctta  30480
tattgttttc tgggtagatg gaaatgaaga ccttcgtatg ggtgatgaat tatctcctat  30540
ctacggatta aaggaaatag tatgaatata attaataaga tttttggaat tcagtacatt  30600
aaggtcacat ataaagtaac agataaaaat ccgtatactg atgaacatga agaaccgcaa  30660
gttgagtcta ttatattaga aaaggaccct aactggccag ttgaatttcg tcttccttgc  30720
tatggtcatt gggctgatgt tgaaattata agcattgaaa atgtctgagt tagagattag  30780
aagcaatttt aggtggccat catgtgcatt aagtaatttc gcccattggc ctttcgttat  30840
ggatggcatt caatttggag gtcttgaagg attcctccaa ggatgcaagg tgaaaaacgt  30900
tgaacaacaa cgtcgtatat ttgggttatc cgggcttgcc gctcaacaag ctggaaggtc  30960
ttatgcaaga gctcaggacc gtgggaccct cttctggctt ggagttccat tttcaagata  31020
ctccccggcg tggaaagaat tatacacaaa tgcatatttt gaagcagcga tccaaaacaa  31080
gggcttccgt gatgcattac aagcctcgaa aggaaaagtt ttgaagcaca gcatggctag  31140
tggtctaaca aaagatgata caatactaac cgaagctgaa tttattgatg tgttaaacct  31200
attaagagac tctctatgaa gcctactatt ttaactgata ttgatggagt atgtttaagc  31260
tggcaatcag gccttcctta ttttgctcag aaatataatc ttccgttaga acatatttta  31320
```

```
aaaatgatcc aggatgagaa atttatttct cctggtaaac tctttaattg tgacgaagaa  31380
cttggcgtta agctaattga aaaatacaat cgttcagatt ttattcgtta cttgtctcca  31440
tataaagatg ctctgtgtgt aattaacaaa ttaaaagaag attataattt tgtagctgtt  31500
acagcattgg gtgattctat tgacgctctg ctgaatcgtc aatttaattt gaacgctctt  31560
tttcctggtg ccttctcaga agtactgatg tgtggtcatg attcttcaaa agaagagttg  31620
ttcaaaaagg caaaagagaa atataacgta atttgttata ttgacgatct cgctcaccat  31680
tgcgatcatg cgagtgaaat attaaatgtt cctgtttatt ggatggctcg aggggagcgt  31740
gacaatattc caaaaactgc tcagcgagtt tatacatgga atgatgtaga gaataagatt  31800
ttttcgccga aggaaaataa agaaagtttt gatcgtgaaa aagctataaa agatgcaatc  31860
gagaagatga ttaaaaacga ttcttttcct tggaacacta cctggagaac gcctggattt  31920
aatccttata atcatctata tcatccatat cagacacatc cgtttcagac atggaactat  31980
attaaacctg gtggcataga gtatttgtat aatagaccta ctagtggtga taatattttc  32040
caaggagcat tctaatgttt gttgttcaca ctatttatga aaatgaaggt aatactacac  32100
gtgattacgg tcacgtaaat caatttttta gatgcaatcc agaattccga gctcaaaaag  32160
acgaacgaat ttttaaaaaa tgtgtagagc aaggtttcat ttacgtcaag cactggatgc  32220
aaggaaataa agttagaacc acatatcata agtctttgac tgagcttaat gatgaattga  32280
tttataatag agctgtaaac caaactctga aggatgaata atgattctta aaattctgaa  32340
cgaaatagca tctattggtt caactaagca gaagcaagca attcttgaaa agaataaaga  32400
taatgaattg cttaaacgag tatatcgtct gacttattct cgtgggttac agtattatat  32460
caagaaatgg cctaaaccgg gtattgctac ccagagtttt ggaatgttga ctcttaccga  32520
tatgcttgac ttcattgaat tcacgttagc tactcggaaa ttgactggaa atgctgcaat  32580
tgaggaatta actggatata ttactgacgg taaaaaagat gatgttgaag ttttgcgtcg  32640
ggtgatgatg cgagaccttg aatgcggtgc ttcagtatct attgcaaaca aagtttggcc  32700
aggtttaatt cctgaacaac ctcaaatgct tgcaagttct tatgatgaaa aaggcattaa  32760
taagaat                                                            32767

SEQ ID NO: 6           moltype = DNA  length = 32767
FEATURE                Location/Qualifiers
source                 1..32767
                       mol_type = genomic DNA
                       organism = Escherichia phage HP3.2
SEQUENCE: 6
ccgccgccgc cgccaccgcc gcctgcaata gctccgccat tattaattct tagtctccca  60
ccaatatcgt tttgaataca atgacctcca gctgaaccag gactattgct accgccatta  120
ccgccacgtc catacatcgt tacgccgtgt atattcaact gaacatattc attcggtgta  180
tctccgtaca tgaagaataa aggaacatct ttagaatatg atactaaatc acctgtaata  240
ttaaacacta taggtgcact acctgcctca aaacatctat ctcggaacca ttgaccattg  300
aagttatggt ctgctccaag cgtgtgaata atttctcgtg agcgacctgc aaattgactc  360
atccagcaag gaacacccaa tcttaattga ccagccgctt gactcatcca gcgctgtcct  420
gtttcatttg cggctgaact tccaatccaa ccaggaacac caactactgc cataatttat  480
actccaaagg gggcatttcc cccttgttgt tagaatttaa aatatttact aattttgcga  540
gcaattttag taaagaaagg agttttcaat tctttaattt cttcactcat ttcctgaata  600
gccttaatta aaagagcatt cacagcagag ttagaaattg tcagaacatc agatccatca  660
acttcaactt tagatacagc ttccggtaat tccttttcaa ggtcctgagc aataatacca  720
acttcacgtt taataacact acggtcttta atagacttaa ctttatcgta aatataaact  780
ttcagtcgac atacttttc aagtgctccg ttttctagct ctttttttatt aatcttaaga  840
cgaccatcgg aacgaatata cacatcgtta aagttaccat taccaggaga atagaaagta  900
ccgtcgtaat gaaattcaaa taccgcgtta gggtgtccag ccgctggcga tgcctccgca  960
gatccaacac gaataattgc ttgcccccaa ttgttaggga cacgacgaat accaagatcg  1020
acggcagtta caaaccccttg attggtgatt acacttcttc ctttgagaat cggataataa  1080
caatcctgtg aaacataacc atgatcgacg aatattggtg cttctactcg ccattggttg  1140
ccccaatcac ccggttgtct agcaatccat ccagaaccgt taatgtgtac acgatcgcgg  1200
ttaacgttaa ccattgcgat attttgtgga tttagcgaaa tctcaccatt gtttgtgata  1260
tgtactgccg cctgagtagc atagctataa aatgctagcg aattatcagc accaccctta  1320
ccaatatacc agttaccact cccgtctacg tcaccacgaa tatgcaaagc attaccagca  1380
gttgttgata atacaataga atcacccgga cgtttaataa tcaatctacc ttcggattca  1440
atttcaccaa aaaatttagt cttaattgca ccagtcgcta aagtacgttc agtggaaaaa  1500
tgaacgcctt tgctgtcttc taactgaata atgttatcgc gcgcattatt actatcaccc  1560
caatgattaa accggaaata atcacgtgat tgcttaccac ccgcttcaaa cgtcagcgta  1620
cctttactta aattaacatc accgctaaag gtagcagcaa gagaatcacg ttctaatttt  1680
aaaacgttag caccactagt accacctaaa gtaacatcac cagttctcaa ttcataacgg  1740
aaaggtctat ttgtattata gtttccattt tgatcatctt cgttggtgga aagaatataa  1800
agattctctc cataagtacg gaaaattgta ccaaaatttc cggcatacat acggaatgca  1860
ttagatgagc gaaatttaac ttctgtttta aaagtggtag tgttattaag gttaacagta  1920
gagttaaaat tggtaggagc accgaagtta actgcgccat taaaatcttg ttgagctgtc  1980
catgtgtggc gaccatcttc aagaacaaca cggcggactg tgcaagttct atttccagaa  2040
ttaccgaaca cacgaacgac aaaataacgg tagtttgtct gggatacagt accgcgccaa  2100
acctgaacag tacgccctgt gctagtgtgt tcgctaggac caacggaaaa cataaccagg  2160
tttccgtcaa tcgtccccca atccatattt gctggcatat tctttatttt gttcaaagga  2220
acactaaaca tactaccagg gacaaaatca aaggtttgcc aatctagctc cgctaattga  2280
gttttaatac cacccatacc caaagtaatt ggcaaagagt aagatgtata tacttcgttc  2340
catgtacccc acgcgccacc ggtatatgca cgctcaaaaa tacgatcgcg agtagttgca  2400
cccgttccgg cagtagtaaa tttttggaaa atagcaccac cagaagcacg ctgtttaact  2460
tccagcaaac caacaataac ggctggtaaa ccttcaccag taggacagtt aataacggca  2520
tcagtgccta aaatgttata taacccagga gttttaaaat cattcagatc tccaccatag  2580
aaagtcgctg gtgtgccatg accaacctgc ttccattcct ccccacttagg tgcactagca  2640
tcccatgcag cagcgagaca acgagtataa accataccca tgcgggtagt ataacgctga  2700
gttctcgtgt ataaaccacc ttcaaatatt tctaaaaatc cttgtgcggc tgatccttct  2760
tctggataat ggcgatcaaa tgatgcgatt gcgcttgaac tgtttcgcca taagccacaa  2820
```

-continued

```
tgttctaatt ctcccaagct attaaggtca atcgtttgtg aaagtggacg agttgacgct  2880
tgaacattac gccacacacc ccatggacca ttgacgccat tccatttagc agataaggaa  2940
cgaatataga cgttaccaga tcttacagta taacgctgag tgccagcaaa ttggccggcc  3000
acaaacactt ctagtacacc tacggcattt tcttctggga atttatttgc tggttgcgca  3060
tttgttgaag tagatttcga ccaaacacca agatattctt caatgggccc atacgtatct  3120
aaattagcat cagtaggtaa ttcgccatta tttttataa atgttgtgct attgacattt  3180
atgtcagatg gagttaaggt aatgtccttt gacccatcaa aagatatacc attaattttc  3240
ctaggtgttt gcaatttagt agctgtgcta gaatttccaa ttaaagttcc agttatattt  3300
tctgtaacct ctaaagaccc atttatagtt cctccatatt ttaaacctaa ttctataaca  3360
ctacctgagt catcttttgt gaaaattgtt ttatctttta agtttatagc caattcacct  3420
tcggctaata ctgaagcagc aggacgttga cctgcagttt tgcttctttt aaattgtatt  3480
tgttttaaag tagccataag tcctcttaat aatagccgaa atcttgaaca gaatccttaa  3540
ttacgatttg gtcaaatcgt ggaacgtgtg aaggttgaga tgcaggattc tgtgaaaaaa  3600
ggtttggcgc agttaaattt cctgtcatag tgtctccaga gcgtaatacc ctagagtttg  3660
catttgctgt aacagtattt attgctccat caacataatc tttgcgagta acatcagatg  3720
ctgcggaagg agtagatgta acagttaccg atggagccgt tacagccctg gtaaatgttg  3780
tcaaaccttc tggcgtaata gtaatttgtc cagtagtgat ttcactacct gctggtctaa  3840
aactaatacc gccagaagag ccaccaacta caagagtatt accagtgccg ccaccagaac  3900
gaattcggat gggggtttca ttattactta attgaagata actatttacc ccgtaattaa  3960
tagtaattgg accggtgtaa gtaccaccat tagctttaga aacgaaatcg ttatcagctg  4020
cctgcggttt attatattct gaatatattt taaatgattt gtagagtaca tcgtcaccgg  4080
ctgaattcaa tggaaaattt ccttgatgcc aaatgacaga tccacctaca gttgaaccta  4140
cttttaaatc agccattata tgcccettta ttttaatatt atttataaag aaaaagggaa  4200
cccgaaggct ccctcagttt aaacttctct aaattcttgc ccaaacactt tgccagtttt  4260
agaagaggct tgtgtaggaa gtaccattat atctggaggt gaagccgatt cgcagacata  4320
attaacgcga ataccgttga cgccaaattc ggcaggtttt gaaatgccgc catttcttga  4380
tacttcagaa aagcttaaat ttctcatgcc gccttgacct gcttgggcag ttctttgtgc  4440
atatatcgta aatcctactg cattttcagg aacaactaca taatcttctt ttaattccca  4500
agacccagct tgcccagtaa actcagcttg ggtcgaggaa atatatccat ttgatgcatc  4560
ataaaaacga atagatatat ttgtagttcc aagatcaagt aaatcagcat cagcatatag  4620
ttgtgcttta agataaagaa catcaccagg aattaaattg tagtcagaaa gtttacttat  4680
agcagctgaa gttggcaatc gcgcaatttc attattagtt cctccaaccg cagacataaa  4740
ttgctcaacg ctttcgtatg ttcttttagg aaatcctgta gctccgacgt cttctaaact  4800
atcaaataca acatctaaaa tagtttgata atcatctgtg ctttttctat tacttagttt  4860
aacatgctct aatgcaatag ctcttttaga agaagtataa aaagcagcat atgatacgtc  4920
aaatcttgac aatactgaat ctgatggaaa aactgaagtt cctgctcccc ttaaccaaga  4980
taccacttca ggaggaaaat taacctttcc gctagttaat atagcagcaa gtctattgtt  5040
tgacaaagaa ttcatgaaac tgacaaaagc agctgatgta gtattatttg aagcagaaaa  5100
agcatatgac ttgctatcaa ctaatgctcc cgtagaaggg tcaaaaactc ttaaatgaag  5160
acctgcacta aatgtttgat ttccaacggg attatcctga aatttaacat atggccccgc  5220
agtagaaagc gggcaagaac ccgctatgct tattttatat cttactgaat tgctttccga  5280
taaaaatggc gtttggacat atccttgtcc aaactctgcc ataaattttt ccataatacc  5340
tcttattcaa cccattcaaa tttaacagtt ttattcactg ggtcaggaat aatgcgaaca  5400
ttaccaattc gtaagaaatc acgaatagta agattaccta ttattccatt atcagatggg  5460
atcgctccta tatctgaagg ttgaggaggg ttacctccgt caaatacctg aacaaaactt  5520
gaccaagagt tttggtttt ctgccatgta cgtgtccagc gagtggtacg tgcttctggg  5580
gtcgttggat aagtaatcca atcttggtaa agcgaatcaa gtgtgttacc aaactgagtc  5640
aatgtaccag gagatttaac ttcttcgcca cgttctaagt atggaagccc agtcacttca  5700
ttagtttttt caaccatttt aaaataaccc gggaactggt tataagtggc tgaatcatta  5760
atatcgattg accagaatcc tacagtatca gatgtcggcg cgcgggtata taaatcagag  5820
gttttagtac cctgagaacg aattctcgag ttaacagtca aaccacccga acttatagta  5880
gcacctttg caatgattaa gctttcacca atcgttactt ggccagatgc attattaata  5940
gctaaaggac gcaatccatt aaatacgcca gtttgatcac ccgatgcagt aagcataaaa  6000
ttcgttactg atccatcatt gcgaacaatg aaaccataat ttccgttaat agcacggaaa  6060
gcatttgcgc ttcgagaaat aatttcacca gttgcagtga ctgaattacc aaatgttgct  6120
acaccatttg cattcaatgt tcctgaagca ttaacattta tcggtgttac tgtaccgttg  6180
atattaaatg ttatatttcc agctttatta cgctgagaat aaaaatgact agacgtttca  6240
tcactaactt caaatacggt agaacgtgtt gtgtctgatt ccccactaaa ttgatttccc  6300
cacactctga ctgtcatcgt ttgagccggg tttgttccag tttgaggtcc tttctcaaaa  6360
atcagacgag ttgccgttcc agtattagaa atagttaatg tactatttgc tgaaactgat  6420
ccaccgaatg tagcagtact agatgataca agaggggcac tcagattcgt ttgttgggtt  6480
aaggttagtg aaccattaac tgtttgtgca atgtccctac gaatgaactg gagcgaatct  6540
agaccatcta ataaattact atctacggct tttgctttta atggcaaata atttgctaat  6600
acgcgattta attcatatgg tgatactgca taaccatttt tctcatatga ttctaatggc  6660
tgtgttgaac cagctgtatc attaccaacg aatgtaattg aaccagacga agttttaaca  6720
aaacctctta tcgcagtagt cgctgcccaa gtaggttcac tctgcacaat ccattttaaa  6780
tttttggag atacagcagt atttgctgac gttccagcta cagtttcaga ccgagttgca  6840
actttaataa cgccttcctg tgcttcagta gatttagtac ctaaaagctt tttaggagtt  6900
attaaaacat tatctaatgt tcctgcagca gcttcaactt gtgtagctac acgaagtgta  6960
ccacgctgtg tctcatttgc ttcaagaata ttaagggtat aatggtccca gagagttcct  7020
gattcaacta atccagatag agcaacaaca gaagtacgat cagtactatt aaatctggtt  7080
ttaattttta atggtgtaga gatacgagta tcgtcgacgc ctgcgtcgaa ttcaacctgt  7140
gtagcaattt cagctatacc acttaaactt tcagttgctc tacggtcatt taaagtttta  7200
ggagtgactg cacgagtata atcagttcct gtattaactt cactttgcgt agcaatttca  7260
attaaaccaa ttcttccatc agttgatgtc tttttatgta acgtttctgg tgttacaacc  7320
gcatttgccc atccttcttg gctttgtcca gcaattactt cactttcaac tgctaaaatt  7380
actgcgcctt gttgcgttgg agtagcttta tactgatcca aagctttagg tgaaacaact  7440
aaattattag tgtttttatt ataaacattc gtaccattta attcacgact agaagctgga  7500
gtagctcctg cagtagatac aaaagttaca atacccgata atgtttcaga accttgacga  7560
```

```
gcttgaagct ttttaggagt gatgattgta gtatcatcga tacctgtatt agtttcctgc  7620
tgcgtagcaa tttcagcaac acctctgcga gtttctgtag cagttctttc attcagcttt  7680
ttaggagtga tgataaggtc atctgcaaaa gagaatgtag tgttctgatt tacttgagca  7740
gtagttgcta ttcttgcaat acctctgcga gtttcagtag cagtacgatt agctaacgtt  7800
tctggagtaa ttgctaattc tttttgtgga gaattttcta aatcagcatt tgcttgagct  7860
tgcgtagcta aagcaattac gcctaatctt gctctagtag aagcatttaa agagtctact  7920
ctttctacag ttggaacgtt ttgctgtaca acccagtatt ttccatcaga atcttctata  7980
taagcaagtt gcaaaactgg tacataatta gtttcaccat taaaaactaa ttcttgaact  8040
gttacccatt cagcttcagg cggatattct gaacgttttg ggaattgcag caattgaact  8100
gaagaagcaa ttttatcttc accagcagct ttgattttaa ctgtttgtcc ttttctcatg  8160
taattcatgg aaattttaac agtatcacca acagaaatat cagtcggaag ctgaagttca  8220
attgtttggg ttgttccatt attcgcgcca aataccatga cttcttcatt tggacgaata  8280
tttgaattag ttgttataat gcgtaaacgt gctttactat ccccgtcaaa caatctccac  8340
aatttctcat tatcgtcaaa catcaagaaa ccgtcaatcg atgtacggcc ttcaatggaa  8400
tgagttccaa cttcttgtac tgaagtcgtt tcatcgtatg tagtaacaat tgtatgataa  8460
agtggattca gtttatctaa atcaacgaaa ttaataatat cgccatgatt agcaaatctc  8520
ggaagtttaa cattaattgg tgcagcagaa gtaaatctac gtacgataaa atcattagat  8580
tgtgcttgat acgcagtcga tggagtaaca atcgcagctt ctctgctata atcagcaaca  8640
tacatttgcc acaaacgatt attaaaaatg aatatcatct gtgactttgg atgagtcatt  8700
aaaactgaac gtacctgttc acctctaaaa ttgacaatac tctgatttga agaatttatt  8760
ttaacctgat ttatgccagg ttttccaccg atatcttgaa ttattacggt ttctccatca  8820
agcggagaag gtggtaaagt aaactcaatg tcattgccaa ctgatgtatc tactgaaatt  8880
gcttctccgg attttaattg atatggtcca gatgatacgg ttgtatatac ggcatcagta  8940
cgtaatgctt tccaacgaat tctattaaaa tttccagcag gttttggaat attatccgtt  9000
gctgcccaaa aacgattatt ataaatgatt acaaaatctt ttaaatatcc acgagttggg  9060
tcatattgct gaactgtgtt ttcttgaatt aagtaatcaa cgttaacacc gtcagttcct  9120
acggtacgat cagctaaagc tacgttgatt attttatcgc cacctgcgtc cagaccatct  9180
tctgctctga actttctttt aatctcggcc attctcccgg gctcctattg tgttttcaat  9240
aataagtatt tatacctgtt tactttaaga tttagatagt atataataga aatctcacta  9300
attgaacgag gttcatatgg atttagaaat gatgctggat gaagattaca aagaaggaat  9360
ttgctttatt gactttagtc aaattgctct ttcaactgct ctggtaaact tcccagataa  9420
agaaaaaatt aatttatcaa tggttcgtca tttgatattg aactcaatta agtttaatgt  9480
caaaaaagca aaaacgcttg gatacactaa aattgtactg tgtattgata acgcgaaatc  9540
tggatactgg cgtcgtgatt tcgcttatta ttataagaaa aaccgtggaa aagcacgaga  9600
agaatctact tgggactggg aaggttattt tgaatccagt cataaagtta tagatgaatt  9660
gaaagcttat atgccataca ttgttatgga tattgataag tatgaagcag atgaccacat  9720
tgctgttctt gttaaaaagt tctctttaga aggacataag attttaatca tttcatcgga  9780
cggtgacttt actcaacttc acaaatatcc aaatgttaag caatggtcac cgatgcacaa  9840
gaaatgggtt aaaattaaaa gcggttctgc tgaaattgat tgtatgacta aaattcttaa  9900
gggtgacaaa aaggataacg ttgcttcagt taaagtacga tctgactttt ggtttaccag  9960
agttgaaggt gaacgaactc cttcaatgaa aacttcaatc gttgaagcta ttgctaatga  10020
ccgtgagcaa gctaaggtgc ttctcacaga atctgaatat aatcgttata aagaaaattt  10080
agttctaatt gattttgatt atattcctga taatattgct tcaaacattg tgaattacta  10140
taattcatat aaattaccac cgcgtggcaa aatttattca tattttgtaa aagcgggtct  10200
ttctaaatta actaatagca ttaatgaatt ttgaggtgaa taatggctaa aaaagaaatg  10260
gttgaatttg atgaagctat ccatggcgaa gacttggcta aatttattaa agaagcatct  10320
gatcataaac tgaaaatttc cggttataat gaactgatta aagatattcg aattcgtgcc  10380
aaagatgaac ttggcgttga tggtaagatg tttaatcgtc tattagcttt gtatcataaa  10440
gataaccgtg atgtgtttga agctgaaact gaagaggtag ttgaacttta tgacacagtt  10500
ttctctaaat gatattcgtc cggtcgatga gaccgggctt tcagaaaaag aactttcaat  10560
taagaaagaa aaggatgaaa ttgcaaagct tcttgaccgc caagaaaatg gatttattat  10620
tgaaaaaatg gtagaagagt ttggaatgag ttatcttgaa gctacaacag cattcttaga  10680
agaaaattct attcctgaaa ctcaatttgc taaatttatt ccttcgggta taattgaaaa  10740
aattcagtca gaagccattg acgaaaatct tttacgtcct tctgttgttc gttgtgaaaa  10800
aactaataca ttagatttc tactatgatt aaactccgca tgcctgctgg tggtgaaaga  10860
tacattgatg gtaaatcagt ttataaatta tacttaatga taaaacaaca tatgaatgga  10920
aagtatgatg ttattaagta taattggtgc atgcgggtgt ctgatgccgc ttatcaaaag  10980
cgaagggata agtatttttt ccagaagtta tcagaaaaat ataaattaaa ggaacttgct  11040
ttaatcttta taagcaatct tgttgctaac caggatgctt ggattggcga catctctgac  11100
gctgatgcac ttgtgtttta tcgtgaatat atcggacgct taaagcaaat taaatttaag  11160
tttgaagaag atattcgcaa catttattat tttagtaaaa aagttgaagt ttctgctttt  11220
aaagaaatct ttgagtataa tccaaaagtt caatcaagtt atatttttaa actacttcaa  11280
tcgaatataa tttcgtttga aacgtttatc ttgcttgatt cgtttttaaa tataattgat  11340
aaacatgatg aacagactga taatttagtc tggaataatt attctataaa gttaaaggct  11400
tatagaaaaa ttttaaatat tgattcacag aaagctaaaa gtgtttttat tgaaactgtg  11460
aaatcttgca agtattgata tgaatatagt atattggttt acatttgaag accgtgtcaa  11520
aaataagact ccaccgtact actatatcgg tagtaaatta aattgctcat ttgagaacgg  11580
aataatatat gactcttccg gaaaggaata ctggagctca tgtaaacaaa aaagattttt  11640
gaatgcgcta atgcttcaaa aaccgagcgt taaaataatt caaattgatg atgacttgga  11700
tgttattgaa gcagaacgaa aataccaact tgaagtaaat gcaagagata atccagacta  11760
ttttaatctg gtatatgctg gtggtggatt tggtgtgagt ggtgaaactc atccagccaa  11820
agacccggaa gttagagagc atatgagatt ggctaattat atgaaccgtg acgattttag  11880
accttggaaa acatcacgag ctaatataga gtcttggaaa ttatctcata ttgcttacga  11940
gaattatgtg ttattattat cctctaatct gtacggtaaa actcctggat ggcgaagagt  12000
taaaggtaat ataaatataa ctgatacaac tgctaaatcg atggtaaagt atttcaactt  12060
aggttggata cctctcgaag acccagagta ttgcgaatta tgccagctat gaggtaaagt  12120
gtcatagcac caactgttaa ttaaattaaa ttaaaaagga aataaaatgt ttaaacgtaa  12180
atctactgct gaacttgctg cacaaatggc taaactgaat ggcaataaag gttttcttc  12240
tgaagataaa ggcgagtgga aactgaaact cgataatgcg ggtaacggtc aagcagtaat  12300
```

-continued

```
tcgttttctt ccgtctaaaa atgatgaaca agcaccattc gcaattcttg taaatcacgg  12360
tttcaagaaa aatggtaaat ggtatattga aacatgttca tctacccatg gtgattacga  12420
ttcttgccca gtatgtcaat acatcagtaa aaatgatctg tacaacactg acaataaaga  12480
gtacagtctt gttaaacgta aaacttctta ctgggctaat attcttgttg taaaagaccc  12540
agctgctcca gaaaatgaag gtaaagtatt taaatatcgt ttcggtaaga aaatctggga  12600
taaaatcaat gcaatgattg cggttgatgt tgaaatgggt gaaactccgg ttgatgtaac  12660
ttgtccgtgg gaaggtgcta actttgtact gaaagttaaa caagtttccg gatttagtaa  12720
ctacgatgaa tctaaattcc tgaatcaatc tgcgattcca aacattgatg atgaatcttt  12780
ccagaaagaa ctgttcgaac aaatggttga cctttctgaa atgacttcta aagataaatt  12840
caaatcgttt gaagaactga gcactaagtt cagtcaagtt atgggaactg ctgctatggg  12900
tggtgccgct gcaactgctg ctaagaaagc tgataaagtt gctgatgatt tggatgcatt  12960
caatgttgat gacttcaata caaaaactga agatgatttt atgagctcaa gctctggcag  13020
ttcatctagt gctgatgaca cagacctgga tgaccttttg aatgaccttt aatagattat  13080
attactaatt aattggggac cctagaggtc cccttttta tttcaaaaat ttttcataaa  13140
acggtttaca tccttgtcct tccatggtac tatacaacta tcggcaatac tgctgataat  13200
taaagaggaa aataatatgg ctaaagttga tattgacatc gttgattttg aatatattga  13260
agaaattatt cgtaatcgtt atcctgaact tagtatcaca agtgtacaag attctaagtt  13320
ttggagtatt caaatcgtta ttgaaggtcc tttagaagtt cttgagcggt ttatggctaa  13380
tgaatactgc gatggtatgg atgctgaaga cgtagaattt tacatgggac tgattgaaca  13440
ataattatca aggggctatt aagcccctat taaaatgagg aaaatcaaaa tggaaatcgg  13500
caaaaaatac gagttaaatc cacatcgtat taaatcttc attgatatta gttcatcaaa  13560
tgctagtatg gtcggcatca ttcaagaaaa tggcggttgg tttgaagtta aatcaatatc  13620
aagtttagat ggctttgatt atgtaaccga aatcatttgt gctaatggtg aaatctataa  13680
tgatgatggt atgggtgatg attattttga acttagtgaa gaagagtttt attgtttccg  13740
cgaatataaa gaaccgactt ctgaagagga tgaagtcaaa gacaaggttt ctggcgtaac  13800
aaaaaattcac tgcattgttg acgaaaacaa tgcagatgaa atcattgaac ttttgcgaaa  13860
aactttcaaa aagtagttta catcagggta gtagtgtgat actattaccc tatcaaaact  13920
aatggagaaa agaaaatgtt cgcaccttat attatggcag cagttatgtt ggtctgttta  13980
tatcttttga ttaaagcttg ctaaggagaa taaaatgaga ttacaacgtc agagtatcaa  14040
agattcagaa gttagaggta aatggtattt taatatcatc ggtaaagatt ctgaacttgt  14100
tgaaaaagct gaacatcttt tacgtgatat gggatgggaa gatgaatgcg atggatgtcc  14160
tctttatgaa gatggagaaa gcgcgggatt ttggatttac tattctgacg ttgaacagtt  14220
taaagctgat tggaaaattg tgaaaaagtc tgtttaagga aaataatatg atttttgtat  14280
ttgaatttat gaatgatgaa ttcgattatg caatttttaa cgcattgcat aatcctgatt  14340
taagtgaatt taatgaaatg ttttctgatg ctttgagtat gtcagaagaa tactgtggag  14400
aatgtcaacg tgtttgtgtg acagtttttg aaaacaaaga aaagacgtat gaagaattat  14460
tctttgatgc taataaagcc actgaatggt ttatcgaaag aggatttgcg taatgattaa  14520
attggtattc gcttattctc caactaaaac agttgaaggc tttgacgaat tagcatttgg  14580
tttaggtgat ggtttaccat ggggacgagt taaaaaggac cttcagaatt ttaaagctcg  14640
tactgaaggt acaattatga ttatgggtgc taaaacgttc cagtcattat ctacattact  14700
tcccggtcgt agccatattg tggtgtgtga ccttgagcgt gattatcctg taactaaaga  14760
cggcgattta gcacatttct atattacttg ggagcaatat ataacttaca tttctggcgg  14820
cgaaattcaa gtgtcaagcc ctaatgtacc attcgagact atgcttgatc agaattccaa  14880
agtaagtgta attggcgggc ctgctctgtt atatgctgcg ttaccttatg cggatgaagt  14940
agttgtttcc cgcattgtta aaaggcatcg tgttaattca acggttcaat tagacgcaag  15000
ttttcttgat gatataagca agcgtgaaat ggttgaaacg cattggtata aaatagatga  15060
agtaacaacc cttacggaat cagtatataa atgaaataac acgtggcgga aaatatgaat  15120
tttaattatt accctattct attagaagaa gacgcgaaac agccaaagtg gcagggtcct  15180
cagtttatta aaggtgtcta tcaattagta gttcctaaag acaagattta tagcagttgt  15240
ttcactgaat ccgcttgcag tattttcggt aatagttctc cgtattggaa ttttgacata  15300
aagctggata gaaatatcga tatttggttg aaagctatgg atattggtaa tatcacgttt  15360
gatgagaata attatcatat tattggtcgc ttttccaaac gcggtaaaga attatatttc  15420
acgcctgaaa ttgagagaaa atttgatgct aaaccgtatt gattatttag cttcataaaa  15480
tgtattataa tttatataag gtactaaatg aaacaatacc aagatttaat taaagacatt  15540
tttgaaaatg gctatgaaac tgatgaccga acgggcacag gaacaattgc tttgttcggt  15600
actaaattac gctgggattt aactaaaggt tttcctgcag taacaactaa gaagctcgcc  15660
tggaaagctt gcattgctga gctactttgg tttttatcag gaagcacaaa tgtcaatgat  15720
ttacgattaa ttcagcatga ttcgttaatc caaggcaaaa cagtttggga tgaaaattac  15780
gaaaatcagg caaaagattt aggataccat agtggtgaac ttggcccaat ttatggaaaa  15840
cagtggcgcg attttggcgg tgtagaccaa attatagaag ttattgatcg tattaaaaaa  15900
ctaccaagtg ataggcgtca aattgtttct gcgtggaatc cagctgaact taaatatatg  15960
gcattaccac cttgtcatat gttctatcag tttaatgtgc gtaatggtta tcttgattta  16020
caatggtatc aacgcagtgt agatgttttc ttgggttaat tgaggcctag gtataaggtg  16080
acttatactt gtaatctatc taaacggggg acctctctag tagacaatcc cgtgctaaat  16140
tgtaggacta ccctttaata atttcatcag gattagttac ttaccgtgta aaatctgata  16200
aatggaattg gttctacata aatgcctaac gactatccct ttggggagta gggtcaagtg  16260
actcgaaacg atagacaact tgctttaaca agttgaagat atagtctgat ctgcatggtg  16320
acatgcagct ggatataatt ccggggtaag attaacgacc ttatctgaac ataatgcttc  16380
catttaatat tgcatcatat gctacgttag ttcatattgt agctaagatg tgtaatctta  16440
ttccgggaga tttgatattt tccggtggta atactcatat ctatatgaat cacgtagaac  16500
aatgtaaaga aattttgcgt cgtgaaccta aagagctttg tgaactggta ataggcggat  16560
tgccttataa attccgctat ctttctacta aagaacaatt ggaatacatt cttaaactca  16620
ggcctaaaga tttcgttctc aaagattatc agtcccacgg cgtcttgaaa ggaaaaatgg  16680
cggtgtaatt tcaatttaat tgcgaggata tatgatttta cgatttaaag atacttctgg  16740
tgcagttctt tttacacttc ctaatccaag tgagctagaa gttccaggac caaatcagcc  16800
tattatcatt tatggcaaaa aatattatac tcataaaatg actcgtgagt attttgataa  16860
taaaatttct acagttaaaa cttcttctga ttgttactat gatattactg ttttaacgga  16920
aaaacaatat gacgaattat caccgcgcgg gccgtctatg tcgggtagtg aataaatata  16980
aatccgactt tgatgtcaat attcaccgcg gtacattttg ggaaattac gtcggtaaag  17040
```

-continued

```
atgctggcag ccgggaggct gccattgaat tattcaaaaa agattttata cgtcgaatta  17100
aatccggaga aataactaaa gcacatttag agcctttacg tggaatgagg ctaggatgca  17160
catgtaaacc aaagccgtgt catggtgata taatagctca tatagttaac cgattgttta  17220
aagacgattt tcaagttgag gacttatgca attaattaat gttatcaaaa gtagtggtgt  17280
ttctcagagc tttgacccgc aaaaaattat taaagtttta tcttgggcag ctgagggaac  17340
atcagtagat ccttatgaat tatatgaaaa tattaaatca tatctccgtg atggaatgac  17400
aactgatgac attcagacta ttgtcattaa ggctgctgcg aattctattt cggttgaaga  17460
acctgattat caatatgtag ctgcacgttg tttaatgttt gctcttcgta agcatgttta  17520
tgggcagtat gaaccacgtt catttattga ccatatttct tactgtgtaa atgaaggtaa  17580
atatgacccc gaattattgt caaaatattc agcagaagaa attacatttt tagaatcaaa  17640
aattaagcac gaacgggata tggaatttac ttattccggg gcgatgcaat taaaagaaaa  17700
atatctagtt aaagataaaa ccactggtca aatttatgaa actccacagt ttgcatttat  17760
gactattgga atggcattgc atcaagatga acctgttgat agattaaaac atgttattcg  17820
tttttatgaa gcagtatcta ctcgacagat ttcattacca actcctatta tggctggttg  17880
ccgtactccg actcgacagt tcagttcatg cgttgttatt gaggcaggag attcattgaa  17940
gtctatcaat aaggcttccg cttcgattgt tgaatatatc tctaaacgcg ctggaattgg  18000
tattaacgtt ggtatgattc gtgctgaagg ttctaagatt ggcatgggtg aagtacgcca  18060
tactggtgtt attccttttt ggaaacattt tcagactgct gttaaatcat gttcacaggg  18120
tggaattcgt ggcggcgctg ctactgctta ttatcctatt tggcatttgg aagttgaaaa  18180
tcttctcgtt ttgaaaaata acaaaggcgt agaagaaaac cgcattcgtc atatggatta  18240
tggtgttcaa ctgaatgatt tgatgatgga acgattcgga aagaacgatt acattacttt  18300
gttcagtccg catgaaatgg gtggagagct ttattattct tattttaaag acaaagaccg  18360
tttccgtgaa ttatacgaag cagcagaaaa agaccctaat attcgtaaaa agcgtattaa  18420
agcccgtgaa ctatttgaat tgctcatgac tgaacgttca ggaacagcaa ggatttatgt  18480
acagttcatt gataatacga ataactatac tccgtttatt cgtgaaaagg cacctattcg  18540
tcagagtaac ttgtgctgtg aaattgctat tccaacaaat gatgtgaata gtcctgatgc  18600
tgaaattgga ttgtgtactc tctctgcatt cgtactagat aattttgact ggcaagacca  18660
agataaaatt aatgaattgg cagaagttca agttcgtgct cttgataatc tgttggatta  18720
ccaaggatat ccagttcctg aagcagaaaa agctaaaaag cgtcgaaatc ttggcgtagg  18780
tgttaccaac tatgcagctt ggctggcaag taactttgct tcttatgaag atgctaacga  18840
tttaacgcat gaactatttg agagattaca gtatggactc attaaagcat ccattaagct  18900
cgccaaagaa aaaggacctt gcgaatatta ttcagacact cgttggtctc gaggcgaatt  18960
acctatcgac tggtacaata aaaagattga ccaaatcgca gctccaaaat acgtttgtga  19020
ctggtcgtcg ctgcgggaag accttaagct ctttggcatc cgtaatagca cattatcagc  19080
acttatgcca tgtgagtcat cttcccaagt ttctaacagt acaaacggta tcgagcctcc  19140
acgtggacca gtctctgtta aagaatcaaa agagggctcc tttaatcaag tcgtgcccaa  19200
tattgagcat aacatagacc tttacgacta tacatggaaa ttagctaaga aaggtaataa  19260
accttatctt acgcaggtag ctattatgct gaaatgggta tgtcaatcag cttcagcgaa  19320
tacatattat gacccgcaga tttttccaaa aggaaaggtt ccaatgtcaa taatgattga  19380
tgacatgcta tacgggtggt attatggcat taaaaatttc tattatcata atacccgtga  19440
tggttctggt actgatgatt atgaaataga aactccaaaa gctgaagatt gttcatcctg  19500
taaattatga tataatttga ctcacggacg agtcaccaac tattaactaa gtggaaaatt  19560
tatgagcaca gtttttaata caaacccagt tgatgtttta aaagaaccta tgttttttgg  19620
ttcaggtctt ggtattgcgc gttatgatat tcaacggcat cgagtatttg aagaacttac  19680
agagaagtcc ttatcatttt tctggcgccc ggaagaagta aacttaatga tggatgctgc  19740
acagtttaat aagcttcctc agtatcagca aaatattttt actaacaact tgaagtatca  19800
atcacttttg gatagcattc agggtcgtgc gccgtctgct gtacttatgt cattaatttc  19860
agacccaagc cttgatacgt ggattgctac atggactttt agtgaaacta ttcacagtcg  19920
ttcatataca catatcatgc gaaatcttta tactgatcca tcgaaggtat ttgatgagat  19980
tgtattagat gaagctatta tgaaacgtgc tgaatccatt ggacgttatt atgatgatgt  20040
tctgattaaa actcgtgaat gggaaaatgc taaagaattt gtagaactat ctaaagaatc  20100
tcctgatgcc gactttcgtt taaaccgagc tattaaacaa gaagccgaag ctaaacgtgc  20160
tttaatgaaa tctctttacc tctgtttgca cgttattaat gcattagaag ctattcgttt  20220
ttatgtatcc tttgcgtgta cctttaactt ccataagaac atggaaatca tggaaggtaa  20280
tgccaagatt atgaagttca ttgcgcgtga tgagcagctt catcttaaag gcacccaata  20340
tattattcgt caacttcaac ttggcactga tggcgatgaa tgggttaaaa ttgctcaaga  20400
gtgtgaacaa gaagcagttg atattttcat ggaagttaac cgccaagaaa aagattgggc  20460
agttcattta tttaaagatg gagatgttcc tggattaaat acaaatagca tgtggagctt  20520
tattgattac ttaactgtat ctcgtatgaa gcagtgtggt cttccatgcc caattaccga  20580
tgctccggtt aaacatccat atccttggat tcgtgaatat cttaattctg ataatgttca  20640
atctgcacca caagaagtag aattgtcatc ttaccttgtt gcacagattg ataatgatgt  20700
tgatgataaa gttatgatga gttttaaaaa atacttttaa ggagtgggcc gcaaggccca  20760
ttttattatg aaagaaattg caacagaata ttcatttatt aaatatactg agctagaatt  20820
agacgacaac ggaagtataa aacaattatc tattccaaac aagtataacg taatttatgc  20880
tattgctata aatgatgagc ttgtttatat tggaaaaact aaaaatttac gtaaaagaat  20940
aaattattat agaactgcta ttaaccgtaa agacaaaacg tctgattcta ctaaatctgc  21000
attaattcat tctgcgctaa aggaaggaag caaagttgaa ttttacgccc gccaatgttt  21060
taatctttct atgacaaatg agttaggtac aatgacaatc gcaacgattg acctagagga  21120
gccgctattc attaaactgt ttaacccgcc ttggaatatt caacacaaga aaaaatgatg  21180
cttccacatg gagtgtggta ctatattcaa aacacaaaag aggatacaca atgcaagaac  21240
tttttaacaa tttaatggaa ctatgtaagg attcacagcg taagtttttt tactcggatg  21300
atgtaagtgc atctggaaga acttatagaa ttttctcata taattatgca tcttattctg  21360
attggttact tccagatgca ctggaatgtc gtggaattat gtttgaaatg gatggagaaa  21420
aaccggtaag aattgcctct cgtcccatgg aaaagttttt taacttgaat gaaaatccat  21480
tcacgatgaa tatcgattta aatgatgttg attacattct aacaaaagaa gacgggtctt  21540
tggtatcaac ttatttagat ggtgatgaaa ttctgttcaa atcaaagggt tcaatcaaat  21600
ctgagcaggc tttaatggct aatgggattt tgatgaatat taatcatcat cggttgcgcg  21660
atagacttaa agaattagct gaagatggat ttactgctaa cttcgaattc gttgctccga  21720
cgaatagaat cgttcttgct taccaagaaa tgaaaattat tttactgaat gttcgtgaaa  21780
```

```
acgaaacggg tgaatacatt tcatacgatg atatttataa agatgctgct cttcgtccat  21840
atctagttga acgattcgaa atcgatagcc ctaaatgggt agaagaagct aaaaatgcag  21900
aaaacatcga aggctatgtt gctgtgatga aagatggttc tcattttaaa attaagtctg  21960
actggtacgt gtctcttcat agtacaaaaa gttcattaga taatccagaa aaattgttta  22020
agactattat tgacggtgca tcagatgatc ttaaagcaat gtacgctgac gatgaatatt  22080
catacagaaa aattgaggcg tttgaaacga cttatctgaa gtacttagac cgagctctgt  22140
ttttagttct tgactgtcac aataagcatt gtggtaaaga tagaaagact tatgcaatgg  22200
aagcgcaagg tgttgctaaa ggtgctggaa tggatcactt gttcggtatc attatgagtc  22260
tataccaggg gtatgatagt caagagaagg ttatgtgcga aatcgaacag aatttttga  22320
aaaattataa aaaatttatc ccagaaggat actaagctgt ttacaagtcc ctcgtgttgt  22380
gttatagtag tcttactgac ataacatgag gactttatga tggatttgca gcttattact  22440
actgaaatgg tcgttaaagc atacggtgat actacagatg ggatttctgt atttaaagga  22500
aatcgtcgag ttggatatat caccgatctt aagaaagatt tagctaagca agtcaagcgg  22560
aaaacgacca ttaaagaata tcgaaatcgt cgtcttgagc aagcccgtga tatgcttcct  22620
gatgcggttg aggagatgaa agtcttttta gaaaatcagc ttgcgaaata tgattgcgat  22680
gtgttcatta atcagactca acctaatgtt catattaaca actgtaaatg ctatatcatc  22740
gttaatcctt taacgggaaa acatcgtctt ggaattagta atccaaatcg tagcgcatcg  22800
gatatggcag aagatgttga ggcatgcttt aaaatttcta aatctccggc tgaacatcat  22860
attttaatta acggtctttc tcaagacgat attatagagg ttattaaaac tttatgcaat  22920
taagtaatac gacagcaggt ttgctattaa ttgtaattgc attaggcgga acttctttaa  22980
ttttaaaaaa taaaattgaa agattagaaa cgtctgttgt agaaattaca aaaacggcca  23040
atgaaaacgc cttagcatta aataatttgc gaattcagta taattatatt gatgcgatga  23100
ataataaaaa tcgtgaggcg attgctgcta ttgagcgtga aaatgaaaaa ctgcgcaaag  23160
atgcaaagaa ggcggatgtg gtggctcgta agccaggatt ggttgaaaaa caaatcaaca  23220
actccttcaa caagttcgca gaagacatcc aggacctttc taaatgatta gactatcagc  23280
agtaatatta tctatcggtc ttctagctgg ttgttcgaca aagcctctag aagtaaagaa  23340
agaaacagtt catcctaatt ggcctgtaca aataaagtca tatgacgaag ctaaattatc  23400
ttggcaagtt aaagttattg atggcaaagc ttgggtcggt atgccatttg aagattctca  23460
ggaatttcgt atttggctta atgatgtaaa acgatatgta catgaccaga aaactatgat  23520
atgttattat cgtcaagagt taaaagagga taaatgtaaa tgatttcatg gcatcaattt  23580
gaacatctca aaggattgat ttatgaatcc gagatggctg caatgattta tggacgccag  23640
attcagcgat tagaatcttt acctccaact aatgatgttt tattagctca atcacgtgct  23700
aatcttaaaa atgaatacca aaataagtgg ggcaaagcat ctaaagacct gcatgattat  23760
attcaatcat tagttgagaa aaataaatga aaactctgct agaacgttat attgaatgct  23820
cagaccgtta cattgatgca tgtcatggtg cagtatacat ggatttggat cgtggaatag  23880
tattaaatga tgaagaccct gctaaagctt tagatgatgc tggtaaagcc ctgcgaaaag  23940
aagcgaaagc tcgtgggctt gatatgtatc agcttaaaaa tcacatgata aaatttattt  24000
catccaatgt tcagagtaaa tcagcgaatc aatcaacagc tgaattgtac aaaggacggt  24060
gtgagcacaa tattcgtatt cttgaagttt tcttaggaat taaatgatga aaaagattat  24120
tttgactatt ggctgtcctg gttctggtaa gagtacttgg gctcgcgaat ttattgctaa  24180
aaatccaggg ttttataata ttaatcgtga tgattatcgt caatccatca tgggtcatga  24240
agaacgcgac gagtataagt ataccaaaaa gaaagaaggt atcgtaactt acatgcagca  24300
tgatgttgct aacatgattc tctgccaaga cgcaacgaag ggtgtaattg tttcagatac  24360
taatctgaat cctgaacgac gtaaggtctg ggaagagttt gccaaagagc ttgggcatca  24420
aattgaatat aaagtgtttg atgttccttg gactgaattg gttaaacgca actcaaaacg  24480
cggaactaaa gcagtaccaa ttgatgtttt acgttcaatg tataaaagca tgcgagagta  24540
tctcggtctt ccggtatata aagggactcc tggtaaacca aaagcagtta tttttgatgt  24600
tgatggcgcg ttagcaaaaa tgaatggtcg tggtccttat gaccttgaaa aatgcgatac  24660
cgatattatt aatccaatgg tcgttgaact atccaagatg tatgctctta tgggttatca  24720
aatcgtagtc gtttcaggcc gtgaaagtgg aaccgaagaa gatccaacga aatattatcg  24780
tatgacccgt aaatgggttg aggacattgc tggtgttcca ttagtcatgc agtgtcaacg  24840
cgaacaaggc gatacccgta aagatgatgt agttaaagaa gaaattttct ggaaacacat  24900
cgcaccacat tttgatgtga aattagctat tgatgaccga actcaagtag ttgaaatgtg  24960
gcgccgcatc ggtgttgaat gctggcaagt cgcttcggga gatttttaat ggcttggcac  25020
catgaaactt gggctattgt tattgtaaat agcggtttag ttggtactag taatgggcaa  25080
ttttgtgtat ttactagtga aaatagagca tgggaggaat gccttaaatt aagagaaaag  25140
aatcctgatg ttgaactagt agtaaagaaa actaaactgc ctttaccatg gaaaacgtat  25200
gaataaccta gaaaagattt atcgtctttg tgataaaatt gaaaaagaaa agaaatatct  25260
attttgtcta tggcctattg ttgacggaag agtaggccta gatgttcttg attatgaaac  25320
agaagacaaa gtagatggcg caacttttga taacgctttg gatgttattg attggctcga  25380
agaaaattat gtgaggtaaa tatgtttccg acttactcta aaatcgtaga agtagtgttt  25440
agccaaatta tcgctaataa tatgtttgaa aaacttgata acgcagctga gcttcgaatc  25500
cacgctcaag tgactcatgt attgaacact ttgcttccag accaggtgga ttctattgcc  25560
attacgttgt atccaggttc cgcgcatatc attgttgtat tcggtcttga tgctgagcta  25620
gttatcaaag gcgacattcg ctttgaatct caaactgcgg aattcaaagc gatttaatgg  25680
tttactttac ggtagagttg tgatattata gctctaccaa aacaaatgag gaaattgaaa  25740
tgagcgaatg gtttgaagaa gataaggttt atcgctttaa aactgggtat aaagatattt  25800
ttaatgaaac ttgcggggct aataaacgaa tcgcccagtt tattggggaa aattcattta  25860
aagtaaaaat tgaccctgca aagaatgtta ttagcattaa acgcgaaatt gatgattgtt  25920
ggtataaagc tgttgatgta atgggtgaat cctataaagt tagcccgtta ttttcaattg  25980
cttatatgtt agaatattct tttttcgaag aagttcaaaa agatgattct gtcagtaaat  26040
ttgaaattaa aactgataaa gaaattaagt ggaaagtagt aggtattact ggttgcatgt  26100
tttatatcta tgctcaaact gatacaaagg aagaagctaa aaagaaagct ctagaatatc  26160
ttgaagagta tgaagaaggc ccggtaatga ttacccaaga tgctgaatta gtttctgtca  26220
aattagttaa aaacgttgaa agtaaggagc tgggatcaac atgctaagcg aaaaaccaat  26280
tactgttaaa gaattccaag aaaaagttaa actatttgct caagaattgg taaataaggt  26340
ttctgaacga tttcctgaaa cgtcggttcg tgttattacc gaaactcctc gttcggtatt  26400
agtaattgtg aatccaggtg atggtgacca aataacacat ctcaaattgg attttgatgg  26460
attagttgaa gcacaaaggg tgtatggcgt actatgatga atttaactga tataattgat  26520
```

-continued

```
aattgtcttg aaaatgatac tggcgatcat agagcgcttg actctgaaac agcaaagttc  26580
attagaataa ctttaatgaa tgatactctg gtgaatagta ttcatccttc tgtgtatgat  26640
gctattattg tgacgaagta tccagttgag cttcacaaaa agatggttgg cgcaattttt  26700
attgataaga aaaaccgctt taaagatggg cagaatataa ttagttctgt tattaaaagt  26760
ataactaaac ttcgtcacga aatttatcgt gttgaaactg ctaaatctgc ttatctggtg  26820
attatgaaat gaaagcgagt acagtacttc aaattgcata tttagtatca caagaatcaa  26880
aatgttgctc ctggaaagta ggagcagtaa ttgaaaagaa tggacgtatt atttctactg  26940
gatataatgg ttcacctgca ggtggtgtga actgctgtga ttatgctgct gagcaaggtt  27000
ggttgctgaa taagcctaaa catactatca ttcaaggtca taagcctgaa tgtgtatcgt  27060
ttggttcaac tgatcgtttt gtattggcga aagaacatcg tagcgcgcac tctgaatggt  27120
cgtctaaaaa tgaaattcat gctgaactaa atgcgatttt gtttgctgca cgaaacggtt  27180
cttcaattga aggtgctact atgtatgtaa cactttctcc ttgcccagat tgtgcaaaag  27240
caatagctca atctggaatt aaaaagctgg tttattgtga aacatacgat aaaaataaac  27300
ctggctggga tgatattctg cgaaatgcag gtattgaagt gtttaatgtt cctaagaaaa  27360
acttaaataa gttaaactgg gaaaatatca acgaattctg tggtgaataa tgaaatttcg  27420
tttggtacag ctcacagcaa ttagttctta ttccaacgag aacatttcat ttgctgtaga  27480
gtataagaag tattttttct ctaaatggaa gcagtattat aagtcaaact gggtttgtat  27540
tgatagacca catagttgga aatctgattt agaaaaatgc caaaaattac tttccactct  27600
taaagaacgt ggaacaactc atattaaaac tgtaataggt aaataaatga aactgacgac  27660
tgaacaaaaa gtagcaattc gtgaaatttt gaaaactaaa ttgtccatgg gtgtttcaaa  27720
cgtagttttt gaaaagtctg atggtactat tcgtgttatg aaaggtactc gcgatgctga  27780
ctttatgcca accatgcaaa ctggtaaatt gactgaatct acccggaaag aatctactga  27840
tatgattcca gtatttgatg ttgaacttgg tgcatggcga ggtttttcta ttgacaaatt  27900
gatttccgtt aatggtatga aagttgagca tttgctccaa tttattggta aataaatgct  27960
ttaagaatta tttgttatta ttaattcatc tgttaacaaa aaggaaaaac gatgtctgaa  28020
gtacaacagc taccaattcg tgctgtcggt gaatatgtta ttttagtttc tgaacctgca  28080
caagccggtg atgaagaagt tacagaatca ggacttatta tcggtaaacg tgttcaaggt  28140
gaagttcctg aactgtgtgt agttcactct gtcggtcctg gtgttcctga aggtttctgt  28200
gaagttggtg atttgacttc tcttccagtt ggtcaaattc gaaacgttcc acaccctttt  28260
gtagctctgg gtcttaagca gccaaaagaa attaaacaaa aattcgttac ctgtcactat  28320
aaagctattc cgtgtcttta taagtgatat aaataataat atgaattggg tgtcggaata  28380
ataagttaac cgaacaattc tatgtggtag tctacaactg agagatctgt cgaaagaaga  28440
tgaaattcag aagaacgtga ctaccgagtt ttaatctcta acgagaattt ttaaatgatt  28500
aaacaattac aacacgctct tgaactgcaa cgaaacgcat ggaataatgg tcacgaaaac  28560
tatggcgcat ctattgatgt tgaagccgaa gctcttgaaa tcctgcgtta tttcaaacat  28620
ctgaatcctg ctcaaactgc attagctgct gagcttcagg aaaaagatga acttaaatat  28680
gctaagcctc tggcttctgc tgcacgaaaa gcagttcgtc actttgtggt aacattgaag  28740
taatttattg gagattcact gccttagtgt gagctaaatc gaggagccgt cgaactgtct  28800
gattaatgat ttgcgaatca ttatagtttt aagaccccgg cagttttacg gtgtacctct  28860
tgaatgtgaa tgatgacggg tttatggtta tcctggtcgt taaatatcca aaaacctatg  28920
ttccccttga gggcttgcgc aggcaatgcc aataagtcct gcattttcat ttaaaagaga  28980
atttataatg gcaaaacaag ctaaagcaaa gaaagcagtt gaaaagaaag ttggtgattc  29040
taaacgcgct ggctacaagc gtgggtcgaa ctctcgtatc aatcaaactg ttgagaagat  29100
catgcgccga gcacgtgcgg ttcttcgaga tgatgcttct cgttttggta agcagaaagc  29160
ataagttgag gactccttcg ggagtccttt tttattttcc aaagattgca taaagttgtt  29220
tacagtatgg ttcctttgtg atagtattat cttacacaaa caaaggagaa taaaatgaaa  29280
acgattaatc tgaacgctgc agttaaaact aaatgcttca atggtaaata tgatgaaact  29340
atgtggttct taatggcagt tgaaggtgat attattgaag tagaaacaac agaaggtatg  29400
ggaacagatt tcacctttac aattcaagtt cataatttct ttactggttg gatttatgaa  29460
ttgaatacag taatcgttgg aaaaattgaa caaaatgaat taggtgaatg gtattatgtt  29520
acagctcgcc aacgtgccga acgcttaatt gagaagatga aaaaagttgg taaacttgat  29580
atgcagcatt ggaaagtagt aaaataattg tttactttgg tacaggatat gatattatat  29640
acctgtaccg caattaaaca tcttggagaa taaaatgaac tacatcaact ttgaacgtaa  29700
atatgtttct aatggtatta caggttctat tgataccatc tgcctttgga aacatcaaaa  29760
tggatcagta tgcgaaattg aacagtacat gactcctaat tacgtttata tgcgatttga  29820
aaacggtatc acggtttcaa tcacgatgga aggttccaac tttaaaatcg ctctggatga  29880
tgatttccgt gaacgcgatt tagggactca tccttgctgg aatggcgtta atcgcaagct  29940
tttggttaaa acttggattc gtcatattct gagtaacaga gctaaacctg agcatcttga  30000
agcaatcttt gatgtagttc ttaacgaatt tgatatttaa aataaatgag gggctttggc  30060
cccttactga ggaaaatgtt atgtttatga ccacttattt tgatactcgt aaaaacttct  30120
gcgaagtagt tttctcaaag gcgcctaaag accttcctgc acatttgcag cctactagcg  30180
aatcgattaa aaactacgtt gatgtggttt gtcctttaga gtttcgtact gtaaatgggc  30240
gcgatacttt agctatcact aaactcaatc gtgaaattga cattgacccc tcaattgcac  30300
gtgaaattaa tagttctgat attaatggcg gtaatgttaa atcgcacggt tttcagatga  30360
ggttttaatg aaattctttt taggtcaaac tgttgaatta aagggagttg gtatacctgg  30420
attaatttct aaggttctac ctccgtttaa atggagtggt attcaaataa aagaggctta  30480
tattgttttc tgggtagatg gaaatgaaga ccttcgtatg ggtgatgaat tatctcctat  30540
ctacggatta aaggaaatag tatgaatata attaataaga tttttggaat tcagtacatt  30600
aaggtcacat ataaagtaac agataaaaat ccgtatactg atgaacatga agaaccgcaa  30660
gttgagtcta ttatattaga aaaggaccct aactggccag ttgaatttcg tcttccttgc  30720
tatggtcatt gggctgatgt tgaaattata agcattgaaa atgtctgagt tagagattag  30780
aagcaatttt aggtggccat catgtgcatt aagtaatttc gcccattggc ctttcgttat  30840
ggatggcatt caatttggag gtcttgaagg attcctccaa ggatgcaagg tgaaaaacgt  30900
tgaacaacaa cgtcgtatat ttgggttatc cgggcttgcc gctcaacaag ctggaaggtc  30960
ttatgcaaga gctcaggacc gtgggaccct cttctggctt ggagttccat tttcaagata  31020
ctccccggcg tggaaagaat tatacacaaa tgcatatttt gaagcagcga tccaaaacaa  31080
gggcttccgt gatgcattac aagcctcgaa aggaaaagtt ttgaagcaca gcatggctag  31140
tggtctaaca aaagatgata caatactaac cgaagctgaa tttattgatg tgttaaacct  31200
attaagagac tctctatgaa gcctactatt ttaactgata ttgatggagt atgtttaagc  31260
```

```
tggcaatcag gccttcctta ttttgctcag aaatataatc ttccgttaga acatatttta  31320
aaaatgatcc aggatgagaa atttatttct cctggtaaac tctttaattg tgacgaagaa  31380
cttggcgtta agctaattga aaaatacaat cgttcagatt ttattcgtta cttgtctcca  31440
tataaagatg ctctgtgtgt aattaacaaa ttaaaagaag attataattt tgtagctgtt  31500
acagcattgg gtgattctat tgacgctctg ctgaatcgtc aatttaattt gaacgctctt  31560
tttcctggtg ccttctcaga agtactgatg tgtggtcatg attcttcaaa agaagagttg  31620
ttcaaaaagg caaaagagaa atataacgta atttgttata ttgacgatct cgctcaccat  31680
tgcgatcatg cgagtgaaat attaaatgtt cctgtttatt ggatggctcg aggggagcgt  31740
gacaatattc caaaaactgc tcagcgagtt tatacatgga atgatgtaga gaataagatt  31800
ttttcgccga aggaaaataa agaaagtttt gatcgtgaaa aagctataaa agatgcaatc  31860
gagaagatga ttaaaaacga ttctttttcct tggaacacta cctggagaac gcctggattt  31920
aatccttata atcatctata tcatccatat cagacacatc cgtttcagac atggaactat  31980
attaaacctg gtggcataga gtatttgtat aatagaccta ctagtggtga taatattttc  32040
caaggagcat tctaatgttt gttgttcaca ctatttatga aaatgaaggt aatactacac  32100
gtgattacgg tcacgtaaat caattttttta gatgcaatcc agaattccga gctcaaaaag  32160
acgaacgaat ttttaaaaaa tgtgtagagc aaggtttcat ttacgtcaag cactggatgc  32220
aaggaaataa agttagaacc acatatcata agtctttgac tgagcttaat gatgaattga  32280
tttataatag agctgtaaac caaactctga aggatgaata atgattctta aaattctgaa  32340
cgaaatagca tctattggtt caactaagca gaagcaagca attcttgaaa agaataaaga  32400
taatgaattg cttaaacgag tatatcgtct gacttattct cgtgggttac agtattatat  32460
caagaaatgg cctaaaccgg gtattgctac ccagagtttt ggaatgttga ctcttaccga  32520
tatgcttgac ttcattgaat tcacgttagc tactcggaaa ttgactggaa atgctgcaat  32580
tgaggaatta actggatata ttactgacgg taaaaaagat gatgttgaag ttttgcgtcg  32640
ggtgatgatg cgagaccttg aatgcggtgc ttcagtatct attgcaaaca aagtttggcc  32700
aggtttaatt cctgaacaac ctcaaatgct tgcaagttct tatgatgaaa aaggcattaa  32760
taagaat                                                             32767

SEQ ID NO: 7           moltype = DNA  length = 32767
FEATURE                Location/Qualifiers
source                 1..32767
                       mol_type = genomic DNA
                       organism = Escherichia phage ES19
SEQUENCE: 7
tttttttttt ttaatgatac ggcgaccacc gagatctaca cttatgcgat cgtcggcagc  60
gtcagatgtg tataagagac agattttaac tgtaggctgt ggctcaattt caatttcacg  120
ggcatgcaaa ccgtagaaaa tttctgggtc tacaaaagag tccactttaa aggttttaga  180
gacaataatt cgtgcttgaa taccatcttc aaaataaata gtacctttat gtgtgccttc  240
aagaatttga tatgctttca tataacctca attagaaaat aattttatcc aagattgttc  300
tttaattaaa aatggctcag aatcatatgc cattaaactt tgagtaatta atcctttaaa  360
tggtccatca ataaattcca tggtaaaata tggaatttta ttcattaatc ttgcattagg  420
agcagtgcac aaaactctgc atcctttgaa tacacctttt tgtaatttgt attgcttggg  480
ataaaattcg ctcaagacgt tgttatttgc caaaatttca aaatgattca ccaatttatt  540
tttaatagtt tttggcgaaa aataaagata ttcgaaaagt tgcgtatctg tcatcattgc  600
attccaatta cgaaaaactg cggacgagta ataccgccaa tgcagcattt actattgcag  660
cagtgttgca cagtttcaat atgaatatcg taaatcttat ccatatcagg agatttgaca  720
ggctcatcaa ttatatacaa aattcgcgaa agcgataaac ctctgaactt gcttccttta  780
ttaccaataa aactgcgtac agaatcagta aataaacgaa aacgtatatc atcattagaa  840
taacgtgaaa attccttttt aatgttattt gcagaaattt tagcgtaagc tgaagtatta  900
gaaagaacaa taactgttcc gccatcatac aaccaattag cagcaaagtt agtcacagca  960
attgatttac cagattgacg tccaccgtct agtcgaagtg tgcaatactg tttaagcaag  1020
tcttcaaatg gcaggatata ttcgttttta caaatttctt ctactctagc atcagaatgg  1080
tgtgtaaaag cattcatcag ggatagataa ggaccagtta aaaatgttct cattttattc  1140
tctctaaatt tgggccattc catggcgcat gaattgtcca tttctgtatt tacccattac  1200
cgcacttggg ctcgacctta ttacaggttg gtgggaatcc ctcacagaat catgaggtcc  1260
aggttattcc catgttattt aaatgtaaat atttttgccg taatacttat accagtgtgg  1320
cttcattaaa attttttcat cgagtcgttg ttgactcaac ttaatagctg atttgcatgg  1380
attataatca tttttccatt ctactggaat atcgctgatg tcaggaactt cagtatcttt  1440
tatactgaac ccgcgtttta agcattccgt tataatgtcc gattgacgct ttcgcaaaaa  1500
ttctaactta tcgtaaaaga aagtaacatg accagaacct aaaataaatt tagaagatat  1560
tttaaaatct ttaacgcgct taccgtttgc cacatgctta cgaactatac caaaaacacg  1620
cggcaattca cggtattctg cgattaaatg ttgatcagca agttcagata ctaaagtcaa  1680
attaatacga gtcattttat ccctccaagt aactgtgaat atactatcac aattctagga  1740
gaaagtaaat agctttatag atttttatac gcgtcccaag ttccagttct aaacgttgca  1800
atgactcgtt ttgcgcggtt aggtgtttga ttataccatc tacttttagc taagttaact  1860
gctgcttcat cccagcgttt ttgctggagc atgcgtaaag aattagtaaa tcctgctacg  1920
ccggtttccc ccatttggaa gaccatgtta atcaatgcac agcggcgaac agcatcaaga  1980
gaatcataaa ctggttttaa tttagcattt ctcagaattc cgcgaacagc agcatcaaca  2040
tcctgattaa agagtttttc ggcctcatct tttgtaatta caccattaca attacgccca  2100
atagctttat ctaattcaga tttagcaaca cttagtgatg gacttttagt aagcaaatga  2160
ccaatgccaa tagtgtaata accttctgtg tctttataga ttttaagtct aagaccttca  2220
tctatacgta acatttcaaa tatattcata atacctccta agtatttata gaaggtattt  2280
ataaattaaa agaggctgtt cattattcgg taaagtgaag gacccatcac atattgccac  2340
tgagtacgag gaataagagc aaaagcatcc atctctggaa tcataacgcc atctttattt  2400
tcaaaataag actcgcaatg gcaatttcta aacatctcat gctctactgg aatcgtataa  2460
taaaataact gtaagtcttt attactagaa tatttaaata cacctaagtc ttctagaagg  2520
tctggattat aatcgataaa accagtctct tctgagcatt ctctttttgc agcttccagt  2580
gcattcaaat cagaactttc tacacgcccc tttggaatat cccagcgatg tgcaatcatt  2640
ccaggtttac gagaaccggt aactcgtccc ataaataaat ctttatcttc tgtcataaag  2700
ataataccag ctgataatgt tttcatttta atttcctgca ttcagtgata aaattattta  2760
```

```
atttttgagc atatttcttt tcatcaaaaa tcttttgttg tctgcgtaaa cgccatggca  2820
tttcaatgaa catacgccat attcctgata atactgctgc tgtaaaaata ttaacaagta  2880
tagttaaaag aacccaatct cctattctgt ccattggatt ttttataaaa aagtaaaata  2940
cgaacgatga tataggaaga ctaatgatat accacagaag aaccttctta tctgtgaacc  3000
aatcagcatt cgttaactta gcgcgaccgt tttgaataca tacgaactta tcatctgtta  3060
cagtaaatgg cttagctgct tgatatccca ttctaaactc cctaatcaac aaatttttca  3120
tatcttcgga acaaccattc cagtcaactc tatcaactga aatgccatca tccccatcat  3180
ctaaatcata ccagcgagtt tttaaaatca tttaattttc ctacaatcac tcacaaactc  3240
tttcattgac tcattttcaa tataagacat gtagctatta tattctttta attgtatttt  3300
gtaatctttt tttctttgcc aatttatttt aaaattatca taatgaaaat ataaaatgat  3360
accaaagaat gaaaacaatg aaataatttt agtataacaa agctcactcc aaacttctgt  3420
tatatttact gtgccgtcga tgtttaaaat aagacagtca attaacaatc caaaaagact  3480
acctgcaaga gctgcagcca acgccacagc aaaaattaaa aatgactcag aaaacgaata  3540
tttgacttta tttagtttg gcttttgcat cgtgattcct taacaaattt cataatttca  3600
tcaaattcat acgcagcaag tttaagctga tgttcctttt taatcttttt acactgtgct  3660
ttccaatcac gtacgcgttt acgataatgc cttccttgat accagtatcc tacccaattt  3720
acgggtacta ataaaagtgg aactattaat ggaagaatta gcattaacac aagtatttcg  3780
ccagaatcaa tatcagtcat aacatctaaa acacctccaa taatcaatag aattacaaat  3840
gatatgagta taacaggacc tattaacaca tcagtagaaa ttatctgacg ctttaattca  3900
tacttcaacg gtttacttgg aaggtatagt gatggctttg acatattctc tacattcctt  3960
aacaaatttt tctagtaata aatcactttc aaaattggga ttttctacaa atttatcaaa  4020
aagatcatca acaatagtta agatattctt tttactaaga atacgtttat tttcatgctt  4080
cgtttcagaa tcaactataa gagtaaagaa atatttcttg ccctgaaatt ttacagtagt  4140
atcaatataa aataaatttg acttttgtaa attacgttta aaccatgcgt cacttaaact  4200
ataaacaccg agataatcaa aatcgtcgtt taaataacaa accgtccatt caggagaaat  4260
gaaatcagta aattcaacat caaaatcaca cgtcaatgaa tgaattgatt caatactgtt  4320
aatgagtatt ccaggacgta ttaaagactt tttacctcta gaaaatcttc cggaaaggct  4380
ttcatcagtt tcatatgaag acccccaata gtaattacgt ccttctgcca tgcgtttaag  4440
agcatttagt aattggtctg gaacatcaac ctgtctttga aactcttcaa acattgaatt  4500
gaaatcactt tgcattttca ttcctattta ctccaagtaa taggggcccg aagcccctta  4560
tcattatttc agagaattaa tatattcctg aacatcggca gaggtagttt caaccccaga  4620
aatattacca ttaaaggttt caactcgagc aagagtatct tcaatatcaa ccttagtcag  4680
tgctgcaatt tcaactacat catcagcagt actaattcca agggcattcg ctgcacgagt  4740
ttcacggata tattccaatt taaccgcaag ttcttgacga gcatcatcta actcaactac  4800
tttcttggcg atttcaattc gcatttcagc ataaccgtca gccttagtag tcaactgctc  4860
agctgttcga cgatatagta aaccgagttt agcatgcatt gttacatctt ggccttcgga  4920
aagaagttta cgaatttcac gctcttttga ttcggcctgt cgattctttt cgataacaag  4980
ttcacgaata cgtttttctt cgttaataga tttaacagaa gcagtttta gatctttaat  5040
tttatcaagt agttttgctg ctgcagcagt atactgttct tcgacagata gatttttagc  5100
catagcagaa ccaagtttag tgcgaataaa ctcaacaatt ttcttcagtg tgttcatagt  5160
atttccttag gttaattgag atttaaaatc cgtaggagta taatactcta tcgtcaaatt  5220
ataggctcat aatatctcaa tcatgagcct gcgtaaactt atttcatatt attgaaatat  5280
tcttctgcga tttcgtcgtt atcatggtaa actttagaag acagtttaac ataaccttct  5340
gctgtgaaca tattaatcac aacttttaca gtataccact gaccgtcttc attacccatt  5400
actgcgtaag tttcaaacat cggatgatca ggaccgataa ctttaatatc attcactgta  5460
cgaccgaaat cttctgaaac gcatttcata aagaagttga acagttcgcc gtaattatcc  5520
atttcattct ccaagttgtt ttctgtatca gtagttgata gttgtatagt accatggaag  5580
aacagagatg taaacagttt tgtgaaaaaa tttttaggga attctagggc agggatgggc  5640
aattaaagga taggataata tattataaag ggtataaact aaatgatgcc tagagaggtc  5700
cagaaaggcc tagataccaa aaagccctat catttagata gggatttaaa attatttacc  5760
tagtttactt attatagctt ctgcagcagc ttttagctta gatgcagtgt taatacgatt  5820
tttaatttca gtatacgcat cgccaagaac atcaaggcta tcagaataaa cacttacact  5880
attgcgttcg ctatttgaaa tagaaccttt agttttgcgg tcaaaatcgg tgtacacgtc  5940
ttgaagatcg cgggctgcct tctttgcatc atccaatgca tcaagagctt tattcaaagc  6000
attaacgtat tttttagtgt cgaacatatt cttagaaatt ttaacaggtg cgcgttcagg  6060
agtagctaac acagatttag gaacctgagc gccagatgcc aatttcttag aaattttgaa  6120
aaatgcttta ttgaatttat tttcttgact cattgtaaaa gaactattat cgatgttgta  6180
catttcaata gctttagctt tccacttaag aaaatcgccg cggtcttttg ggtccaattg  6240
gaagaatact ttagtaagat ctgcttcaga tggtaatttt gctgcttcgg ttaaaaattc  6300
ggcataggtt ttcatttaaa atccttgaaa taatttatcg gttggttatt aattatttat  6360
tactttgtta ctatccgtaa cagcgttatc cgagtgattc aaactaaaaa gccccaacct  6420
ttcggtcggg gctaagaatg tcatttgatt tgtttagcag accaaatgcg gtctttaata  6480
attttttgga tgtcttcaac atactcaaga gagtgaacat gtggattatc tttgaaacta  6540
taagcacggg ctaactttg gccttcggtt ttgattacta aaagctcttt aaggatagct  6600
tcatatttag cgataattcc tttaacgata ttttttcttt gtgccgcttt aggatctgct  6660
ttaggagcag gtttacccga agcctttgca aaagcagcgc cagtagcaac taaacttttc  6720
caggccatac taactgcatt tcccgtaaat ccttccgctt tcatgtcgcg tgcaaactgg  6780
aatcgtgatt catcagaagc atctttatag gaatatttac ccgcggcaat ggcagctttt  6840
gcaacagctt gaatttcggt gctagatgct tcatttaaca ccgcttcatt taaaaattga  6900
gtatatgatt tcatcttatt tcctgtttta atttgtagat ttaatatact aatatttata  6960
ccaaaaagcc ccaacctttc ggtcggggct aagccttgcg gcaaccttgt cggggttcca  7020
cctgctaagg caagtgtttg tacgaaacgc cgggattcga acccggttat taagtagttg  7080
acgctactca atatttttaa aaggccatat ctcgaccata tccgaacgtt ccgtcaaaaa  7140
cgctactcgg cttacggcaa agatatttcc tcgaatcgat aattcggtgc gccgtttctg  7200
ctgtgatagt aaagagccag aacacagtaa aactgtggga ggaaactata ctccagggaa  7260
catcagtccg acgacttacc ggtagcgacc cggtttctta atattctttt aaagaatcaa  7320
tatattcacg gcgtttacgc cacaaatcaa ttgcttcata cgcggattca gcatttcgaa  7380
ttagccggca tttatgtaaa gacttatgat tttgatattg tgtagataac ggaattgtat  7440
ctaaaaggtc tttacgatca aaatattcgt aaccatctaa accaaatgaa cgatttttga  7500
```

-continued

```
gaaattgcca atgaccatat tcgttttcga cataaacata atctgcatgc tgataaagca  7560
aattaattac acgttcagaa ataacagtat cattatgatt aaaatagaat gttaaatcat  7620
gaactactaa ataaacatta cctttcatat tttcctcact tataattggt cgaggcagta  7680
gggatcgaac ctacgaccta ggacttagaa ggtccttgct cttccttctg agctatgccc  7740
cgtaattggg gtgaccgatg ggagtcgaac ccatgactac gagaatcaca atctcgagtt  7800
ctaccaactg aactacggcc acattaatac ctactccaac aatcaagatg tcttcacacg  7860
aaattaagag aagagtgatc agttcaaccc ctataatcgc gtcaagtaga tattaatgtg  7920
acagttgtca caaatttggc ggacgtgata ggattcgaac ctataaccaa tcgcttaaca  7980
ggcgatcgct ctgccattga gctacacatc caaattggtg gggagtggtg gagtcgaacc  8040
acccgagtcg caatgacaat ggatttacag tccacaccgc tacctctacg ggataactcc  8100
ccaaattaat ttggtggccc tgggtggaat tgaaccacca tctggcgatt atgagtcgct  8160
tgcttgaacc ttccagctac agggccttgg tgctgattga cggaatcgaa ccgccgacct  8220
tctcattaca agtgagttgc tctacctact gagctaaatc agcaaaactg gcggaggcga  8280
taggatttga acctatgagt cgccggagcg actgccggtt ttcaagaccg gtgcattaaa  8340
ccactctgcc acgcctccag tctccgtggc aggatttgaa cctacgacat tctgctccca  8400
aagcagacgc tctaccaaac tgagctacac ggagtaaatt aaattggagc ggataatgag  8460
aatcgaactc acatcatcag attggaagtc tgaggtaata ccattatacg atatccgcaa  8520
atttggtgcg agaagtggga ctcgaaccca caaggaaatc attccgcagc attttaagtg  8580
ctgtgccttt accaatttgg ccattctcgc gctgggaata aaggactcga acctttgcat  8640
cctggaatca aaatccagtg ccttaccaac ttggctaatt cccaattatt aacaaaggct  8700
cttaagcaag aacccttgat gatagaggt attaatcagt gcgatatgag ttaataataa  8760
caaataattc ttaaagcata tttaccattt ataataatac atatttacga tgcattcaag  8820
acccaaagga ttcttgaaaa tatcatattc aagaggacct ttttctgttt caataaagaa  8880
atcaaaattt actgtattaa atttacgttc ttccttcact aatttaactt gagaagatga  8940
acggtcaatg taaacctttt caacttcaaa acatgttaaa atgccataat catcaatcaa  9000
agctttagcc gcgtcttgat catatttata tccattttca atggatgata ctttcgcata  9060
aagaatcatt atcagccttc atcaacaata gtgtgagtat tagcatttac gatttgccac  9120
caatcaaagc gattagaatc catcggtttg ttttcatttt ctttgataat gtcacggagt  9180
tcatcttcag agaatgcttt agcaattaaa tcggtatacc caccacgggg ataataatta  9240
tcacctgcaa acaaaaggaa atttaccttc ccggaagcaa catatgcttc cttaggatac  9300
ttgtttcctg cgtggtcaac cacttcaata taacggtaag gaatatcggt tctttcagcc  9360
cattgccatg ccgccgcagg ggaatcgaaa gcatctacac ctaaacgatt atcttcatct  9420
ttagacggat tattttcgta atccgcatat acataatatt caacgttcat tattcacctt  9480
tagaaatttt atccataaca atagcaatta aaccaattaa aaatgctact acaagtgaaa  9540
acacatttc tgctgtagtc aataatccac atataaatcc aacaaacatt gaaaaactaa  9600
aagcggaagc agaaattgca atagcaacat ttcgaattaa ttcacaacgt ttcattttat  9660
tctcctcagt agtagatagg gtaatagtat cactacccta tctaaaagta aacttatttt  9720
ttacgaaaaa ttgatttatt ttctgctgcc catttttcaa taactgcagc aggaccagta  9780
acaacaattt tatcaccgta atcttctgcg gcgagttgac cgaaattatc taatgcatca  9840
cgaagaactc catgaggcat ttcacccatt ttatctttct tgccagtgta aataaactca  9900
acttttacat cagcagtttc agcaataaat tcttggtaag ttttcatttt gatttccatt  9960
tggttttgtt ttgatagggt aatagtatca caactaaaac cctatgtaaa caactttgtg  10020
aaattatttt aaatcttcta atcgtttctt catcttagaa ccatttttag caatttctcc  10080
tgcatcggag cataatgcta aaagtgcttt aactttagtt tggtctcctt taaaagatga  10140
aggatcgacc gcagcagcaa gttctttaat acgagagaaa agacgctcag cttcagctaa  10200
agccattcca agctttactt ccataccgtg ggaagattca gtgatagtag tttttgtagc  10260
aaactctttg aaagttttca tttttatttt cctaattaat tttgatgagg taatagtatc  10320
actacctcat cagtatgtaa acaactttgt gaaattattt taaatcatct gcccaatcga  10380
gtttaagagg ctctttgtat tcacggtcaa gtacaaccgg aatttgtaca tcaccgctaa  10440
atgataaggg cccaacatta taagacaatg ttatatgcgg tgtgtaatca tcaaaatcgt  10500
gtgtagcacc tagtgcccgc gcatacatgt gtcgacagcg cagatattca gaatctagca  10560
caagtacaag agtcgatcca tcttgtgttt tccacacttc taaatgtcca gaagaagcta  10620
cttcaaaact tccactcgat ggaacatatg gaacatttac tctcgaataa catatggtcg  10680
aatgaatttt ttctctagga actggattag gaacacgtaa agagcgctgg agttcttcca  10740
gcgcgtcaag tgttaattct gaaaacttag ctgctacata aagacccgtt gaaaagtctt  10800
taaattccat cattcttcat ctgcagattc agcagtaaga ttcttgacag cttcaacgat  10860
ttcttcaact ttaatagtat cgccagtgat acctactgca tgagcaattt cagccaaagt  10920
tccttgcaga attttggatt cttccatcag acgagccgct tggtcctgcg tatcaagaat  10980
acgagatttc agagttacga tttcagcaga cagtttttgt tcaatagttt gttcagacat  11040
tatagtacct ttagtgtatt tttaatttta gaaaaaagtt cttcaagaga accatcgttt  11100
gtaattacta aatcgccatc acgaattggc aatccagctt ctgtaatatg tgtatcattg  11160
gatttttgac caggacgaac tacatgaatt actgtagcac ccatcgccct agccgcatcc  11220
atttcatgat cttgacgggt atcaggaacg atataataat cataacctga gttaaattta  11280
tcaagataat ctaaagcaaa taattttacc cagtacatgc ggtcgaagtt attaacaatc  11340
aaatccgtac ctagggcttg catcagacga cggactgacc attgatcttc aatattattt  11400
ataacgtcag taattttgtt aaatgctacg aaattaactg attcttttcc ttcgtcatca  11460
aaaacaaaca cacctttaat tgggctttta ccattaagat agcaaaatgc ttgttccata  11520
atcataatta cttctaattt agtcaaattc aaattagtct cacgatcata gtcaattcct  11580
tcaaactctc tacgagttaa gcaaggatag tcagtgtttg ctgcaaatac accccatgca  11640
taagccaatg catctttaat aggaccagca agttgatatt taactgcaga ataattattc  11700
atgataaaat ctgcagtagt atcttttcca ctacgcttta caccacttaa aaagattagt  11760
ttcatgtgtt tctcctcaaa tttagttaag attataacac atgaaactga agcattaaac  11820
ttctgctata attttgccat ctttttctac ttgaaaatac gtataaggaa tcgttgctgt  11880
gcatactaaa gctgggtctg aatcttccgt gtagctaaat tctacttcag acaggtcaga  11940
aacccaaggc ttataaaaat ttattgacat cacgatttca gttttactat tatctaaaat  12000
gtaaagcgta atgtattcag gacctgtttt ttgggcagta ttttcgcctg taagatagtt  12060
actagttcct agcatccatt catacattcc tatccacgac ttaagctctt cgtcaactat  12120
aaatctcacg atgagtggat cgtattcaaa tgtaactcct ggacgttgtg ctctgcctag  12180
tccaaacggc ccagtcacgg tatcagtaac aggtatccta attcctggaa taggaactga  12240
```

-continued

```
ctgagcattt aaagtaaaag cagatgtagt attactatgt ggtattgata ctacaaagtt  12300
agttgtattt gcttggttaa aaatttgttg cagagcttgc gacatatatt cctcataatg  12360
ctttataact gttggtggta taatgggtct aagtcccttc cattcaattc catttagaac  12420
aaacaacaga aaagaatgga agataataga attaaatatt tgaccagact ttgtttgcag  12480
agaaacgttt tccttttgaa acgaactgct gaagtggcat caatacaacg ttcgcccagt  12540
ctttcggggc gatttcaaca aggctaccca taatattacc aggtatatat gccttaatca  12600
tttggtctgc acccctaaat cctttcactt gactccaatc aatttttaat ttcgttttat  12660
tagtaatagt aggtgtattt gaatattgct ttaaaagctc ttctaggaat tgctggcgag  12720
ctttaggtgg aatatagtgc aagttcaatc cgtacattaa attatgctta cctaaaccaa  12780
ggtaaattat caaaggaaat ttatcccagt aaggaagagt ttccttgtgt ttagcatcat  12840
aagcaaaagc atatattcgt cccggctgcg ggcgaacaac tttatgtcct tttacttgct  12900
taatagtttc agcaaaccac tttctggttt tattattaat tgctgcgcct tcattacgaa  12960
ttttatcacg caatgtttgc ctgaatgaat ttatcataag cagttgtctt tcttgcttat  13020
tgagtttatt cattggtttt gattcaagct tttgaatctt ttcagctgtt ttaattcctg  13080
aagcatattt tgacattgcc gaagtaaacg tagagtattt gattcctctt tcttcagcaa  13140
attgctttcc tgtcattcct tttgctttgg cctttttata ttcaagacct atctgaatcc  13200
atttcttttc gtttaatgat tgcttaacct ttggaacttg gggagtgctt tcattaatta  13260
tttgaaaaat agccattatg ccccccttaaa gccaagagct cgtaatccat cttctgtcag  13320
aattctaaat tttattccac gcttttcagc taaagcttga gctgctttcc atttgtcggt  13380
attaacagaa tatgtataaa tttcattcat aaatcttttc ttcgctgcgg ttgttagatg  13440
tgctggttta actggtggtt gtgtttcttt tttaggtttt atttcaataa aaaattcttg  13500
tccagaagaa tctttcatcc aaatatccat gaagtatcta cgtttttttcc cttctgcatt  13560
acaaaaataa ggaattactg ctgtttcact accccatgca ataatttctg gatttttatc  13620
taaccattca aaaaagaatt tttcccaatt tgatctatac gtaatttttt tagggtcacc  13680
tctatacttt gatatatttt taggaaccca ttttccagaa tatgccattg gattctcctt  13740
ataaatagat aatatattta taaacaggag ggcccatgct ctttacattt tttgatccga  13800
ttgaatatgc ggccaaaacg gtgaataaaa acgcgccgac tattcctatg acagatattt  13860
ttagaaacta taaagactat tttaaacgcg ctcttgcggg ataccgatta cgtacttatt  13920
atatcaaagg ttcaccacgc ccggaagaat tagcaaatac tatatatgga aatccacagt  13980
tgtattgggt tttattgatg tgtaatgata attatgaccc atattatgga tggattactt  14040
cacaagaagc agcttatcaa gcatctatac aaaaatacaa aaatgtaggt ggagaccaaa  14100
tagtatatca tgtgaatgag aacggtgaaa aattttataa tttaatatca tacgatgata  14160
atccatatgt ttggtatgat aaaggtgata aagctagaaa atatcctcaa tatgaaggag  14220
cacttgctgc tgttaatacg tatgaagatg ctgttcttga aaatgaaaaa cttcgtcaaa  14280
taaaaataat agcaaaatca gacattaatt catttatgaa cgaccttata cgtataatgg  14340
agaaatctta tggaaatgat aagtaataac cttaattggt ttgttggtgt tgttgaagat  14400
agaatggacc cattaaaatt aggtcgtgtt cgtgttcgtg tggttggtct gcatccacct  14460
caaagagcac aaggcgatgt aatgggtatt ccaactgaaa aattaccatg gatgtcagtt  14520
attcaaccta taacttctgc agcaatgtct ggaattggag gttctgttac tggaccggta  14580
gaaggaacta gagtttatgg tcattttttta gacaaatgga aaactaacgg aattgtcctt  14640
ggcacgtatg gtggaatagt tcgcgaaaaa ccgaatagac ttgaaggatt ttctgaccca  14700
actgggcaat atcctagacg tttaggaaat gatactaatg tattaaacca aggcggagaa  14760
gtaggatatg attcgtcttc taacattatc caagatagta acttagacac tgcaataaat  14820
cccgatgata gaccactatc agagattcca accgatgata atccaaatat gtcaatggct  14880
gaaatgcttc gccgtgatga aggattaaga ttaaaagttt attgggatac cgaaggatat  14940
ccgacaattg gtattggtca tcttatcatg aagcagccag ttcgtgatat ggctcaaatt  15000
aataaagttt tatcaaaaca agttggtcgt gaaattactg gaaacccagg ttctattacg  15060
atggaagagg cgacgacttt atttgaacgt gatttggctg atatgcaacg ggacattaaa  15120
tcacattcta aagtaggacc agtctggcaa gctgtcaacc gttctcgtca aatggcgtta  15180
gaaaatatgg catttcagat gggtgttggt ggtgtagcta aatttaacac aatgttaact  15240
gctatgttag caggagattg ggaaaaagcg tataaagctg gtcgtgattc attatggtat  15300
caacaaacaa aaggccgtgc atcccgtgtt accatgatta ttcttacggg aaatttagaa  15360
tcatatggcg ttgaagtgaa aaccccagct aggtctctat cagcaatggc tgctactgta  15420
gctaaatctt ctgaccctgc tgaccctcct attccaaatg actcgagaat tttattcaaa  15480
gaaccagttt cttcatataa aggtgaatat ccttatgtgc atacaatgga aactgaaagt  15540
ggacatattc aggaatttga tgatacccct gggcaagaac gatacagatt agttcatcca  15600
actggaactt atgaagaagt atcaccgtca ggaagaagaa caagaaaaac tgttgataat  15660
ttgtatgata taaccaacgc tgatggtaat tttttggtag ccggtgataa aaagactaac  15720
gtcggtggat cagaaattta ttacaacatg gataatcgtc ttcaccagat agatggaagc  15780
aatacaatat ttgtacgtgg cgacgaaacg aaaactgttg aaggcaatgg aactatccta  15840
gttaaaggta atgttactat tgtagttgaa ggtaatgctg acattacagt taaaggagat  15900
gctaccactt tagttgaagg aaatcaaact aacacagtaa atggaaatct ttcttggaaa  15960
gttgctggga cagttgattg ggacgttggt ggtgattgga cagaaaaaat ggcatctatg  16020
agttctattt catctggtca atacacaatt gatggatcga ggattgacat tggctaatat  16080
acttccaatg agcgctgatt taggagaatc catggaaggt tcttctatcg acgtcacctt  16140
taccgctcaa ttagaaacag gtgaaacgtt agtatctata aatataacta gttacgaaga  16200
aactcctggg gttttagtag aagaaaatcg cttatacgga acatatgaat ctgtgtttgg  16260
atttggaaat gacgcgttga aatatcgttt aggcgatgaa tttaaaactg ctgcttcatg  16320
ggaagaactt cctactgatt ctgatactca gttgtattta tggaaagctc ctcaaaacct  16380
ccagaagaca ttcacttacg aagtaacatt aatatatgac taccaagaac aaagtgaatc  16440
tggaggttct ggcagtaatt ctaggtcatc ttctgatact actgaaccga cagatcctcc  16500
tgctccagta agaaaaactc tcgttaaaaa ttatactaaa actatagttg gaaattggag  16560
tcgttgggct aataaattaa gaagctatgt gtatgagagg tcatagatgt caggattaag  16620
ttatgataag tgtgttactg ccggccatga agcatggcct ccaacagttg tgaatgctac  16680
acaaagtaaa gtattcactg gaggaattgc tgttctcgta gcaggtgatc caattacaga  16740
acatacagaa attaaaaagc catatgaaac acatggcgga gtgacacaac ctagaacttc  16800
taaggtatat gtcactggaa agaaagcggt tcaaatggct gatccaatat catgcggtga  16860
tactgtggct caggcatcat ctaaagtatt cattaaatag gatttaaaat ggcaaatacc  16920
cctgtaaatt atcaattaac aagaacagca aatgctattc ccgagatatt cgtcgggggt  16980
```

```
acatttgctg aaataaaaca aaacctcatt gaatggctta atggccaaaa tgaatttttg  17040
gattatgatt ttgaaggctc aagattaaac gttctgtgcg acctttggc ttataatacg  17100
ctgtacattc aacagtttgg taatgctgct gtgtatgaaa gctttatgcg tactgctaac  17160
ttacgaagtt cagttgttca agctgcacaa gataacggat atttacctac ttcaaaatcc  17220
gctgcgcaga ccgaaattat gttaacatgc accgacgcat tgaataggaa ttacattact  17280
attcctcgcg gaactcgctt tttagcatat gcaaaagata cttctgttaa tccatataac  17340
ttcgtttcta ccgaagacgt tattgctatt cgtgataaaa ataaccaata ttttccgcgt  17400
ttaaaattgg cccagggacg tatagtaaga actgaaatca tttatgataa attaacacct  17460
attatcattt atgataaaaa tattgataga aaccaggtta aattatacgt tgatggagca  17520
gaatggatta actggacaag aaagtcaatg gttcatgctg gttctacatc gacaatttac  17580
tacatgcgtg aaactattga tggaaatact gaattctatt ttggtgaagg tgaaatttct  17640
gttaatgctt ctgaaggagc tttgaccgct aattatatcg gaggtcttaa acctactcag  17700
aactctacga ttgttattga gtacatcagt actaatggcg ctgacgcgaa cggagcagtc  17760
ggattttcat acgcagatac attaacaaat ataactgtca tcaatattaa tgaaaatcca  17820
aacgatgacc cagatttttgt tggggcagat ggcggcggtg atccagaaga tattgagcgt  17880
atccgcgaat tgggtactat taaacgcgaa acccagcaac gctgcgtaac tgcgactgac  17940
tatgatacat tcgtttcaga gagatttggt tctattattc aagcagttca gactttcact  18000
gattctacta aacctggtta tgcatttatt gctgctaaac ctaaatcagg tctgtattta  18060
actactgtac agcgtgaaga tattaaaaat tatctcaaag actataattt agctcctatt  18120
acgccatcaa ttatttctcc taattatctt tttattaaga ctaatttaaa agtcacatat  18180
gctttaaata agctgcaaga atccgaacag tggctcgaag gtcaaataat tgataaaatt  18240
gatcgttatt ataccgaaga cgtagaaatt tttaattcat ctttcgctaa atctaagatg  18300
ttgacatatg tagatgatgc agatcattct atcattggct catcagcgac aattcaaatt  18360
gttcgtgaag tacaaaactt ctataaaacg cctgaagcag gtattaaata caataatcaa  18420
ataaaagatc gttctatgga atctaatacg ttttcattta attctggacg aaaggttgta  18480
aatcctgata ctggtttaga agaagatgta ttatatgacg ttcgcatagt atcaacagac  18540
cgagattcta aaggaattgg taaagttatt attggtccat ttgcttctgg cgatgttaca  18600
gaaaatgaaa acattcagcc atatacaggc aacgatttta acaaattagc aaattctgat  18660
ggacgcgaca aatactatgt tatcggtgaa ataaattatc cagctgatgt gatttattgg  18720
aatatcgcta aaattaattt aacatctgaa aaatttgaag ttcagaccat cgaattatat  18780
tctgacccaa ccgatgatgt tatctttact cgcgacggtt cactgattgt atttgaaaat  18840
gacttacgtc cacaatactt aactatcgat ttggagccta tatcacaatg acagtaaaag  18900
caccttcagt cactagtctc agaatttcca agttatccgc aaatcaggtg caagtacgct  18960
gggatgacgt tggtgctaat ttctactatt ttgtagaaat cgctgagaca aaaacgaact  19020
cgggggaaaa tctcccgagt aatcaataca gatggattaa cttaggatat actgcaaata  19080
acagcttctt ttttgatgat gctgacccat tgacatcata cattatcaga gtagctacag  19140
ctgcgcaaga ttttgagcag tctgattgga tttataccga agagtttgaa acttttgcta  19200
caaatgctta tacatttcaa aacatgattg aaatgcaatt agccaataaa ttcattcagg  19260
aaaaatttac tcttaataat tctgattatg ttaattttaa caatgacact ataatggctg  19320
cattgatgaa tgaatcattt caattcagcc catcgtatgt tgatgtttca tcaataagta  19380
attttattat tggtgaaaat gagtatcatg aaatacaagg ttctattcag caagtatgta  19440
aggatattaa ccgagtttat ttgatggaat cagaaggaat tctatatctt tttgagcgct  19500
atcaacctgt agttaaagta tccaatgata aaggacaaac ctggaaagcc gtaaagctct  19560
tcaatgaccg tgtaggatat cctttatcta agacagtata ttaccaatct gcgaacacaa  19620
catacgttct aggatacgac aagattttct atggccgtaa atcgactgac gttagatggt  19680
cagcagatga tgtcagattc agttcgcagg atataacatt tgctaaactt ggcgaccagt  19740
tacatttagg atttgatgta gaaatctttg gtacttatgc gactttacca gcgaatgtat  19800
atcgtatagc tgaagccatt acttgtacgg atgattatat ctatgttgtt gccagagata  19860
aagttagata tataaaaacg agcaatgcac ctatagattc tgatccatta tttccaacat  19920
attcggaaag gctatttgaa cctgatacaa tgactataac tggaaatcct aaagcagtat  19980
gctataaaat ggattctatt ggtgataaag tttttgctct tattatcggt gaagttgaaa  20040
cattaaatgc taatcctaga acgtcaaaaa taattgattc tactgataaa ggaatatatg  20100
ttttaaatca tgacacaaaa acgtggaaaa gagtttttgg caacactgaa gaagaaagaa  20160
gacgtattca acctgggtat gcgaatatgt caactgatgg taaattagtt tctctatctt  20220
cgagtaattt taaattttta aatgataacg ttgttaatga ccctgaaact gtagcaaaat  20280
atcagttaat cggtgccgtt aaatatgaat ttcctcgtga atggttagct gataagcatt  20340
atcatatgat ggcatttata gcagatgaaa agtctgattg ggaaactttt acgcctcagc  20400
caatgaaata ctatgcagaa ccattcttta actggtctaa aaagtctaat acacggtgct  20460
ggataaacaa ctctaataga gctgtagtag tttatgctga tttaaaatac actaaagtta  20520
tagaaaatat tccggaaaca tcaccagata gattagttca tgaatactgg gatgatggtg  20580
attgtacgat agtaatgcca aatgttaaat tcacgggatt taaaaaatat gcgtctggga  20640
tgcttttta taaatcttct ggtgaaataa tttcttatta tgattttaac tatcgtgtga  20700
gagatacagt agaaattatt tggaagccga ctggagtatt tttaaaagca tttttacaaa  20760
accaagagca tgagactcct tggtcgccag aagaagagca tggattagct gaccctgatt  20820
taagaccatt aattggcaca atgatgcctg attcttattt gttgcaggat tcgaattttg  20880
aggcatttg tgaagcatat attcaatatc tttctgacgg atacggaact cagtataata  20940
atttacgaaa tttaattcgt aatcagtatc cacgagaaga gcatgcgtgg gaatatttgt  21000
ggtcagagat atataaaaga aacatttatt taaatgctga caaacgtgat gctgttgcaa  21060
gattttttga atcacgtagt tatgattttt attctactaa aggaattgaa gcatcataca  21120
aatttctttt taaagttctt tataatgaag aagttgaaat tgaaattgaa tctggggctg  21180
gtactgaata tgacataatc gttcaatctg attctttgac tgaagattta gtaggacaaa  21240
cgatttatac agccacagga agatgtaatg ttacttatat agaaagaagt tattctaatg  21300
gtaaattgca atggaccgta actattcata atcttttggg aagattaatt gctggtcaag  21360
aagttaaagc agaaagactc cctagttttg aaggcgaaat tattcgtgga gttaaaggaa  21420
aggatttgct tcaaaacaat atagactata ttaatagaag tagatcatac tatgtaatga  21480
aaattaaatc caatttacct tcttcccgct ggaaatctga cgttattcgt tttgttcatc  21540
cagtaggatt tggatttata gcaattaccc ttttaacgat gtttattaat gttggtttaa  21600
ctcttaaaca tacagagact ataattaata aatacaaaaa ctataaatgg gattctggat  21660
tgcctactga atatgctgat agagtagcta aattaactcc aaccggtgaa attgagtatg  21720
```

```
attcagtaac aggcgaagca atttatgagc ctggcccaat ggctggtgta gaatatcctc  21780
ttcctgatga ctataatgct gaaaataata attcaatatt tcaaggtcaa ttgccgtctg  21840
aacgacgtaa attaatgagt cccctatttg atgcttctgg aacaacattt gcgcaattta  21900
gggatttagt taataaacgt ctaaaagata atataggaaa tccaagagac cctgaaaatc  21960
caacacaggt taaaatagat gaatgattca agtgttatct atcgtgcgat agttacttca  22020
aaatttagaa cagaaaaaat gctgaatttt tataattcaa ttggaagtgg tccggataaa  22080
aacactatct ttatcacatt tggaagatca gaaccgtggt catcaaatga aaatgaggtg  22140
ggctttgccc caccttatcc aaccgattct gtattaggcg taactgacat gtggacgcat  22200
atgatgggaa cagtaaaagt tcttccatca atgcttgatg ctgttattcc tcgcagagat  22260
tggggagata ctagatatcc ggatccatac acatttagaa ttaacgatat tgtagtgtgt  22320
aactcagctc cttacaacgc tactgaatca ggcgcaggct ggttagtata tcgttgttta  22380
gatgttcctg ataccggaat gtgttcaata gcatctttaa ctaataagga tgaatgcctc  22440
aaattaggcg gaaaatggac tccttctgtt aggtcaatga ctcctcctga aggtcgagga  22500
gatgcggaag gaacaatcga acctggagac ggatatgttt gggaatatct ttttgagatt  22560
ccgcccgatg tatctataaa tagatgcaca aatgaatata tcgtagttcc ttggcctgag  22620
gaattaaaag aagacccaac tagatggggg tatgaagata atctcacttg gcaacaagat  22680
gattttggat taatttaccg ggttaaggca aatactatcc gttttaaagc atatttagat  22740
tcagtttact ttcctgatgc tgcattgcca ggaaataaag gatttagaca aatatcaata  22800
atcacaaatc ctcttgaagc taaagctcat ccaaatgacc caaatgttaa agctgaaaag  22860
gattattatg atccagaaga tttaatgagg cattcgggcg aaatgattta tatggaaaat  22920
aggccaccta ttatcatggc aatggatcag acagaagaaa tcaatattct gtttacattt  22980
taaattaagg gagcccatgg gctccctttt tctttataaa tactataaac tcataaggaa  23040
accgctatgt tcattcaaga accaaagaaa ttgattgata ccggcgaaat tggtaacgct  23100
tctactggtg atatcttatt cgacggtggt aataaaatta atagtgattt taacgcaatt  23160
tataatgcgt ttggcgatca gcgtaaaatg gcagtagcaa atggcactgg agcagatggt  23220
caaattatcc atgctactgg atattatcaa aagcactcta tcgcggagta cgcaactcca  23280
gtgaaagttg gcactagaca tgatattgat acctctactg taggtgttaa agttattatt  23340
gaaagaggag aacttggcga ttgtgttgaa ttcattaact ctaatggatc aatatcagtt  23400
actaatcctt taacgattca ggctattgat tcaattaaag gtgtttcggg taatttggta  23460
gtaactagcc catatagtaa agttacttta cgttgtattt catctgataa ttctacgtca  23520
gtttggaatt attctattga aagtatgttt ggccaaaagg aatcaccggc cgaaggtaca  23580
tggaatattt ctacatctgg gtcagttgac attccattgt ttcatcgtac tgaatataac  23640
atggctaaat tgttagttac atgccaatca gtagatggaa gaaaaattaa aacggcagaa  23700
ataaatattc ttgtagatac tgttaattca gcggtcattt cttctgaata tgctgtcatg  23760
cgggttggaa atgaaacaga agaagacgaa atcgctaata ttgcatttag tattaaagaa  23820
aattatgtaa cggcaactat aagttcttca actgtcggta tgagagcagc agttaaagtt  23880
atcgctacgc agaaaatcgg ggtggctcaa taatgaaaca aaatattaat atcggtaatg  23940
ttgttgatga tggtaccggt gactacctgc gtaaaggtgg tataaaaata aatgaaaact  24000
ttgatgaact ttattatgaa cttggcgatg gagatgttcc atattcagcc ggtgcctgga  24060
aaacttataa tgcttcatcc ggtcaaacat taaaagctaa gtggggaaaa tcatacgcta  24120
ttaatacctc ttctggaaga gtaactttac aacttcctaa aggaactgtt aatgattata  24180
ataaagtaat tagagctagg gatgtatttg caacatggaa cattaatcca gttactttag  24240
tagctgcttc tggggataca attaaagggt cgtcatcgtc agttgaaatt aatattcaat  24300
ttagtgattt agagctcgtt tattgtgctc caggacgttg ggaatatgtc aaaaacaaac  24360
aaattgacaa aattattagt tcagatatta gtaatgtagc acgtaaagaa tttttagtcg  24420
aagttcaagg acaaacagac tttttagatg ttttccgcgg aactagctat aatgttaata  24480
acatccgagt aaaacaccgc ggtaacgaat tatattacgg cgatgtattt agtgaaaaca  24540
gtgactttgg ctctcctggg gaaaatgaag gagaattaat tcctcttgat ggatttaata  24600
ttaggttaag acagccttgt aatattggcg acactgttca aattgaaacg tttatggatg  24660
gtgtatcaca atggagaagt tcatatacaa gacgccaaat aaaagtgtta gattcaaaac  24720
taacatcaaa gacttcttta gaaggaagca tttatgttac tgatttatcg gcgatgaaat  24780
caattccatt ttcagctttt ggattaattc ctggcgaacc cattaatcct aattctcttg  24840
aggttcgttt taatggaatt ttacagcaac aggctggaac agctgggtat cctctgtttt  24900
tgtgcgaagg cgctaattca gatacgcaag aaggatgtat atctcttggt ggcgaatgga  24960
aagaatcaaa tacagattat tctatagaat atgaagatgg aaaacctacc agtcttttat  25020
ttgatagaaa atttgaatca ggcgatataa tcgttataac gtggttcaat aatgatttag  25080
gaactctttt agaaaaagat gacatcattg aattgactga tgaccgttat gttagcaaag  25140
gatcgtctac cgaagttact ggcgatgtag ccttaacaga ttttgataaa attggctggc  25200
caaatgttga aaaagttgat tcttatacta gaacgtataa ttcaatatca tctattttcg  25260
atagcattta tcctgtaggt tcaatttatg aaaatgctat aaacccaaat aatccggtga  25320
cttatatggg gtttggttcg tggaaattat ttggtaaagg acaagtttta gtaggatgga  25380
atgatgatgt tacagatcca aactttgcat taaacaataa tgatttagat tctagcggaa  25440
atccttcaca cactgccggt ggaacagttg gaacaacgtc agtaacgctt gaaaatgcaa  25500
atcttcctgc gactaaaact gacgaaagag ttttaattga agatgaaaat ggatcagtta  25560
ttattggagg ttgtcaatat gacccagatg aaactggtcc tatatataca aaatatcgtg  25620
aagactatgc aacaacaaac tcttcacata ctcctcctac taatattagt aatattcaac  25680
cgtctattac tgtataccgt tggataagga ttgcataatg agtttactta ataataaagc  25740
gggagttatt tcccgcttag cggattttct tggttttaga actaagaaaa atgatatttc  25800
gattatgaat aatcagccag taggcgctgt aacaatttca caaatatcaa aaggttttta  25860
tgattcaaat gtagaatctg ctatcaatga cgttagaaat atggcagagc aaccggttgg  25920
agctgtatta gttaatataa gcggcgtatc tcctactggc gtgcaacaaa ccgactattg  25980
gtcatttgaa ggaactgtta ctgatacttc agtcaaatca ggtgacccag ttattgttaa  26040
catgtttggt attccagtta aagctactaa tggaatgact tcaattgaat ttactagtgc  26100
cgttagaata gctctacagg aaatggttgt aaaatttatt gcaattgatt catttgaaga  26160
ccatcctacc ataggaaata aaatacaagt taagtattta gataaccaag aacatatctt  26220
agaacaatac tctgataaag gaattacttt caaacaggaa ataatttctc cttctaaacc  26280
tgggtatgga acttggcaat tattaggtgc gcaaactgtt acgctagata gtcacacaca  26340
acctacagta ttttattatt ttgagagagt agcatgagta acaatacata tcagcacgta  26400
tcaaatgaat caaaatatgt taaattcgat ccagtaggat cgaattttcc tggcactgtt  26460
```

```
acgacagtac agtctgcatt atcaaaaata agtaatatcg gcgtaaatgg tattcctgat  26520
gcaactatgg aagttaaagg aatagcaatg attgcgtcag aacaagaggt tttagatgga  26580
actaataact ctaaaatcgt tacaccagct acattagcaa caagattatt gtatccaaat  26640
gctactgaaa ctaaatatgg tttaacgcgt tattcaacaa atgaagaaac attaaaaggc  26700
tcagataata attcatcaat aacaccacaa aaactgaaat accacactga cgatgtgttc  26760
aaaaatagat attcgtctga gtcatcaaac ggggttatta aaatatcatc tacacctgca  26820
gctttggctg gagttgatga tactactgcg atgactccgc taaaaaccca aaaacttgca  26880
ataaaattaa tttcgcaaat agctccttca gaagacactg caacagaatc ggtgagagga  26940
gtagttcaat tatctactgt tgcacaaatt cgtcaaggaa ctctccgcga aggatatgca  27000
atttccccgt ataccttat gaattctgtt gcaacacatg aatataaggg tgttatacgc  27060
ctaggaacgc agactgaaat taataataat ttgggtggtg ttgcagtaac aggtgaaaca  27120
ctaaatggtc gaggagctac cggttctatg cgtggagtag ttaaattaac gacgcaagcc  27180
ggtattgccc ctgaaggtga tagctctgga gcattagcat ggaacgcaga tgtaattaat  27240
actcgtggtg gacaaactat taatggttct ttaaatttag accatcttac agcaaatgga  27300
atttggtcac gcggtggaat gtggaaaaat ggcgatcaac ctgttgccac tgaaagatat  27360
gcgtccgaac gagttccggt tggaactatt atgatgtttg cgggtgattc agcacctcca  27420
ggttggatta tgtgtcatgg tggaaccgtg tcaggtgacc aatttcctga ttatagaaat  27480
gtagttggaa caagatttgg tggcgattgg aataatcctg gcgttcctga tatgcggggt  27540
cttttcgtca gaggagccgg cacaggcggt catattttaa atcaacgtgg acaagatggc  27600
tatggaaagg atagactggg cgtaggatgt gacggaatgc atgttggtgg tgttcaggca  27660
caacaaatgt cataccataa acatgctggt ggttggggtg aatattacag aagtgaaggc  27720
ccatttggcg cgtcagttta tcaaggatat cttggaacta gaaaatattc cgactgggat  27780
aatgcttcat acttcactaa tgatggattt gaattaggtg gaccgagaga tgctcatggt  27840
acacttaatc gtgaaggatt aattggttat gaaactagac catggaatat atcattaaac  27900
tatattatta aagttcatta ctaaggatta caaatgattg aattaaaaga gttacctttt  27960
gttgatagcg ttcctgacga aggtcaggaa cgtatttcat ggattaaaaa tggtgaagaa  28020
atattaggag ctagtactaa gtatggaaat gatggatcaa tgaatagacc aattgtttcc  28080
gtgtttaaaa acgtcgaagt tcttgatgaa aatgtgggaa ttcttaaaac tgccattgaa  28140
acatcacaga aagatattaa aacaattcaa ggagttttag atgtatcagg agatatagaa  28200
gcactatcgc agatcagtgt taataaaaat gacatatcga atttaaagac acttaccagt  28260
gaacacactg atatattaac tggaactaat aatacagttg acaaaattat tgctgatata  28320
ggtccattta atgatgaaga aaactctgtt tatagaacaa ttagaaatga tttattgtgg  28380
attaaacagg aattaggaca atattctggc caagacatta acggtcttcc tgttgttggt  28440
aatgctagca caggaatgaa acacagaata ataacaaata gtacattatt atcttcacag  28500
ggcattcgtt taagcgaatt agaaaataaa tttactgaat ctgacgtagg atcattaact  28560
gttgaagttg gtaaattacg tgatgaactt ggtaataaac cagtagattt tgggccaaat  28620
atttataata gattaaacac tatagatgat aaacaaactt taataaattc tgatatagca  28680
gaaattaaat cttctattgg atacccagaa aatgtttcta taataacaga aattaataat  28740
aacaaaagta gcattgaatc tattaataat gaattaaatc agagtgaagg tgttaaacag  28800
cgcttaacgg ctattgaaac ttctataggt tcagatgata ttccttctag tattaaagga  28860
aaaattaaaa atcacacaac ttctattgag tctttaaacg gaattgttgg tgaaaacact  28920
tcgtctggtt taagagcgaa tgtttcgtgg ttaaatcaaa ttgttggaac tgactccagc  28980
ggaggacaac cgtctccttc tggatctcta ttaaataaag tttcagtgct tgaaggagaa  29040
gtttcagttt taaacaataa tgttcaaaat atacaagttg aaataggaaa taatagaaca  29100
ggaattaaag gtcaagttat tgaacttact tcacttataa atggaaataa tcctgacgga  29160
tcaactgttg aagaacgagg attaactaat tctataaaaa cgaatgaaac taacattgcg  29220
gtagtcacgc atgaagtaaa tacagctaaa gacaatatat cctctttaca gagcagcgtt  29280
caagctctac aagaagcagg ttatattcct gaagctccaa aagatggcca agcttacgtt  29340
cgtaaagacg gcgaatgggt actactttct accttttat caccagcata acatggggcc  29400
gcagggcccc aaaggatttt aaatgtcagg atataattct cagaatccaa aggaactcaa  29460
agatgtcatt ctaagacgtt taggggctcc aattatcaat gttgagttaa cacccgatca  29520
aatttatgat tgcatccagc gtgccctaga attatacggt gaataccatt ttgatggact  29580
taacaaaggt tttcatgtat tttatgtagg agatgacgaa gaaaaatata aaaccggagt  29640
cttcgattta agaggttcaa atgtattcgc agtaactcgc attttgcgaa caaatattgg  29700
atcaataacg tcaatggacg gaaacgctac atatccatgg tttactgatt ttcttttagg  29760
aatggctggt attaatggcg gtatggggac ttcttgtaat agattttatg gaccaaatgc  29820
ctttggagct gatttaggat attttaccca gcttaccagt tacatgggaa tgatgcaaga  29880
tatgctctct cctattccag acttttggtt taattcagca aatgaacagc tcaaagtcat  29940
gggaaacttc caaaaatatg atttaattat cgtagaaagc tggactaaat catacattga  30000
tactaataaa atggttggaa atacagtagg atatggaaca gtcggtccac aagatagctg  30060
gtcattatct gaacgatata ataacccaga ccacaattta gttggtcgag ttgttggtca  30120
agatccgaat gttaaacagg gtgcttataa taatcgttgg gtgaaagact atgctacagc  30180
tttagctaaa gaattgaatg gtcaaatttt agcacgtcat caaggtatga tgcttcctgg  30240
cggtgttacg attgatggac aacgcttaat agaagaagct cgattagaaa aagaagcatt  30300
acgtgaagaa ttatacttgc tcgatcctcc atttggaatt ttggtaggtt aatatggcta  30360
cttatgataa aaatcttttt gctaaattgg aaaaccgcac tggttattct cagaccaatg  30420
aaactgaaat actaaatcct tatgtaaatt tcaatcatta taaaaacagt caaatattag  30480
ctgatgtatt agtagctgaa agcattcaaa tgcgaggtgt agaatgctat tatgttccaa  30540
gagagtatgt ttcccctgat ttgatatttg gcgaagactt aaaaaataaa tttactaaag  30600
cttggaaatt cgctgcatat ttaaattcat ttgaaggata tgaaggagct aaatcgttct  30660
ttagtaactt tggtatgcaa gtacaggatg aagttacttt gtccattaat ccaaacttgt  30720
ttaaacacca agttaatgga aaagaaccga aagaaggcga tttgatatat tttcctatgg  30780
ataacagctt atttgaaatt aactgggttg aaccatatga tccattttat caattaggcc  30840
aaaacgctat tcgtaaaatt acagcaggta aattcattta ttctggagaa gaaattaatc  30900
cagttctaca gaaaaatgaa ggaattaaca ttccagaatt tagtgaatta gaattaaatc  30960
ctgttcgcaa tcttaacggt attcatgaca ttaatattga tcagtatgct gaagtagatc  31020
aaattaattc tgaagctaaa gaatatgttg aaccttatgt tgttgtcaat aacagaggca  31080
aatctttcga atctagccca tttgataatg atttcatgga ttaataaata ttataaacta  31140
attaaagccc agattaggag aaatcatgtt tggttatttt tataattcgt cttttagacg  31200
```

-continued

```
atatgctacc ttgatgggcg atttgttttc aaatatccaa atcaaacgtc agttagaatc  31260
tggtgataag tttatacgtg ttcctattac gtatgcatca aaggaacact ttatgatgaa  31320
attgaataaa tggacatcga taaattcaca agaagatgtg gccaaggttg aaactattct  31380
acctcgtata aatttgcatt tagttgattt tagctataat gctccattta aaacaaacat  31440
tttaaatcag aatttactgc aaaaaggcgc aacttctgta gtatcacagt ataatccatc  31500
tcctattaaa atgatttatg aattgagtat ctttactcgt tacgaagacg atatgtttca  31560
aatagttgaa cagattcttc catattttca acctcatttt aatacaacta tgtacgaaca  31620
gtttggaaat gatattccat ttaaaaggga tattaaaatt gtactgatgt ctgctgctat  31680
agatgaagct atagatggag ataatttatc tcgtcgtaga atcgaatggt cactaacatt  31740
tgaagtaaac ggatggatgt atcctccagt agatgatgca gaaggattaa ttcgtactac  31800
ttatacagat tttcacgcca atacaagaga tttgcctgat ggcgaaggtg tttttgaatc  31860
tgttgatagc gaagttgttc ctcgagatat taacccagag gactgggatg gaacagtaaa  31920
acaaactttc actagcaatg taaatagacc aacaccgcca gaacctcctg gcccaagaac  31980
atagaggtta ttatggaagg tcttgatata aacaaacttt tagatatttc tgacctcccc  32040
ggaatcgacg gggaggaaat taaagtatat gaacctctac aattagtaga agttaaaagc  32100
aatcctcaaa accgtactcc tgacttagaa gatgattatg gagtagttcg tcgaaatatg  32160
cattttcaac aacaaatgct aatggacgca gccaagattt ttcttgagac ggcaaagaat  32220
gctgattctc ctcgtcacat ggaagtattt gcaactctta tggggcaaat gactacgacg  32280
aacagagaaa tactgaagct tcataaagat atgaaagata ttacatctga gcaggttggc  32340
actaaaggcg ctgttcctac aggtcaaatg aatattcaga acgcgacagt attcatgggt  32400
tcaccaacag aattaatgga cgaaattggt gatgcttacg aggctcaaga agctcgtgag  32460
aaggtgataa atggaacaac cgattaatgc attaaatgat ttccatccat taaatgaagc  32520
tggaaaaatt ttaataaaac acccaagctt agcagaaaga aaagatgaag atggaattca  32580
ttggataaaa tcacagtggg atggaaaatg gtatcctgaa aaattcagtg attatcttcg  32640
tttacacaaa atagtaaaaa tcccaaataa ttctgataag cctgaattat ttcaaactta  32700
taaagataag aataataaaa gatctcggta tatgggtctt cctaacttaa aacgagctaa  32760
tattaaa                                                            32767
```